US012788922B2

(12) United States Patent
Deubel et al.

(10) Patent No.: US 12,788,922 B2
(45) Date of Patent: Nov. 10, 2026

(54) PATIENT INTERFACE WITH HEAT AND MOISTURE EXCHANGER AND VENT

(71) Applicant: RESMED PTY LTD, Bella Vista (AU)

(72) Inventors: Sebastien Deubel, Sydney (AU); Sophie Evelyn Foster, Sydney (AU); Luke Andrew Stanislas, Sydney (AU)

(73) Assignee: RESMED PTY LTD, Bella Vista (AU)

( * ) Notice: Subject to any disclaimer, the term of this patent is extended or adjusted under 35 U.S.C. 154(b) by 531 days.

(21) Appl. No.: 18/554,116

(22) PCT Filed: Apr. 7, 2022

(86) PCT No.: PCT/AU2022/050308
§ 371 (c)(1),
(2) Date: Oct. 5, 2023

(87) PCT Pub. No.: WO2022/213151
PCT Pub. Date: Oct. 13, 2022

(65) Prior Publication Data

US 2024/0374852 A1 Nov. 14, 2024

(30) Foreign Application Priority Data

Apr. 8, 2021 (AU) ................................ 2021901019
Apr. 8, 2021 (AU) ................................ 2021901021

(51) Int. Cl.
*A61M 16/06* (2006.01)
*A61M 16/08* (2006.01)
*A61M 16/10* (2006.01)

(52) U.S. Cl.
CPC .... *A61M 16/0616* (2014.02); *A61M 16/0816* (2013.01); *A61M 16/1045* (2013.01);
(Continued)

(58) Field of Classification Search
CPC ...... A41D 13/11; A41D 13/1138; A61B 5/03; A61B 5/087; A61B 5/097; A61B 5/4836;
(Continued)

(56) References Cited

U.S. PATENT DOCUMENTS 4,782,832 A 11/1988 Trimble et al.
4,944,310 A 7/1990 Sullivan
(Continued)

FOREIGN PATENT DOCUMENTS

CN 105636632 A 6/2016
CN 110382030 A 10/2019
(Continued)

OTHER PUBLICATIONS

"Respiratory Physiology", by John B. West, Lippincott Williams & Wilkins, 9th edition published 2012 (8 pages).
(Continued)

*Primary Examiner* — Annette Dixon
(74) *Attorney, Agent, or Firm* — NIXON & VANDERHYE, PC

(57) ABSTRACT

A patient interface may include: a plenum chamber pressurisable to a therapeutic pressure, a seal-forming structure connected to the plenum chamber and constructed and arranged to seal with a region of the patient's face, a positioning and stabilising structure configured to hold the seal-forming structure in a therapeutically effective position on the patient's head, a frame assembly connected to the plenum chamber, a heat and moisture exchanger material positioned within the frame assembly, a conduit connector connected to the frame assembly and configured to be connected to a conduit, and a plurality of vent holes constructed and arranged to allow for washout of exhaled gases to ambient continuously throughout the patient's respiratory cycle, a first portion of the vent holes being positioned
(Continued)

radially on the frame assembly to direct a first portion of exhaled gases to ambient in a radial direction without passing through the heat and moisture exchanger material.

23 Claims, 118 Drawing Sheets

(52) U.S. Cl.
CPC ............... *A61M 2205/3334* (2013.01); *A61M 2210/0618* (2013.01)

(58) Field of Classification Search
CPC .............. A61M 16/00; A61M 16/0003; A61M 16/0051; A61M 16/0057; A61M 16/0066; A61M 16/0069; A61M 16/0072; A61M 16/022; A61M 16/024; A61M 16/026; A61M 16/047; A61M 16/06; A61M 16/0605; A61M 16/0611; A61M 16/0616; A61M 16/0622; A61M 16/0627; A61M 16/0633; A61M 16/0666; A61M 16/0672; A61M 16/0683; A61M 16/0688; A61M 16/08; A61M 16/0808; A61M 16/0816; A61M 16/0825; A61M 16/0833; A61M 16/0858; A61M 16/0875; A61M 16/0883; A61M 16/10; A61M 16/1005; A61M 16/1045; A61M 16/105; A61M 16/1055; A61M 16/106; A61M 16/1065; A61M 16/107; A61M 16/1085; A61M 16/109; A61M 16/1095; A61M 16/12; A61M 16/16; A61M 16/161; A61M 16/162; A61M 16/20; A61M 16/201; A61M 16/204; A61M 16/206; A61M 16/207; A61M 16/208; A61M 16/209; A61M 2016/0018; A61M 2016/0027; A61M 2016/003; A61M 2016/0033; A61M 2016/0036; A61M 2016/0039; A61M 2016/0661; A61M 2016/1025; A61M 2202/0007; A61M 2202/0085; A61M 2202/0208; A61M 2202/0225; A61M 2205/02; A61M 2205/0216; A61M 2205/0238; A61M 2205/0272; A61M 2205/18; A61M 2205/21; A61M 2205/276; A61M 2205/332; A61M 2205/3331; A61M 2205/3334; A61M 2205/3344; A61M 2205/3355; A61M 2205/3365; A61M 2205/3368; A61M 2205/3379; A61M 2205/3553; A61M 2205/3584; A61M 2205/3592; A61M 2205/3653; A61M 2205/42; A61M 2205/50; A61M 2205/502; A61M 2205/505; A61M 2205/52; A61M 2205/581; A61M 2205/582; A61M 2205/583; A61M 2205/586; A61M 2205/587; A61M 2205/59; A61M 2205/6045; A61M 2205/702; A61M 2205/7518; A61M 2205/7527; A61M 2205/7536; A61M 2205/8206; A61M 2206/10; A61M 2206/14; A61M 2207/00; A61M 2207/10; A61M 2209/06; A61M 2209/086; A61M 2210/0606; A61M 2210/0618; A61M 2210/0625; A61M 2230/432; A61M 39/24; A62B 18/02; A62B 18/025; A62B 23/02; A62B 23/025; A62B 7/10; A62B 9/003; A62B 9/06; B05B 13/06; B29C 39/10; B29C 39/42; B29K 2083/00; B29K 2105/0809; B29L 2023/00; B29L 2031/753; B33Y 80/00; F16K 15/145; G16H 20/40; G16H 40/60; G16H 40/63; Y02A 90/10; Y10S 55/35
See application file for complete search history.

(56) References Cited

U.S. PATENT DOCUMENTS

| | | | | |
|---|---|---|---|---|
| 5,595,173 | A | 1/1997 | Dodd | |
| 5,687,715 | A | 11/1997 | Landis | |
| 5,921,239 | A | 7/1999 | McCall | |
| 6,374,826 | B1 | 4/2002 | Gunaratnam et al. | |
| 6,491,034 | B1 | 12/2002 | Gunaratnam et al. | |
| 6,532,959 | B1 | 3/2003 | Berthon-Jones | |
| 6,581,594 | B1 | 6/2003 | Drew et al. | |
| 6,907,882 | B2 | 6/2005 | Ging et al. | |
| 7,210,481 | B1 | 5/2007 | Lovell et al. | |
| 7,302,950 | B2 | 12/2007 | Berthon-Jones et al. | |
| 7,353,827 | B2 | 4/2008 | Geist | |
| 7,658,189 | B2 | 2/2010 | Davidson et al. | |
| 7,861,715 | B2 | 1/2011 | Jones et al. | |
| 7,866,944 | B2 | 1/2011 | Kenyon et al. | |
| 7,967,013 | B2 | 6/2011 | Ging et al. | |
| 8,636,479 | B2 | 1/2014 | Kenyon et al. | |
| 8,638,014 | B2 | 1/2014 | Sears et al. | |
| 8,733,349 | B2 | 5/2014 | Bath et al. | |
| 10,232,137 | B2 | 3/2019 | Romagnoli et al. | |
| 10,695,521 | B2 | 6/2020 | Harrington et al. | |
| 10,729,870 | B2 * | 8/2020 | Martin | A61M 16/16 |
| 10,773,044 | B2 | 9/2020 | Dantanarayana et al. | |
| 10,792,450 | B2 | 10/2020 | Holley et al. | |
| 11,077,273 | B2 | 8/2021 | Finch et al. | |
| 11,351,324 | B2 | 6/2022 | Dantanarayana et al. | |
| 11,420,008 | B2 | 8/2022 | Dantanarayana et al. | |
| 11,497,874 | B2 | 11/2022 | Gupta et al. | |
| 2007/0044804 | A1 | 3/2007 | Matula et al. | |
| 2009/0044808 | A1 | 2/2009 | Guney et al. | |
| 2009/0050156 | A1 | 2/2009 | Ng et al. | |
| 2010/0000534 | A1 | 1/2010 | Kooij et al. | |
| 2012/0097156 | A1 | 4/2012 | Bowman et al. | |
| 2012/0325205 | A1 | 12/2012 | Allum et al. | |
| 2014/0276177 | A1 | 9/2014 | Brambilla et al. | |
| 2016/0228663 | A1 | 8/2016 | Harrison | |
| 2016/0250438 | A1 * | 9/2016 | Harwood | A61M 16/0875 128/201.13 |
| 2018/0133426 | A1 | 5/2018 | Hallett et al. | |
| 2019/0184126 | A1 | 6/2019 | Todd et al. | |
| 2020/0405994 | A1 * | 12/2020 | Shirley | A61M 16/1045 |
| 2022/0233803 | A1 | 7/2022 | Wong et al. | |

FOREIGN PATENT DOCUMENTS

| | | | |
|---|---|---|---|
| WO | WO 98/04310 | A1 | 2/1998 |
| WO | WO 98/34665 | A1 | 8/1998 |
| WO | WO 00/38772 | A1 | 7/2000 |
| WO | WO 00/78381 | A1 | 12/2000 |
| WO | WO 2004/073778 | A1 | 9/2004 |
| WO | WO 2005/063328 | A1 | 7/2005 |
| WO | WO 2006/074513 | A1 | 7/2006 |
| WO | WO 2006/130903 | A1 | 12/2006 |
| WO | WO 2009/052560 | A1 | 4/2009 |
| WO | WO 2010/135785 | A1 | 12/2010 |
| WO | WO 2012/171072 | A1 | 12/2012 |
| WO | WO 2013/020167 | A1 | 2/2013 |
| WO | WO 2015/052681 | A1 | 4/2015 |
| WO | WO 2020/188495 | A1 | 9/2020 |

OTHER PUBLICATIONS

International Search Report dated Jun. 17, 2022 issued in International Application No. PCT/AU2022/050308 (7 pages).
Written Opinion of the International Searching Authority dated Jun. 17, 2022 issued in International Application No. PCT/AU2022/050308 (13 pages).

(56) References Cited

OTHER PUBLICATIONS

Office Action with English translation issued in Chinese Application No. 202280027241.8, dated Nov. 25, 2025 (20 pages).
International Preliminary Report on Patentability dated Oct. 10, 2023 issued in International Application No. PCT/AU2022/050308 (14 pages).
Office Action dated May 16, 2026 and English translation issued in Chinese Application No. 202280027241.8, 13 pp.

* cited by examiner

Copyright 2012 ResMed Limited

Copyright 2012 ResMed Limited

Copyright 2012 ResMed Limited

Copyright 2012 ResMed Limited

Copyright 2012 ResMed Limited

Copyright 2012 ResMed Limited

Copyright 2012 ResMed Limited

Copyright 2012 ResMed Limited

Copyright 2012 ResMed Limited

Relatively Large
Positive Curvature

Relatively Small
Positive Curvature

Zero Curvature

Relatively Small
Negative Curvature

Relatively Large
Negative Curvature

Copyright 2015 ResMed Limited

Copyright 2015 ResMed Limitec

Copyright 2015 ResMed Limited

Copyright 2015 ResMed Limited

PATIENT INTERFACE WITH HEAT AND MOISTURE EXCHANGER AND VENT

A portion of the disclosure of this patent document contains material which is subject to copyright protection. The copyright owner has no objection to the facsimile reproduction by anyone of the patent document or the patent disclosure, as it appears in Patent Office patent files or records, but otherwise reserves all copyright rights whatsoever.

1 CROSS-REFERENCE TO RELATED APPLICATIONS

This application is the U.S. national phase of International Application No. PCT/AU2022/050308 filed Apr. 7, 2022 which designated the U.S. and claims priority to Australian Provisional Application No. 2021901021, filed Apr. 8, 2021, and Australian Provisional Application No. 2021901019, filed Apr. 8, 2021, the entire contents of each of which are hereby incorporated by reference.

2 BACKGROUND OF THE TECHNOLOGY

2.1 Field of the Technology

The present technology relates to one or more of the screening, diagnosis, monitoring, treatment, prevention and amelioration of respiratory-related disorders. The present technology also relates to medical devices or apparatus, and their use.

2.2 Description of the Related Art

2.2.1 Human Respiratory System and its Disorders

The respiratory system of the body facilitates gas exchange. The nose and mouth form the entrance to the airways of a patient.

The airways include a series of branching tubes, which become narrower, shorter and more numerous as they penetrate deeper into the lung. The prime function of the lung is gas exchange, allowing oxygen to move from the inhaled air into the venous blood and carbon dioxide to move in the opposite direction. The trachea divides into right and left main bronchi, which further divide eventually into terminal bronchioles. The bronchi make up the conducting airways, and do not take part in gas exchange. Further divisions of the airways lead to the respiratory bronchioles, and eventually to the alveoli. The alveolated region of the lung is where the gas exchange takes place, and is referred to as the respiratory zone. See "*Respiratory Physiology*", by John B. West, Lippincott Williams & Wilkins, 9th edition published 2012.

A range of respiratory disorders exist. Certain disorders may be characterised by particular events, e.g. apneas, hypopneas, and hyperpneas.

Examples of respiratory disorders include Obstructive Sleep Apnea (OSA), Cheyne-Stokes Respiration (CSR), respiratory insufficiency, Obesity Hyperventilation Syndrome (OHS), Chronic Obstructive Pulmonary Disease (COPD), Neuromuscular Disease (NMD) and Chest wall disorders.

Obstructive Sleep Apnea (OSA), a form of Sleep Disordered Breathing (SDB), is characterised by events including occlusion or obstruction of the upper air passage during sleep. It results from a combination of an abnormally small upper airway and the normal loss of muscle tone in the region of the tongue, soft palate and posterior oropharyngeal wall during sleep. The condition causes the affected patient to stop breathing for periods typically of 30 to 120 seconds in duration, sometimes 200 to 300 times per night. It often causes excessive daytime somnolence, and it may cause cardiovascular disease and brain damage. The syndrome is a common disorder, particularly in middle aged overweight males, although a person affected may have no awareness of the problem. See U.S. Pat. No. 4,944,310 (Sullivan).

2.2.2 Therapies

Various respiratory therapies, such as Continuous Positive Airway Pressure (CPAP) therapy, Non-invasive ventilation (NIV), Invasive ventilation (IV), and High Flow Therapy (HFT) have been used to treat one or more of the above respiratory disorders.

2.2.2.1 Respiratory Pressure Therapies

Respiratory pressure therapy is the application of a supply of air to an entrance to the airways at a controlled target pressure that is nominally positive with respect to atmosphere throughout the patient's breathing cycle (in contrast to negative pressure therapies such as the tank ventilator or cuirass).

Continuous Positive Airway Pressure (CPAP) therapy has been used to treat Obstructive Sleep Apnea (OSA). The mechanism of action is that continuous positive airway pressure acts as a pneumatic splint and may prevent upper airway occlusion, such as by pushing the soft palate and tongue forward and away from the posterior oropharyngeal wall. Treatment of OSA by CPAP therapy may be voluntary, and hence patients may elect not to comply with therapy if they find devices used to provide such therapy one or more of: uncomfortable, difficult to use, expensive and aesthetically unappealing.

2.2.3 Respiratory Therapy Systems

These respiratory therapies may be provided by a respiratory therapy system or device. Such systems and devices may also be used to screen, diagnose, or monitor a condition without treating it.

A respiratory therapy system may comprise a Respiratory Pressure Therapy Device (RPT device), an air circuit, a humidifier, a patient interface, an oxygen source, and data management.

2.2.3.1 Patient Interface

A patient interface may be used to interface respiratory equipment to its wearer, for example by providing a flow of air to an entrance to the airways. The flow of air may be provided via a mask to the nose and/or mouth, a tube to the mouth or a tracheostomy tube to the trachea of a patient. Depending upon the therapy to be applied, the patient interface may form a seal, e.g., with a region of the patient's face, to facilitate the delivery of gas at a pressure at sufficient variance with ambient pressure to effect therapy, e.g., at a positive pressure of about 10 $cmH_2O$ relative to ambient pressure. For other forms of therapy, such as the delivery of oxygen, the patient interface may not include a seal sufficient to facilitate delivery to the airways of a supply of gas at a positive pressure of about 10 $cmH_2O$. For flow therapies such as nasal HFT, the patient interface is configured to insufflate the nares but specifically to avoid a complete seal. One example of such a patient interface is a nasal cannula.

Certain other mask systems may be functionally unsuitable for the present field. For example, purely ornamental masks may be unable to maintain a suitable pressure. Mask systems used for underwater swimming or diving may be configured to guard against ingress of water from an external higher pressure, but not to maintain air internally at a higher pressure than ambient.

Certain masks may be clinically unfavourable for the present technology e.g. if they block airflow via the nose and only allow it via the mouth.

Certain masks may be uncomfortable or impractical for the present technology if they require a patient to insert a portion of a mask structure in their mouth to create and maintain a seal via their lips.

Certain masks may be impractical for use while sleeping, e.g. for sleeping while lying on one's side in bed with a head on a pillow.

The design of a patient interface presents a number of challenges. The face has a complex three-dimensional shape. The size and shape of noses and heads varies considerably between individuals. Since the head includes bone, cartilage and soft tissue, different regions of the face respond differently to mechanical forces. The jaw or mandible may move relative to other bones of the skull. The whole head may move during the course of a period of respiratory therapy.

As a consequence of these challenges, some masks suffer from being one or more of obtrusive, aesthetically undesirable, costly, poorly fitting, difficult to use, and uncomfortable especially when worn for long periods of time or when a patient is unfamiliar with a system. Wrongly sized masks can give rise to reduced compliance, reduced comfort and poorer patient outcomes. Masks designed solely for aviators, masks designed as part of personal protection equipment (e.g. filter masks), SCUBA masks, or for the administration of anaesthetics may be tolerable for their original application, but nevertheless such masks may be undesirably uncomfortable to be worn for extended periods of time, e.g., several hours. This discomfort may lead to a reduction in patient compliance with therapy. This is even more so if the mask is to be worn during sleep.

CPAP therapy is highly effective to treat certain respiratory disorders, provided patients comply with therapy. If a mask is uncomfortable, or difficult to use a patient may not comply with therapy. Since it is often recommended that a patient regularly wash their mask, if a mask is difficult to clean (e.g., difficult to assemble or disassemble), patients may not clean their mask and this may impact on patient compliance.

While a mask for other applications (e.g. aviators) may not be suitable for use in treating sleep disordered breathing, a mask designed for use in treating sleep disordered breathing may be suitable for other applications.

For these reasons, patient interfaces for delivery of CPAP during sleep form a distinct field.

2.2.3.1.1 Seal-Forming Structure

Patient interfaces may include a seal-forming structure. Since it is in direct contact with the patient's face, the shape and configuration of the seal-forming structure can have a direct impact the effectiveness and comfort of the patient interface.

A patient interface may be partly characterised according to the design intent of where the seal-forming structure is to engage with the face in use. In one form of patient interface, a seal-forming structure may comprise a first sub-portion to form a seal around the left naris and a second sub-portion to form a seal around the right naris. In one form of patient interface, a seal-forming structure may comprise a single element that surrounds both nares in use. Such single element may be designed to for example overlay an upper lip region and a nasal bridge region of a face. In one form of patient interface a seal-forming structure may comprise an element that surrounds a mouth region in use, e.g. by forming a seal on a lower lip region of a face. In one form of patient interface, a seal-forming structure may comprise a single element that surrounds both nares and a mouth region in use. These different types of patient interfaces may be known by a variety of names by their manufacturer including nasal masks, full-face masks, nasal pillows, nasal puffs and oro-nasal masks.

A seal-forming structure that may be effective in one region of a patient's face may be inappropriate in another region, e.g. because of the different shape, structure, variability and sensitivity regions of the patient's face. For example, a seal on swimming goggles that overlays a patient's forehead may not be appropriate to use on a patient's nose.

Certain seal-forming structures may be designed for mass manufacture such that one design fit and be comfortable and effective for a wide range of different face shapes and sizes. To the extent to which there is a mismatch between the shape of the patient's face, and the seal-forming structure of the mass-manufactured patient interface, one or both must adapt in order for a seal to form.

One type of seal-forming structure extends around the periphery of the patient interface, and is intended to seal against the patient's face when force is applied to the patient interface with the seal-forming structure in confronting engagement with the patient's face. The seal-forming structure may include an air or fluid filled cushion, or a moulded or formed surface of a resilient seal element made of an elastomer such as a rubber. With this type of seal-forming structure, if the fit is not adequate, there will be gaps between the seal-forming structure and the face, and additional force will be required to force the patient interface against the face in order to achieve a seal.

Another type of seal-forming structure incorporates a flap seal of thin material positioned about the periphery of the mask so as to provide a self-sealing action against the face of the patient when positive pressure is applied within the mask. Like the previous style of seal forming portion, if the match between the face and the mask is not good, additional force may be required to achieve a seal, or the mask may leak. Furthermore, if the shape of the seal-forming structure does not match that of the patient, it may crease or buckle in use, giving rise to leaks.

Another type of seal-forming structure may comprise a friction-fit element, e.g. for insertion into a naris, however some patients find these uncomfortable.

Another form of seal-forming structure may use adhesive to achieve a seal. Some patients may find it inconvenient to constantly apply and remove an adhesive to their face.

A range of patient interface seal-forming structure technologies are disclosed in the following patent applications, assigned to ResMed Limited: WO 1998/004,310; WO 2006/074,513; WO 2010/135,785.

One form of nasal pillow is found in the Adam Circuit manufactured by Puritan Bennett. Another nasal pillow, or nasal puff is the subject of U.S. Pat. No. 4,782,832 (Trimble et al.), assigned to Puritan-Bennett Corporation.

ResMed Limited has manufactured the following products that incorporate nasal pillows: SWIFT™ nasal pillows mask, SWIFT™ II nasal pillows mask, SWIFT™ LT nasal pillows mask, SWIFT™ FX nasal pillows mask and MIRAGE LIBERTY™ full-face mask. The following patent applications, assigned to ResMed Limited, describe examples of nasal pillows masks: International Patent Application WO2004/073,778 (describing amongst other things aspects of the ResMed Limited SWIFT™ nasal pillows), US Patent Application 2009/0044808 (describing amongst other things aspects of the ResMed Limited SWIFT™ LT nasal pillows); International Patent Applications WO 2005/063,328 and WO 2006/130,903 (describing amongst other things aspects of the ResMed Limited MIRAGE LIBERTY™ full-face mask); International Patent Application WO 2009/052,560 (describing amongst other things aspects of the ResMed Limited SWIFT™ FX nasal pillows).

2.2.3.1.2 Positioning and Stabilising

A seal-forming structure of a patient interface used for positive air pressure therapy is subject to the corresponding force of the air pressure to disrupt a seal. Thus a variety of techniques have been used to position the seal-forming structure, and to maintain it in sealing relation with the appropriate portion of the face.

One technique is the use of adhesives. See for example US Patent Application Publication No. US 2010/0000534. However, the use of adhesives may be uncomfortable for some.

Another technique is the use of one or more straps and/or stabilising harnesses. Many such harnesses suffer from being one or more of ill-fitting, bulky, uncomfortable and awkward to use.

2.2.3.2 Respiratory Pressure Therapy (RPT) Device

A respiratory pressure therapy (RPT) device may be used individually or as part of a system to deliver one or more of a number of therapies described above, such as by operating the device to generate a flow of air for delivery to an interface to the airways. The flow of air may be pressure-controlled (for respiratory pressure therapies) or flow-controlled (for flow therapies such as HFT). Thus RPT devices may also act as flow therapy devices. Examples of RPT devices include a CPAP device and a ventilator.

2.2.3.3 Air Circuit

An air circuit is a conduit or a tube constructed and arranged to allow, in use, a flow of air to travel between two components of a respiratory therapy system such as the RPT device and the patient interface. In some cases, there may be separate limbs of the air circuit for inhalation and exhalation. In other cases, a single limb air circuit is used for both inhalation and exhalation.

2.2.3.4 Humidifier

Delivery of a flow of air without humidification may cause drying of airways. The use of a humidifier with an RPT device and the patient interface produces humidified gas that minimizes drying of the nasal mucosa and increases patient airway comfort. In addition, in cooler climates, warm air applied generally to the face area in and about the patient interface is more comfortable than cold air.

A range of artificial humidification devices and systems are known, however they may not fulfil the specialised requirements of a medical humidifier.

Medical humidifiers are used to increase humidity and/or temperature of the flow of air in relation to ambient air when required, typically where the patient may be asleep or resting (e.g. at a hospital). A medical humidifier for bedside placement may be small. A medical humidifier may be configured to only humidify and/or heat the flow of air delivered to the patient without humidifying and/or heating the patient's surroundings. Room-based systems (e.g. a sauna, an air conditioner, or an evaporative cooler), for example, may also humidify air that is breathed in by the patient, however those systems would also humidify and/or heat the entire room, which may cause discomfort to the occupants. Furthermore, medical humidifiers may have more stringent safety constraints than industrial humidifiers While a number of medical humidifiers are known, they can suffer from one or more shortcomings. Some medical humidifiers may provide inadequate humidification, some are difficult or inconvenient to use by patients.

2.2.3.5 Vent Technologies

Some forms of treatment systems may include a vent to allow the washout of exhaled carbon dioxide. The vent may allow a flow of gas from an interior space of a patient interface, e.g., the plenum chamber, to an exterior of the patient interface, e.g., to ambient.

The vent may comprise an orifice and gas may flow through the orifice in use of the mask. Many such vents are noisy. Others may become blocked in use and thus provide insufficient washout. Some vents may be disruptive of the sleep of a bed partner 1100 of the patient 1000, e.g. through noise or focussed airflow.

ResMed Limited has developed a number of improved mask vent technologies. See International Patent Application Publication No. WO 1998/034,665; International Patent Application Publication No. WO 2000/078,381; U.S. Pat. No. 6,581,594; US Patent Application Publication No. US 2009/0050156; US Patent Application Publication No. 2009/0044808.

Table of noise of prior masks (ISO 17510-2: 2007, 10 cmH2O pressure at 1 m)

| Mask name | Mask type | A-weighted sound power level dB(A) (uncertainty) | A-weighted sound pressure dB(A) (uncertainty) | Year (approx.) |
|---|---|---|---|---|
| Glue-on (*) | nasal | 50.9 | 42.9 | 1981 |
| ResCare (*) standard | nasal | 31.5 | 23.5 | 1993 |
| ResMed MirageTM (*) | nasal | 29.5 | 21.5 | 1998 |
| ResMed UltraMirageTM | nasal | 36 (3) | 28 (3) | 2000 |
| ResMed Mirage ActivaTM | nasal | 32 (3) | 24 (3) | 2002 |
| ResMed Mirage MicroTM | nasal | 30 (3) | 22 (3) | 2008 |
| ResMed MirageTM SoftGel | nasal | 29 (3) | 22 (3) | 2008 |
| ResMed MirageTM FX | nasal | 26 (3) | 18 (3) | 2010 |
| ResMed Mirage SwiftTM (*) | nasal pillows | 37 | 29 | 2004 |
| ResMed Mirage SwiftTM II | nasal pillows | 28 (3) | 20 (3) | 2005 |
| ResMed Mirage SwiftTM LT | nasal pillows | 25 (3) | 17 (3) | 2008 |
| ResMed AirFit P10 | nasal pillows | 21 (3) | 13 (3) | 2014 |

((*) one specimen only, measured using test method specified in ISO 3744 in CPAP mode at 10 cmH2O)

Sound pressure values of a variety of objects are listed below

| Object | A-weighted sound pressure dB(A) | Notes |
|---|---|---|
| Vacuum cleaner: Nilfisk Walter Broadly Litter Hog: B+ Grade | 68 | ISO 3744 at 1 m distance |
| Conversational speech | 60 | 1 m distance |
| Average home | 50 | |

-continued

| Object | A-weighted sound pressure dB(A) | Notes |
|---|---|---|
| Quiet library | 40 | |
| Quiet bedroom at night | 30 | |
| Background in TV studio | 20 | |

3 BRIEF SUMMARY OF THE TECHNOLOGY

The present technology is directed towards providing medical devices used in the screening, diagnosis, monitoring, amelioration, treatment, or prevention of respiratory disorders having one or more of improved comfort, cost, efficacy, ease of use and manufacturability.

A first aspect of the present technology relates to apparatus used in the screening, diagnosis, monitoring, amelioration, treatment or prevention of a respiratory disorder.

Another aspect of the present technology relates to methods used in the screening, diagnosis, monitoring, amelioration, treatment or prevention of a respiratory disorder.

An aspect of certain forms of the present technology is to provide methods and/or apparatus that improve the compliance of patients with respiratory therapy.

An aspect of the present technology is directed to a patient interface that may comprise: a plenum chamber pressurisable to a therapeutic; a seal-forming structure connected to the plenum chamber and being constructed and arranged to seal with a region of the patient's face; a positioning and stabilising structure comprising at least one tie configured to hold the seal-forming structure in a therapeutically effective position on the patient's head; a frame assembly; a heat and moisture exchanger material; a conduit connector; and a vent having a plurality of vent holes constructed and arranged to allow for washout of exhaled gases and to direct a first portion of exhaled gases to ambient without passing through the heat and moisture exchanger material.

An aspect of the present technology is directed to a patient interface that may comprise: a plenum chamber pressurisable to a therapeutic; a seal-forming structure connected to the plenum chamber and being constructed and arranged to seal with a region of the patient's face; a positioning and stabilising structure comprising at least one tie configured to hold the seal-forming structure in a therapeutically effective position on the patient's head; a frame assembly connected to the plenum chamber; a heat and moisture exchanger material positioned within the frame assembly; a conduit connector connected to the frame assembly and configured to be connected to a conduit; and a vent having a plurality of vent holes constructed and arranged to allow for washout of exhaled gases to ambient continuously throughout the patient's respiratory cycle, a first portion of the vent holes being positioned radially on the frame assembly to direct a first portion of exhaled gases to ambient in a radial direction without passing through the heat and moisture exchanger material.

Another aspect of the present technology is directed to a patient interface that may comprise: a plenum chamber pressurisable to a therapeutic pressure of at least 4 cmH2O above ambient air pressure by a flow of air at the therapeutic pressure for breathing by a patient, the plenum chamber further comprising a lip that forms a plenum chamber hole, and the plenum chamber forming a cavity; a seal-forming structure connected to the plenum chamber, the seal-forming structure being constructed and arranged to seal with a region of the patient's face that at least partly surrounds an entrance to the patient's airways, the seal-forming structure having a nasal hole therein to deliver the flow of air at the therapeutic pressure to at least the patient's nares during use, the seal-forming structure being constructed and arranged to maintain the therapeutic pressure within the plenum chamber throughout the patient's respiratory cycle in use; a positioning and stabilising structure comprising at least one tie configured to hold the seal-forming structure in a therapeutically effective position on the patient's head; a frame assembly connected to the lip of the plenum chamber; a heat and moisture exchanger material positioned within the frame assembly; a conduit connector connected to the frame assembly and configured to be connected to a conduit to receive the flow of air at the therapeutic pressure; and a vent having a plurality of vent holes constructed and arranged to allow for washout of exhaled gases to ambient continuously throughout the patient's respiratory cycle, a first portion of the vent holes being positioned radially on the frame assembly to direct a first portion of exhaled gases to ambient in a radial direction without passing through the heat and moisture exchanger material, wherein the patient interface is configured to leave the patient's mouth uncovered, or the seal-forming structure is configured to seal around the patient's mouth and the patient interface is configured to allow the patient to breath from ambient in the absence of the flow of air at the therapeutic pressure.

Another aspect of the present technology is directed to a frame assembly configured to be connected to a lip of a plenum chamber of a patient interface and comprising: a heat and moisture exchanger material positioned within the frame assembly; a conduit connector connected to the frame assembly and configured to be connected to a conduit to receive the flow of air at the therapeutic pressure; and a vent having a plurality of vent holes constructed and arranged to allow for washout of exhaled gases to ambient continuously throughout the patient's respiratory cycle, a first portion of the vent holes being positioned radially on the frame assembly to direct a first portion of exhaled gases to ambient in a radial direction without passing through the heat and moisture exchanger material.

In examples, (a) the frame assembly may comprise an anterior frame and a posterior frame releasably connected to the anterior frame to join the frame assembly to the plenum chamber at the plenum chamber hole, (b) the heat and moisture exchanger material may be positioned between the anterior frame and the posterior frame, (c) the frame assembly may be configured to support the heat and moisture exchanger material inside of the cavity formed by the plenum chamber, (d) the posterior frame may comprise a plurality of radial spacers extending radially inward to contact a circumferential surface of the heat and moisture exchanger material and form gaps between the posterior frame and the heat and moisture exchanger material to allow gases to flow around the heat and moisture exchanger material, (e) the posterior frame may comprise one or more posterior frame supports that form openings to allow gas to flow between the frame assembly and the plenum chamber, (f) the posterior frame may comprise one or more clips to releasably connect the posterior frame to the anterior frame, (g) the anterior frame may comprise an anterior annular rim and a posterior annular rim that together form an annular channel that receives the lip of the plenum chamber, (h) the one or more clips may be configured to releasably connect to the posterior annular rim, (i) the one or more clips may be configured to releasably connect to the posterior annular rim with a snap fit, (j) the first portion of the vent holes may be positioned radially on the anterior frame, (k) the frame assembly may comprise a bypass frame positioned between the anterior frame and the heat and moisture exchanger material, (l) the bypass frame may comprise one or more bypass channels configured to direct gas into and out of the plenum chamber without passing through the heat and moisture exchanger material, (m) the bypass frame may comprise a tab configured to contact the anterior frame, (n) the posterior frame may comprise one or more alignment notches configured to receive a corresponding one of the bypass channels to align the bypass frame with the posterior frame, (o) the bypass frame may comprise a central hole to allow the flow of air to pass through the bypass frame to reach the heat and moisture exchanger material and to allow exhaled gases to pass through the bypass frame after passing through the heat and moisture exchanger material, (p) the heat and moisture exchanger material may comprise an anterior surface and a posterior surface, (q) the anterior surface and the posterior surface may be substantially flat, (r) the anterior surface may be convex in shape and the posterior surface may be concave in shape, (s) the bypass frame may contact the anterior surface and the posterior frame supports may contact the posterior surface when the frame assembly is assembled, (t) when the frame assembly is assembled the anterior frame may contact the anterior surface and the posterior frame supports contact the posterior surface, (u) the anterior frame may comprise a central hole configured to receive the flow of air during therapy, (v) the posterior frame may include one or more posterior lip retainers extending radially from the posterior frame to form a lip retaining channel that retains the lip of the plenum chamber to join the frame assembly to the plenum chamber, (w) the frame assembly may be configured to support the heat and moisture exchanger material outside of the cavity formed by the plenum chamber, (x) the conduit connector may be removably connected to the anterior frame, (y) the conduit connector may comprise a second portion of the vent holes configured to direct a second portion of exhaled gases from the plenum chamber to ambient after passing through the heat and moisture exchanger material, (z) the conduit connector may include a conduit connection tube configured to releasably connect to the conduit, and the second portion of the vent holes may be positioned on the conduit connector radially around the conduit connection tube, (aa) the second portion of the vent holes may be oriented on the conduit connector axially relative to the flow of air through conduit connection tube, (bb) the anterior frame may include a cage, a membrane may be positioned between the cage and the conduit connector and may be freely movable between the cage and the conduit connector, and the membrane may be configured to be urged against the conduit connector in response to an increase in pressure within the patient interface to at least partially occlude a portion of the second portion of the vent holes while leaving another portion of the second portion of the vent holes unoccluded, (cc) the second portion of the vent holes may comprise inner axial vent holes and outer axial vent holes that are positioned radially outward of the inner axial vent holes, (dd) the membrane may be shaped and dimensioned to at least partially cover the inner axial vent holes while leaving the outer axial vent holes uncovered, (ee) the membrane may include a membrane hole configured to allow the flow of air at the therapeutic pressure to travel from the conduit connector, through the anterior frame, and into the plenum chamber, (ff) the heat and moisture exchanger material, when positioned within the cavity of the anterior frame, may be spaced from the conduit connector such that a portion of the flow of air at the therapeutic pressure travels through the second portion of the vent holes to atmosphere without passing through the heat and moisture exchanger material, (gg) the anterior surface may be concave in shape and the posterior surface may be convex in shape, (hh) the posterior frame may comprise one or more flow directors extending radially therefrom, (ii) each of the flow directors may form a flow directing hole to direct gas into and out of the cavity of the plenum chamber without passing through the heat and moisture exchanger material, (jj) the posterior frame may comprise one or more connection tabs configured to releasably connect the posterior frame to the anterior frame, (kk) each of the connection tabs may extend in an axial direction and may be configured to engage an interior surface of the anterior frame, (ll) the posterior frame may comprise one or more axial spacers extending axially to contact a posterior surface of the heat and moisture exchanger material and form gaps between the posterior frame and the heat and moisture exchanger material to allow gases to flow around the heat and moisture exchanger material, (mm) a posterior flow directing structure may have one or more flow directing tabs and one or more connection tabs to releasably connect the posterior flow directing structure to the posterior frame, the posterior frame may include one or more axial flow directing walls and two or more radial flow directing walls, and when the posterior flow directing structure may be releasably connected to the posterior frame, corresponding ones of the flow directing tabs, the axial flow directing walls, and the radial flow directing walls form a flow directing channel to direct gas into and out of the cavity of the plenum chamber without passing through the heat and moisture exchanger material, (nn) an anti-asphyxia valve may be included, (oo) the anti-asphyxia valve may be positioned on the conduit connector, (pp) the conduit connector may be an elbow, (qq) the elbow may be rotatable 360 degrees, (rr) the heat and moisture exchanger material may be foam, paper, or a combination of foam and paper, (ss) the heat and moisture exchanger material may be treated with a salt, (tt) the seal-forming structure and the plenum chamber may be formed in one piece, (uu) the seal-forming structure and the plenum chamber may be formed from a single, homogeneous piece of material, (vv) the seal-forming structure and the plenum chamber may be constructed from silicone, and/or (ww) the frame assembly may be constructed from a plastic material that is more rigid than silicone.

An aspect of the present technology is directed to a patient interface comprising: a plenum chamber pressurisable to a therapeutic pressure, the plenum chamber further comprising a lip that forms a plenum chamber hole; a seal-forming structure connected to the plenum chamber, the seal-forming structure being constructed and arranged to seal with a region of the patient's face; a positioning and stabilising structure comprising at least one tie configured to hold the seal-forming structure in a therapeutically effective position on the patient's head; a vent constructed and arranged to allow for washout of exhaled gases to ambient; and a conduit connector assembly comprising: a posterior frame having a posterior connector; an anterior frame having an anterior connector configured to be connected to the posterior connector; and a conduit connector connected to the anterior frame and configured to be connected to a conduit, wherein when the posterior connector and the anterior connector are connected, the lip is positioned between the posterior frame and the anterior frame.

Another aspect of the present technology is directed to a patient interface comprising: a plenum chamber pressurisable to a therapeutic pressure of at least 4 cmH2O above ambient air pressure by a flow of air at the therapeutic pressure for breathing by a patient, the plenum chamber further comprising a lip that forms a plenum chamber hole; a seal-forming structure connected to the plenum chamber, the seal-forming structure being constructed and arranged to seal with a region of the patient's face that at least partly surrounds an entrance to the patient's airways, the seal-forming structure having nasal a hole therein to deliver the flow of air at the therapeutic pressure to at least the patient's nares during use, the seal-forming structure being constructed and arranged to maintain the therapeutic pressure within the plenum chamber throughout the patient's respiratory cycle in use; a positioning and stabilising structure comprising at least one tie configured to hold the seal-forming structure in a therapeutically effective position on the patient's head; a vent constructed and arranged to allow for washout of exhaled gases to ambient, the vent having a plurality of vent holes; and a conduit connector assembly comprising: a posterior frame positioned within the plenum chamber and having a posterior connector; an anterior frame having an anterior connector configured to be connected to the posterior connector; and a conduit connector connected to the anterior frame and configured to be connected to a conduit to receive the flow of air at the therapeutic pressure, wherein when the posterior connector and the anterior connector are connected, the lip is positioned between the posterior frame and the anterior frame, and wherein the patient interface is configured to leave the patient's mouth uncovered, or the seal-forming structure is configured to seal around the patient's mouth and the patient interface is configured to allow the patient to breath from ambient in the absence of the flow of air at the therapeutic pressure.

Another aspect of the present technology is directed to a conduit connector assembly comprising: a posterior frame configured to be positioned within a plenum chamber of a patient interface and having a posterior connector; an anterior frame having an anterior connector configured to be connected to the posterior connector; and a conduit connector connected to the anterior frame and configured to be connected to a conduit to receive the flow of air at the therapeutic pressure, wherein when the posterior connector and the anterior connector are connected, a lip of the plenum chamber is positioned between the posterior frame and the anterior frame In examples of any of the aspects of the preceding paragraphs, (a) one of the posterior connector and the anterior connector may be a female bayonet connector and the other of the posterior connector and the anterior connector may be a male bayonet connector, (b) the posterior connector and the anterior connector may be configured to be connected to one another inside of the plenum chamber, (c) the anterior frame may be configured to extend through the plenum chamber hole to allow the anterior connector to connect to the posterior connector, (d) the lip may be compressed between the posterior frame and the anterior frame when the posterior connector and the anterior connector are connected, (e) the lip may be secured radially between the posterior frame and the anterior frame, (f) the posterior frame may be positioned radially outward of the lip and the anterior frame may be positioned radially inward of the lip, (g) the anterior frame may comprise an annular rim, and the lip may be secured axially between the anterior connector and the annular rim, (h) the posterior connector and the anterior connector may be configured to be releasably connected, (i) the posterior connector and the anterior connector may be configured to be permanently connected, (j) the posterior frame may comprise a plurality of posterior connectors and the anterior frame may comprise a plurality of anterior connectors, each of the posterior connectors corresponding to one of the anterior connectors, (k) the vent holes may be positioned on the anterior frame, (l) a heat and moisture exchanger cartridge may be positioned inside of the anterior frame, (m) when the heat and moisture exchanger cartridge is positioned inside of the anterior frame, the heat and moisture exchanger cartridge may be positioned externally of the plenum chamber, (n) the positioning and stabilising structure may comprise a frame configured to be connected to the plenum chamber and headgear straps configured to be connected to the frame, (o) the posterior frame may include a plate positioned centrally thereon to block a portion of the flow of air at the therapeutic pressure passing from the heat and moisture exchanger cartridge into the plenum chamber, (p) an anti-asphyxia valve may be included, and/or (q) the anti-asphyxia valve may be positioned on the conduit connector.

An aspect of the present technology is directed to a patient interface comprising: a plenum chamber pressurisable to a therapeutic pressure; a seal-forming structure connected to the plenum chamber, the seal-forming structure being constructed and arranged to seal with a region of the patient's face; a positioning and stabilising structure comprising at least one tie configured to hold the seal-forming structure in a therapeutically effective position on the patient's head; a heat and moisture exchanger cartridge; and a vent and conduit connector assembly comprising: an anterior frame configured to receive the heat and moisture exchanger cartridge; a conduit connector configured to receive the flow of air at the therapeutic pressure; a first plurality of vent holes configured to direct a first portion of gas exhaled by the patient from the plenum chamber to atmosphere after passing through the heat and moisture exchanger cartridge; and a second plurality of vent holes configured to direct a second portion of gas exhaled by the patient from the plenum chamber to atmosphere without passing through the heat and moisture exchanger cartridge.

Another aspect of the present technology is directed to a patient interface comprising: a plenum chamber pressurisable to a therapeutic pressure of at least 4 cmH2O above ambient air pressure by a flow of air at the therapeutic pressure for breathing by a patient; a seal-forming structure connected to the plenum chamber, the seal-forming structure being constructed and arranged to seal with a region of the patient's face that at least partly surrounds an entrance to the patient's airways, the seal-forming structure having a nasal hole therein to deliver the flow of air at the therapeutic pressure to at least the patient's nares during use, the seal-forming structure being constructed and arranged to maintain the therapeutic pressure within the plenum chamber throughout the patient's respiratory cycle in use; a positioning and stabilising structure comprising at least one tie configured to hold the seal-forming structure in a therapeutically effective position on the patient's head; a heat and moisture exchanger cartridge including a heat and moisture exchanger material positioned within a heat and moisture exchanger cartridge frame; a vent and conduit connector assembly connected to the plenum chamber and comprising: an anterior frame that forms a cavity configured to receive the heat and moisture exchanger cartridge; a conduit connector configured to receive the flow of air at the therapeutic pressure; a first plurality of vent holes configured to direct a first portion of gas exhaled by the patient from the plenum chamber to atmosphere after passing through the heat and moisture exchanger cartridge; and a second plurality of vent holes configured to direct a second portion of gas exhaled by the patient from the plenum chamber to atmosphere without passing through the heat and moisture exchanger cartridge, wherein the patient interface is configured to leave the patient's mouth uncovered, or the seal-forming structure is configured to seal around the patient's mouth and the patient interface is configured to allow the patient to breath from ambient in the absence of the flow of air at the therapeutic pressure.

Another aspect of the present technology is directed to a vent and conduit connector assembly configured to be connected to a plenum chamber of a patient interface and comprising: an anterior frame that forms a cavity configured to receive a heat and moisture exchanger cartridge including a heat and moisture exchanger material positioned within a heat and moisture exchanger cartridge frame; a conduit connector configured to receive the flow of air at the therapeutic pressure; a first plurality of vent holes configured to direct a first portion of gas exhaled by the patient from the plenum chamber to atmosphere after passing through the heat and moisture exchanger cartridge; and a second plurality of vent holes configured to direct a second portion of gas exhaled by the patient from the plenum chamber to atmosphere without passing through the heat and moisture exchanger cartridge.

In examples of any of the aspects of the preceding paragraphs, (a) the plenum chamber may comprise a plenum chamber hole, and the vent and conduit connector assembly may comprise a posterior frame configured to be releasably connected to the anterior frame to join the vent and conduit connector assembly to the plenum chamber at the plenum chamber hole, (b) the vent and conduit connector assembly may be configured such that the heat and moisture exchanger cartridge is positioned externally of the plenum chamber when received in the cavity of the anterior frame, (c) the heat and moisture exchanger cartridge may be configured to be releasably connected to the posterior frame, (d) the posterior frame may be configured to retain the heat and moisture exchanger cartridge within the cavity of the anterior frame, (e) the anterior frame may comprise an annular wall around the cavity, (f) the second plurality of vent holes may be positioned on the annular wall, (g) the annular wall and the heat and moisture exchanger cartridge may form a path, when the heat and moisture exchanger cartridge is positioned within the cavity, to allow the second portion of gas exhaled by the patient to travel from the plenum chamber to atmosphere without passing through the heat and moisture exchanger cartridge, (h) the second plurality of vent holes may be positioned radially around the annular wall, (i) the conduit connector may be positioned on the anterior frame, (i) the first plurality of vent holes may be positioned on the conduit connector, (j) the first plurality of vent holes may be oriented on the conduit connector axially relative to the flow of air therethrough, (k) the conduit connector may comprise a conduit connection tube configured to be connected to a conduit to receive the flow of air at the therapeutic pressure, and the first plurality of vent holes may be positioned radially outward of the conduit connection tube on the conduit connector, (l) the first plurality of vent holes may comprise inner axial vent holes and outer axial vent holes that are positioned radially outward of the inner axial vent holes, (m) the anterior frame may include a cage, a membrane may be positioned between the cage and the conduit connector and may be freely movable between the cage and the conduit connector, and the membrane may be configured to be urged against the conduit connector in response to an increase in pressure within the patient interface to at least partially occlude a portion of the first plurality of vent holes while leaving another portion of the first plurality of vent holes unoccluded, (n) the membrane may be shaped and dimensioned to at least partially cover the inner axial vent holes while leaving the outer axial vent holes uncovered, (o) the membrane may include a membrane hole configured to allow the flow of air at the therapeutic pressure to travel from the conduit connector, through the anterior frame, and into the plenum chamber, (p) the heat and moisture exchanger cartridge, when positioned within the cavity of the anterior frame, may be spaced from the conduit connector such that a portion of the flow of air at the therapeutic pressure travels through the first plurality of vent holes to atmosphere without passing through the heat and moisture exchanger cartridge, (q) a diffuser material may be positioned opposite the anterior frame relative to the conduit connector such that a first portion of a vent flow passing through the first plurality of vent holes is directed into the diffuser material, (r) the diffuser material may be spaced from the conduit connector such that a second portion of the vent flow passing through the plurality of vent holes travels to atmosphere without being directed into the diffuser material, (s) the posterior frame may include a plate positioned centrally thereon to block a portion of the flow of air at the therapeutic pressure passing from the heat and moisture exchanger cartridge into the plenum chamber, (t) an anti-asphyxia valve may be included, and/or (u) the anti-asphyxia valve is positioned on the conduit connector.

An aspect of the present technology is directed to a patient interface comprising: a plenum chamber pressurisable to a therapeutic pressure of at least 4 cmH2O above ambient air pressure by a flow of air at the therapeutic pressure for breathing by a patient, the plenum chamber further comprising a plenum chamber hole through which the flow of air passes during use; a seal-forming structure connected to the plenum chamber, the seal-forming structure being constructed and arranged to seal with a region of the patient's face that at least partly surrounds an entrance to the patient's airways, the seal-forming structure having a nasal hole therein to deliver the flow of air at the therapeutic pressure to at least the patient's nares during use, the seal-forming structure being constructed and arranged to maintain the therapeutic pressure within the plenum chamber throughout the patient's respiratory cycle in use; a positioning and stabilising structure comprising at least one tie configured to hold the seal-forming structure in a therapeutically effective position on the patient's head; a flow director positioned inside of the plenum chamber, the flow director comprising an anterior channel wall, a posterior channel wall, and a channel between the anterior channel wall and the posterior channel wall, the channel having a proximal opening inside of the plenum chamber and configured to be positioned proximal to the patient during use, the channel having a distal opening configured to be positioned distal from the patient during use, and the flow director having a port through which the flow of air passes into the plenum chamber during use; and a plurality of vent holes configured to washout exhaled gases to ambient continuously throughout the patient's respiratory cycle during use, wherein the channel is configured to direct exhaled gases from the distal opening to the plurality of vent holes without passing through the port of the flow director.

Another aspect of the present technology is directed to a patient interface comprising: a plenum chamber pressurisable to a therapeutic pressure; a seal-forming structure connected to the plenum chamber, the seal-forming structure being constructed and arranged to seal with a region of the patient's face; a positioning and stabilising structure comprising at least one tie configured to hold the seal-forming structure in a therapeutically effective position on the patient's head; a flow director positioned inside of the plenum chamber, the flow director comprising a channel; and a plurality of vent holes configured to washout exhaled gases to ambient, wherein the channel is configured to direct exhaled gases to the plurality of vent holes.

Another aspect of the present technology is directed to a flow director configured to be positioned inside of a plenum chamber of a patient interface, the flow director comprising an anterior channel wall, a posterior channel wall, and a channel between the anterior channel wall and the posterior channel wall, the channel having a proximal opening inside of the plenum chamber and configured to be positioned proximal to the patient during use, the channel having a distal opening configured to be positioned distal from the patient during use, and the flow director having a port through which the flow of air passes into the plenum chamber during use.

In examples of any of the aspects of the preceding paragraphs, (a) the flow director may be removably connected to an interior surface of the plenum chamber, (b) a heat and moisture exchanger material may be positioned on the flow director at the port such that the flow of air passing through the port passes through the heat and moisture exchanger material, (c) the channel may be configured to direct exhaled gases from the distal opening to the plurality of vent holes without passing through the heat and moisture exchanger material, (d) the flow director may comprise an anterior shell joined to a posterior shell, (e) the anterior shell may comprise the anterior channel wall and the posterior shell comprises the posterior channel wall, (f) the anterior shell may comprise a plurality of the anterior channel walls and the posterior shell comprises a plurality of the posterior channel walls, and a plurality of channels may be formed between corresponding ones of the plurality of anterior channel walls and the plurality of posterior channel walls, (g) the plurality of channels may extend radially around the flow director, (h) a retainer may be joined to the flow director to retain the heat and moisture exchanger material on the flow director at the port, (j) the heat and moisture exchanger material may be shaped and dimensioned to completely cover the port such that the flow of air passing through the port must pass through the heat and moisture exchanger material to reach the interior of the plenum chamber, (k) a vent ring may be connected to the plenum chamber at the plenum chamber hole, the vent ring comprising the plurality of vent holes, (l) the plenum chamber may have a lip that forms the plenum chamber hole, (m) the vent ring may comprise an anterior annular rim and a posterior annular rim that form an annular channel, and the lip may extend into the annular channel to removably connect the vent ring to the plenum chamber, (n) the vent ring may be configured to be removably connected to an elbow or an air delivery conduit, (o) the vent ring may have a central hole configured to receive the flow of air from the elbow or the air delivery conduit and direct the flow of air to the port of the flow director, (p) each channel may be configured to direct exhaled gases to the plurality of vent holes on the vent ring, (q) the flow director may be configured to be removably connected to the vent ring, (r) each of the anterior shell, the posterior shell, and the retainer may be constructed from a polymer, (s) the polymer of each of the anterior shell, the posterior shell, and the retainer may be one of: Polycarbonate (PC), Polypropylene (PP), Acrylic (PMMA), Acrylonitrile butadiene styrene (ABS), Polyethylene (PE), Polyethylene terephthalate glycol (PETG), and Polystyrene (PS), (t) one or more of the anterior shell, the posterior shell, and the retainer may be formed by vacuum forming, thermoforming, or pressure forming, (u) one or more of the anterior shell, the posterior shell, and the retainer may have a uniform wall thickness throughout, (v) one or more of the anterior shell, the posterior shell, and the retainer may have a variable wall thickness throughout, (w) one or more of the anterior shell, the posterior shell, and the retainer may have a wall thickness of approximately 0.25 mm that is constant throughout, (x) one or more of the anterior shell, the posterior shell, and the retainer may have a wall thickness that is less than approximately 1.00 mm to approximately 1.25 mm and that is uniform throughout, (y) the HMX material may be foam, paper, or a combination of foam and paper, (z) the HMX material may include a salt applied thereto, (aa) the anterior shell, the posterior shell, and the retainer may be permanently joined by heat staking, (bb) the HMX material may be positioned between the retainer and the posterior shell, (cc) the flow director may comprise one or more protrusions configured to engage an interior surface of the plenum chamber, and/or (dd) the patient interface may comprise an anti-asphyxia valve.

Another aspect of one form of the present technology is a patient interface that is moulded or otherwise constructed with a perimeter shape which is complementary to that of an intended wearer.

An aspect of one form of the present technology is a method of manufacturing apparatus.

An aspect of certain forms of the present technology is a medical device that is easy to use, e.g. by a person who does not have medical training, by a person who has limited dexterity, vision or by a person with limited experience in using this type of medical device.

An aspect of one form of the present technology is a portable RPT device that may be carried by a person, e.g., around the home of the person.

An aspect of one form of the present technology is a patient interface that may be washed in a home of a patient, e.g., in soapy water, without requiring specialised cleaning equipment. An aspect of one form of the present technology is a humidifier tank that may be washed in a home of a patient, e.g., in soapy water, without requiring specialised cleaning equipment.

The methods, systems, devices and apparatus described may be implemented so as to improve the functionality of a processor, such as a processor of a specific purpose computer, respiratory monitor and/or a respiratory therapy apparatus. Moreover, the described methods, systems, devices and apparatus can provide improvements in the technological field of automated management, monitoring and/or treatment of respiratory conditions, including, for example, sleep disordered breathing.

Of course, portions of the aspects may form sub-aspects of the present technology. Also, various ones of the sub-aspects and/or aspects may be combined in various manners and also constitute additional aspects or sub-aspects of the present technology.

Other features of the technology will be apparent from consideration of the information contained in the following detailed description, abstract, drawings and claims.

4 BRIEF DESCRIPTION OF THE DRAWINGS

The present technology is illustrated by way of example, and not by way of limitation, in the figures of the accompanying drawings, in which like reference numerals refer to similar elements including:

4.1 Respiratory Therapy Systems

FIG. 1A shows a system including a patient 1000 wearing a patient interface 3000, in the form of nasal pillows, receiving a supply of air at positive pressure from an RPT device 4000. Air from the RPT device 4000 is humidified in a humidifier 5000, and passes along an air circuit 4170 to the patient 1000. A bed partner 1100 is also shown. The patient is sleeping in a supine sleeping position.

FIG. 1B shows a system including a patient 1000 wearing a patient interface 3000, in the form of a nasal mask, receiving a supply of air at positive pressure from an RPT device 4000. Air from the RPT device is humidified in a humidifier 5000, and passes along an air circuit 4170 to the patient 1000.

FIG. 1C shows a system including a patient 1000 wearing a patient interface 3000, in the form of a full-face mask, receiving a supply of air at positive pressure from an RPT device 4000. Air from the RPT device is humidified in a humidifier 5000, and passes along an air circuit 4170 to the patient 1000. The patient is sleeping in a side sleeping position.

4.2 Respiratory System and Facial Anatomy

Figure 1A:
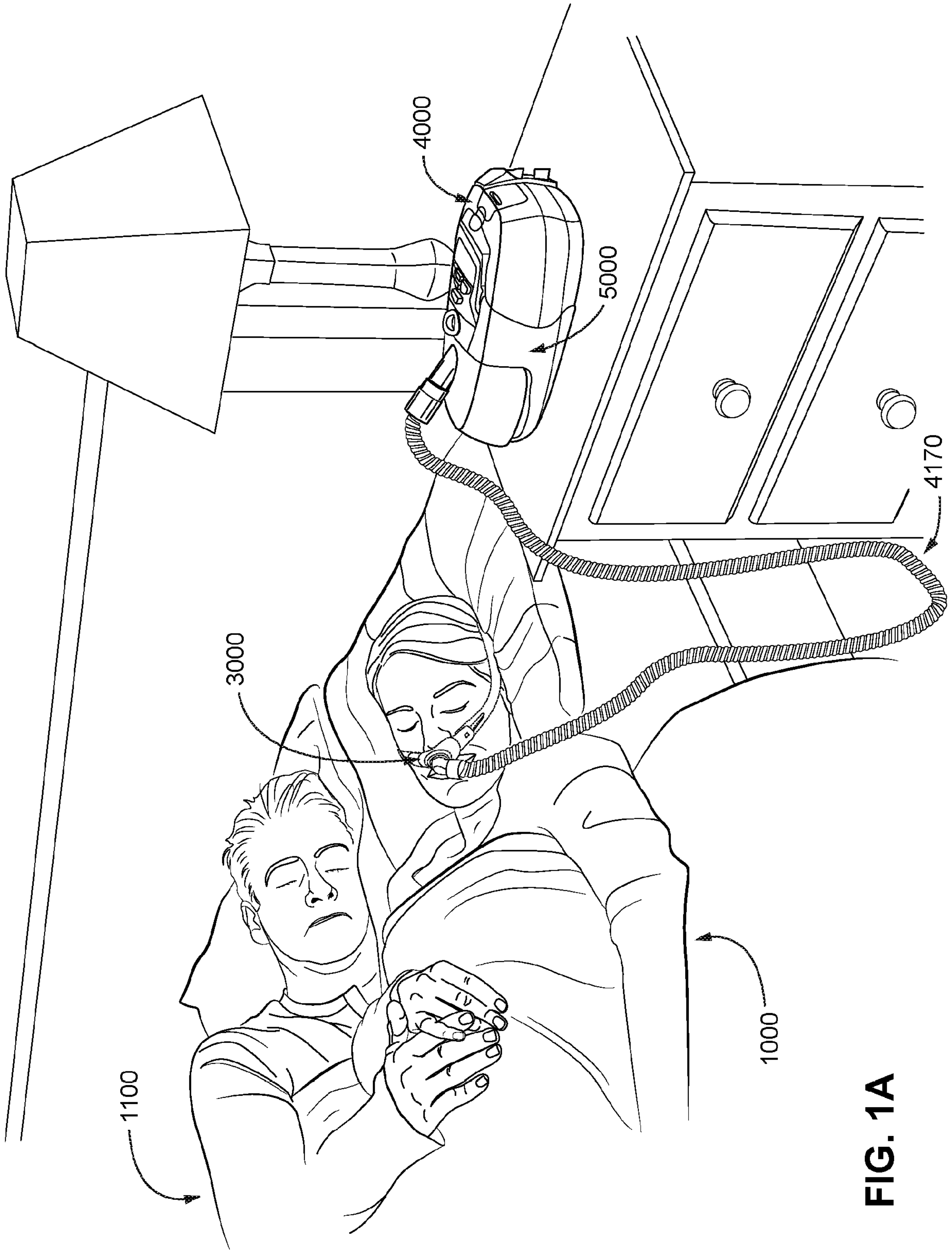
Figure 1B:
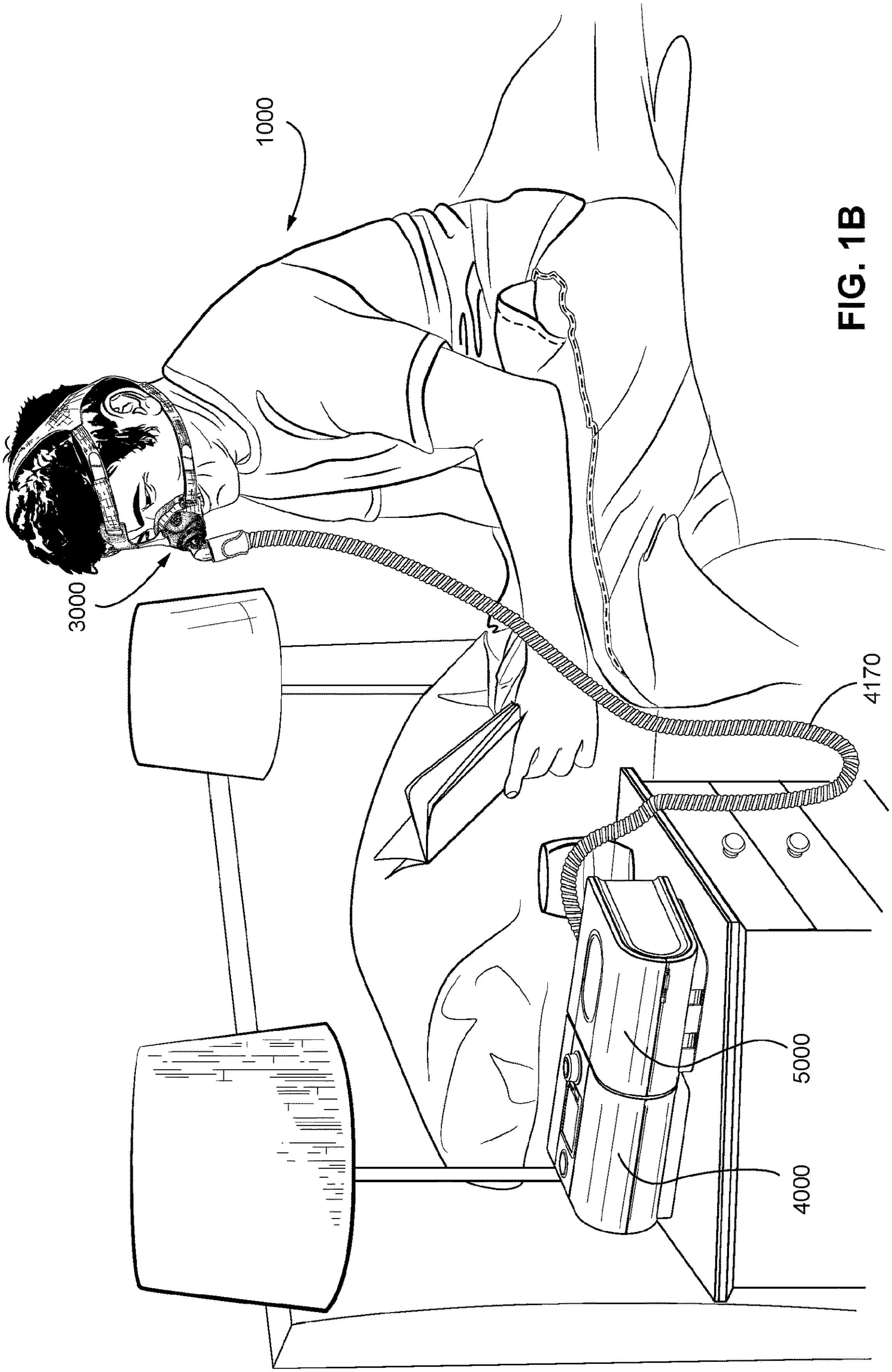
Figure 1C:
Figure 2A:
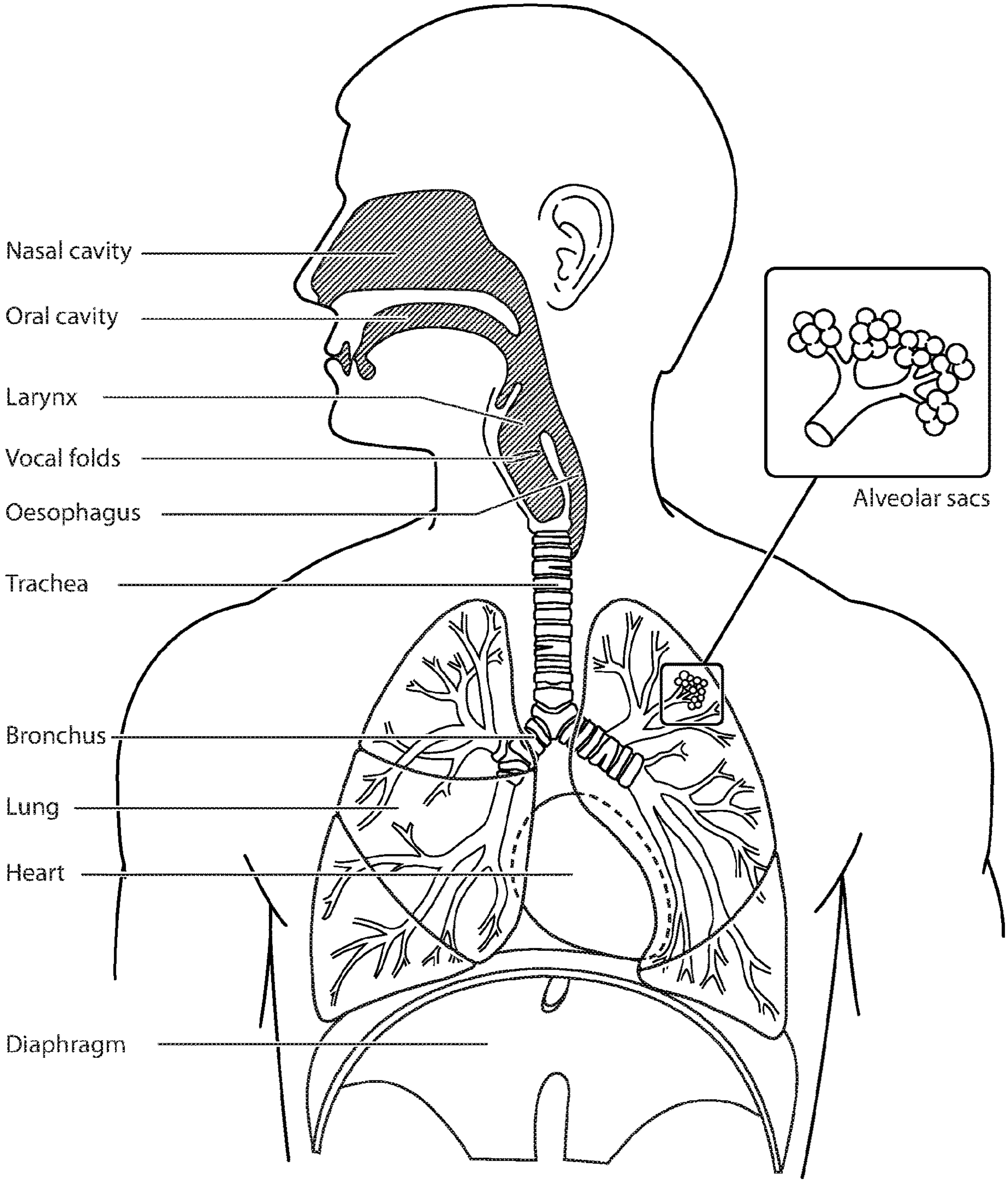
FIG. 2A shows an overview of a human respiratory system including the nasal and oral cavities, the larynx, vocal folds, oesophagus, trachea, bronchus, lung, alveolar sacs, heart and diaphragm.
Figure 2B:
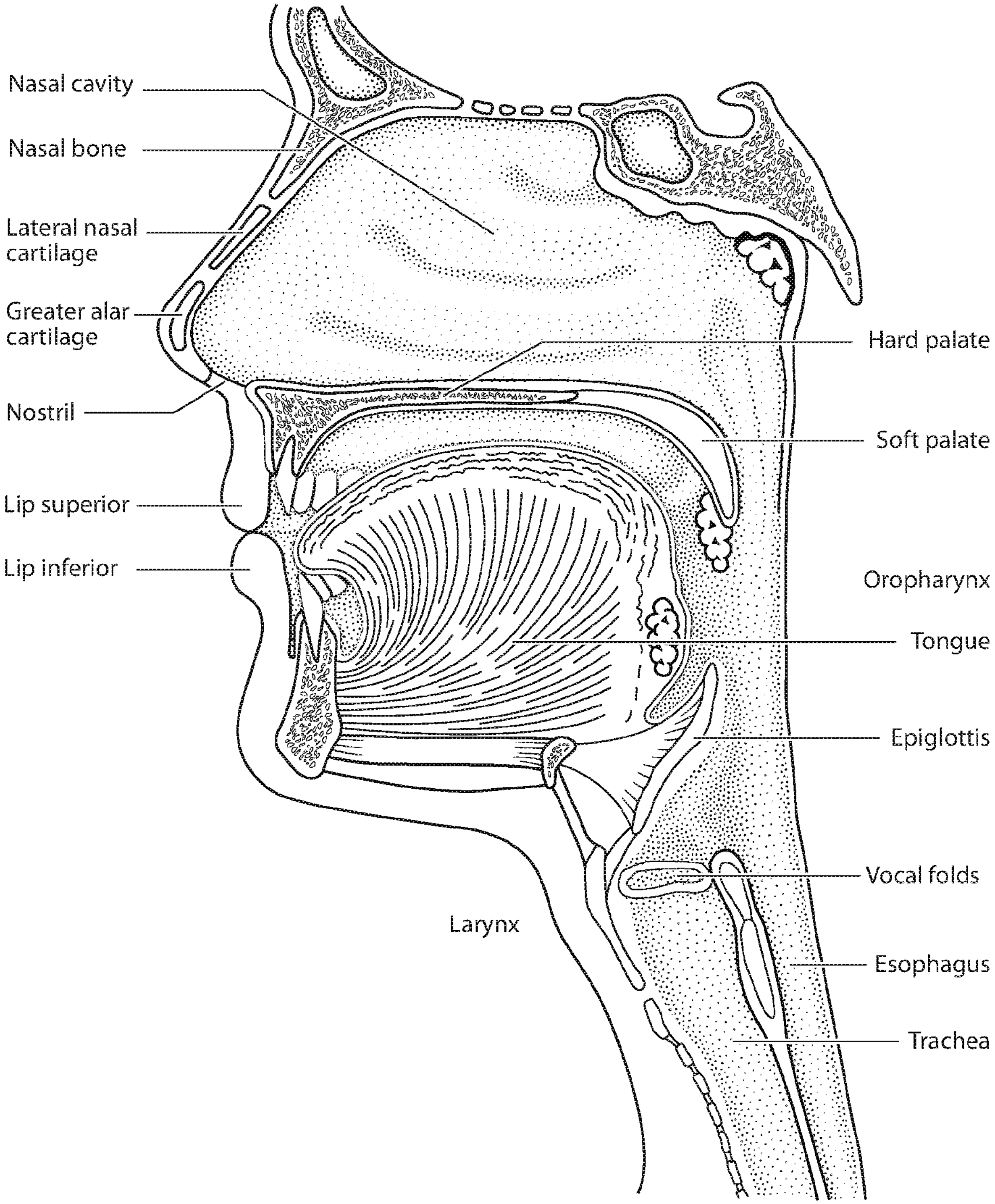
FIG. 2B shows a view of a human upper airway including the nasal cavity, nasal bone, lateral nasal cartilage, greater alar cartilage, nostril, lip superior, lip inferior, larynx, hard palate, soft palate, oropharynx, tongue, epiglottis, vocal folds, oesophagus and trachea.
Figure 2C:
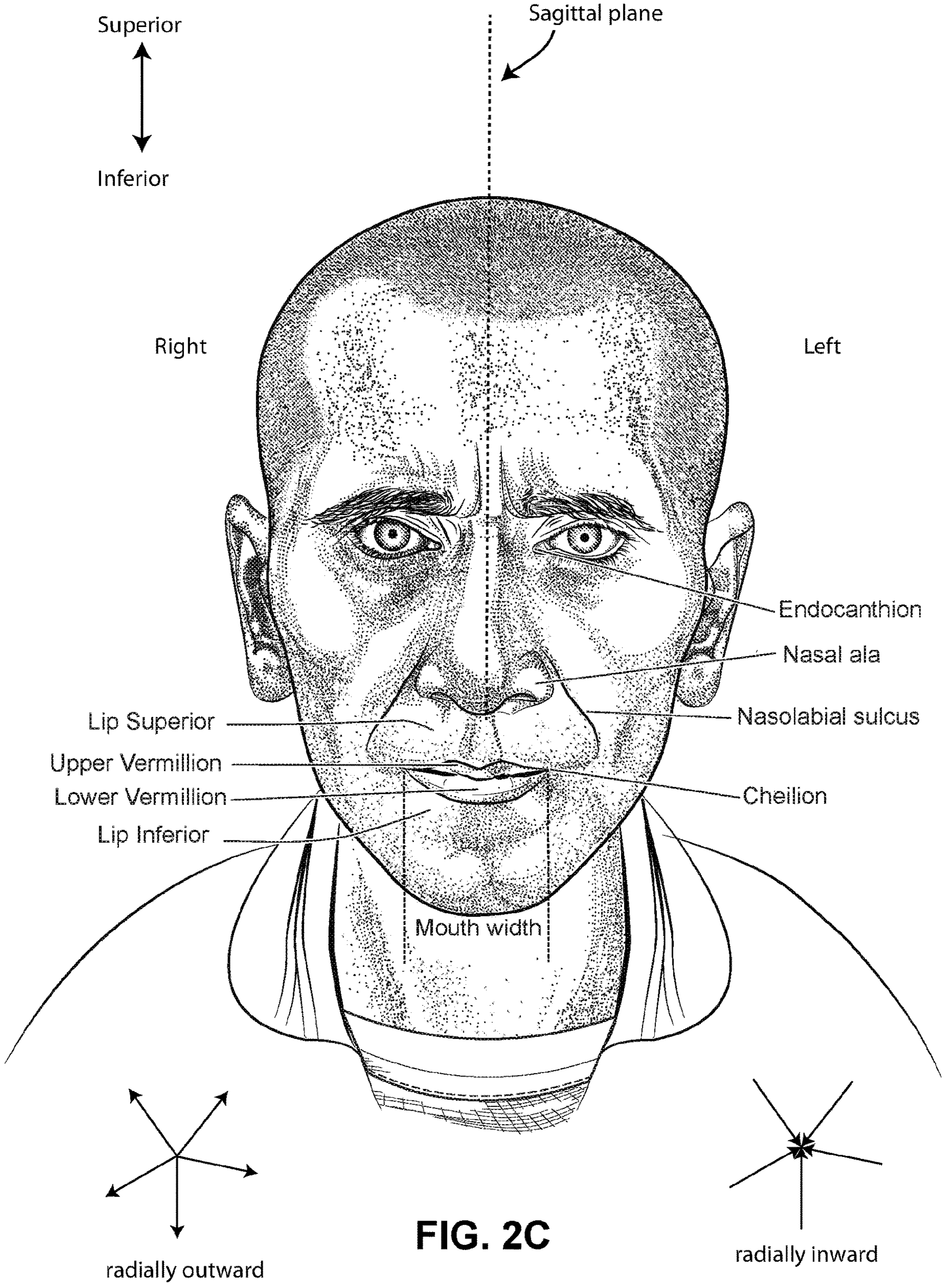
FIG. 2C is a front view of a face with several features of surface anatomy identified including the lip superior, upper vermilion, lower vermilion, lip inferior, mouth width, endocanthion, a nasal ala, nasolabial sulcus and cheilion. Also indicated are the directions superior, inferior, radially inward and radially outward.
Figure 2D:
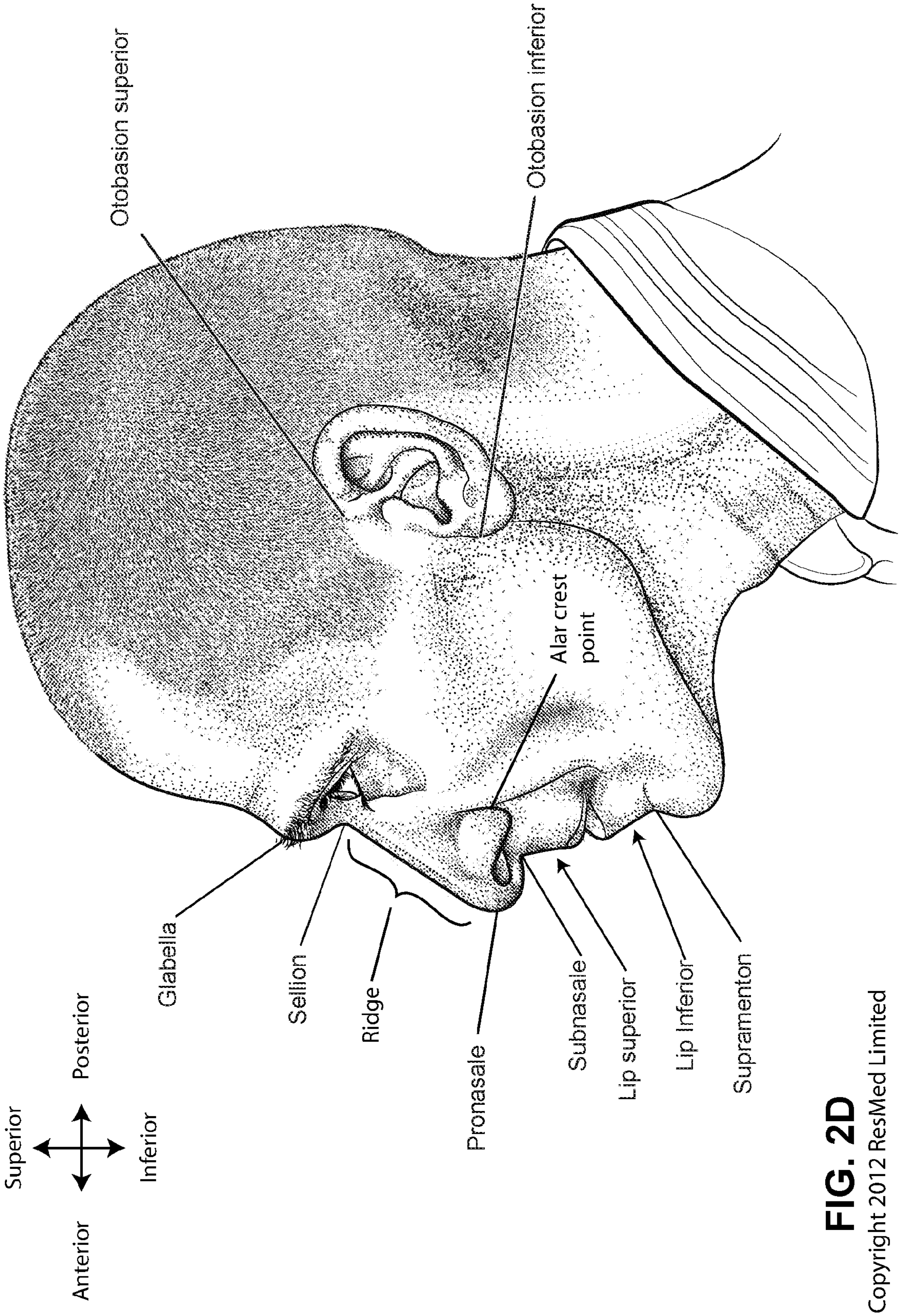
FIG. 2D is a side view of a head with several features of surface anatomy identified including glabella, sellion, pronasale, subnasale, lip superior, lip inferior, supramenton, nasal ridge, alar crest point, otobasion superior and otobasion inferior. Also indicated are the directions superior & inferior, and anterior & posterior.
Figure 2E:
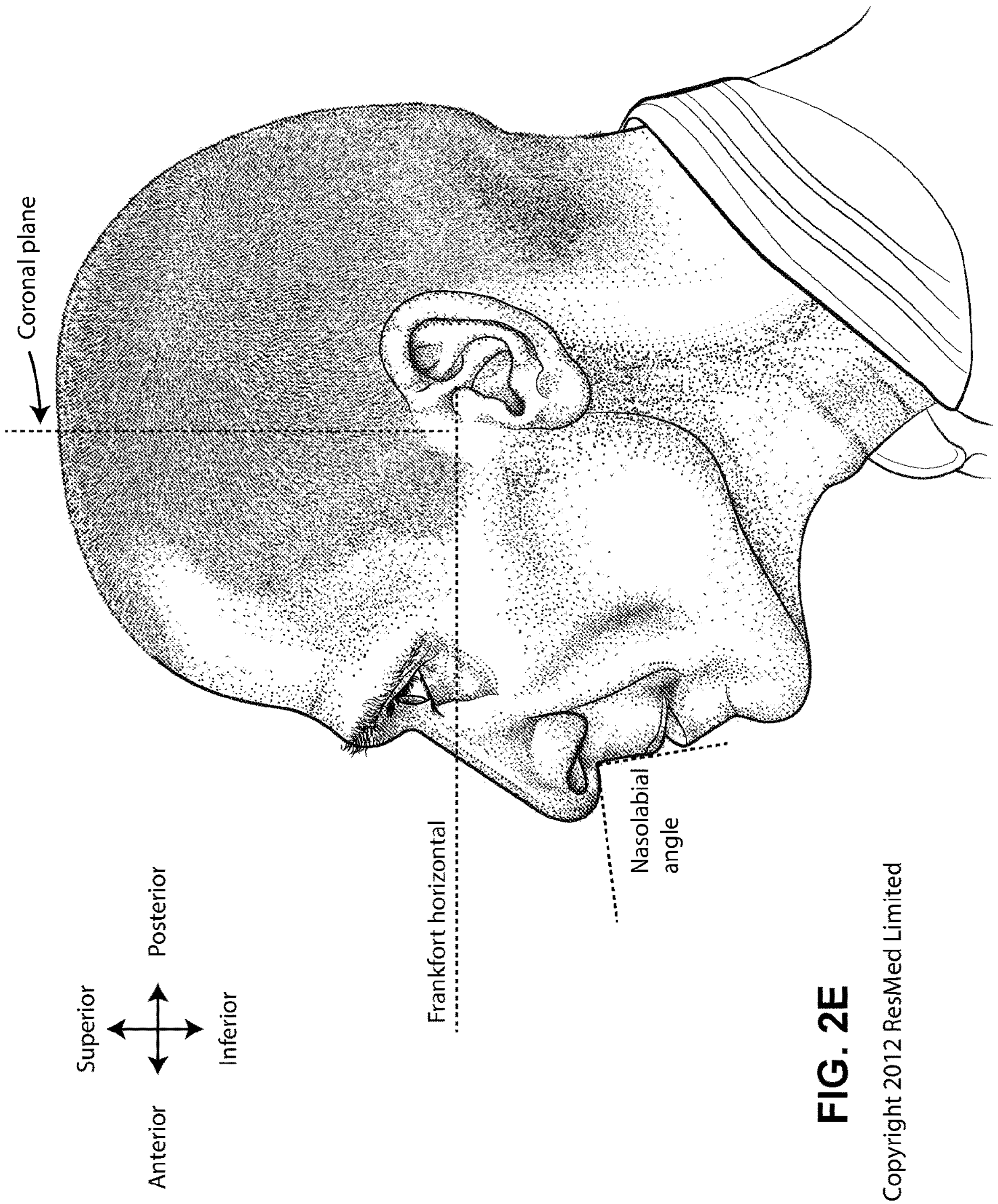

FIG. 2E is a further side view of a head. The approximate locations of the Frankfort horizontal and nasolabial angle are indicated. The coronal plane is also indicated.

Figure 2F:
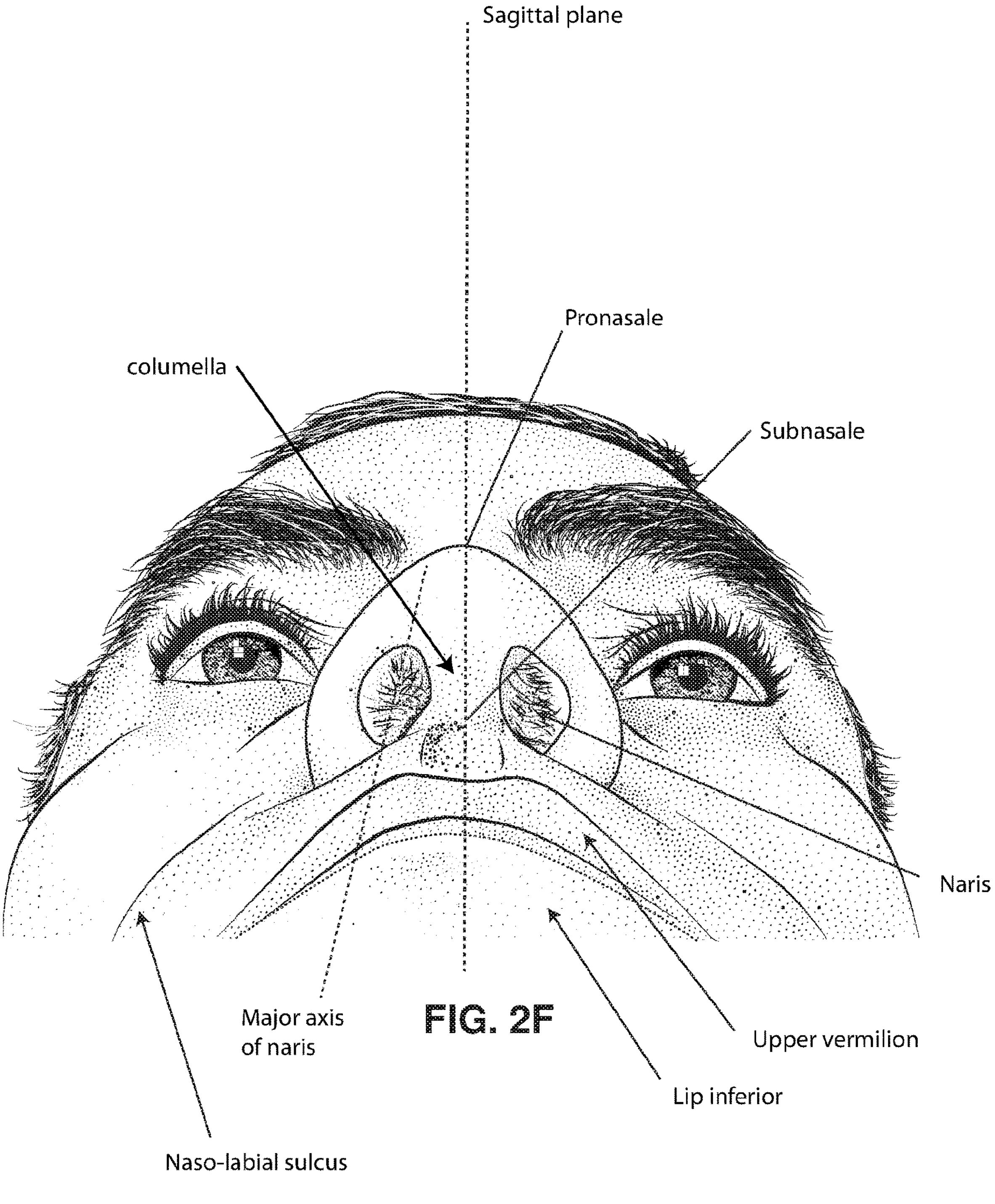

FIG. 2F shows a base view of a nose with several features identified including naso-labial sulcus, lip inferior, upper Vermilion, naris, subnasale, columella, pronasale, the major axis of a naris and the midsagittal plane.

Figure 2I:
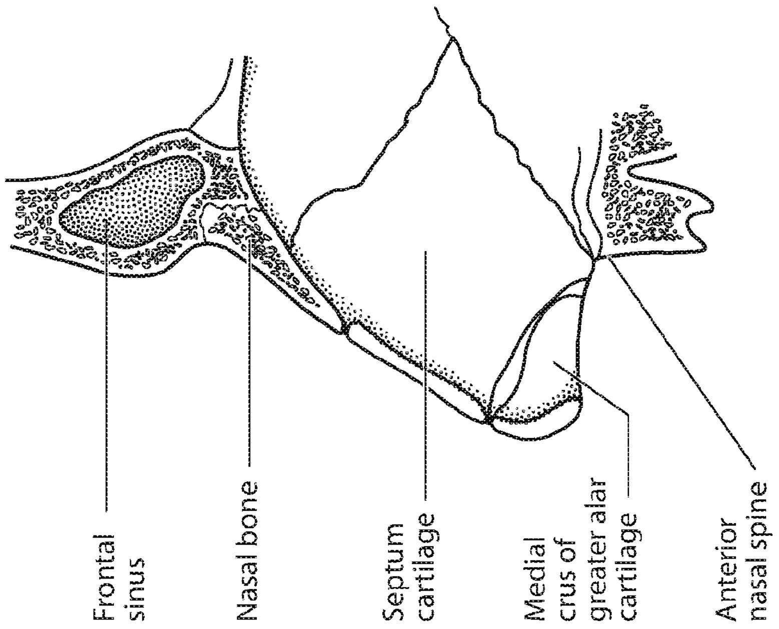
Figure 2H:
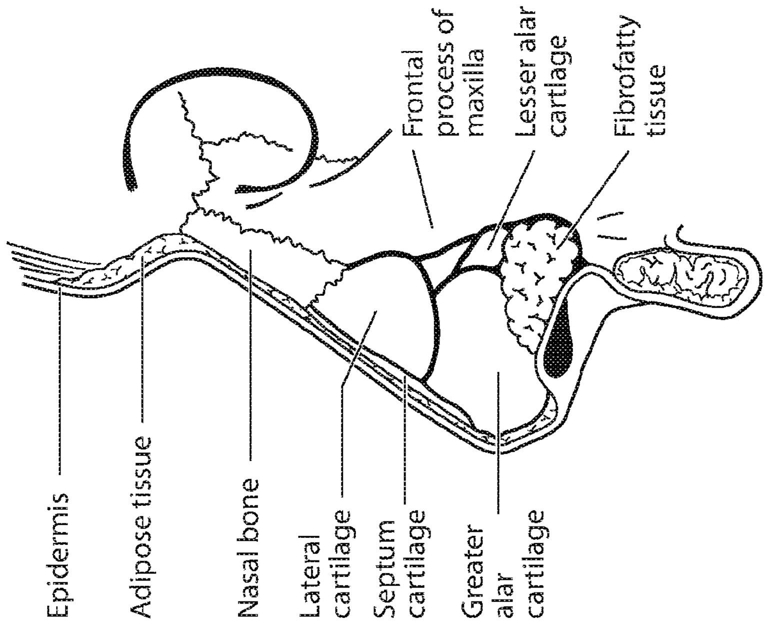
Figure 2G:
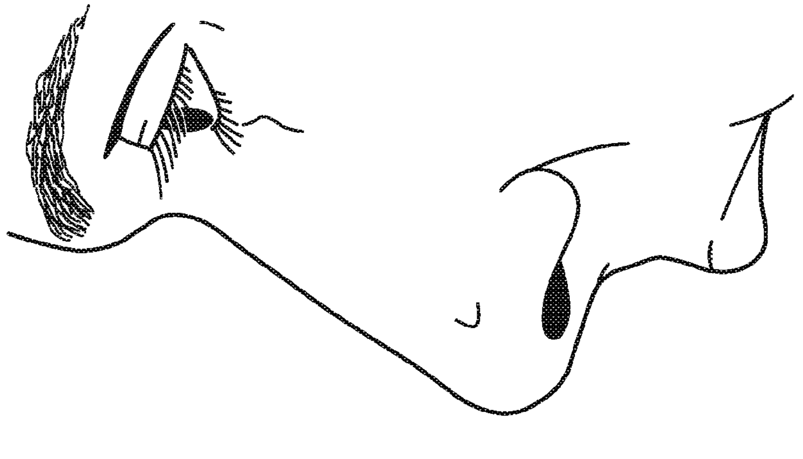

FIG. 2G shows a side view of the superficial features of a nose.

FIG. 2H shows subcutaneal structures of the nose, including lateral cartilage, septum cartilage, greater alar cartilage, lesser alar cartilage, sesamoid cartilage, nasal bone, epidermis, adipose tissue, frontal process of the maxilla and fibrofatty tissue.

FIG. 2I shows a medial dissection of a nose, approximately several millimeters from the midsagittal plane, amongst other things showing the septum cartilage and medial crus of greater alar cartilage.

Figures 2J, 2K:
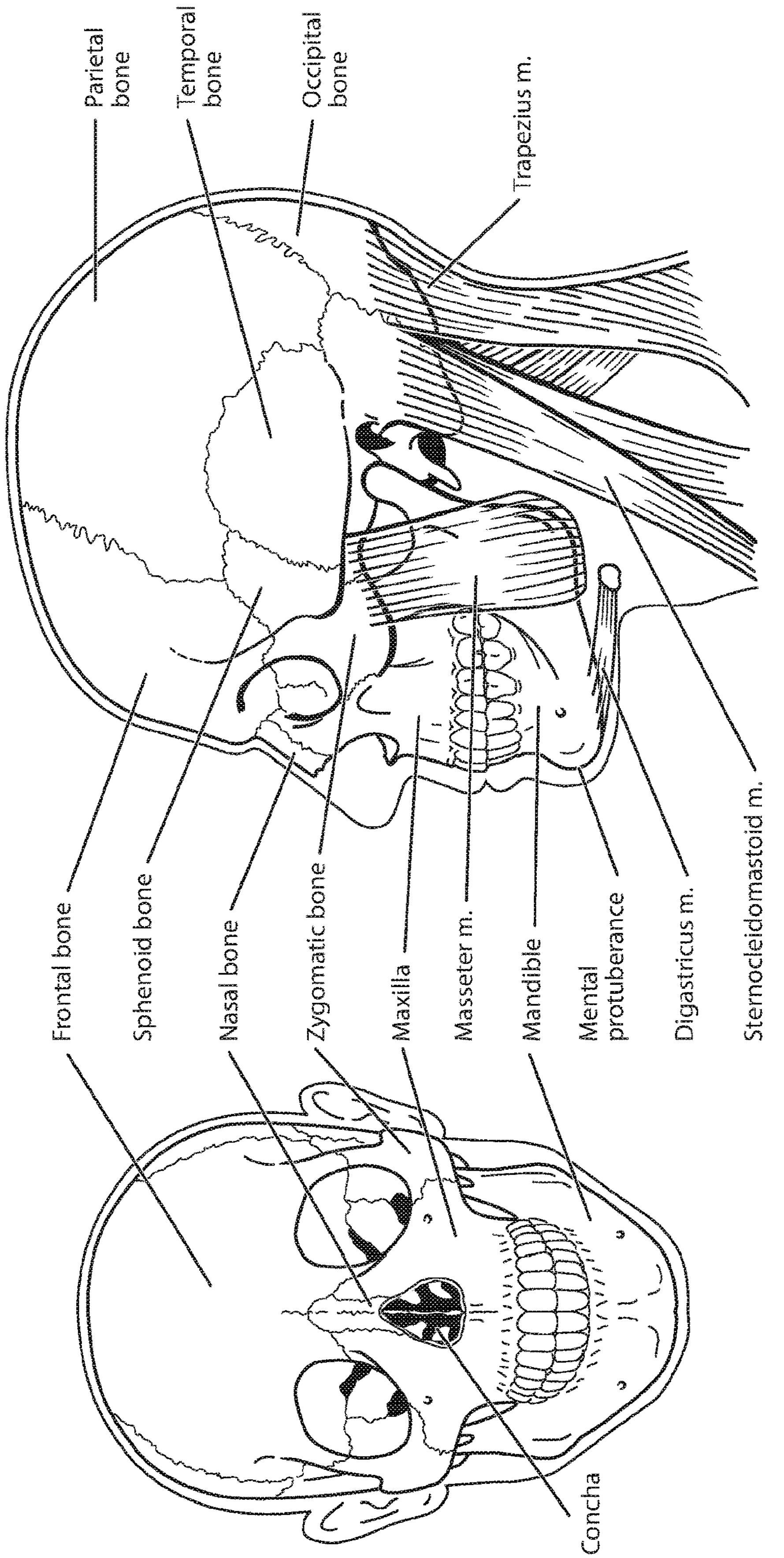

FIG. 2J shows a front view of the bones of a skull including the frontal, nasal and zygomatic bones. Nasal concha are indicated, as are the maxilla, and mandible.

FIG. 2K shows a lateral view of a skull with the outline of the surface of a head, as well as several muscles. The following bones are shown: frontal, sphenoid, nasal, zygomatic, maxilla, mandible, parietal, temporal and occipital. The mental protuberance is indicated. The following muscles are shown: digastricus, masseter, sternocleidomastoideo trapezius.

Figure 2L:
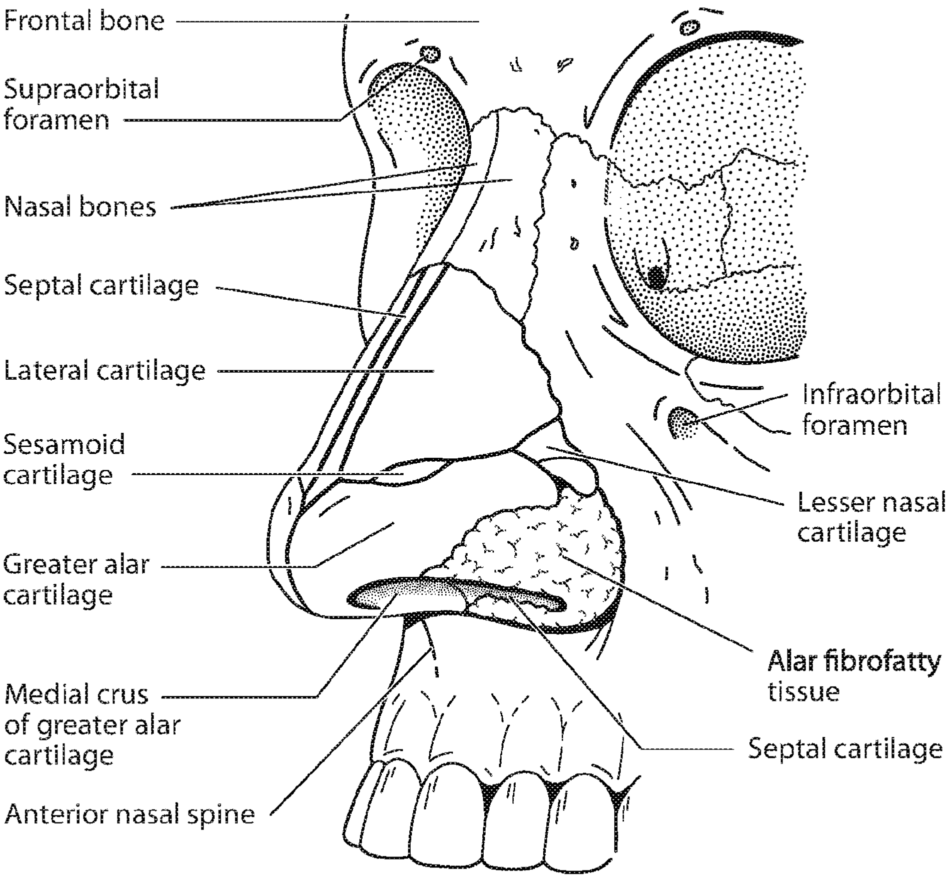

FIG. 2L shows an anterolateral view of a nose.

4.3 Patient Interface

Figure 3A:
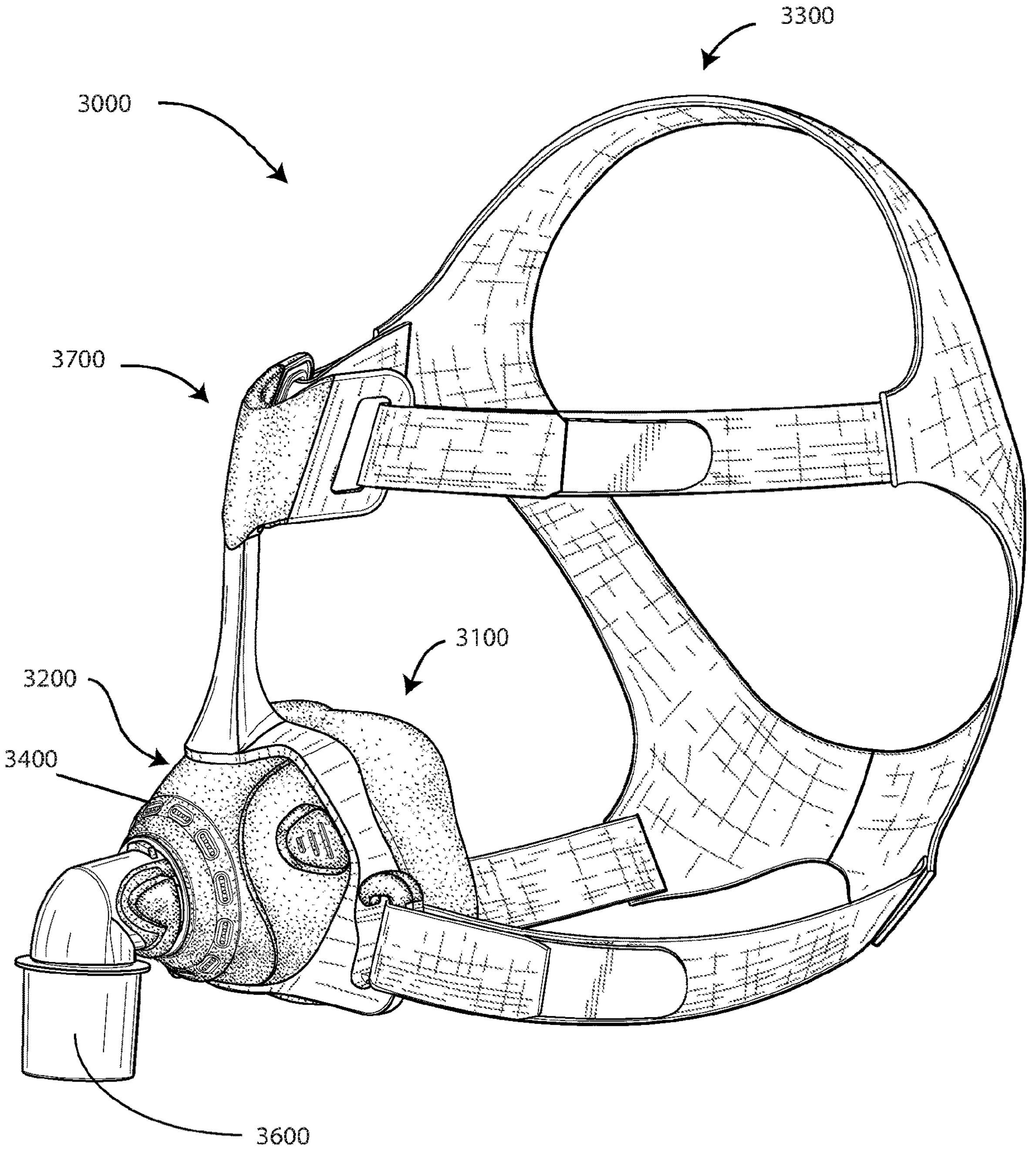

FIG. 3A shows a patient interface in the form of a nasal mask in accordance with one form of the present technology.

Figure 3B:
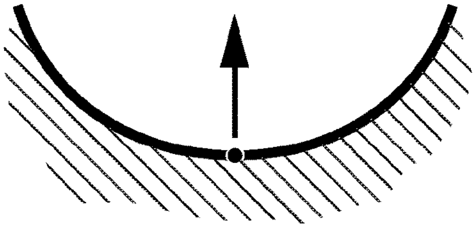

FIG. 3B shows a schematic of a cross-section through a structure at a point. An outward normal at the point is indicated. The curvature at the point has a positive sign, and a relatively large magnitude when compared to the magnitude of the curvature shown in FIG. 3C.

Figure 3C:
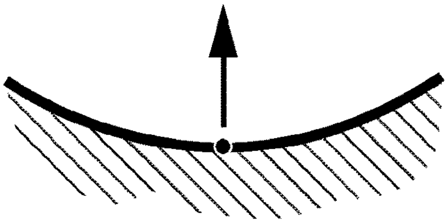

FIG. 3C shows a schematic of a cross-section through a structure at a point. An outward normal at the point is indicated. The curvature at the point has a positive sign, and a relatively small magnitude when compared to the magnitude of the curvature shown in FIG. 3B.

Figure 3D:
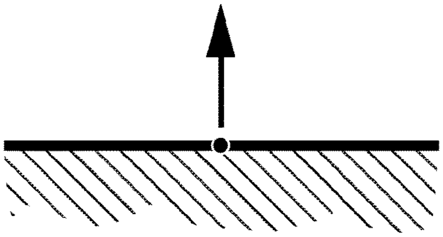

FIG. 3D shows a schematic of a cross-section through a structure at a point. An outward normal at the point is indicated. The curvature at the point has a value of zero.

Figure 3E:
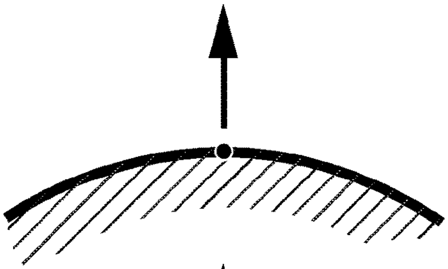

FIG. 3E shows a schematic of a cross-section through a structure at a point. An outward normal at the point is indicated. The curvature at the point has a negative sign, and a relatively small magnitude when compared to the magnitude of the curvature shown in FIG. 3F.

Figure 3F:
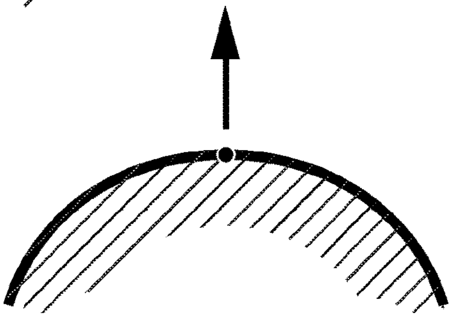

FIG. 3F shows a schematic of a cross-section through a structure at a point. An outward normal at the point is indicated. The curvature at the point has a negative sign, and a relatively large magnitude when compared to the magnitude of the curvature shown in FIG. 3E.

Figure 3H:
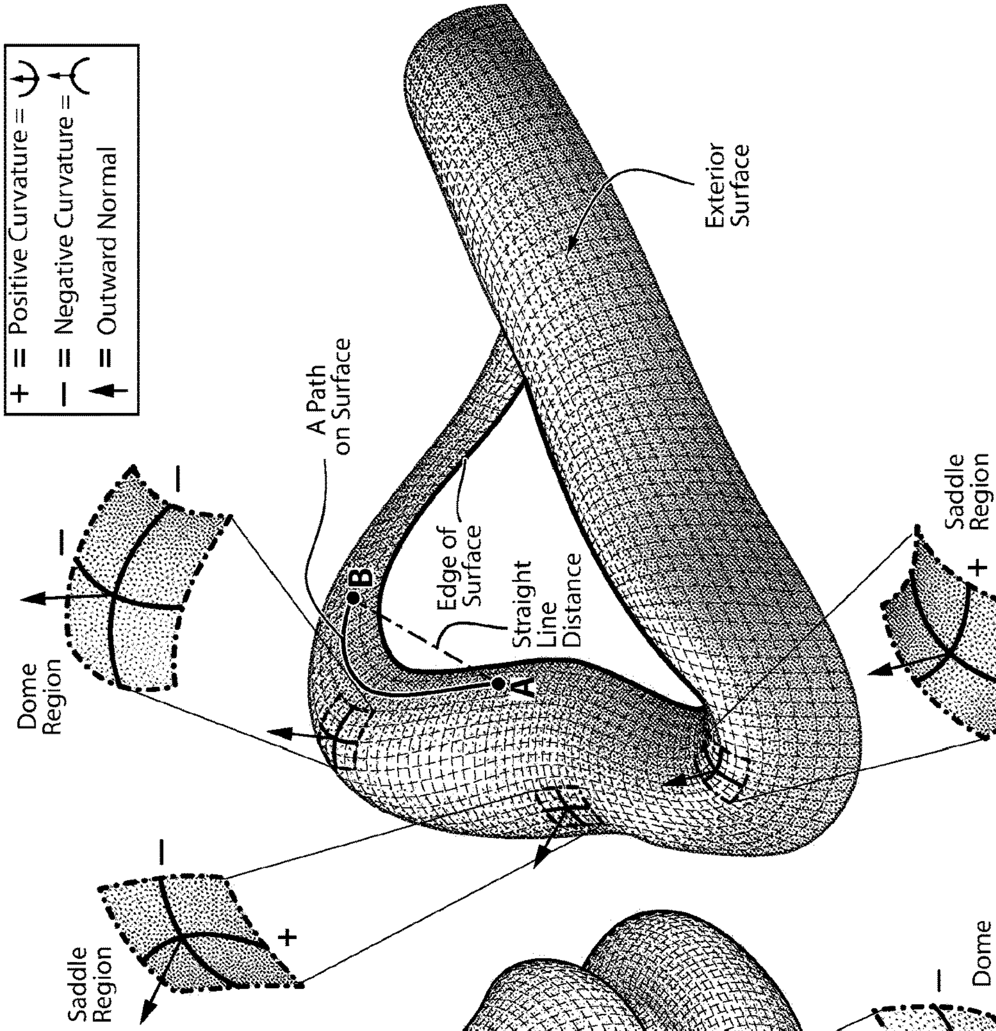
Figure 3G:
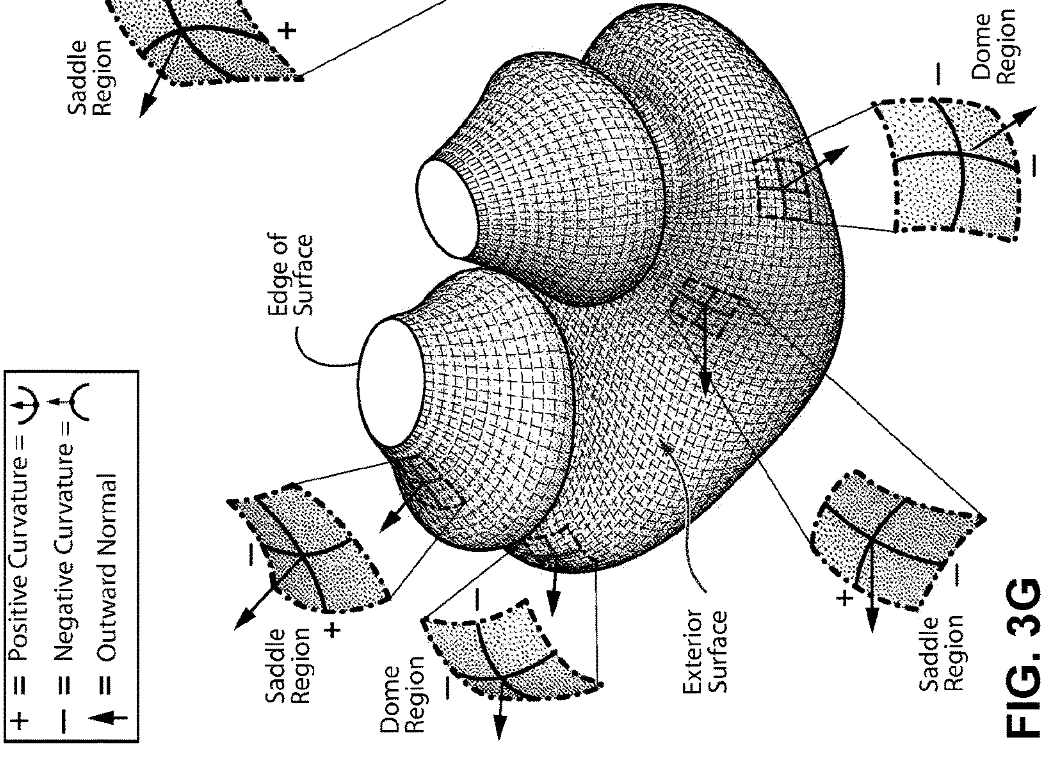

FIG. 3G shows a cushion for a mask that includes two pillows. An exterior surface of the cushion is indicated. An edge of the surface is indicated. Dome and saddle regions are indicated.

FIG. 3H shows a cushion for a mask. An exterior surface of the cushion is indicated. An edge of the surface is indicated. A path on the surface between points A and B is indicated. A straight line distance between A and B is indicated. Two saddle regions and a dome region are indicated.

Figure 3I:
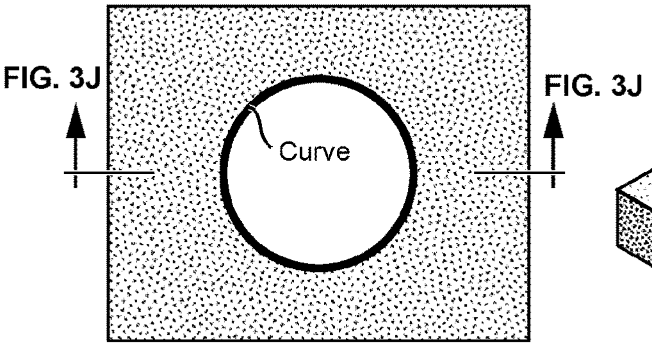

FIG. 3I shows the surface of a structure, with a one dimensional hole in the surface. The illustrated plane curve forms the boundary of a one dimensional hole.

Figure 3K:
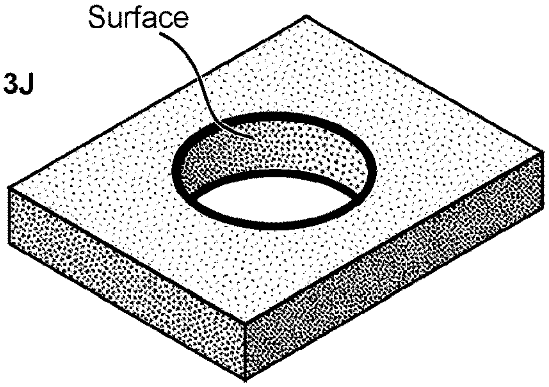
Figure 3J:
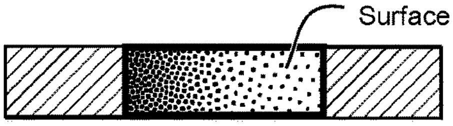

FIG. 3J shows a cross-section through the structure of FIG. 3I. The illustrated surface bounds a two dimensional hole in the structure of FIG. 3I.

FIG. 3K shows a perspective view of the structure of FIG. 3I, including the two dimensional hole and the one dimensional hole. Also shown is the surface that bounds a two dimensional hole in the structure of FIG. 3I.

Figure 3L:
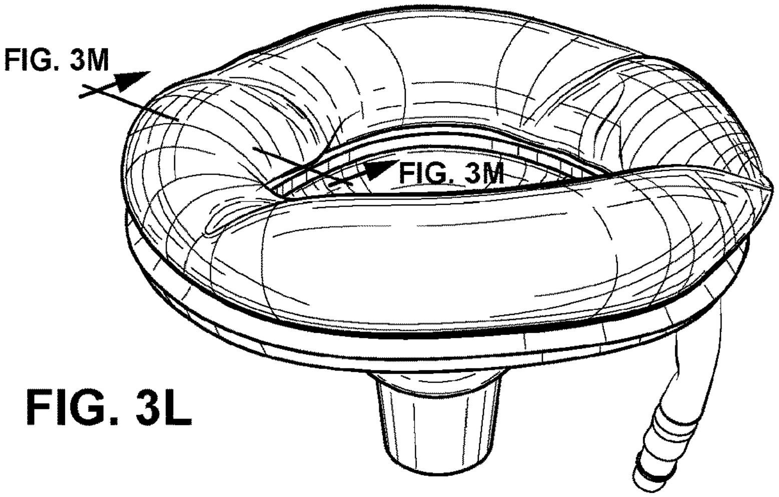

FIG. 3L shows a mask having an inflatable bladder as a cushion.

Figure 3M:
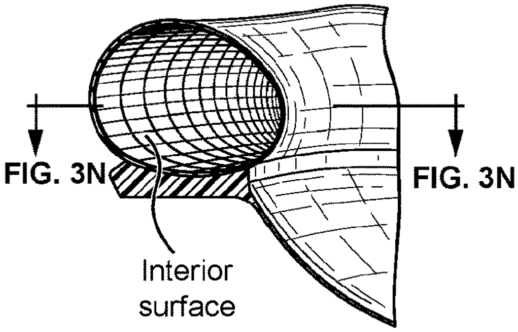

FIG. 3M shows a cross-section through the mask of FIG. 3L, and shows the interior surface of the bladder. The interior surface bounds the two dimensional hole in the mask.

Figure 3N:
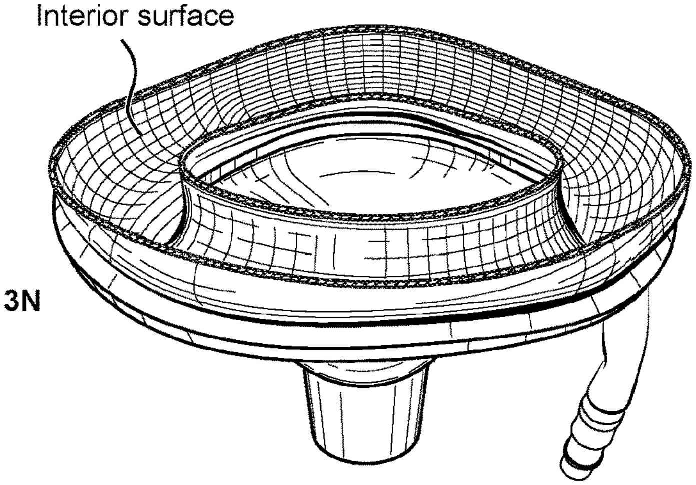

FIG. 3N shows a further cross-section through the mask of FIG. 3L. The interior surface is also indicated.

Figure 3O:
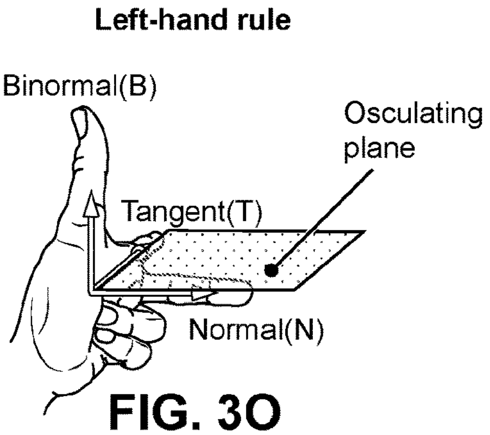

FIG. 3O illustrates a left-hand rule.

Figure 3P:
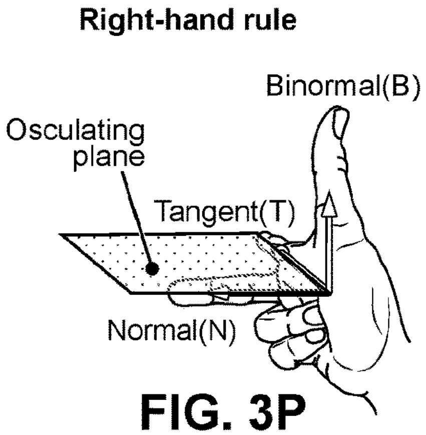

FIG. 3P illustrates a right-hand rule.

Figure 3Q:
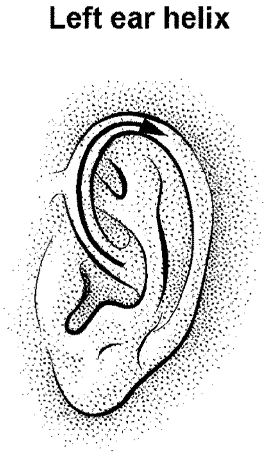

FIG. 3Q shows a left ear, including the left ear helix.

Figure 3S:
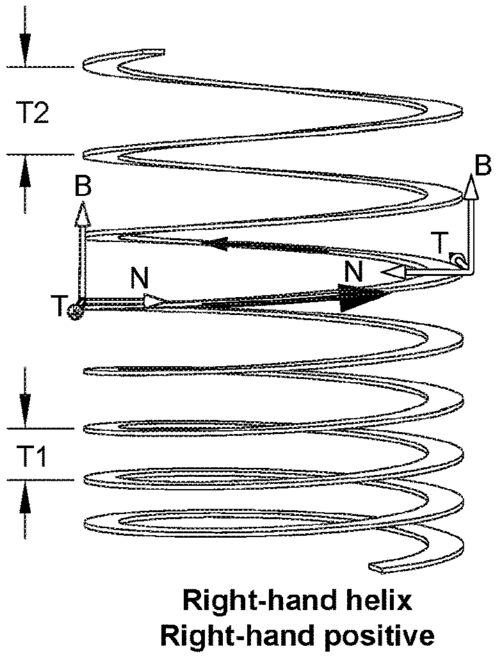
Figure 3R:
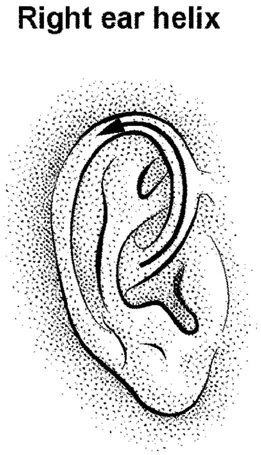

FIG. 3R shows a right ear, including the right ear helix.

FIG. 3S shows a right-hand helix.

Figure 3T:
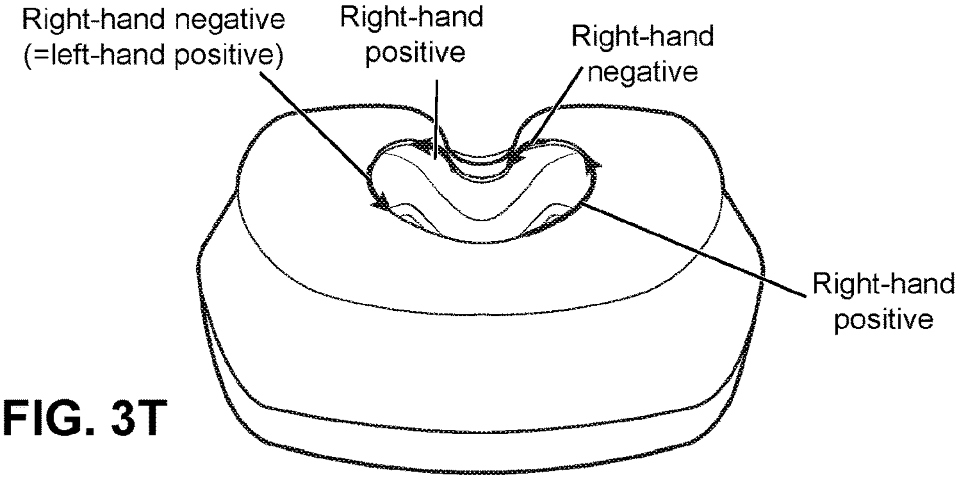

FIG. 3T shows a view of a mask, including the sign of the torsion of the space curve defined by the edge of the sealing membrane in different regions of the mask.

4.4 RPT Device

Figure 4A:
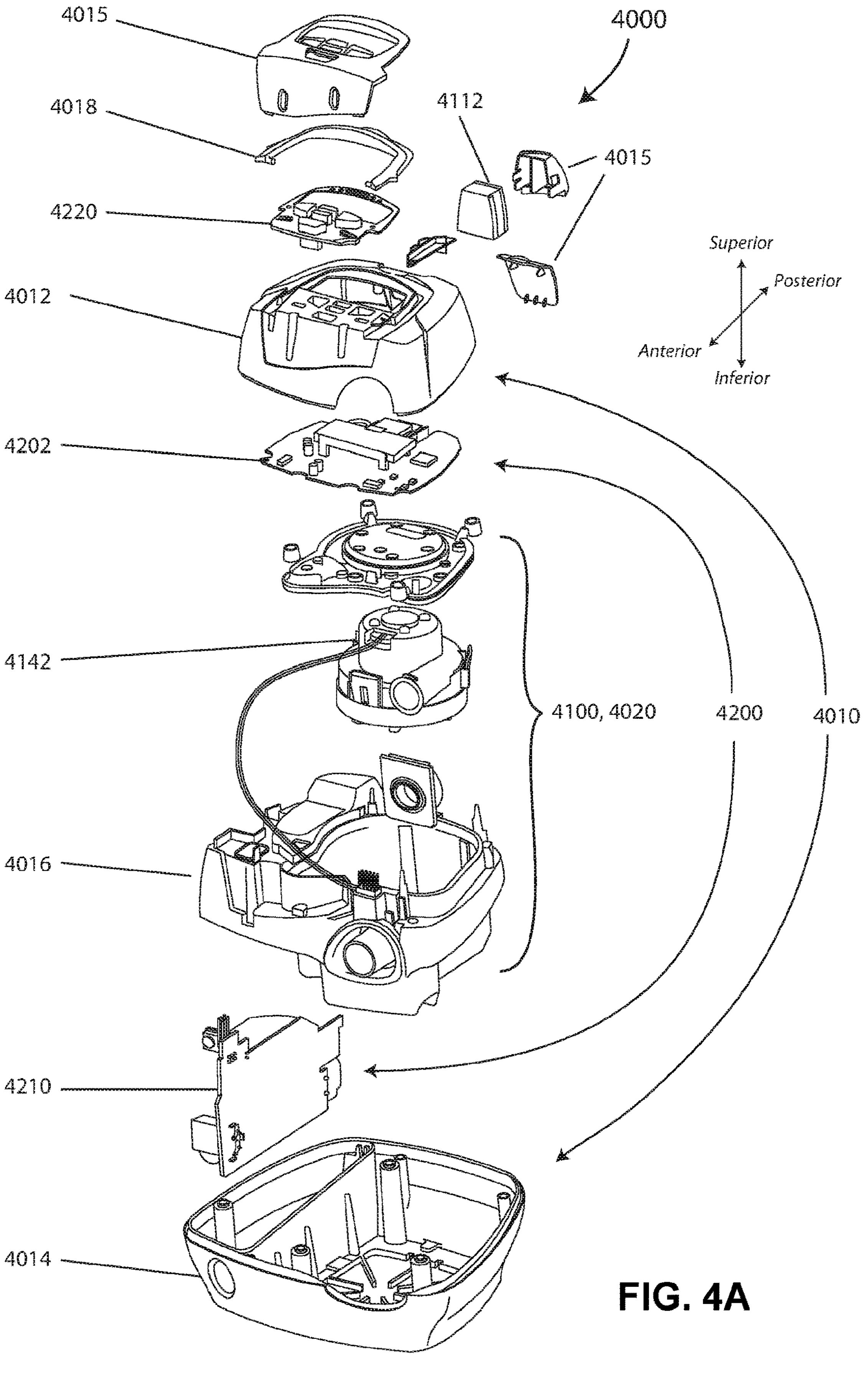

FIG. 4A shows an RPT device in accordance with one form of the present technology.

Figure 4B:
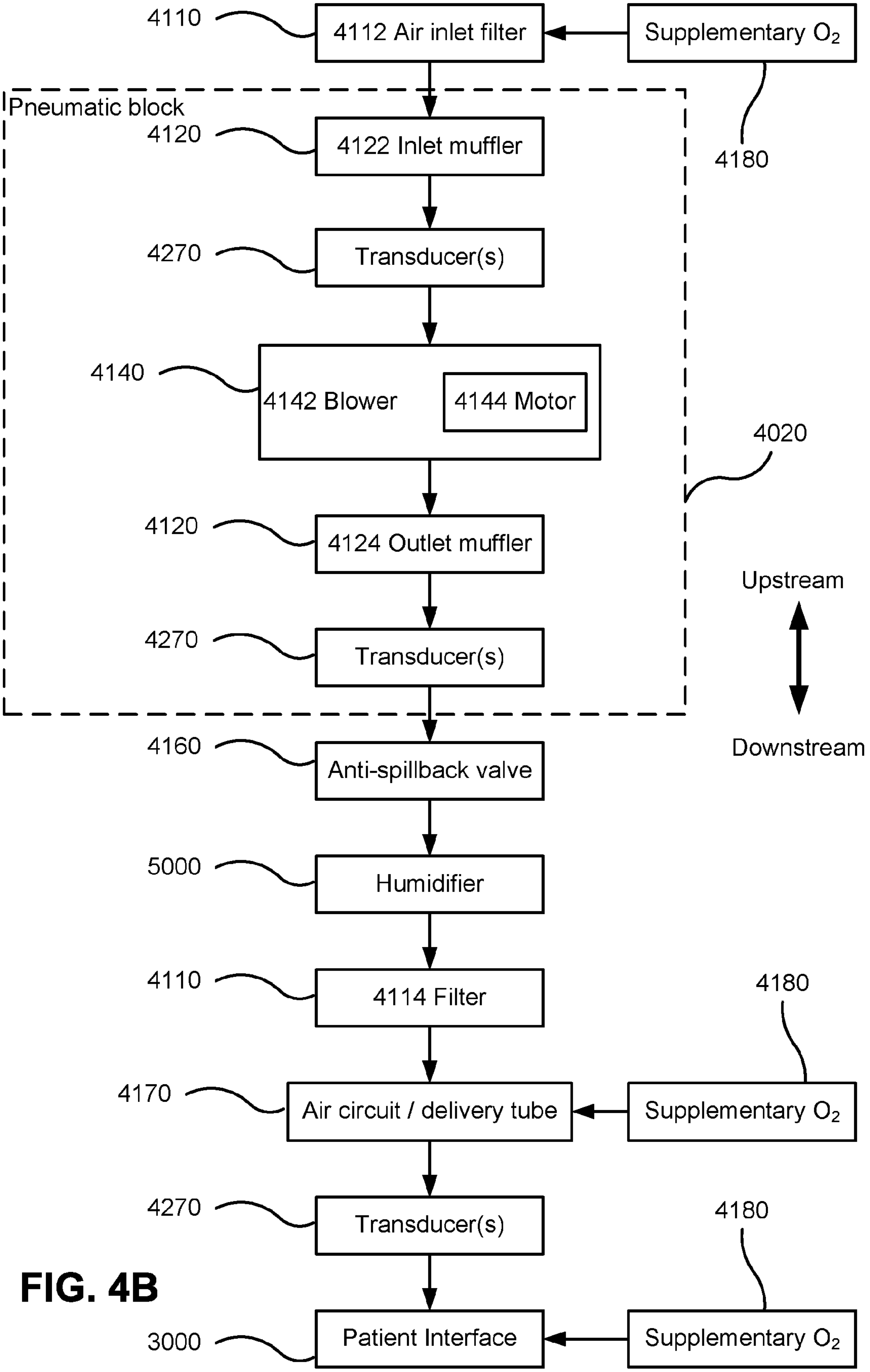

FIG. 4B is a schematic diagram of the pneumatic path of an RPT device in accordance with one form of the present technology. The directions of upstream and downstream are indicated with reference to the blower and the patient interface. The blower is defined to be upstream of the patient interface and the patient interface is defined to be downstream of the blower, regardless of the actual flow direction at any particular moment. Items which are located within the pneumatic path between the blower and the patient interface are downstream of the blower and upstream of the patient interface.

4.5 Humidifier

Figure 5A:
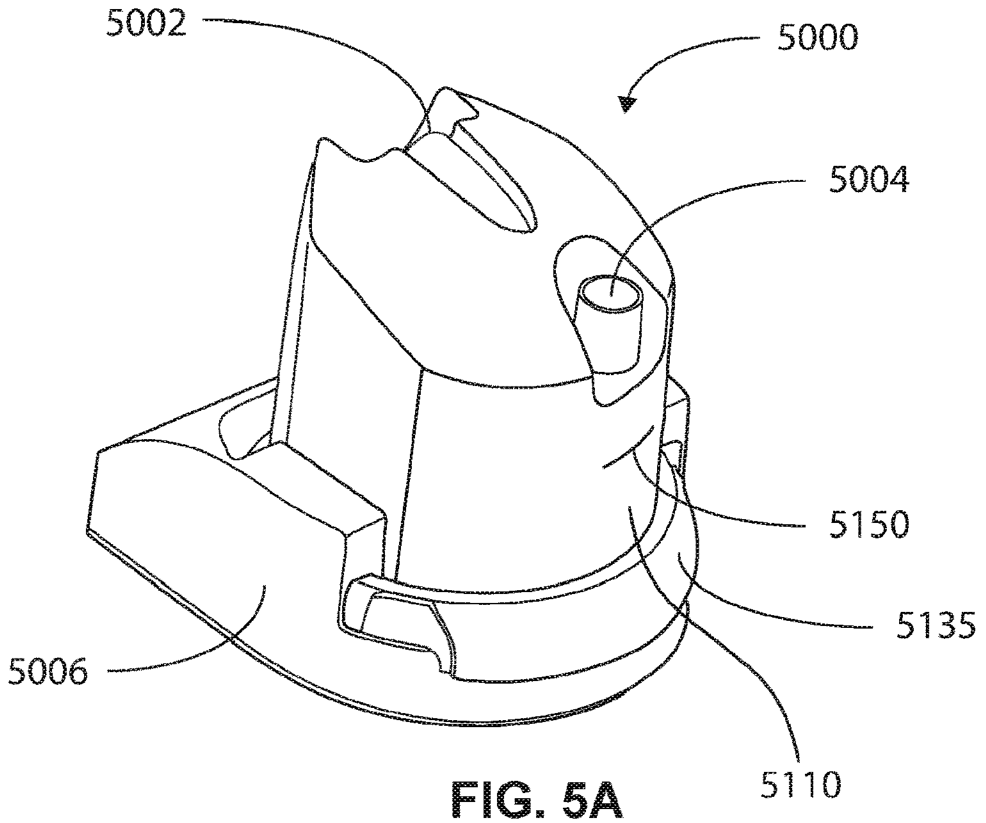

FIG. 5A shows an isometric view of a humidifier in accordance with one form of the present technology.

Figure 5B:
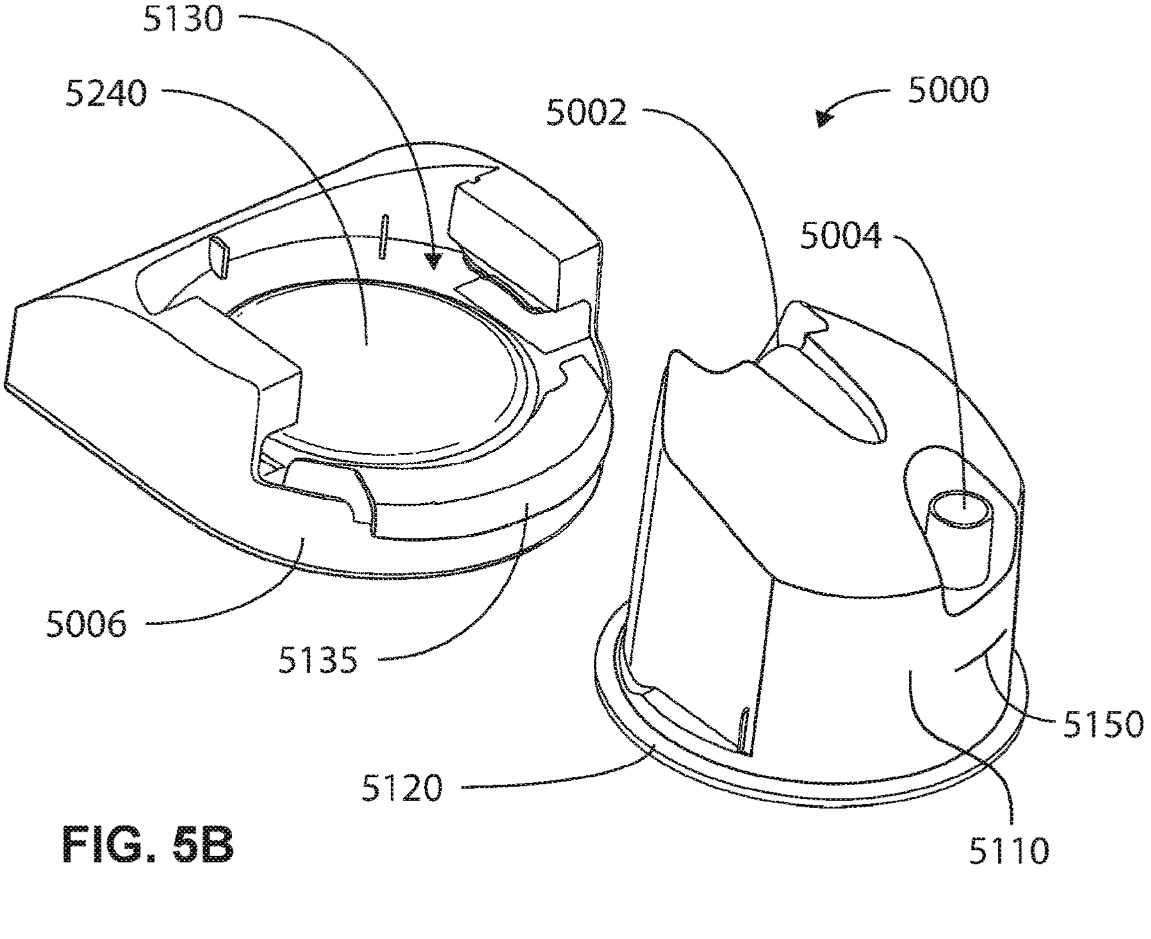

FIG. 5B shows an isometric view of a humidifier in accordance with one form of the present technology, showing a humidifier reservoir 5110 removed from the humidifier reservoir dock 5130.

4.6 Breathing Waveforms

Figure 6:
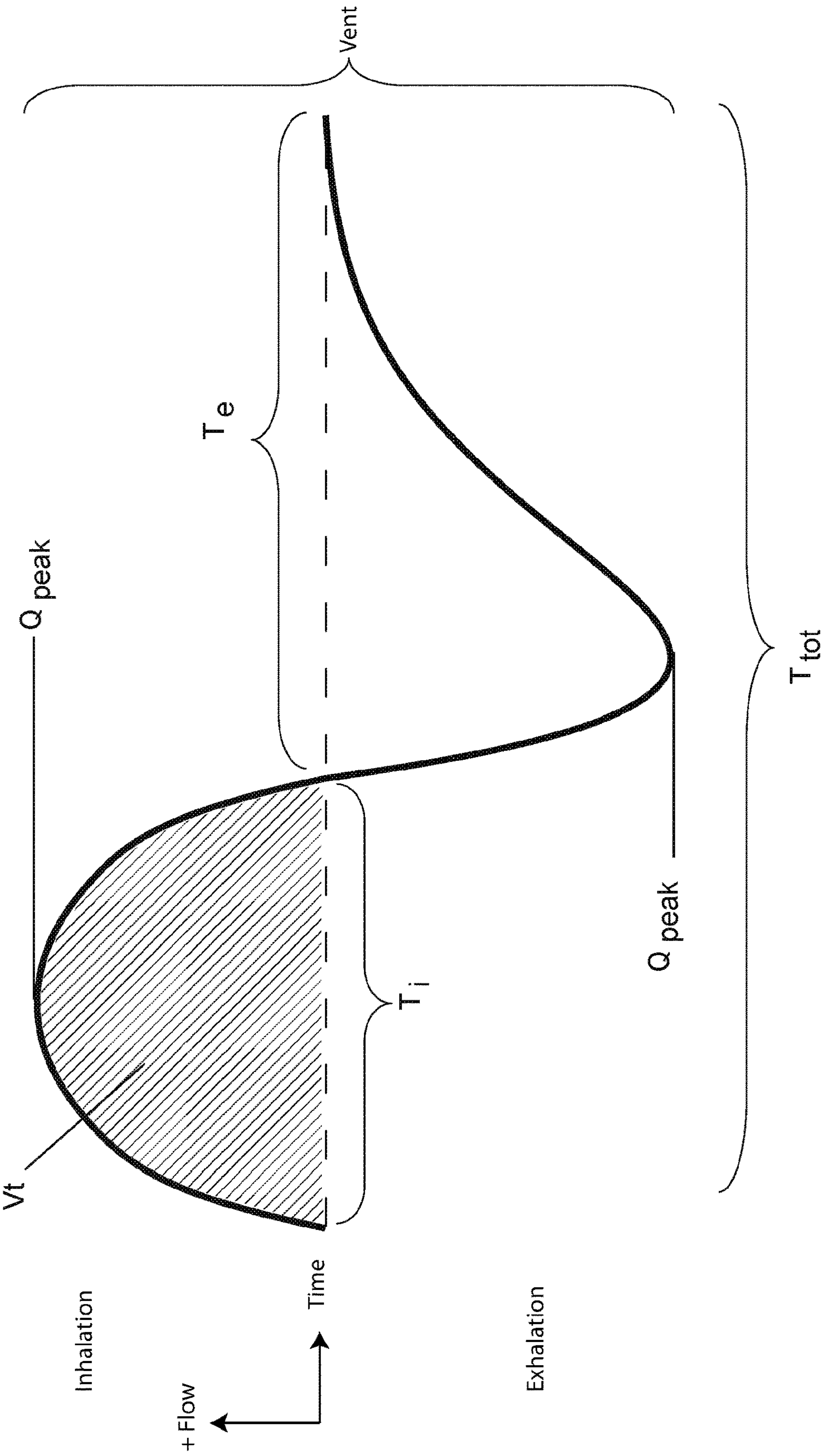

FIG. 6 shows a model typical breath waveform of a person while sleeping.

4.7 Further Patient Interface Example

Figure 7A:
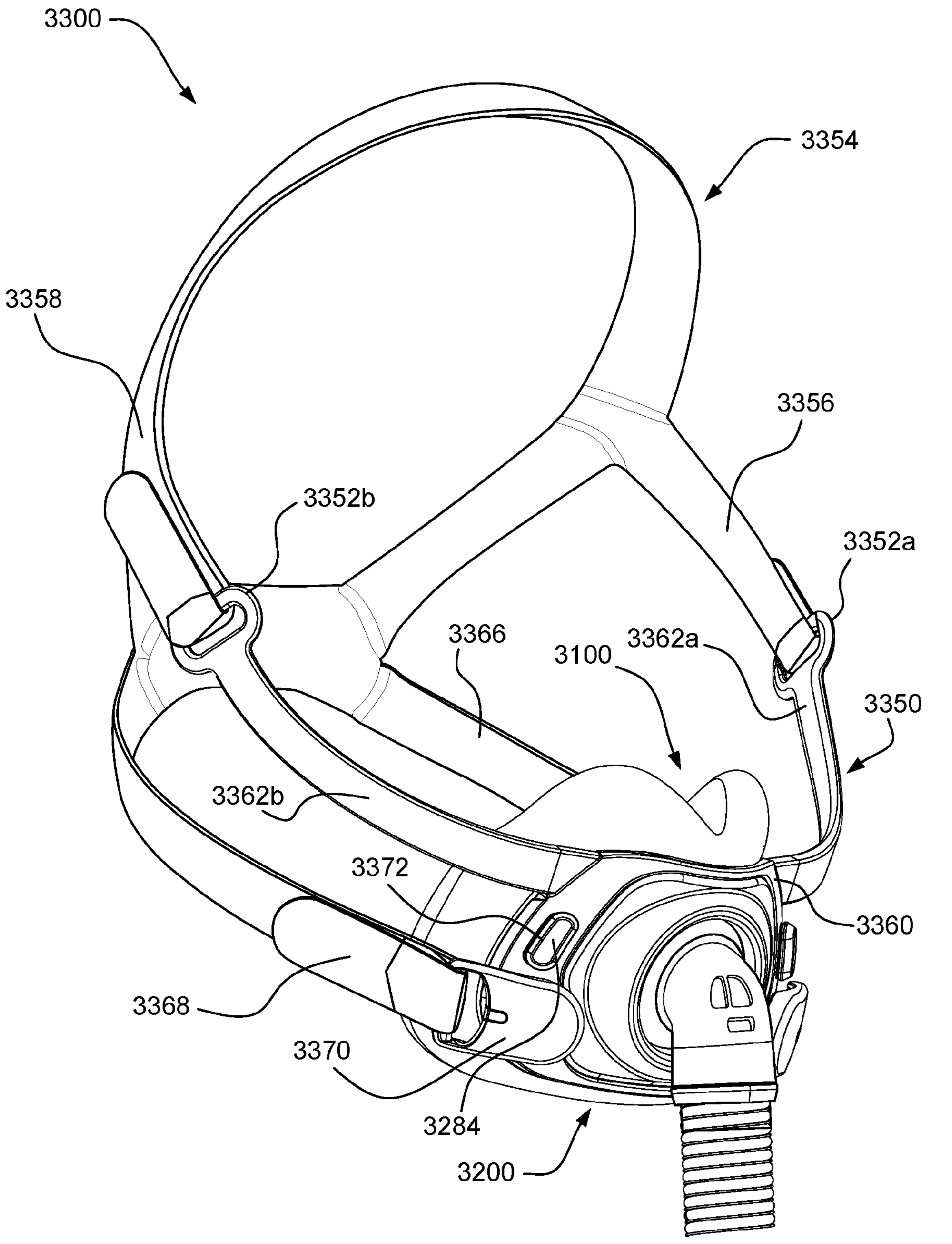

FIG. 7A shows a perspective view of a patient interface.

Figure 7B:
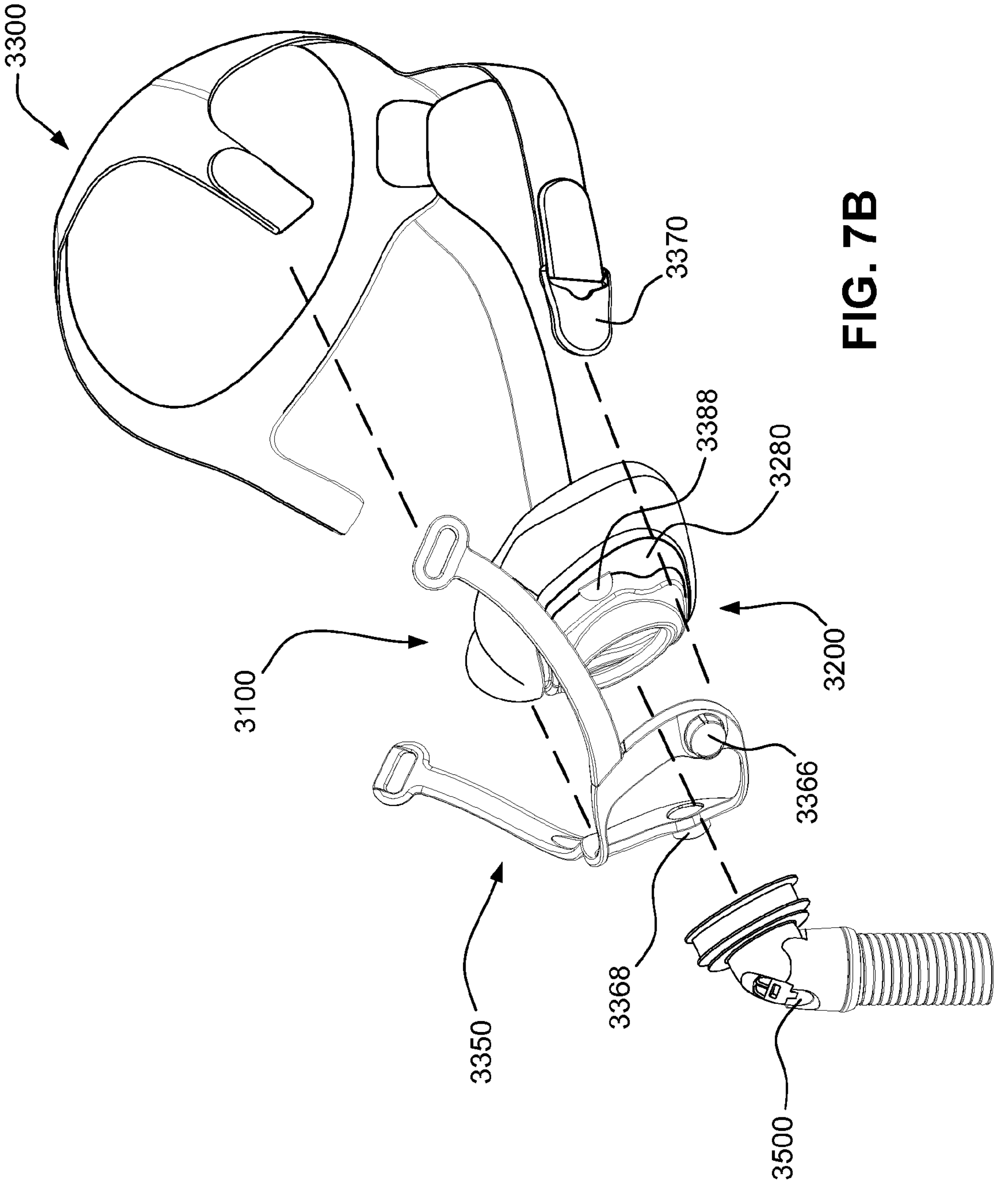

FIG. 7B shows an exploded view of a patient interface.

Figure 7C:
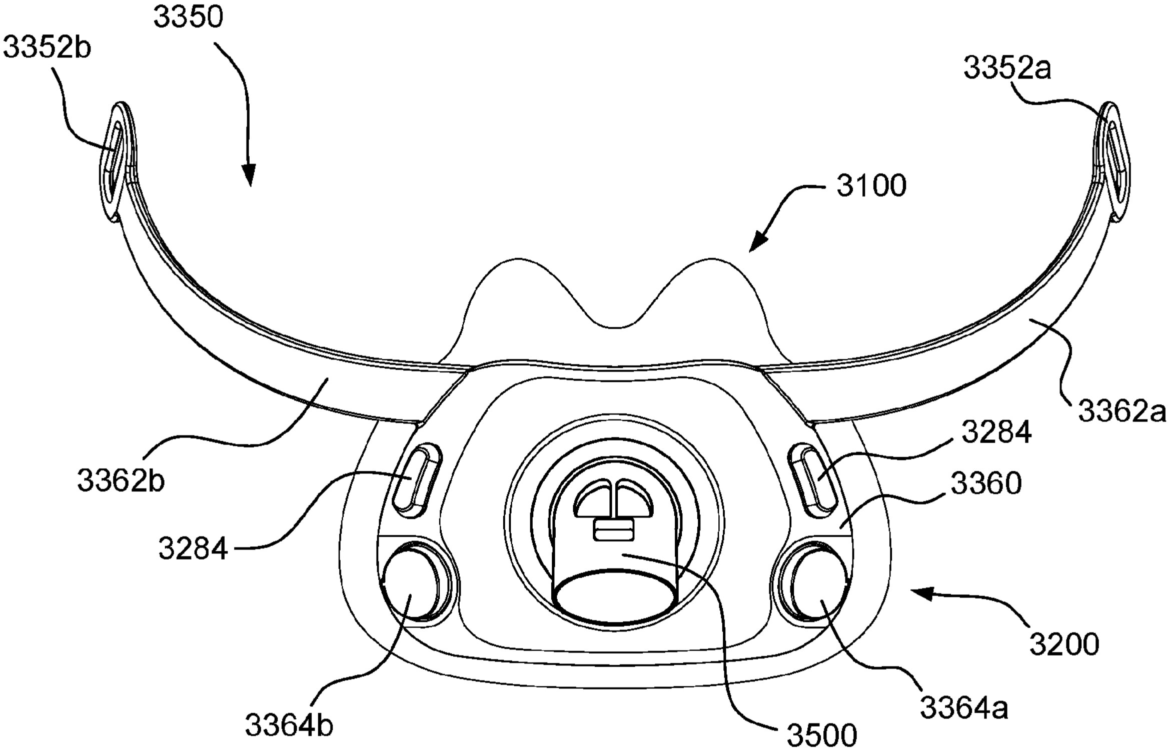

FIG. 7C shows an anterior view of a patient interface.

4.8 HMX and Patient Interface System

Figure 8A:
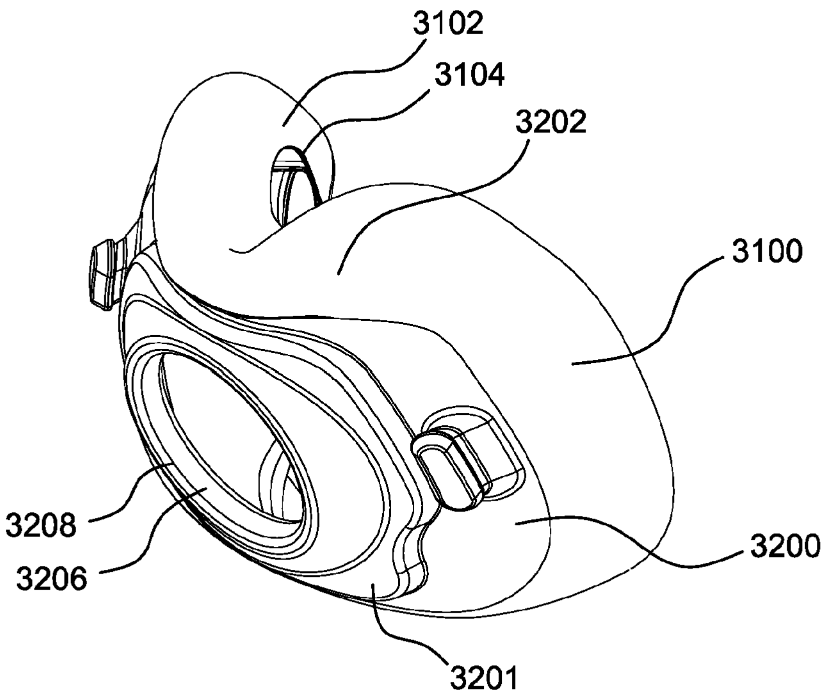

FIG. 8A shows a perspective view of a seal-forming structure and a plenum chamber according to an example of the present technology.

Figure 8B:
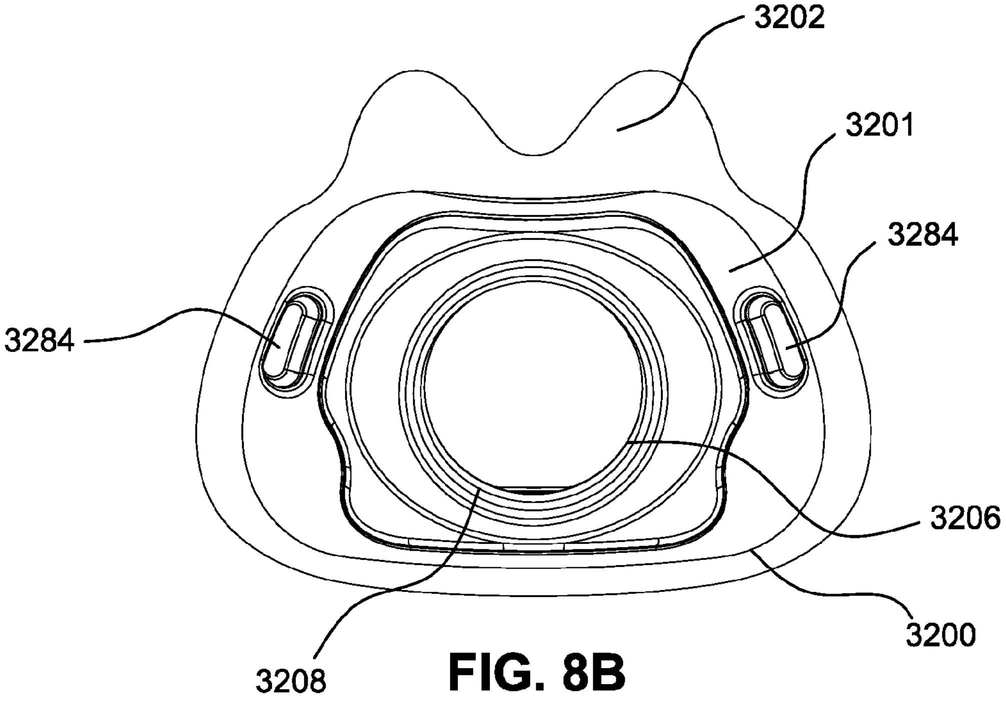

FIG. 8B shows an anterior view of a seal-forming structure and a plenum chamber according to an example of the present technology.

Figure 8C:
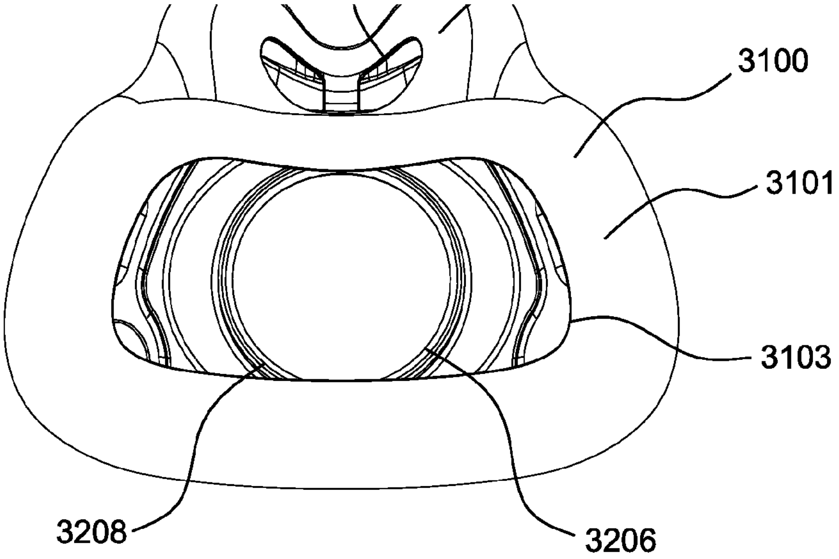

FIG. 8C shows a posterior view of a seal-forming structure and a plenum chamber according to an example of the present technology.

Figure 9A:
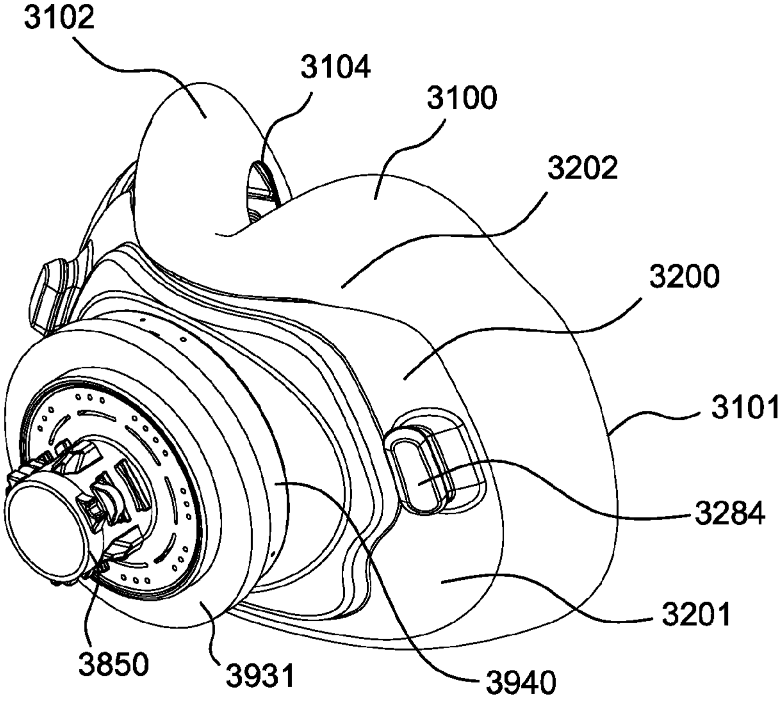

FIG. 9A shows a perspective view of an HMX and a patient interface according to an example of the present technology.

Figure 9B:
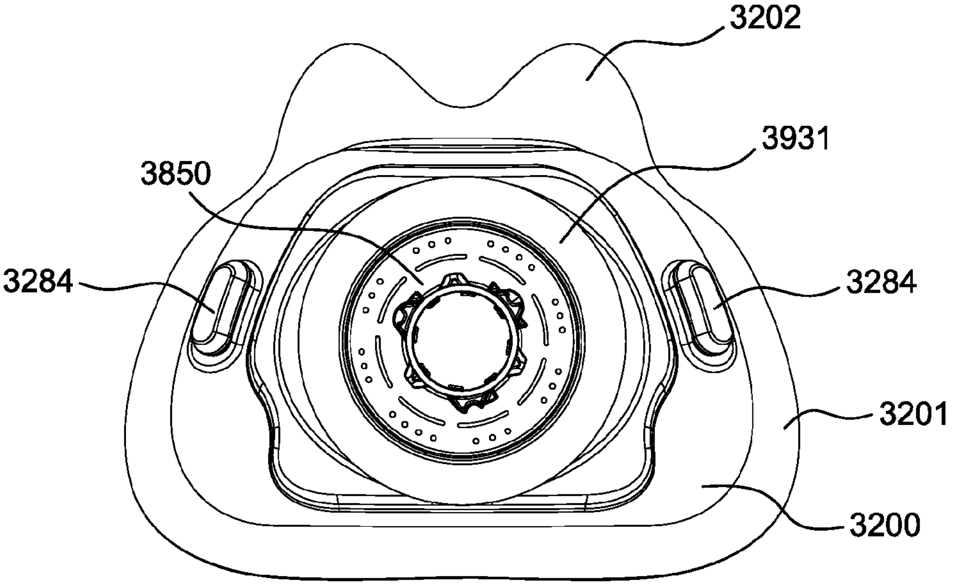

FIG. 9B shows an anterior view of an HMX and a patient interface according to an example of the present technology.

Figure 9C:
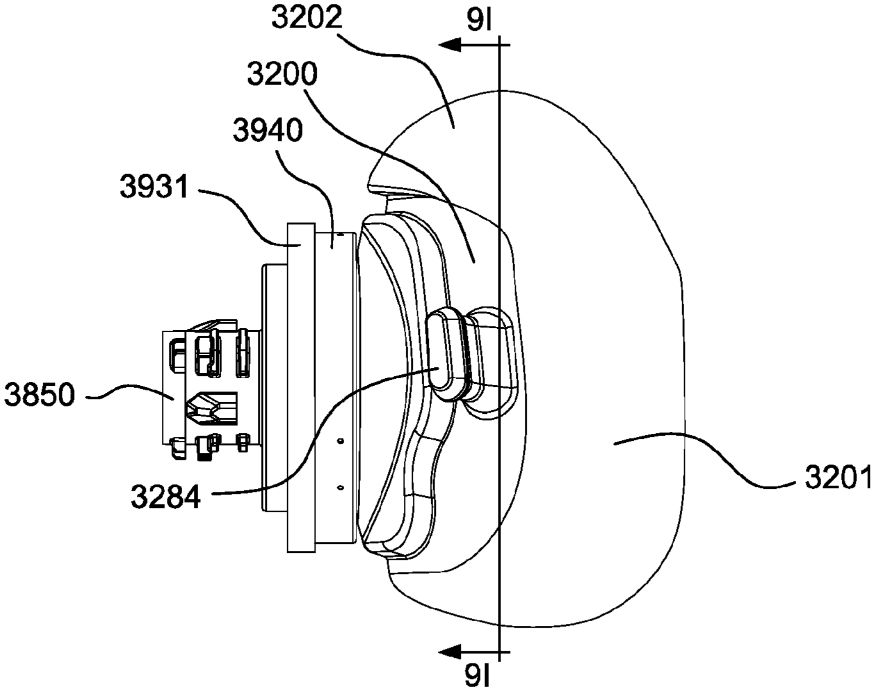

FIG. 9C shows a lateral view of an HMX and a patient interface according to an example of the present technology.

Figure 9D:
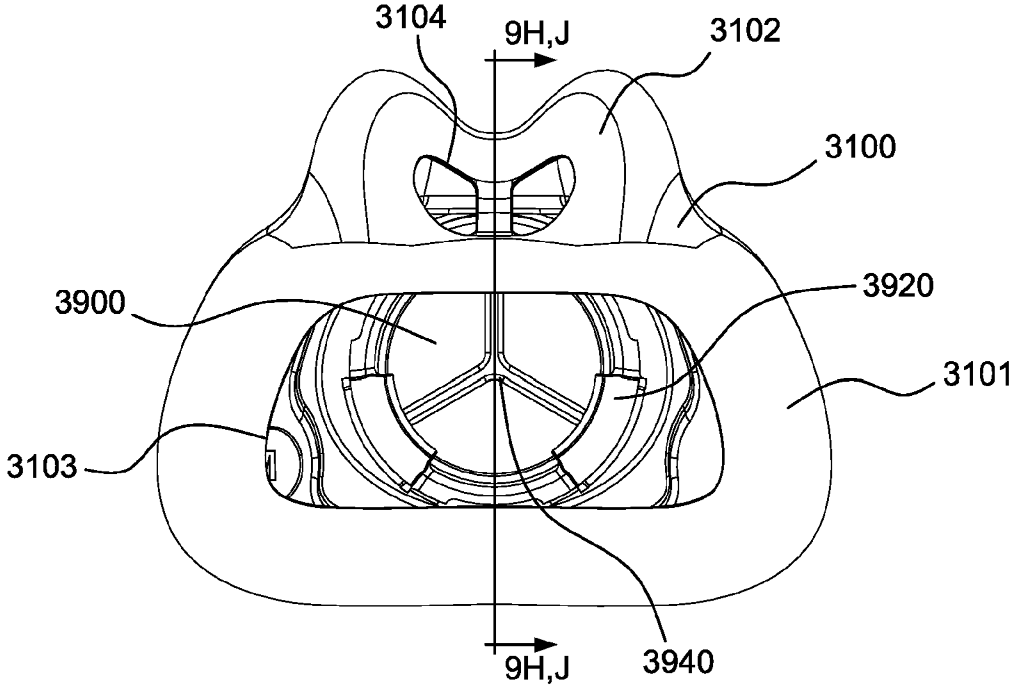

FIG. 9D shows a posterior view of an HMX and a patient interface according to an example of the present technology.

Figure 9E:
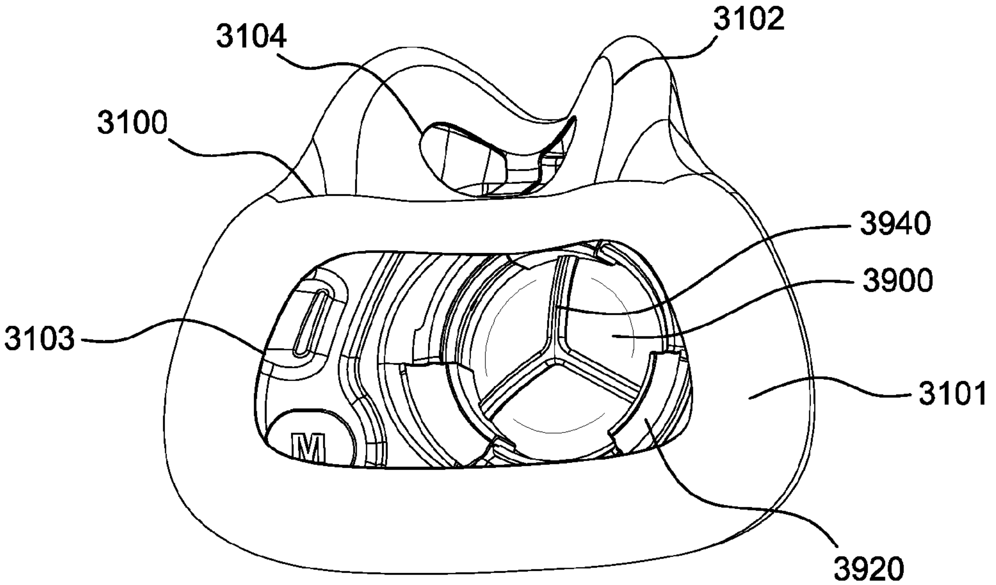

FIG. 9E shows another perspective view of an HMX and a patient interface according to an example of the present technology.

Figure 9F:
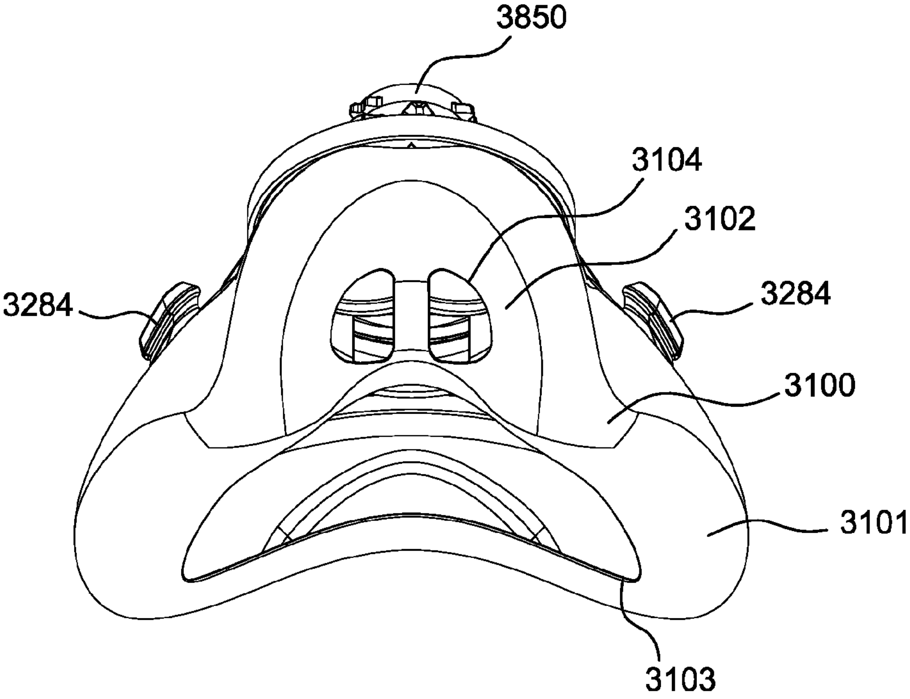

FIG. 9F shows a superior view of an HMX and a patient interface according to an example of the present technology.

Figure 9G:
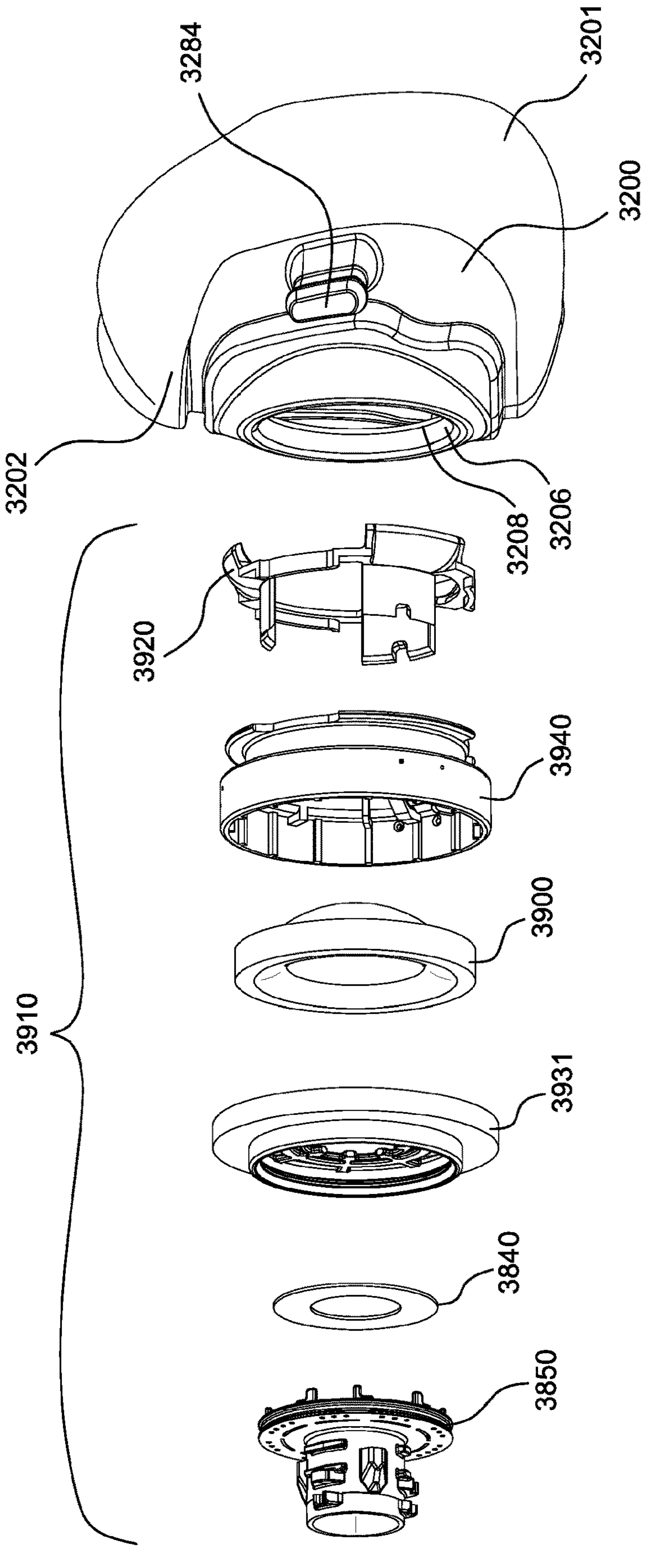

FIG. 9G shows an exploded view of an HMX and a patient interface according to an example of the present technology.

Figure 9H:
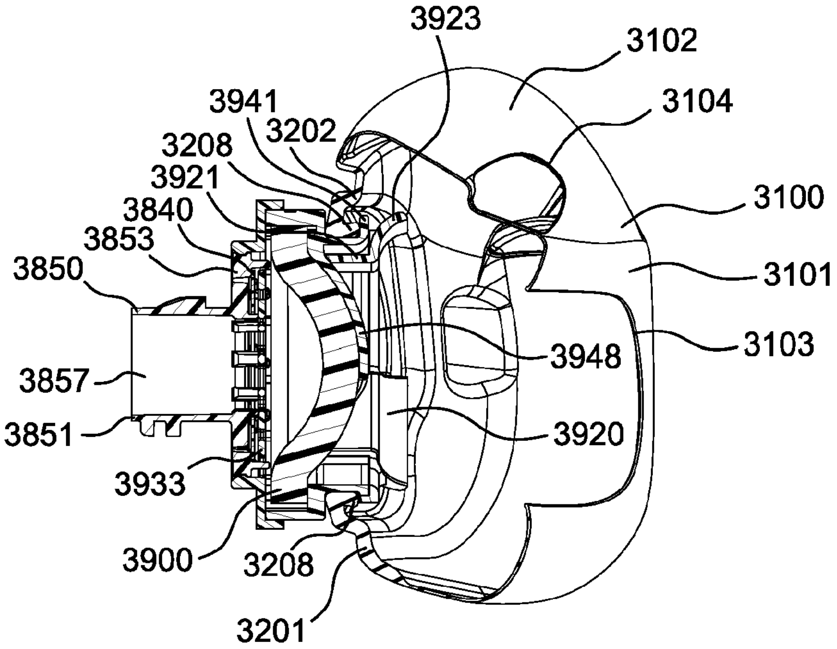

FIG. 9H shows a cross-sectional view of an HMX and a patient interface according to an example of the present technology taken through line 9H, J-9H, J of FIG. 9D.

Figure 9I:
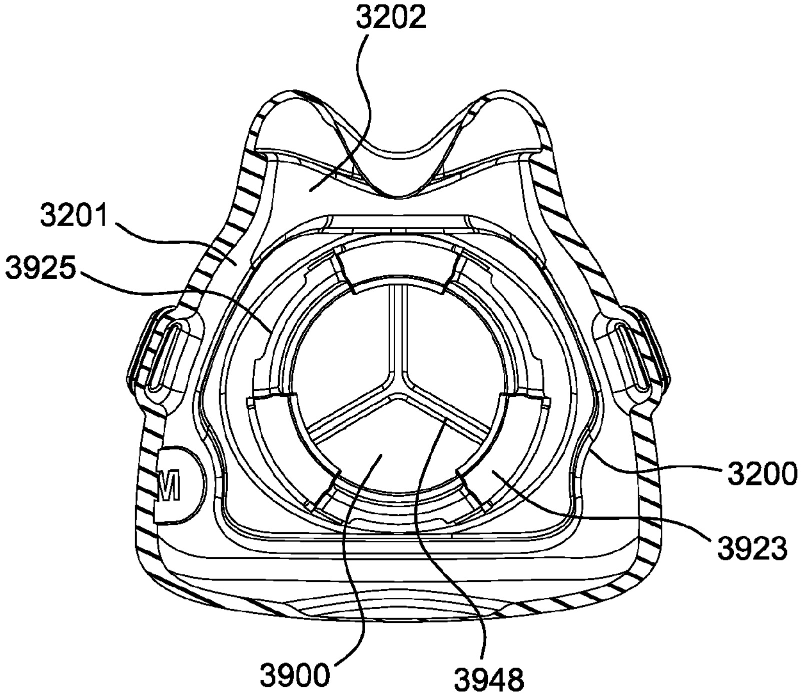

FIG. 9I shows a cross-sectional view of an HMX and a patient interface according to an example of the present technology taken through line 9I-91 of FIG. 9C.

Figure 9J:
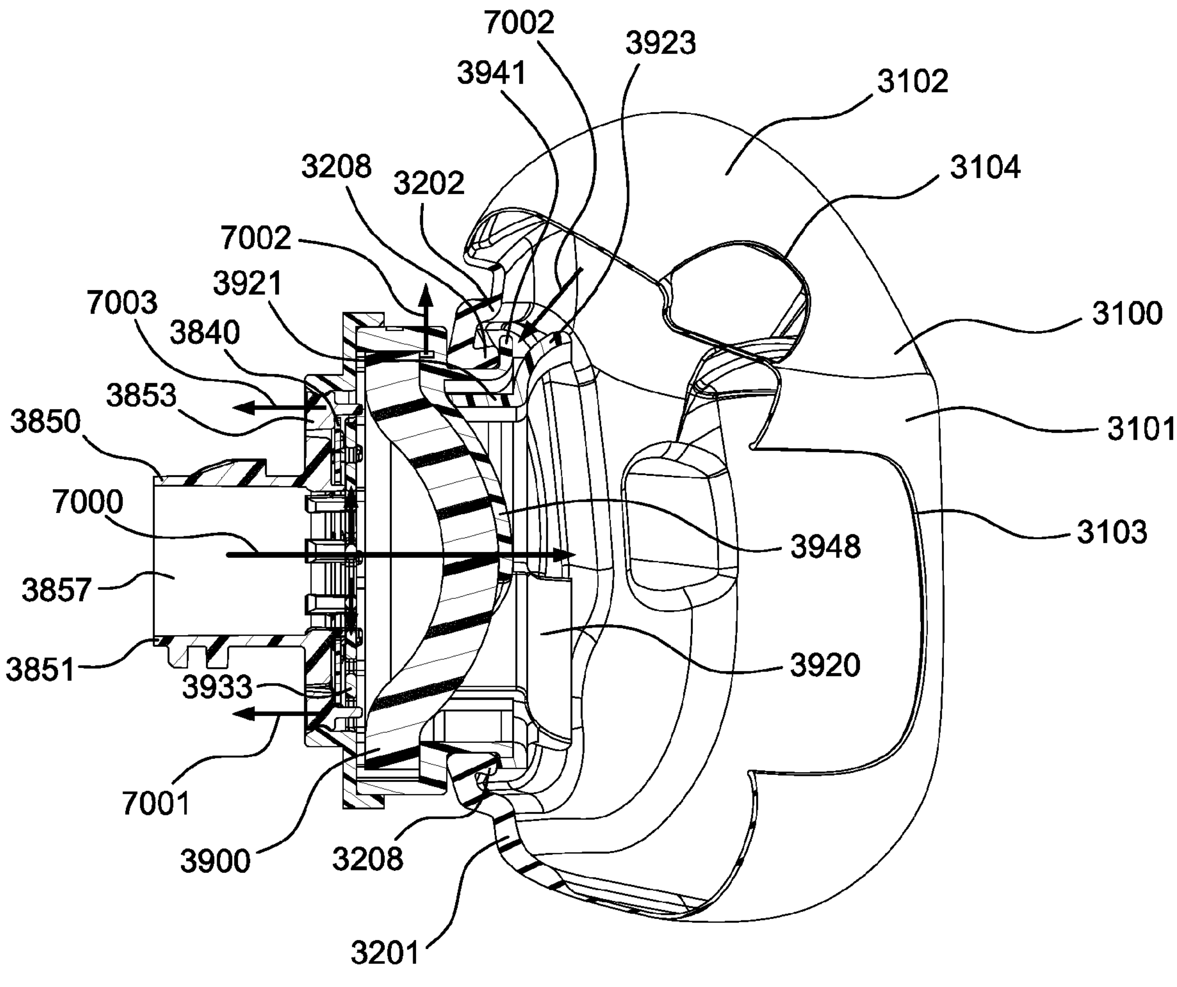

FIG. 9J shows a cross-sectional view of an HMX and a patient interface according to an example of the present technology taken through line 9H, J-9H, J of FIG. 9D.

Figure 10A:
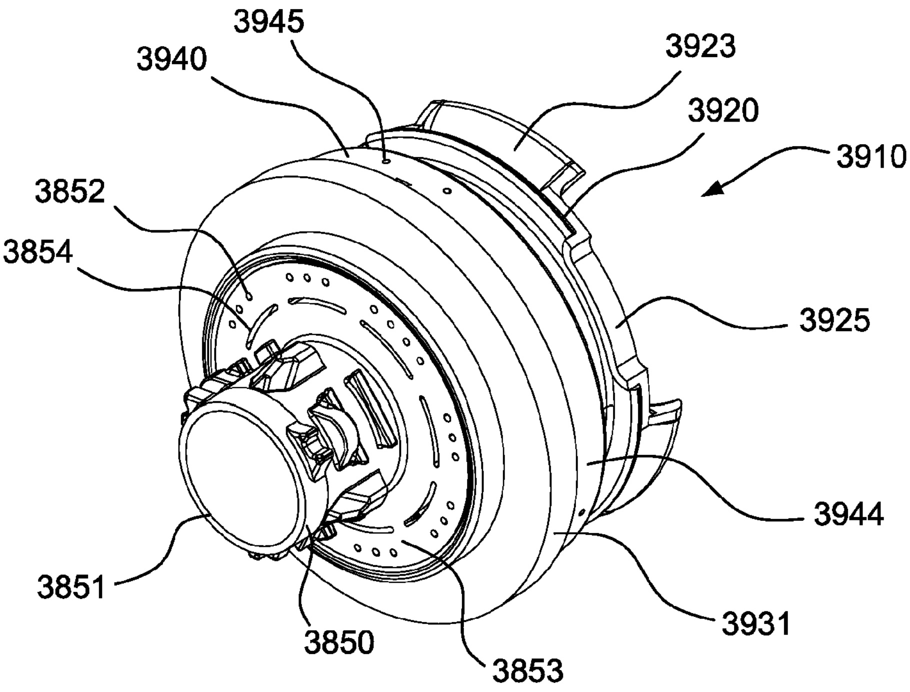

FIG. 10A shows a perspective view of a vent and conduit connector assembly and an HMX material according to an example of the present technology.

Figure 10B:
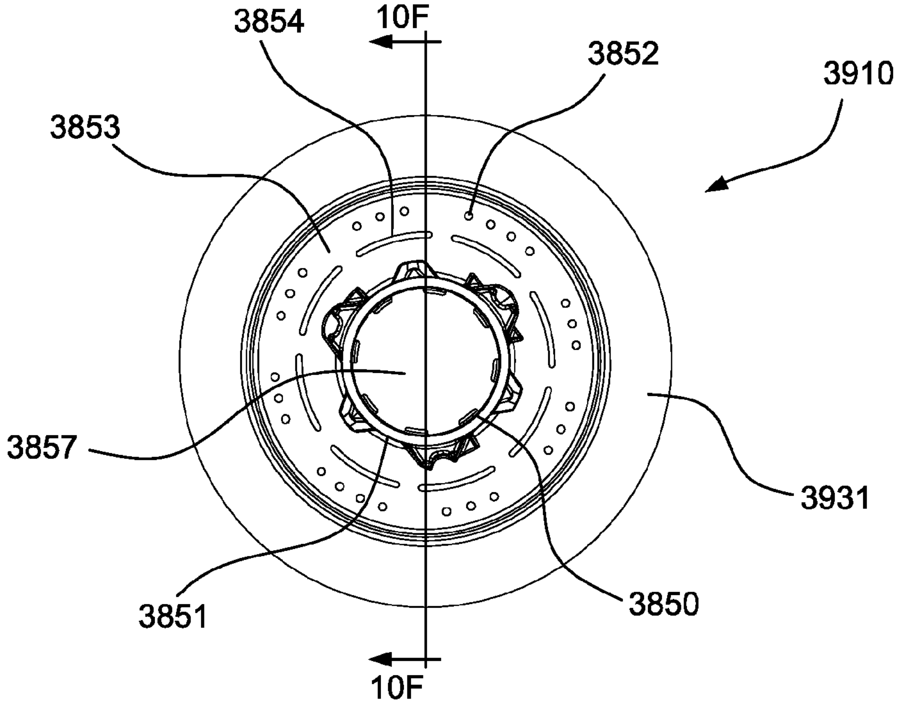

FIG. 10B shows an anterior view of a vent and conduit connector assembly and an HMX material according to an example of the present technology.

Figure 10C:
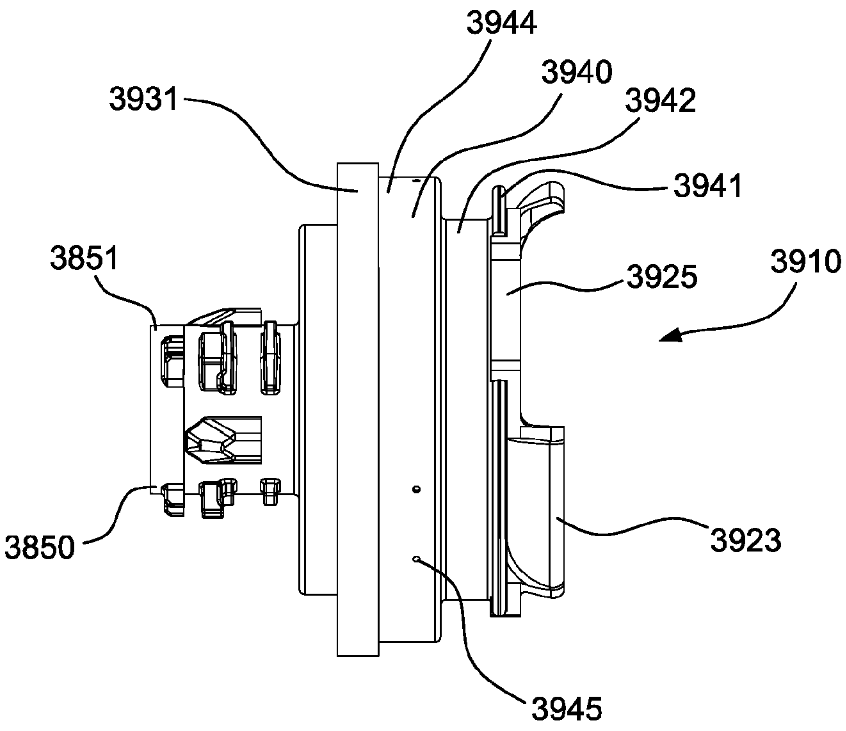

FIG. 10C shows a lateral view of a vent and conduit connector assembly and an HMX material according to an example of the present technology.

Figure 10D:
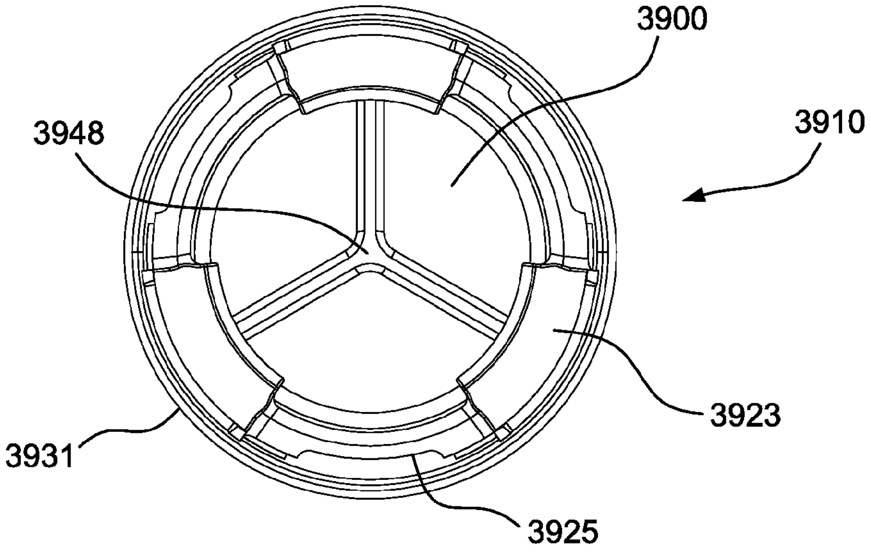

FIG. 10D shows a posterior view of a vent and conduit connector assembly and an HMX material according to an example of the present technology.

Figure 10E:
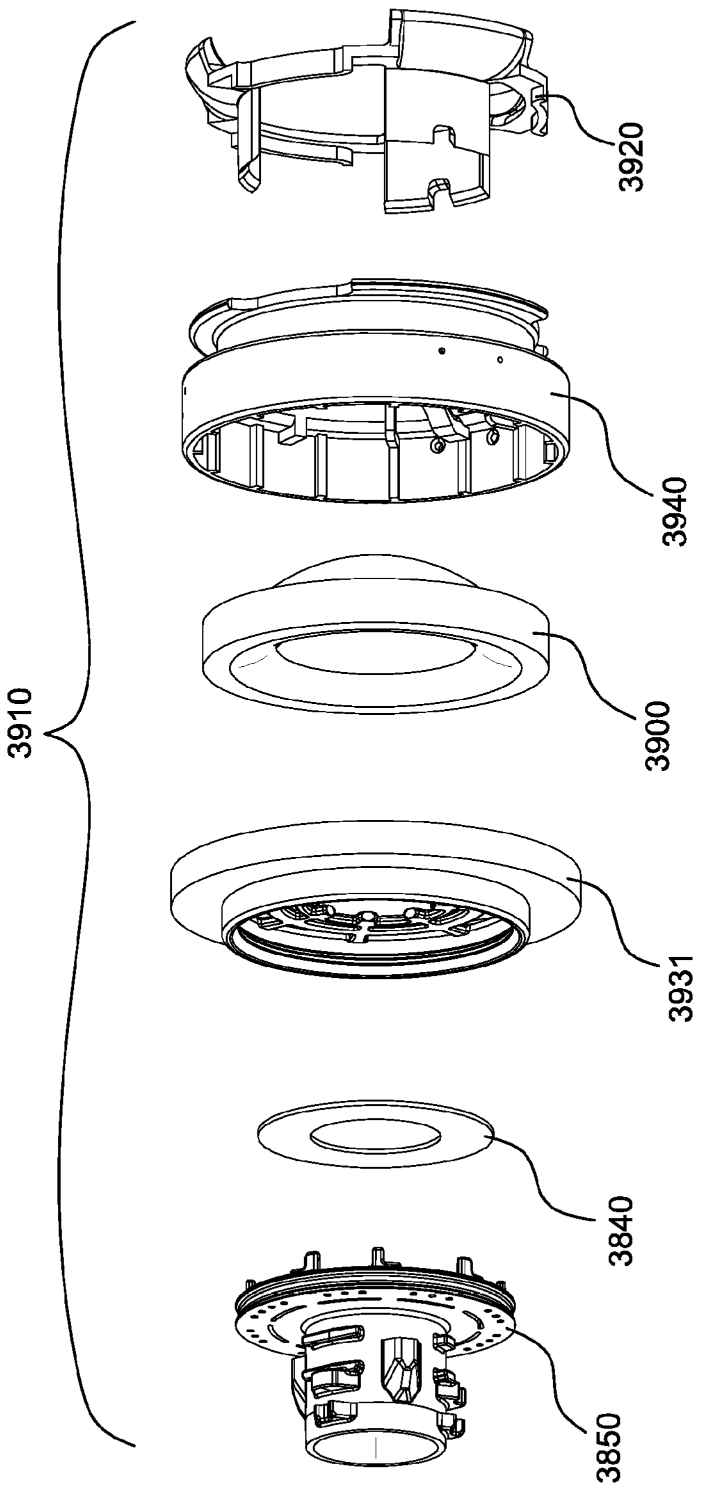

FIG. 10E shows an exploded view of a vent and conduit connector assembly and an HMX material according to an example of the present technology.

Figure 10F:
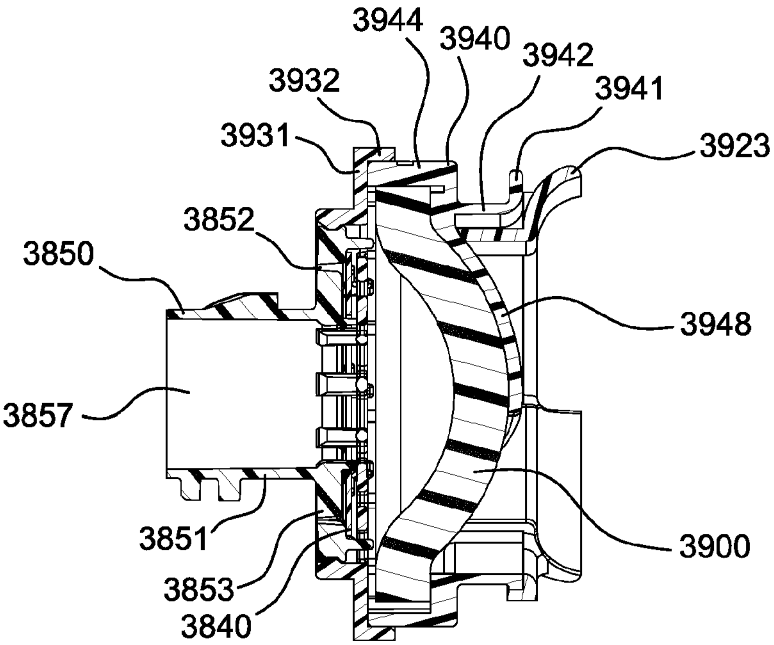

FIG. 10F shows a cross-sectional view of a vent and conduit connector assembly and an HMX material according to an example of the present technology taken through line 10F-10F of FIG. 10B.

Figure 11A:
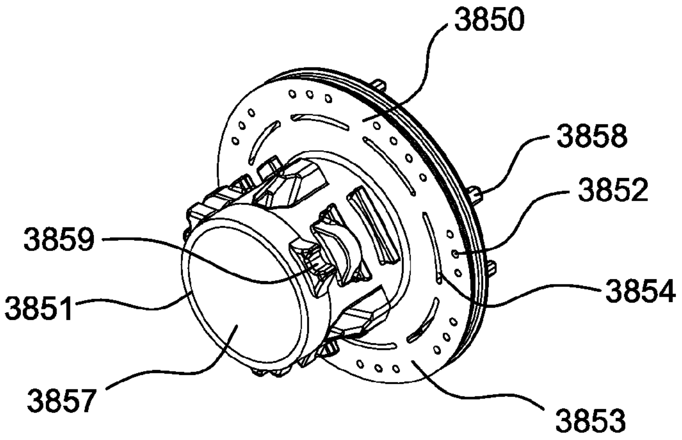

FIG. 11A shows a perspective view of a conduit connector according to an example of the present technology.

Figure 11B:
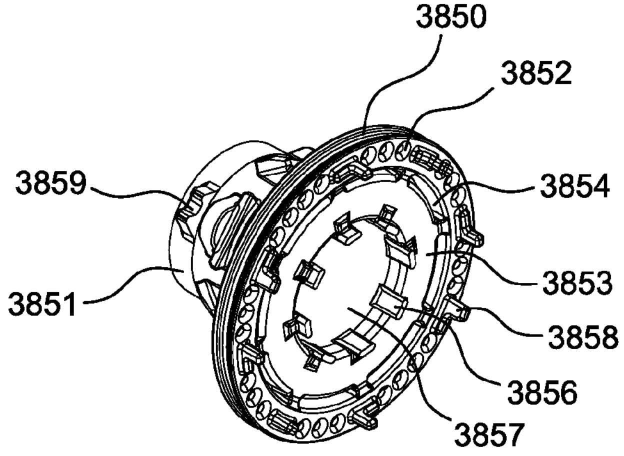

FIG. 11B shows another perspective view of a conduit connector according to an example of the present technology.

Figure 12:
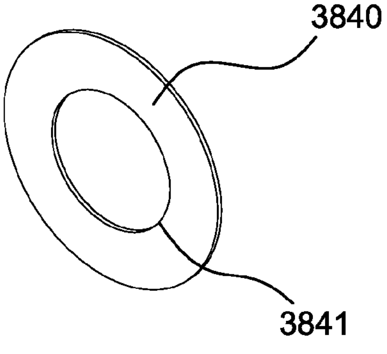

FIG. 12 shows a perspective view of a membrane according to an example of the present technology.

Figure 13A:
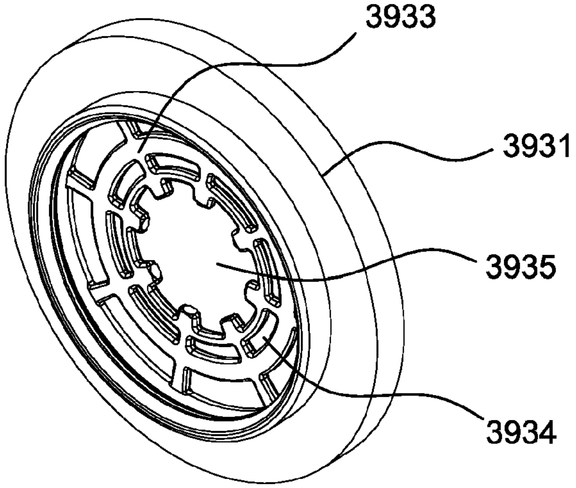

FIG. 13A shows a perspective view of an anterior HMX frame according to an example of the present technology.

Figure 13B:
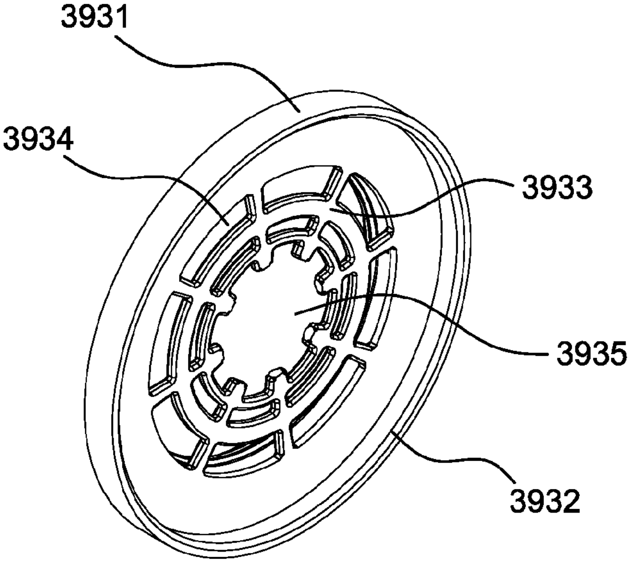

FIG. 13B shows another perspective view of an HMX frame according to an example of the present technology.

Figure 14A:
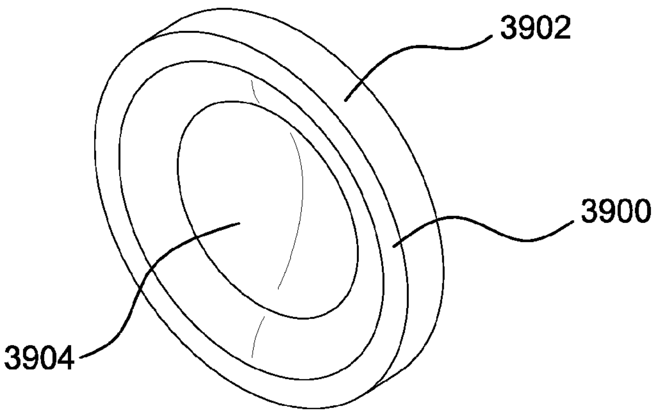

FIG. 14A shows a perspective view of an HMX material according to an example of the present technology.

Figure 14B:
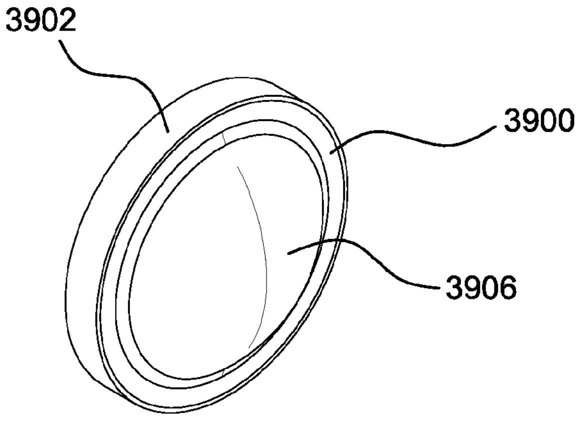

FIG. 14B shows another perspective view of an HMX material according to an example of the present technology.

Figure 15A:
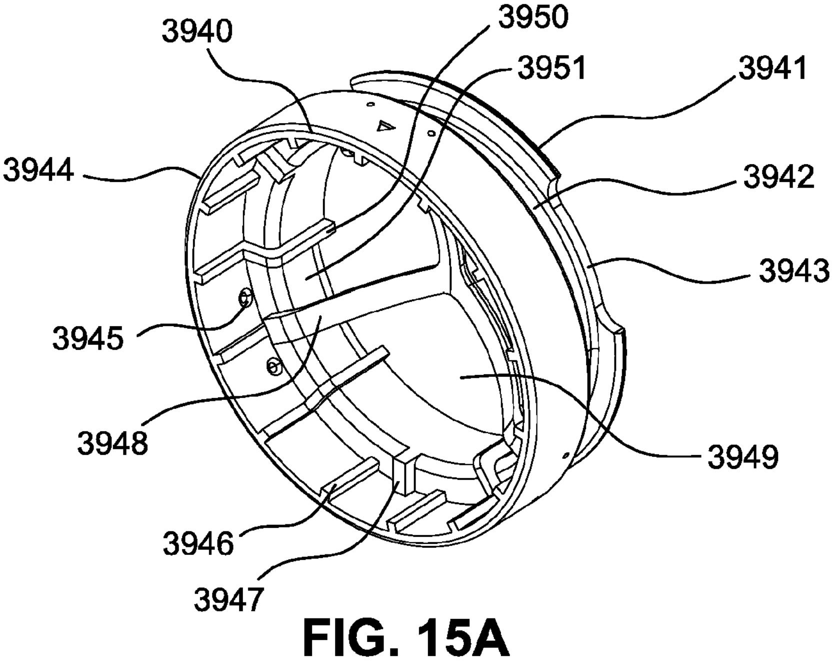

FIG. 15A shows a perspective view of a posterior HMX frame according to an example of the present technology.

Figure 15B:
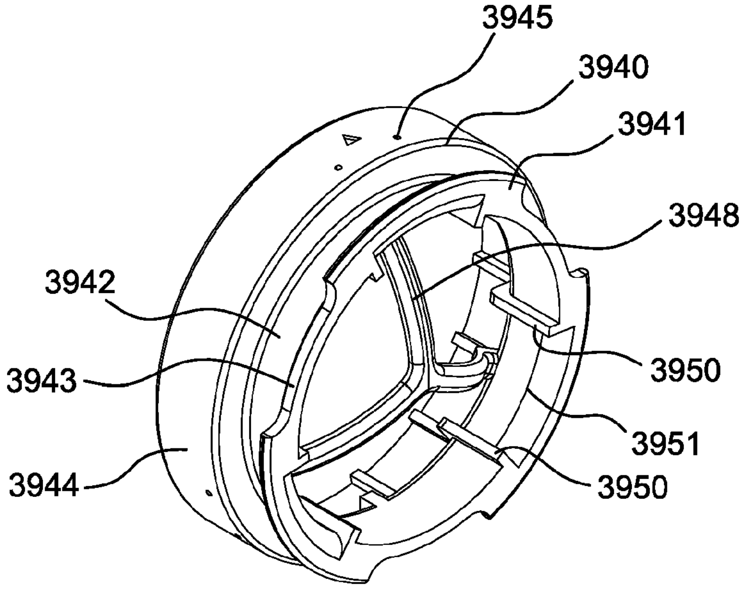

FIG. 15B shows another perspective view of a posterior HMX frame according to an example of the present technology.

Figure 16A:
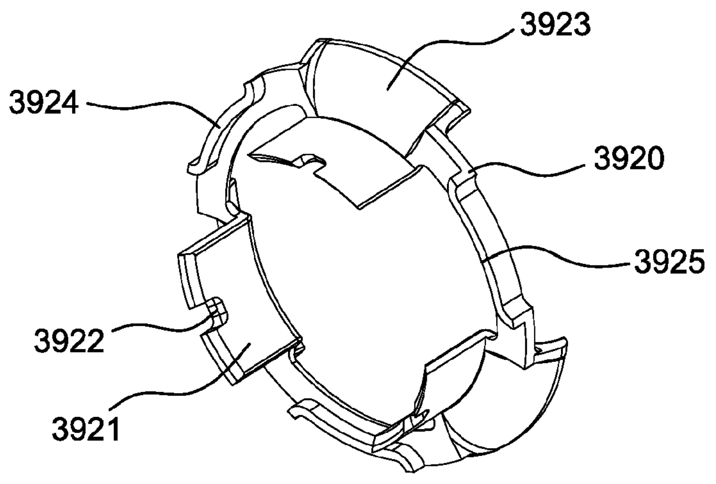

FIG. 16A shows a perspective view of a posterior flow directing structure according to an example of the present technology.

Figure 16B:
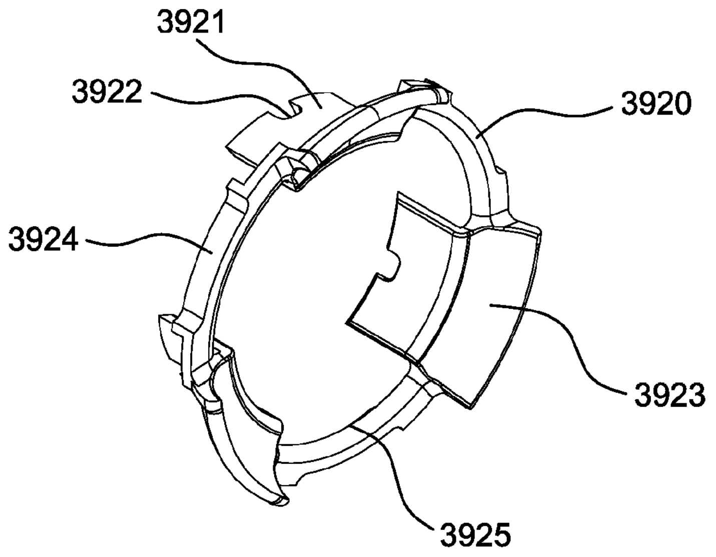

FIG. 16B shows another perspective view of a posterior flow directing structure according to an example of the present technology.

Figure 17A:
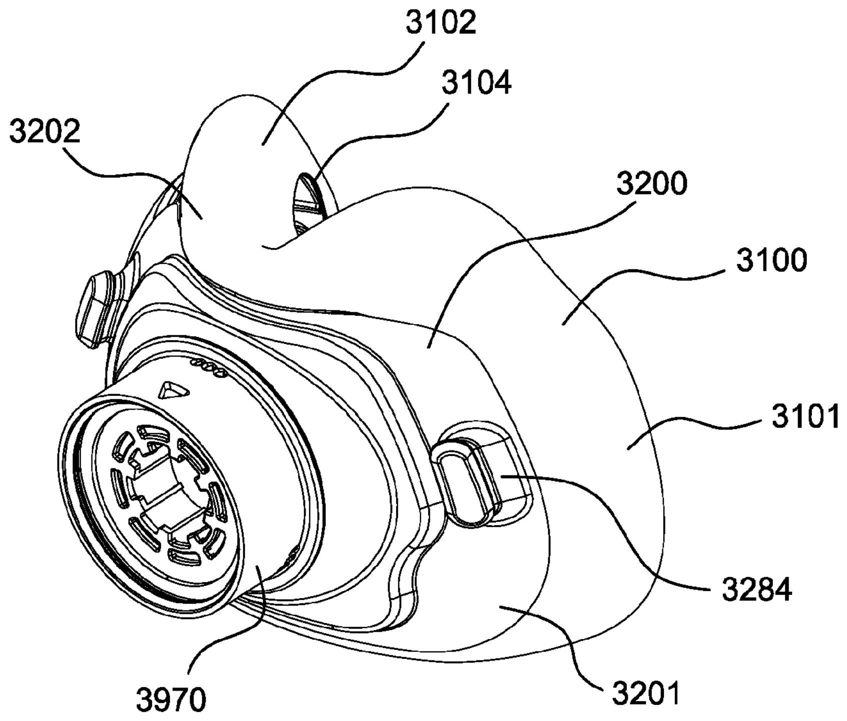

FIG. 17A shows a perspective view of an HMX and a patient interface according to an example of the present technology.

Figure 17B:
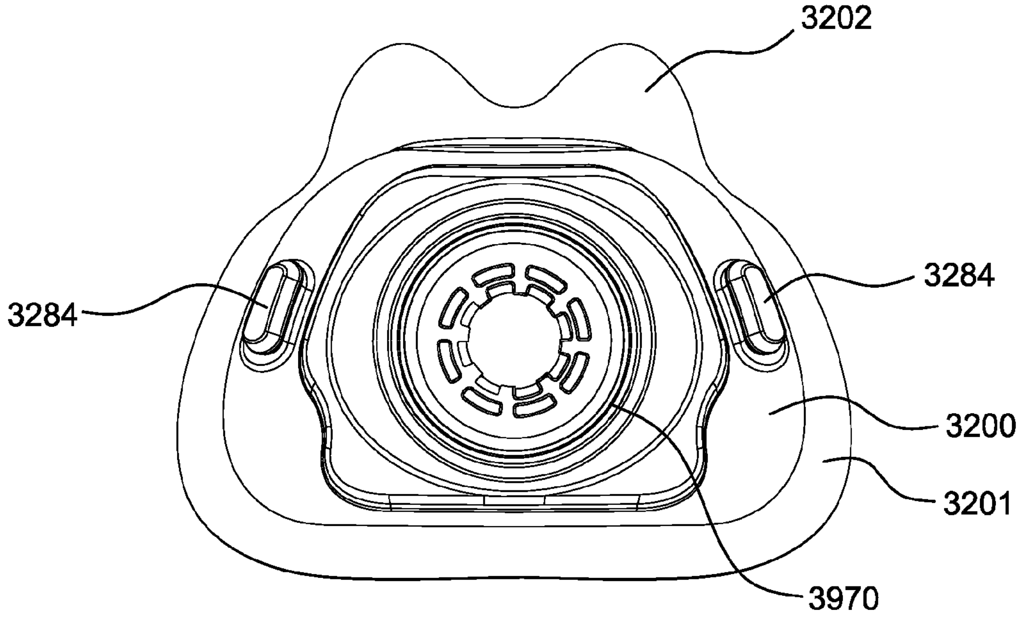

FIG. 17B shows an anterior view of an HMX and a patient interface according to an example of the present technology.

Figure 17C:
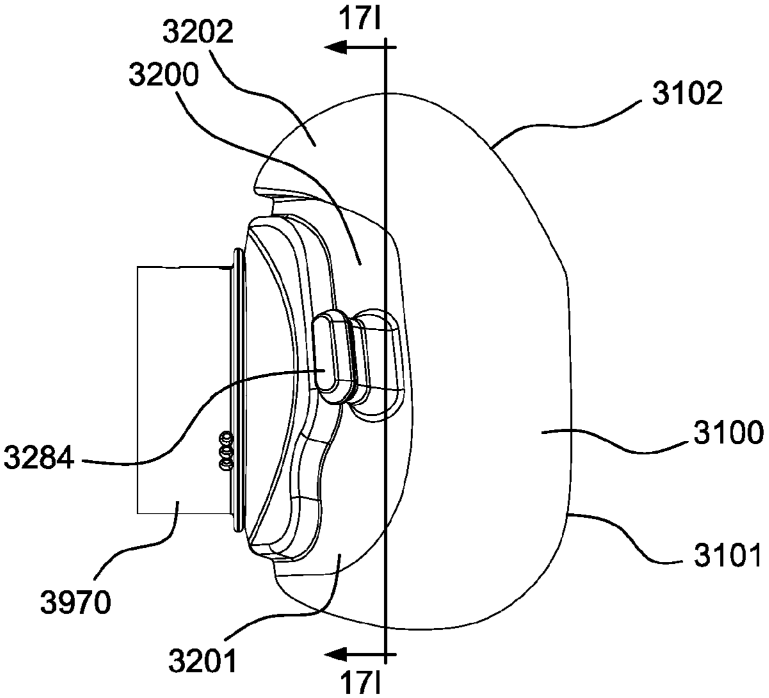

FIG. 17C shows a lateral view of an HMX and a patient interface according to an example of the present technology.

Figure 17D:
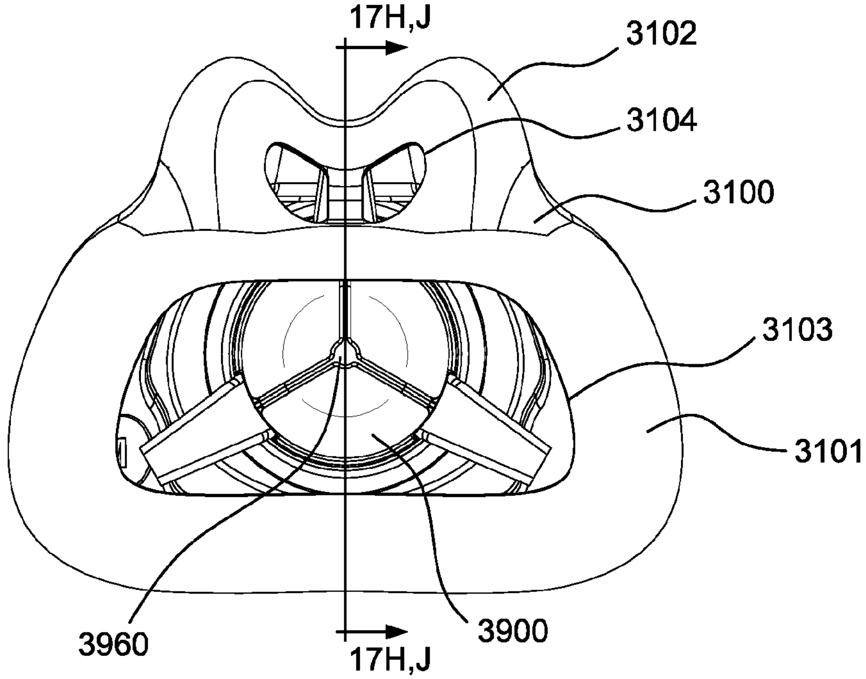

FIG. 17D shows a posterior view of an HMX and a patient interface according to an example of the present technology.

Figure 17E:
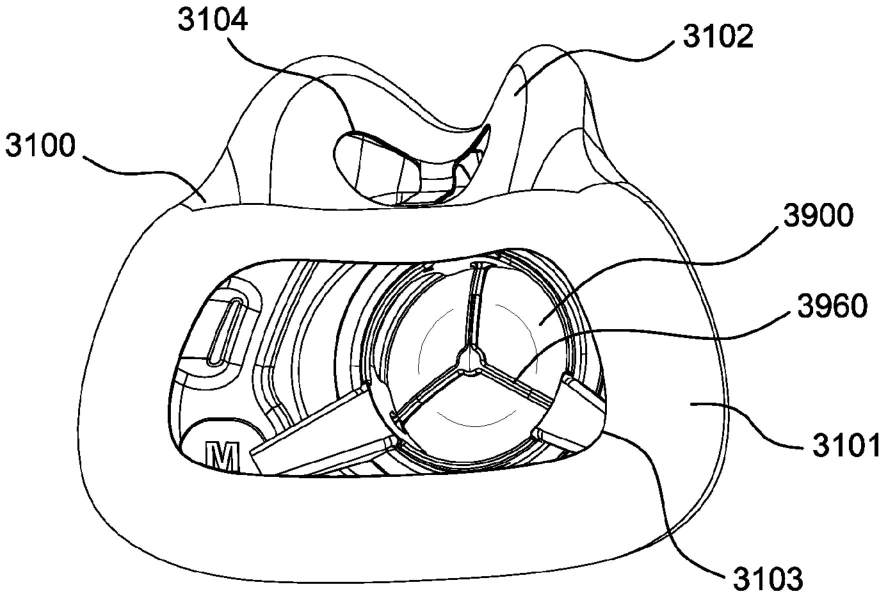

FIG. 17E shows another perspective view of an HMX and a patient interface according to an example of the present technology.

Figure 17F:
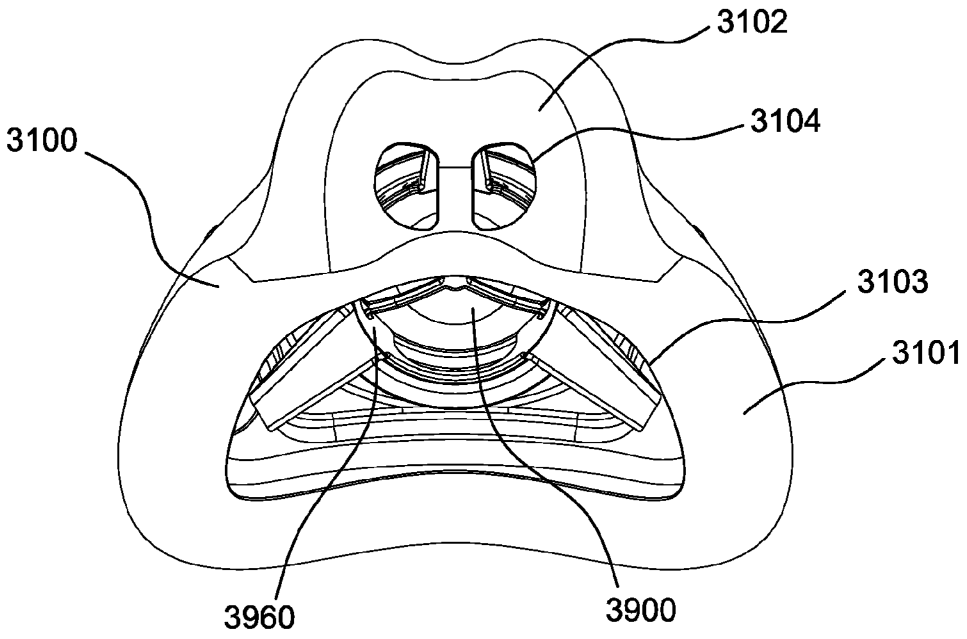

FIG. 17F shows a superior view of an HMX and a patient interface according to an example of the present technology.

Figure 17G:
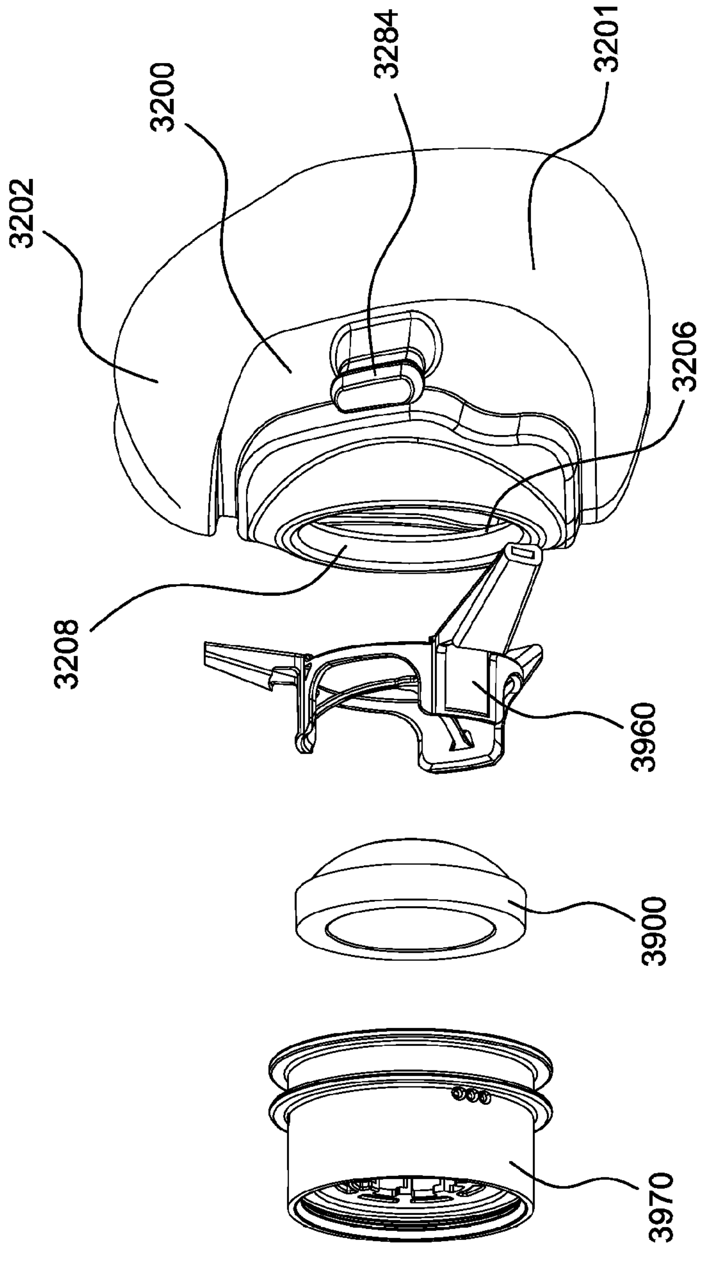

FIG. 17G shows an exploded view of an HMX and a patient interface according to an example of the present technology.

Figure 17H:
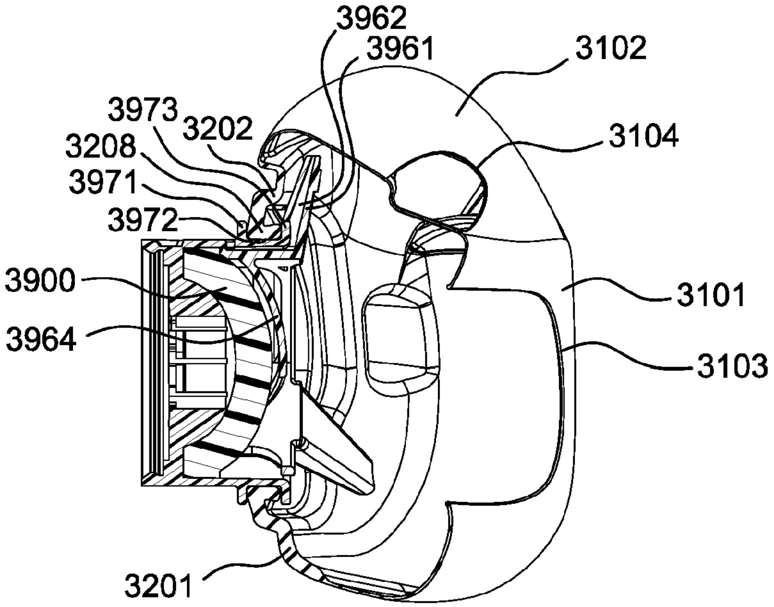

FIG. 17H shows a cross-sectional view of an HMX and a patient interface according to an example of the present technology taken through line 17H, J-17H, J of FIG. 17D.

Figure 17I:
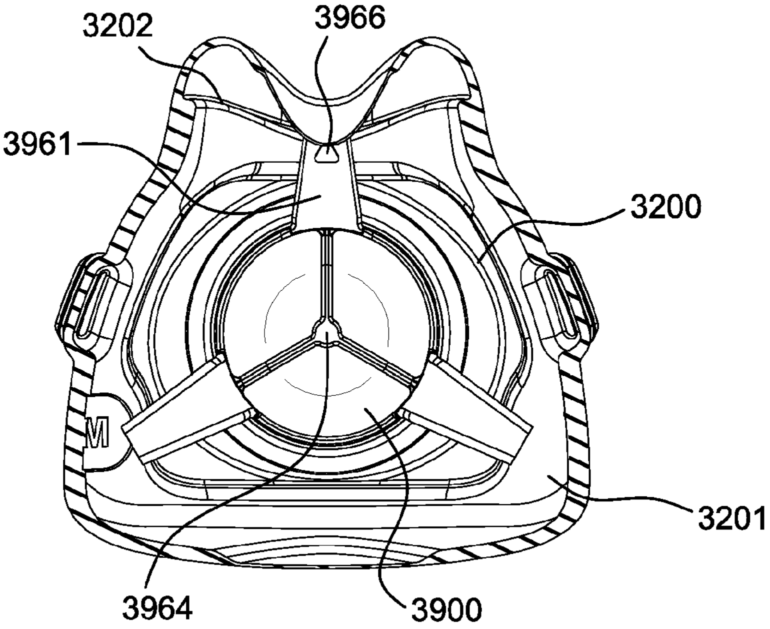

FIG. 17I shows a cross-sectional view of an HMX and a patient interface according to an example of the present technology taken through line 17I-17I of FIG. 17C.

Figure 17J:
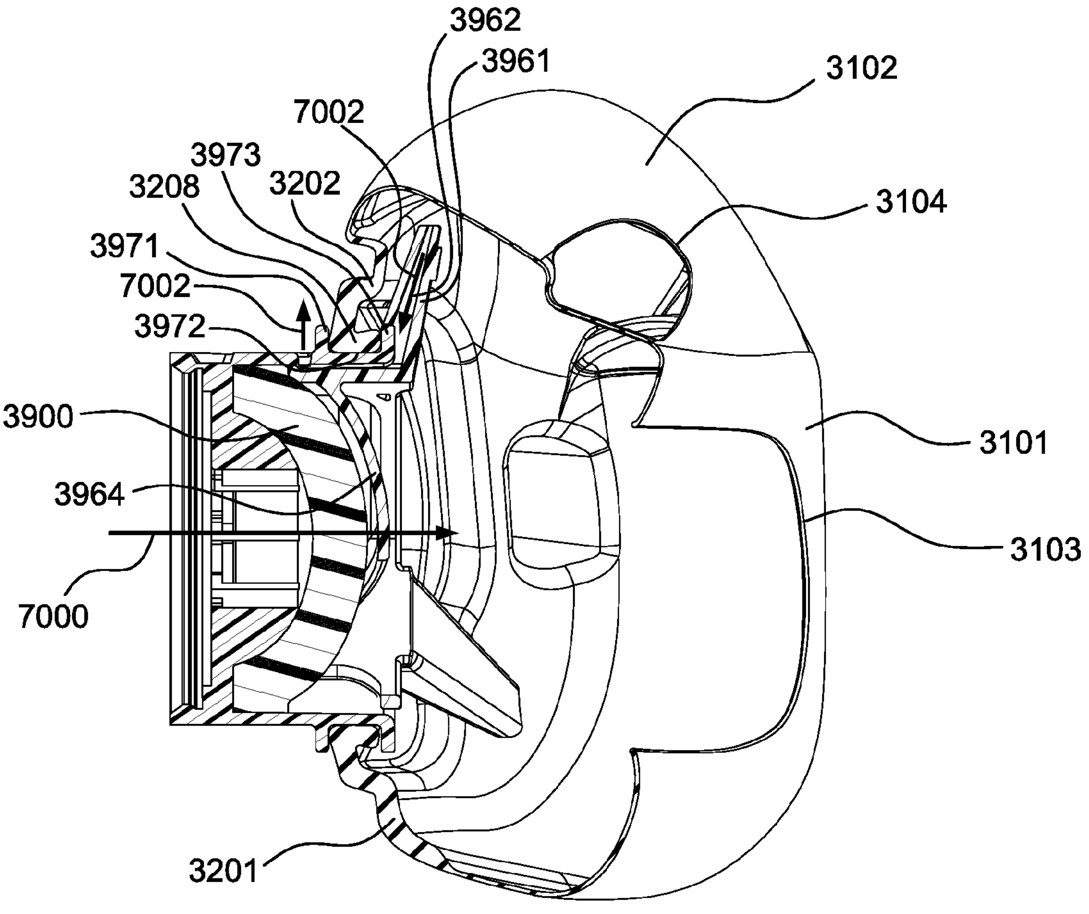

FIG. 17J shows a cross-sectional view of an HMX and a patient interface according to an example of the present technology taken through line 17H, J-17H, J of FIG. 17D.

Figure 18A:
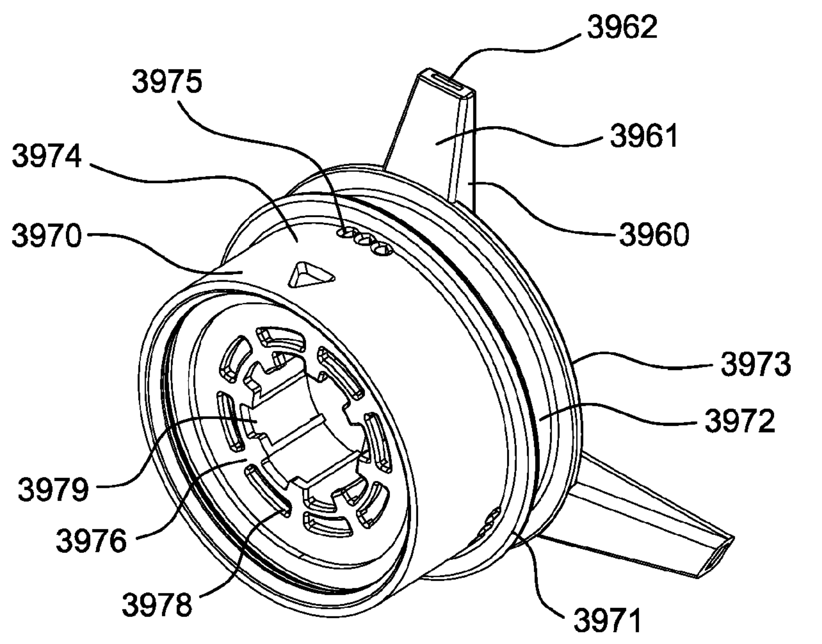

FIG. 18A shows a perspective view of a vent and conduit connector assembly and an HMX material according to an example of the present technology.

Figure 18B:
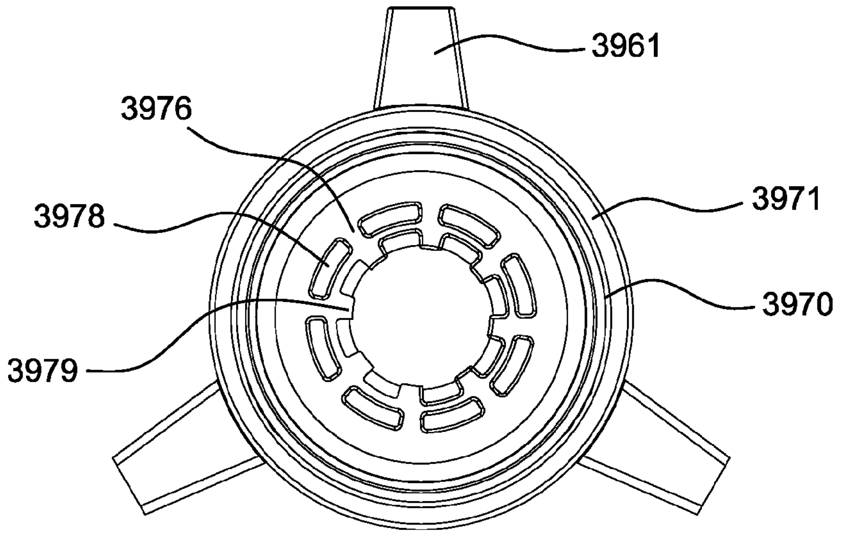

FIG. 18B shows an anterior view of a vent and conduit connector assembly and an HMX material according to an example of the present technology.

Figure 18C:
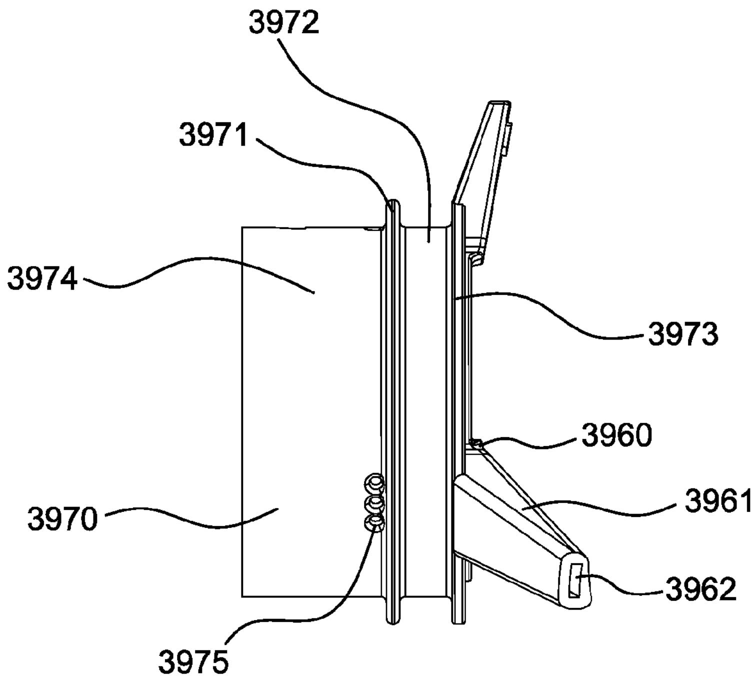

FIG. 18C shows a lateral view of a vent and conduit connector assembly and an HMX material according to an example of the present technology.

Figure 18D:
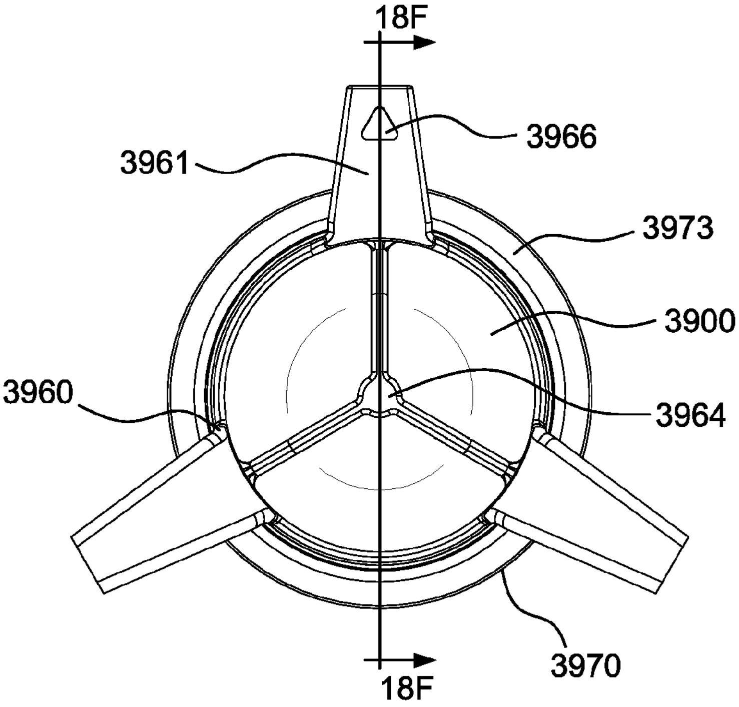

FIG. 18D shows a posterior view of a vent and conduit connector assembly and an HMX material according to an example of the present technology.

Figure 18E:
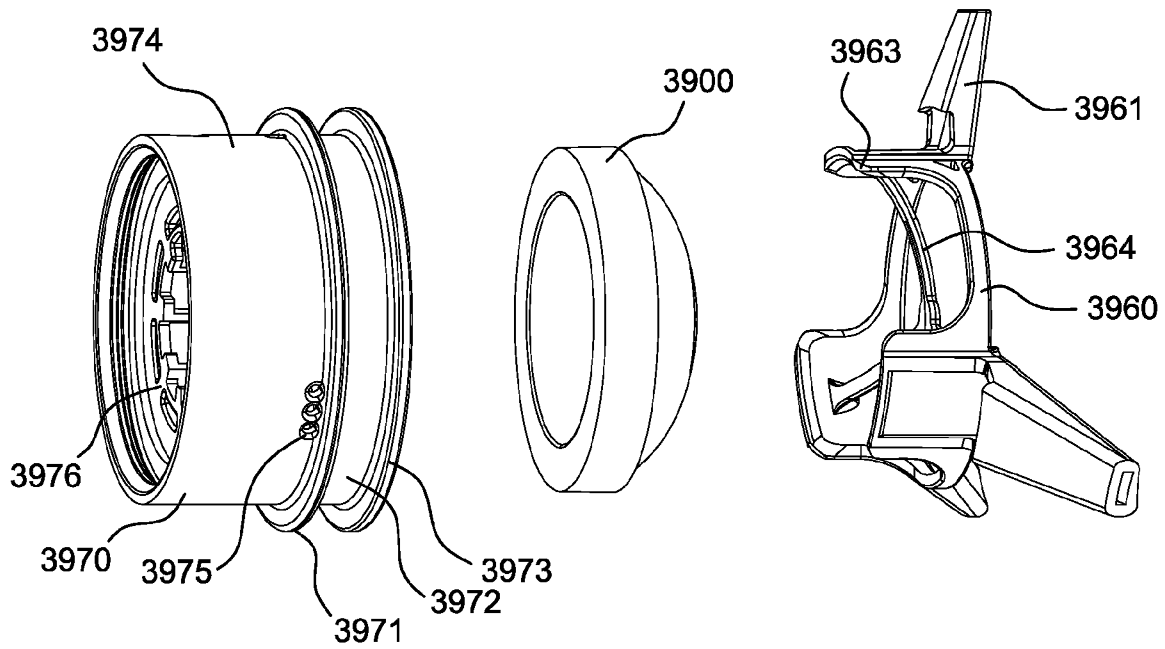

FIG. 18E shows an exploded view of a vent and conduit connector assembly and an HMX material according to an example of the present technology.

Figure 18F:
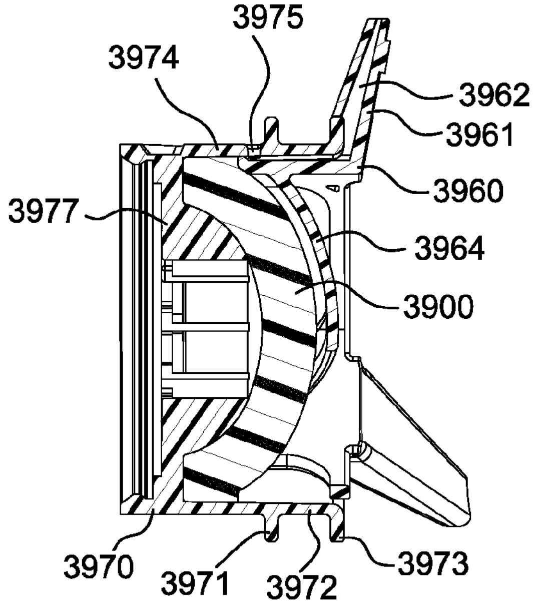

FIG. 18F shows a cross-sectional view of a vent and conduit connector assembly and an HMX material according to an example of the present technology taken through line 18F-18F of FIG. 18D.

Figure 19A:
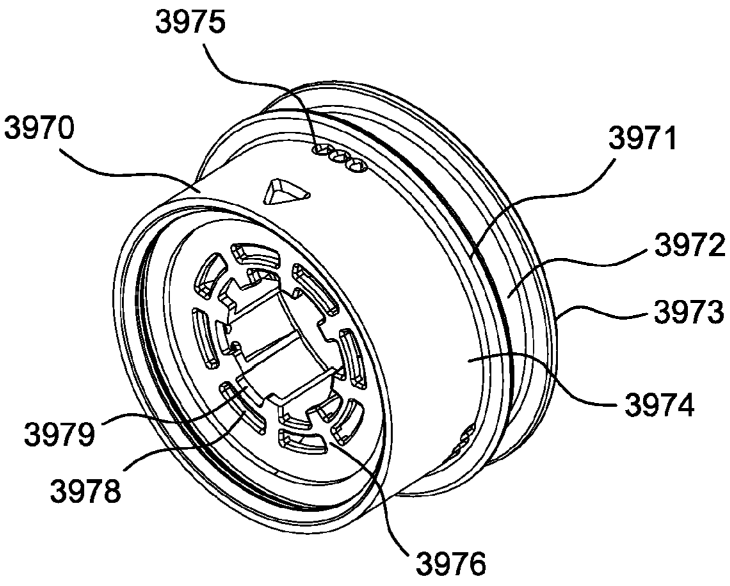

FIG. 19A shows a perspective view of an anterior HMX frame according to an example of the present technology.

Figure 19B:
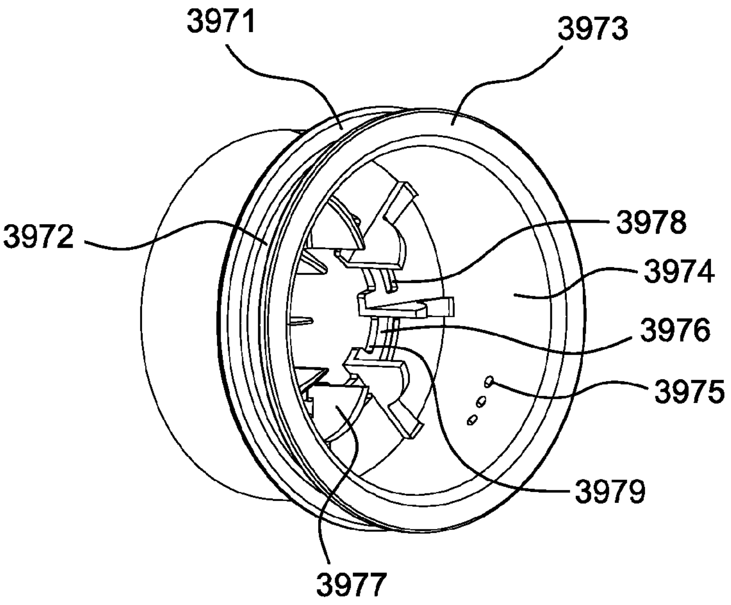

FIG. 19B shows another perspective view of an HMX frame according to an example of the present technology.

Figure 19C:
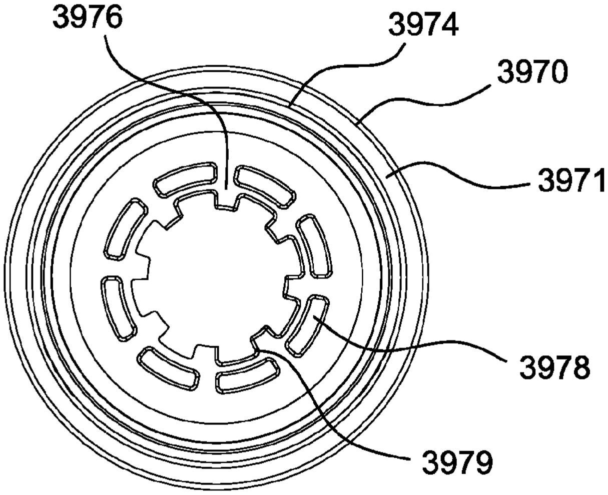

FIG. 19C shows an anterior view of an anterior HMX frame according to an example of the present technology.

Figure 19D:
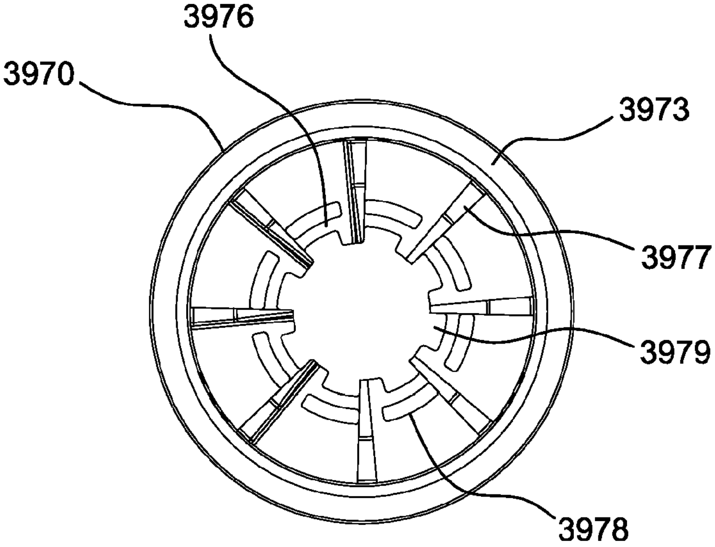

FIG. 19D shows a posterior view of an HMX frame according to an example of the present technology.

Figure 20A:
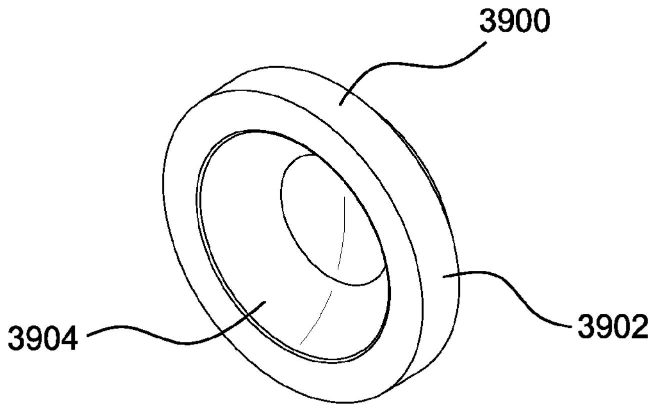

FIG. 20A shows a perspective view of an HMX material according to an example of the present technology.

Figure 20B:
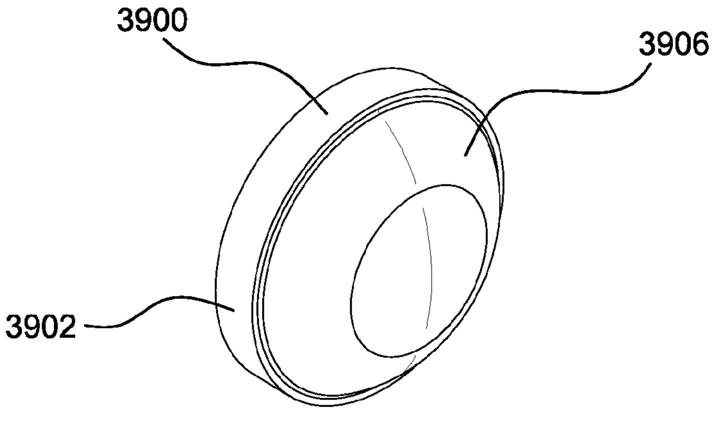

FIG. 20B shows another perspective view of an HMX material according to an example of the present technology.

Figure 21A:
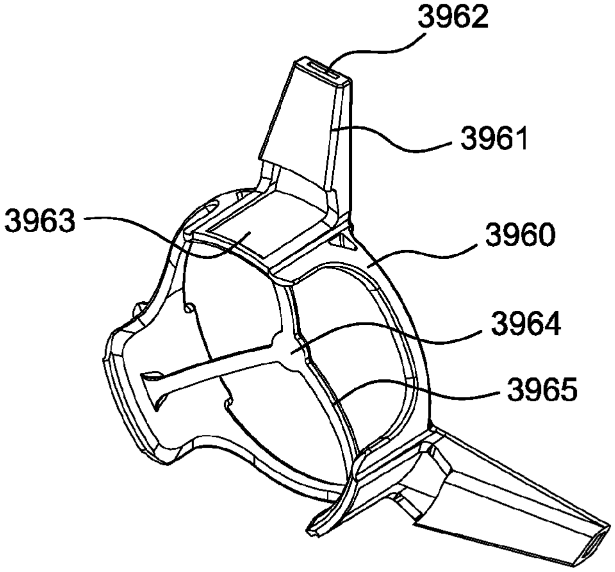

FIG. 21A shows a perspective view of a posterior HMX frame according to an example of the present technology.

Figure 21B:
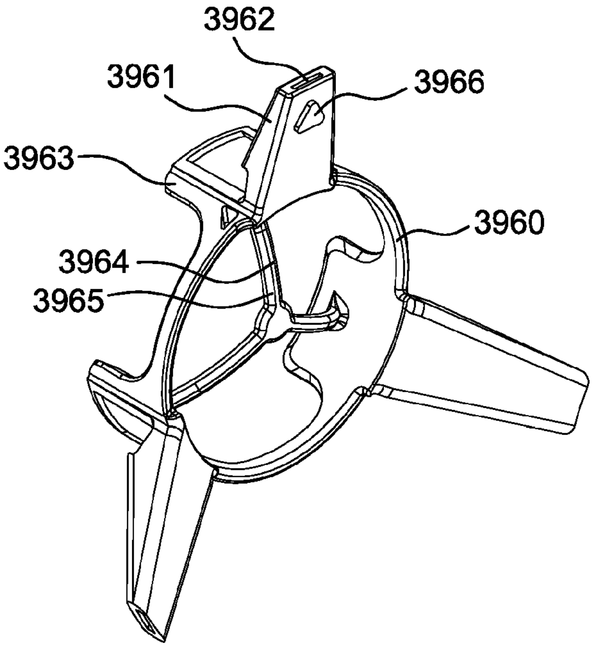

FIG. 21B shows another perspective view of a posterior HMX frame according to an example of the present technology.

Figure 22A:
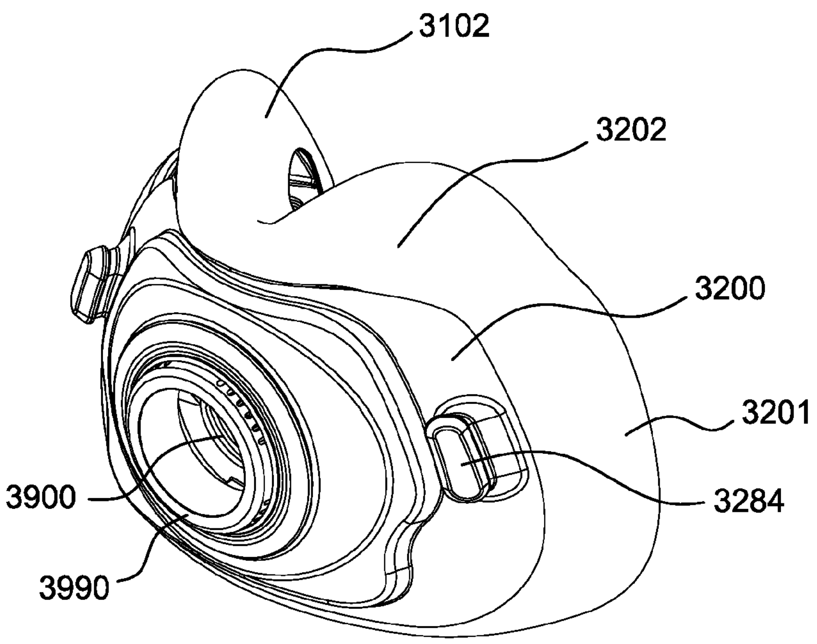

FIG. 22A shows a perspective view of an HMX and a patient interface according to an example of the present technology.

Figure 22B:
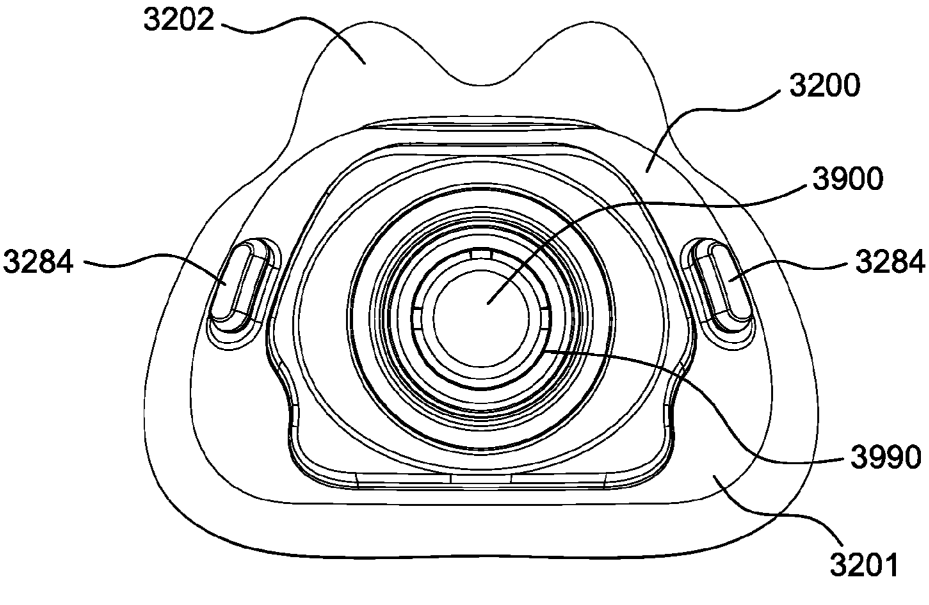

FIG. 22B shows an anterior view of an HMX and a patient interface according to an example of the present technology.

Figure 22C:
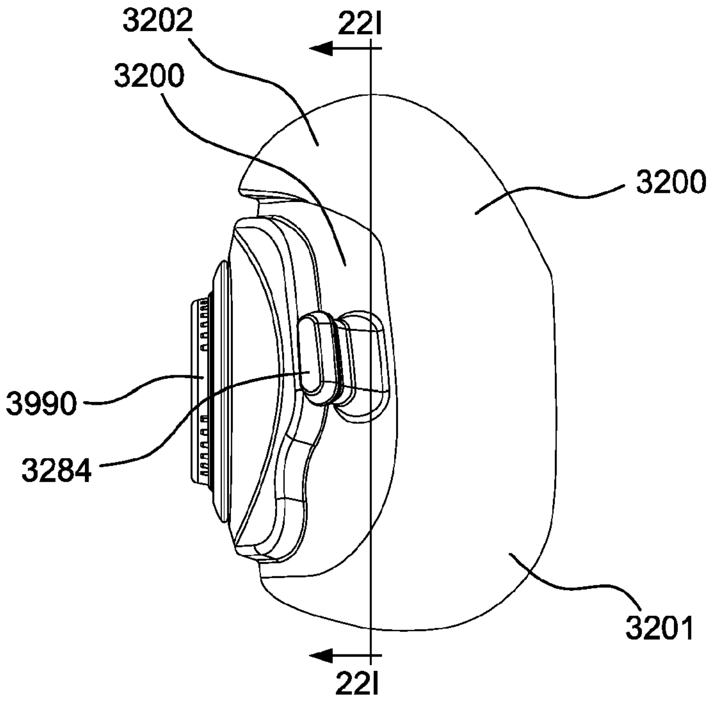

FIG. 22C shows a lateral view of an HMX and a patient interface according to an example of the present technology.

Figure 22D:
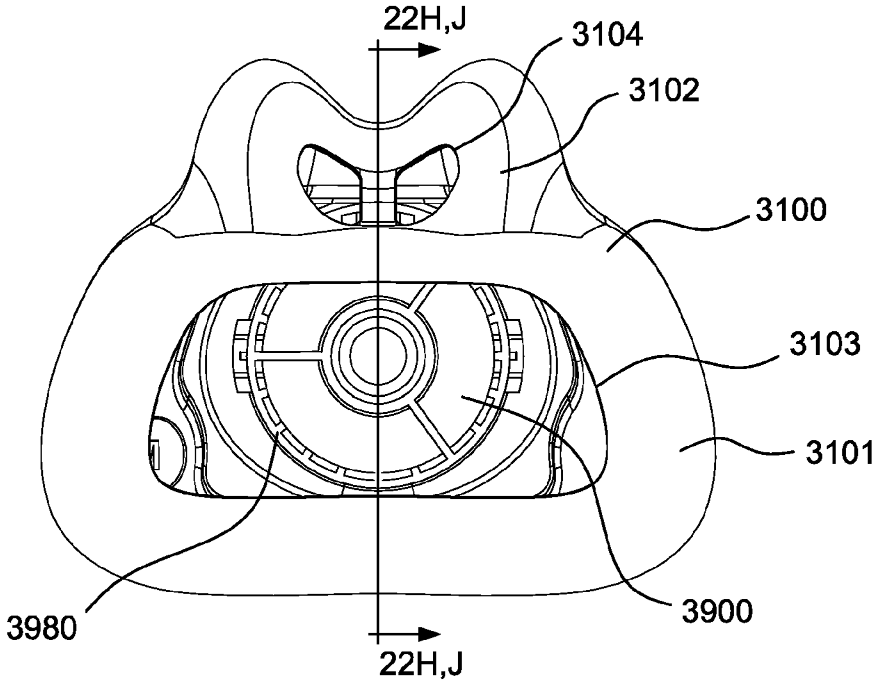

FIG. 22D shows a posterior view of an HMX and a patient interface according to an example of the present technology.

Figure 22E:
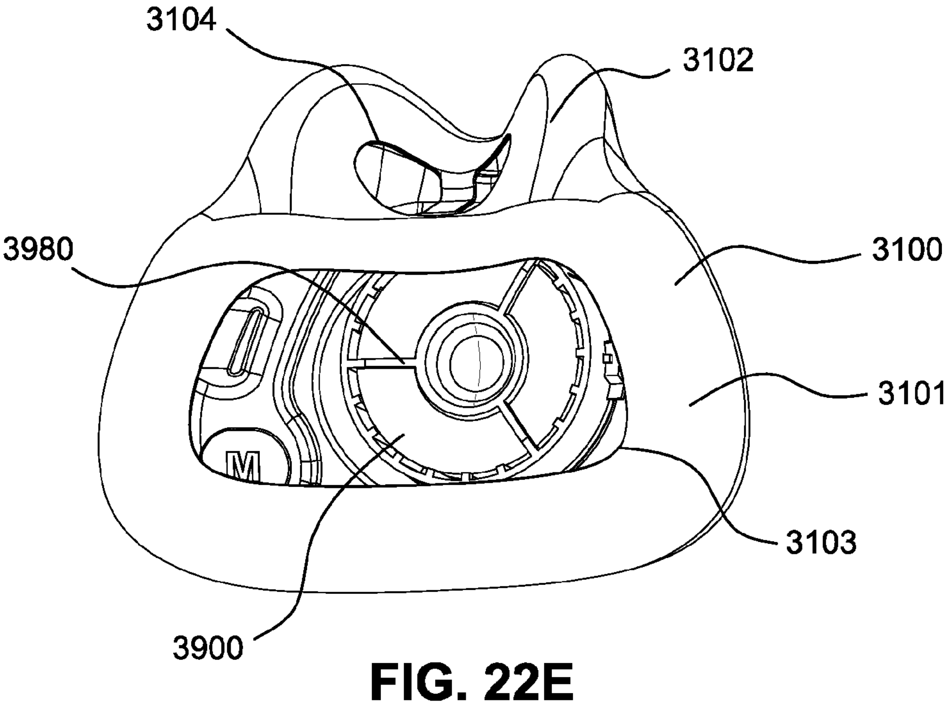

FIG. 22E shows another perspective view of an HMX and a patient interface according to an example of the present technology.

Figure 22F:
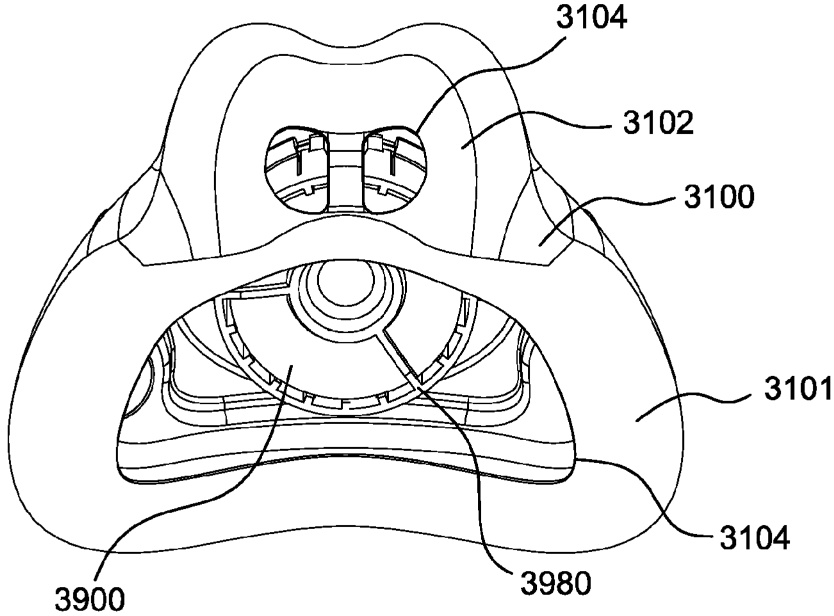

FIG. 22F shows a superior view of an HMX and a patient interface according to an example of the present technology.

Figure 22G:
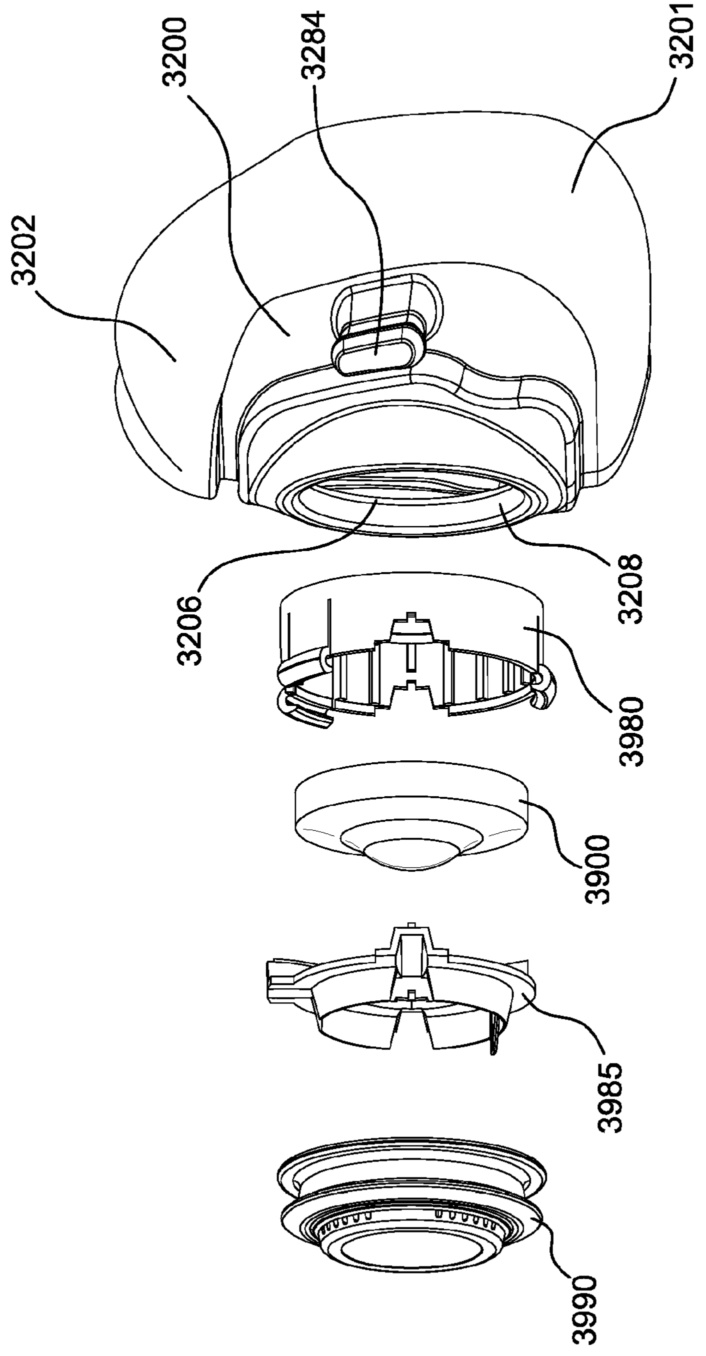

FIG. 22G shows an exploded view of an HMX and a patient interface according to an example of the present technology.

Figure 22H:
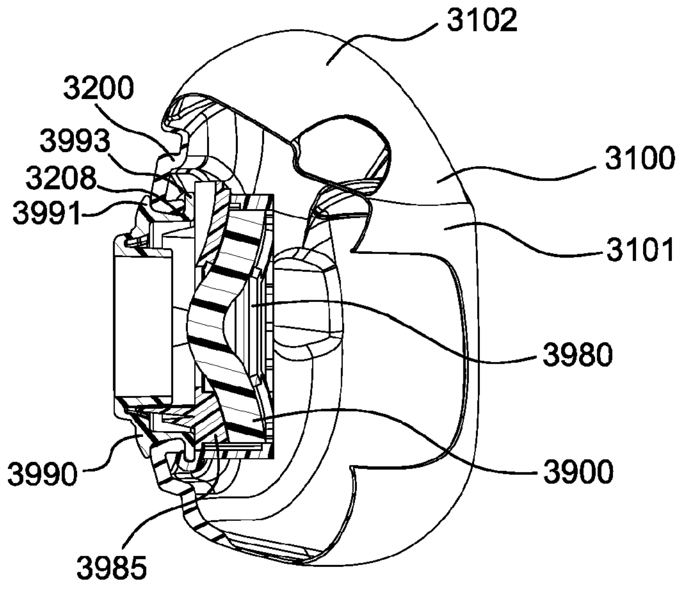

FIG. 22H shows a cross-sectional view of an HMX and a patient interface according to an example of the present technology taken through line 22H, J-22H, J of FIG. 22D.

Figure 22I:
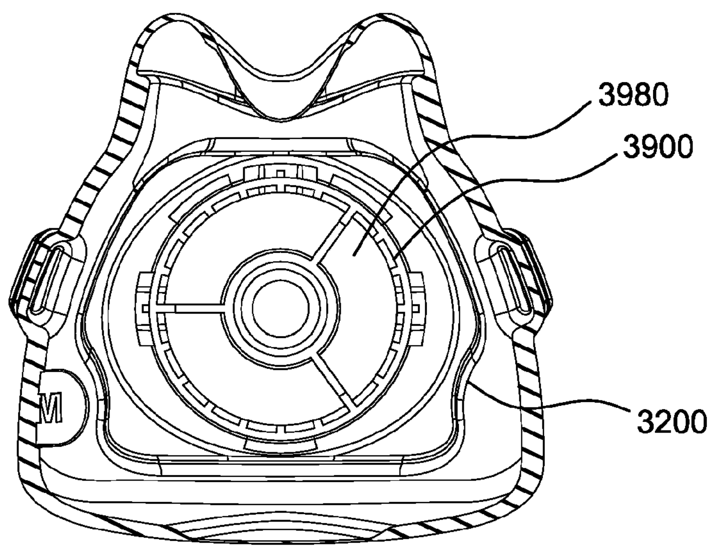

FIG. 22I shows a cross-sectional view of an HMX and a patient interface according to an example of the present technology taken through line 22I-22I of FIG. 22C.

Figure 22J:
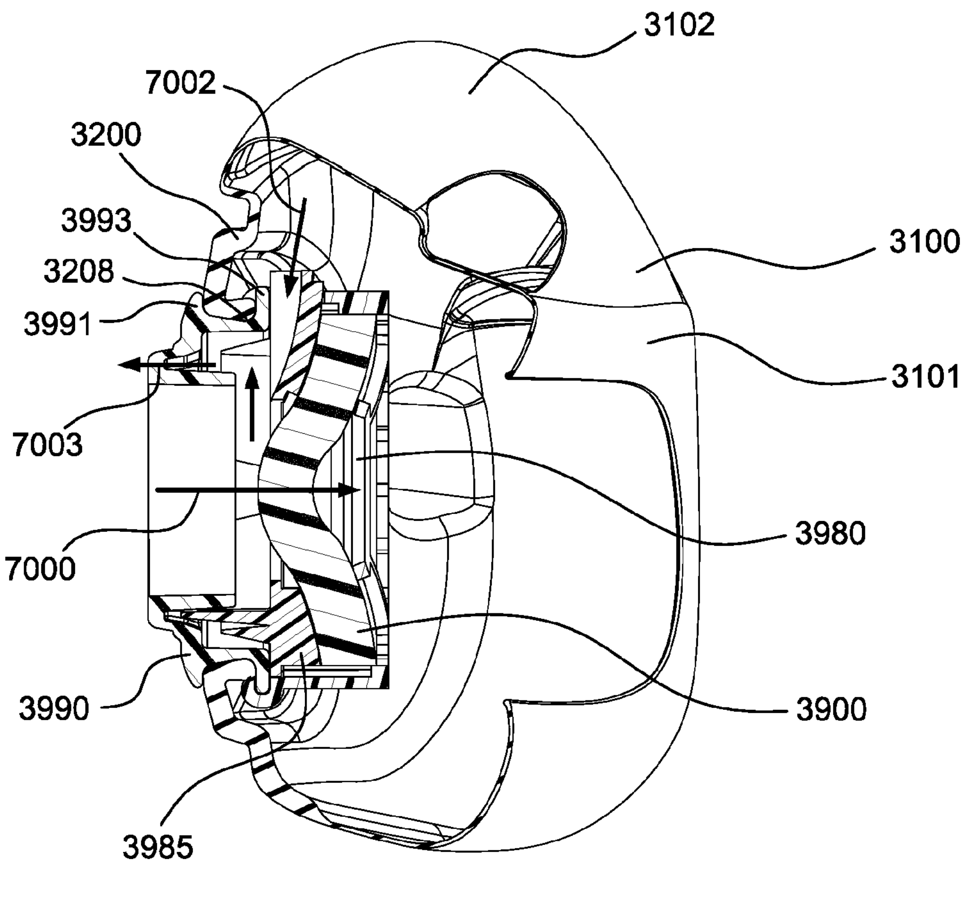

FIG. 22J shows a cross-sectional view of an HMX and a patient interface according to an example of the present technology taken through line 22H, J-22H, J of FIG. 22D.

Figure 23A:
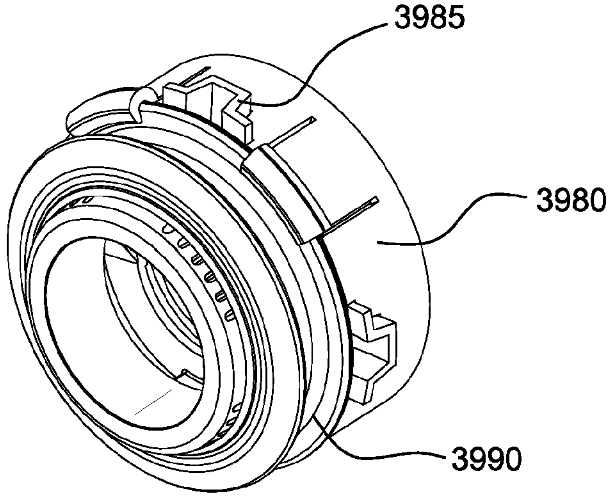

FIG. 23A shows a perspective view of a vent and frame assembly and an HMX material according to an example of the present technology.

Figure 23B:
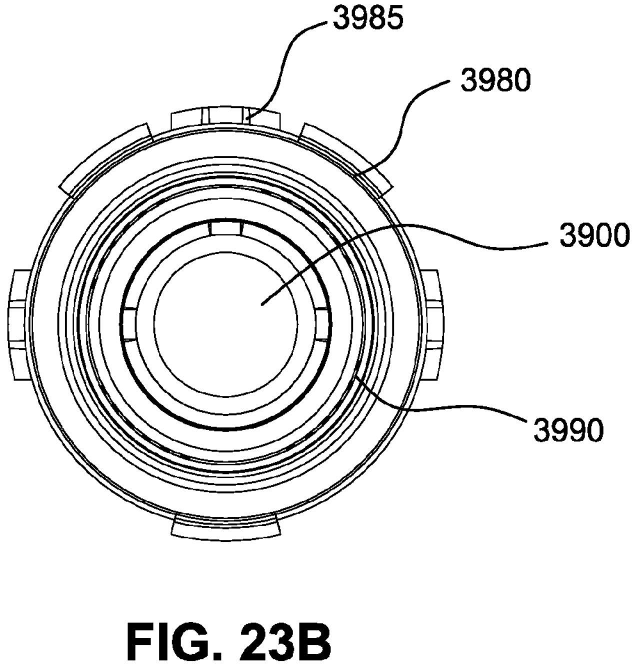

FIG. 23B shows an anterior view of a vent and frame assembly and an HMX material according to an example of the present technology.

Figure 23C:
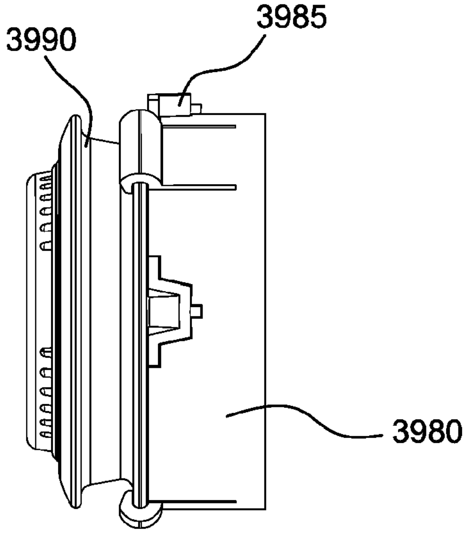

FIG. 23C shows a lateral view of a vent and frame assembly and an HMX material according to an example of the present technology.

Figure 23D:
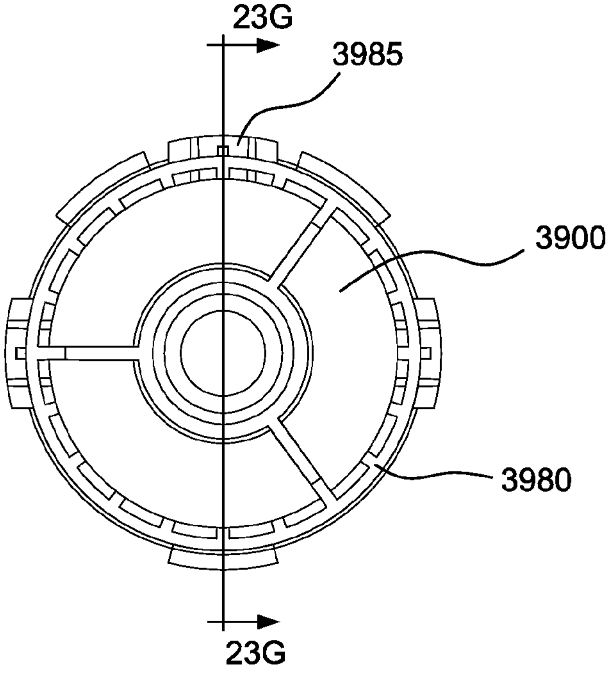

FIG. 23D shows a posterior view of a vent and frame assembly and an HMX material according to an example of the present technology.

Figure 23E:
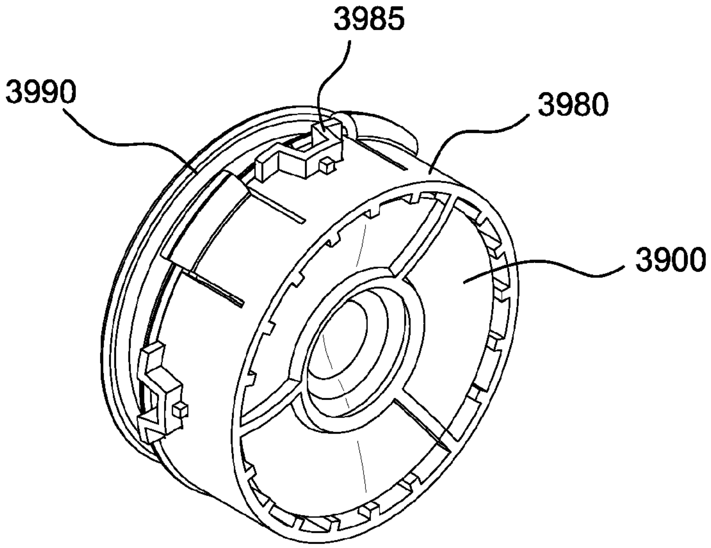

FIG. 23E shows a perspective view of a vent and frame assembly and an HMX material according to an example of the present technology.

Figure 23F:
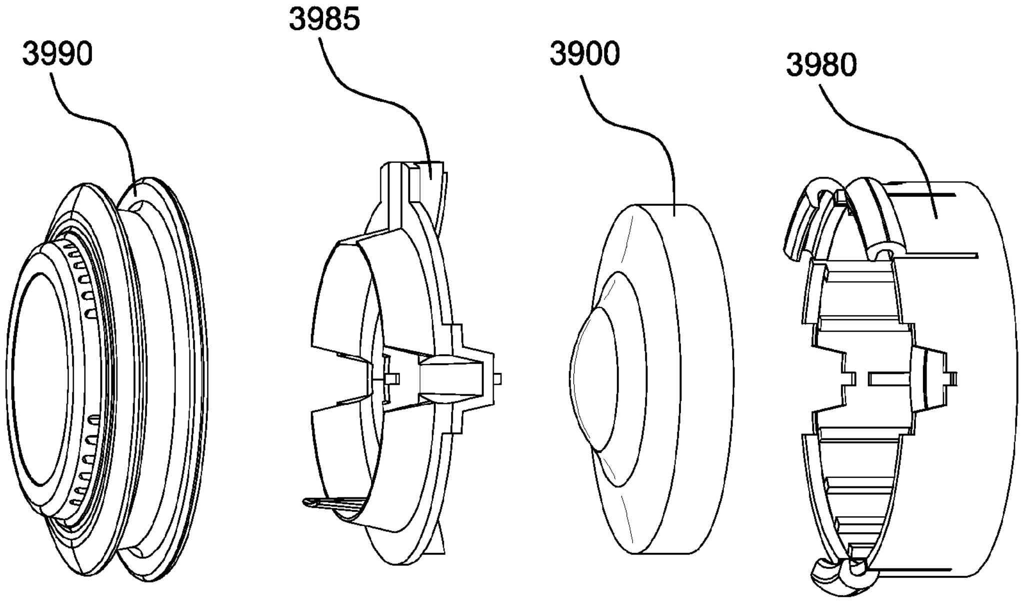

FIG. 23F shows an exploded view of a vent and frame assembly and an HMX material according to an example of the present technology.

Figure 23G:
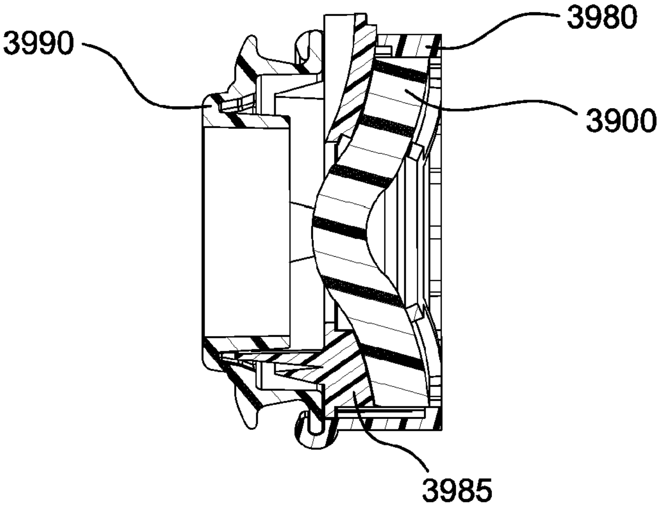

FIG. 23G shows a cross-sectional view of a vent and frame assembly and an HMX material according to an example of the present technology taken through line 23G-23G of FIG. 23D.

Figure 24A:
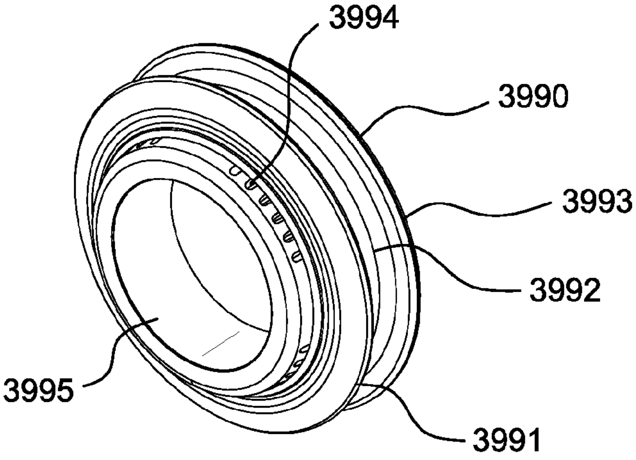

FIG. 24A shows a perspective view of an anterior HMX frame according to an example of the present technology.

Figure 24B:
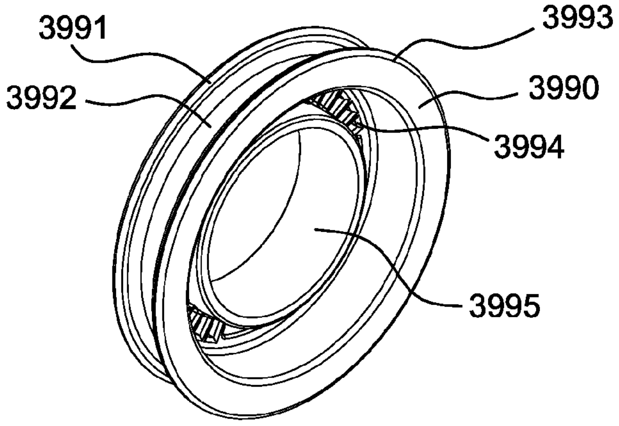

FIG. 24B shows another perspective view of an anterior HMX frame according to an example of the present technology.

Figure 24C:
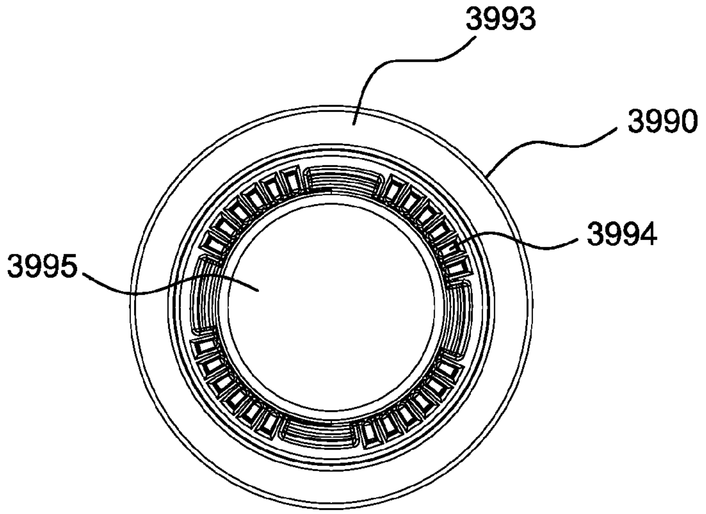

FIG. 24C shows a posterior view of an anterior HMX frame according to an example of the present technology.

Figure 25A:
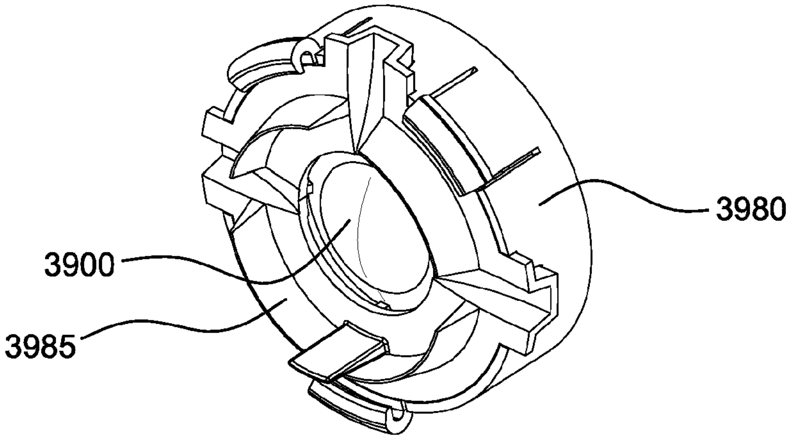

FIG. 25A shows a perspective view of a bypass frame, an HMX material, and a posterior HMX frame according to an example of the present technology.

Figure 25B:
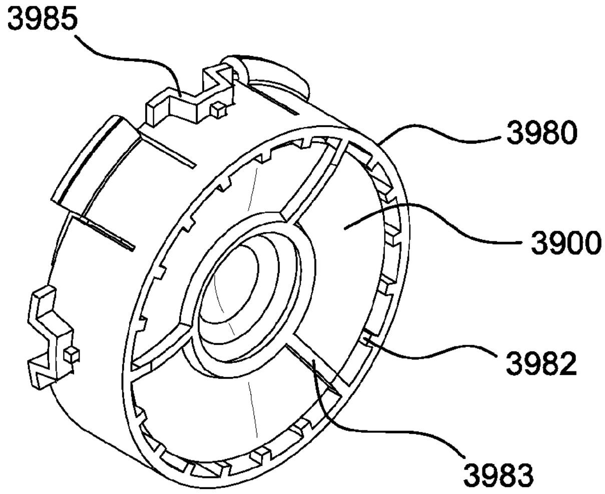

FIG. 25B shows another perspective view of a bypass frame, an HMX material, and a posterior HMX frame according to an example of the present technology.

Figure 25C:
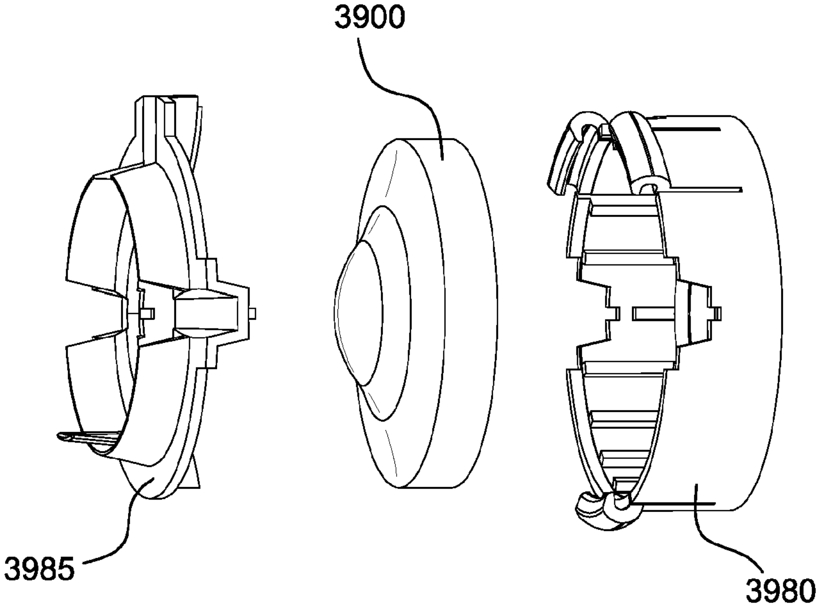

FIG. 25C shows an exploded view of a bypass frame, an HMX material, and a posterior HMX frame according to an example of the present technology.

Figure 26A:
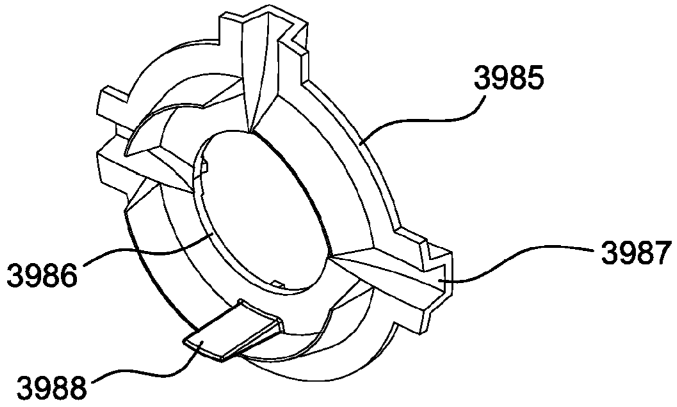

FIG. 26A shows a perspective view of a bypass frame according to an example of the present technology.

Figure 26B:
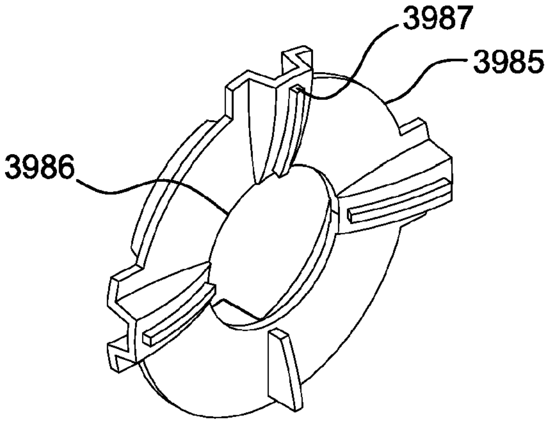

FIG. 26B shows another perspective view of a bypass frame according to an example of the present technology.

Figure 27A:
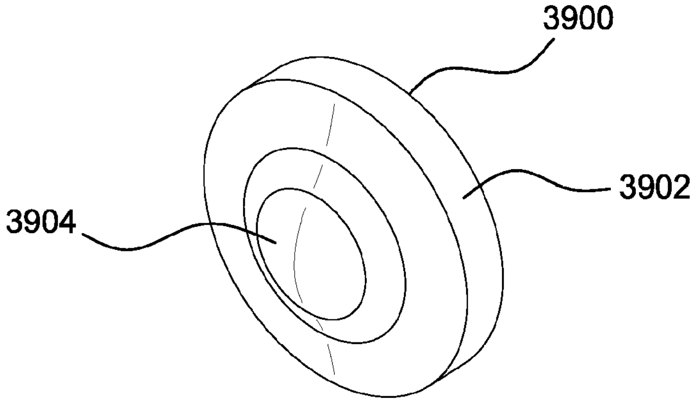

FIG. 27A shows a perspective view of an HMX material according to an example of the present technology.

Figure 27B:
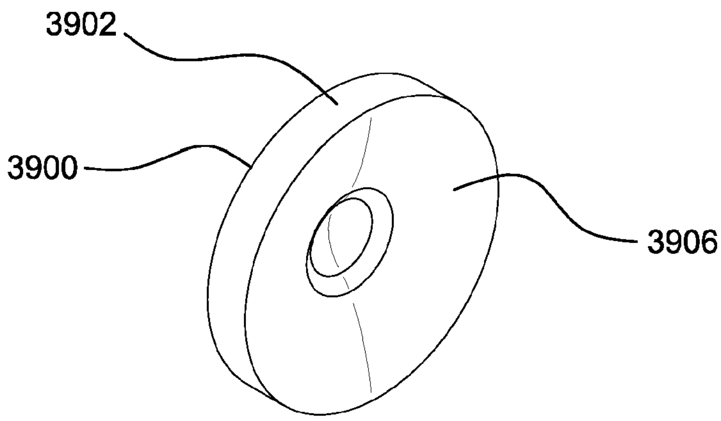

FIG. 27B shows another perspective view of an HMX material according to an example of the present technology.

Figure 28A:
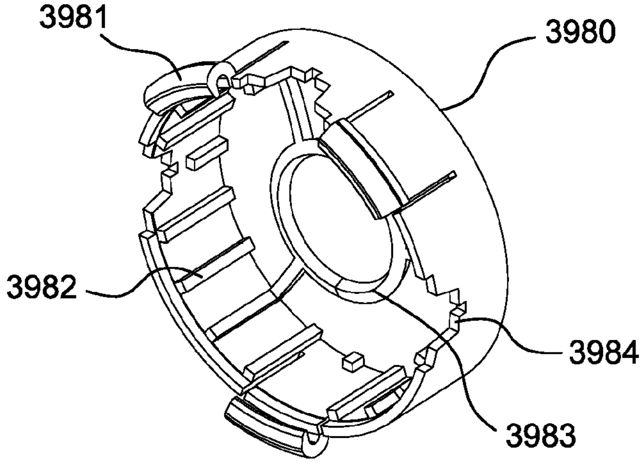

FIG. 28A shows a perspective view of a posterior HMX frame according to an example of the present technology.

Figure 28B:
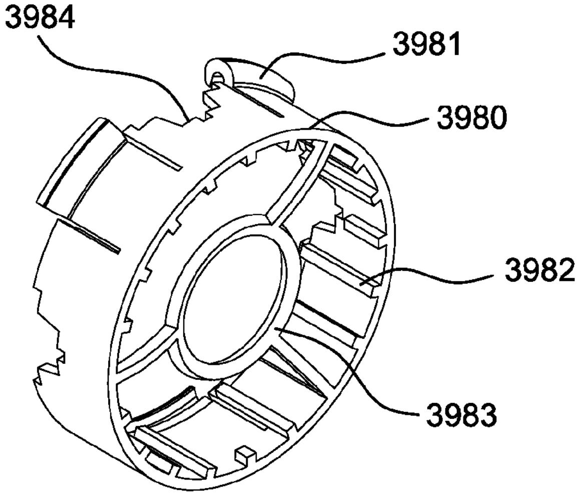

FIG. 28B shows another perspective view of a posterior HMX frame according to an example of the present technology.

Figure 29A:
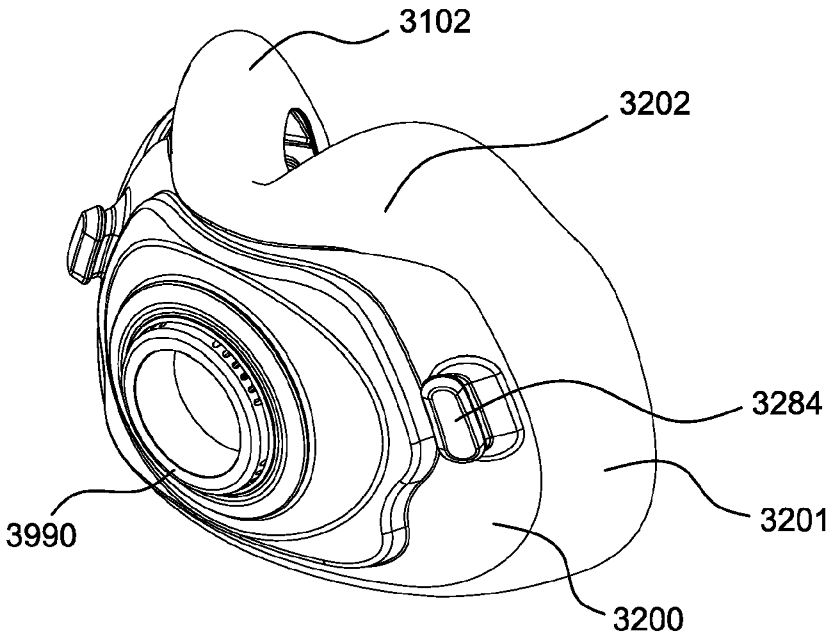

FIG. 29A shows a perspective view of an HMX and a patient interface according to an example of the present technology.

Figure 29B:
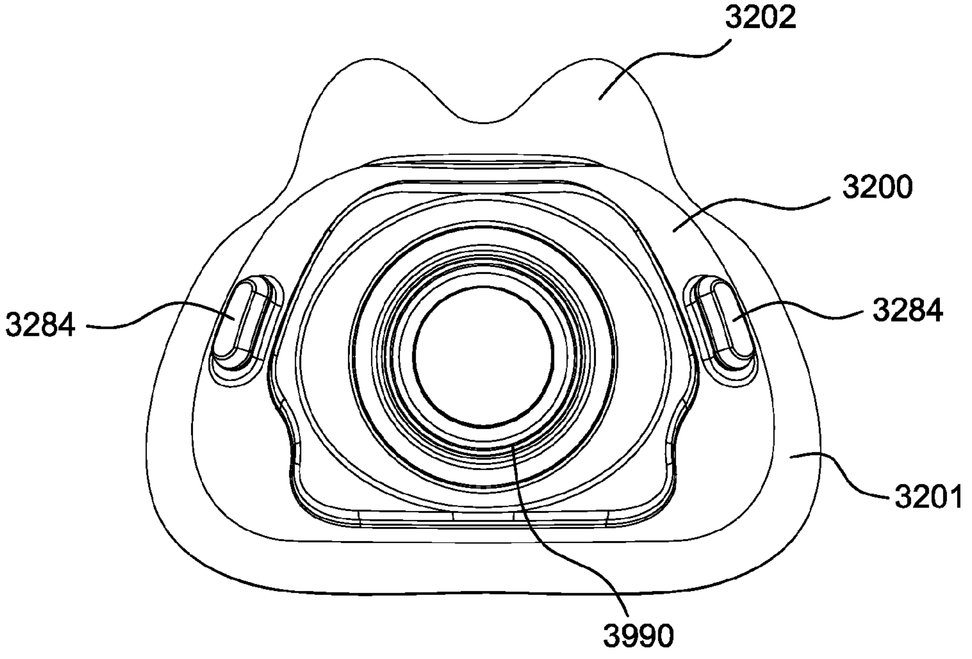

FIG. 29B shows an anterior view of an HMX and a patient interface according to an example of the present technology.

Figure 29C:
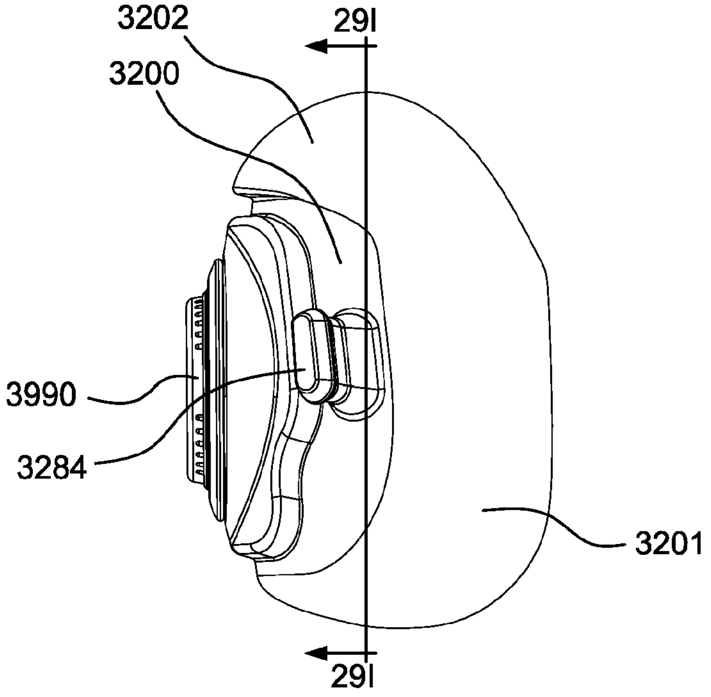

FIG. 29C shows a lateral view of an HMX and a patient interface according to an example of the present technology.

Figure 29D:
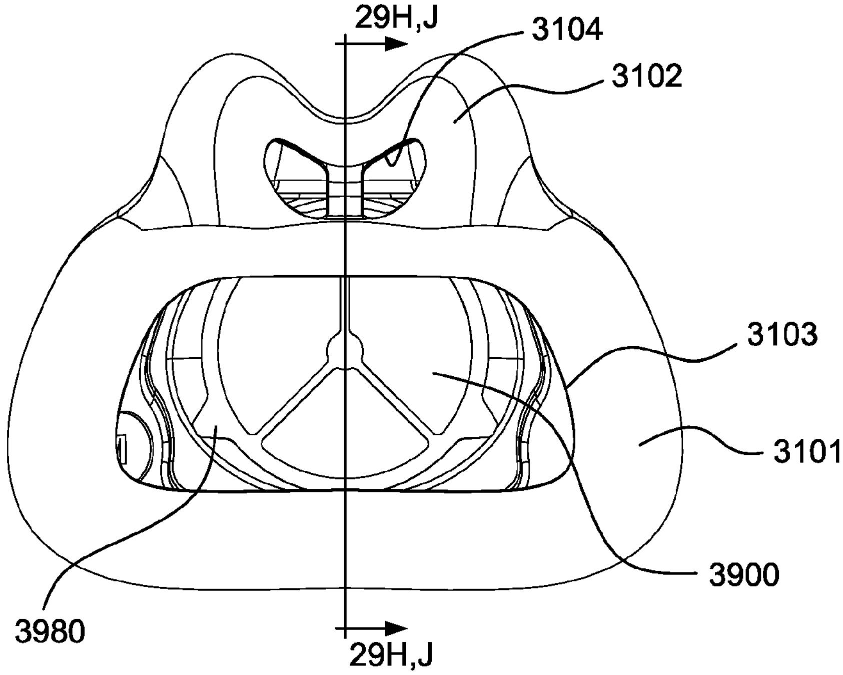

FIG. 29D shows a posterior view of an HMX and a patient interface according to an example of the present technology.

Figure 29E:
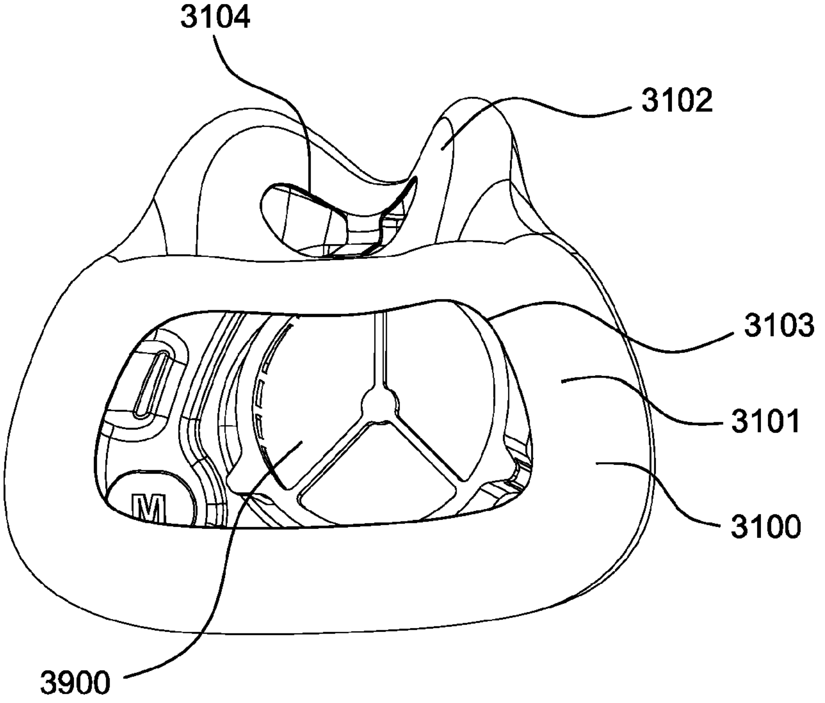

FIG. 29E shows another perspective view of an HMX and a patient interface according to an example of the present technology.

Figure 29F:
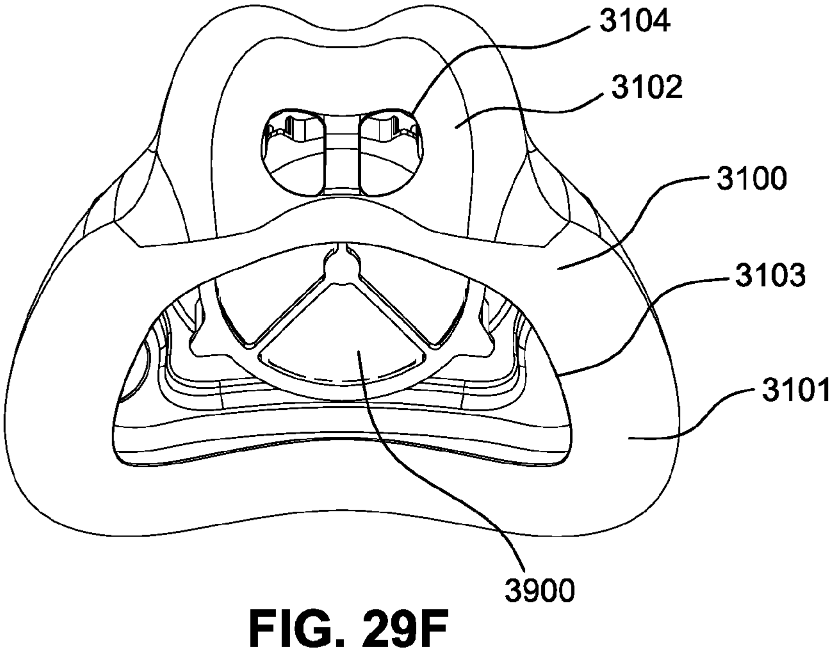

FIG. 29F shows a superior view of an HMX and a patient interface according to an example of the present technology.

Figure 29G:
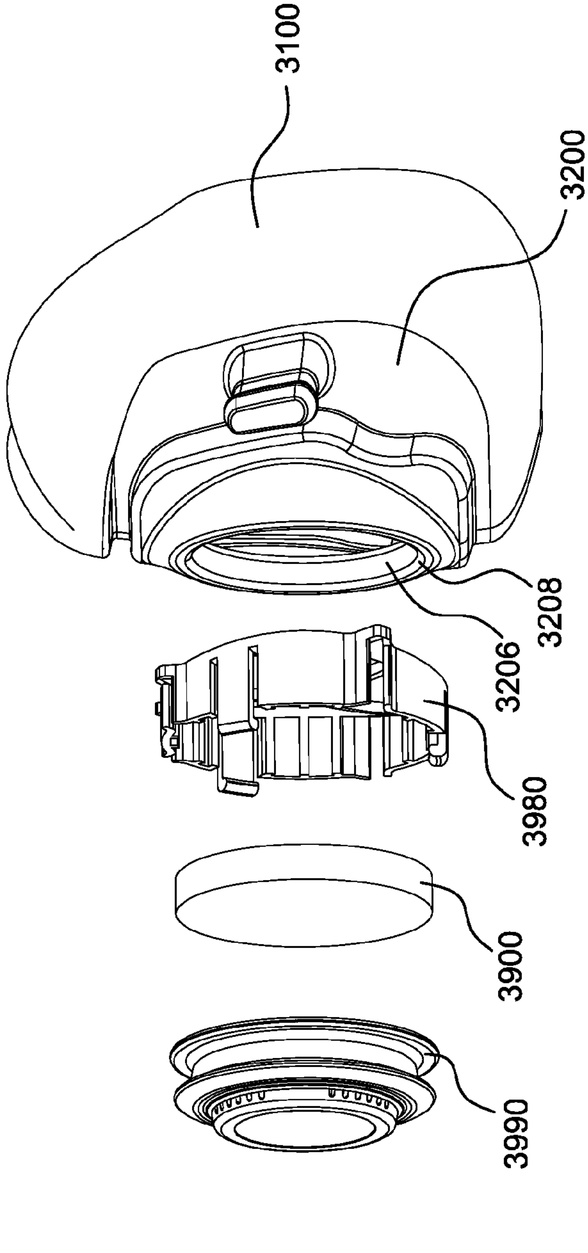

FIG. 29G shows an exploded view of an HMX and a patient interface according to an example of the present technology.

Figure 29H:
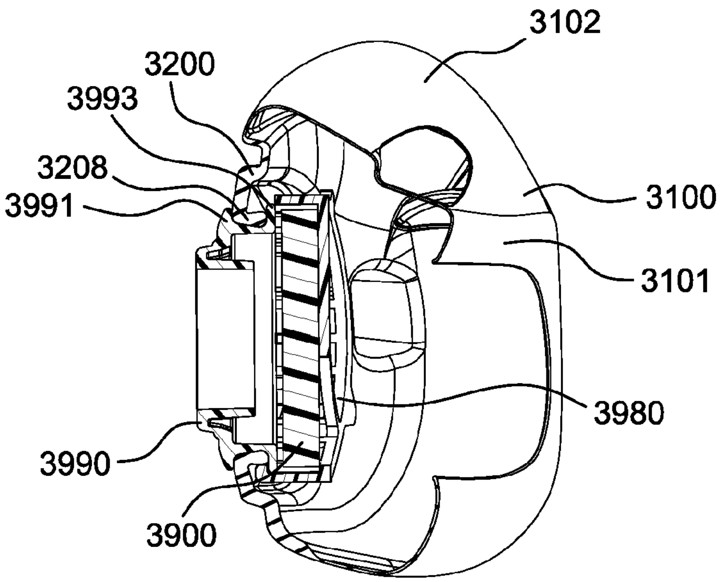

FIG. 29H shows a cross-sectional view of an HMX and a patient interface according to an example of the present technology taken through line 29H, J-29H, J of FIG. 29D.

Figure 29I:
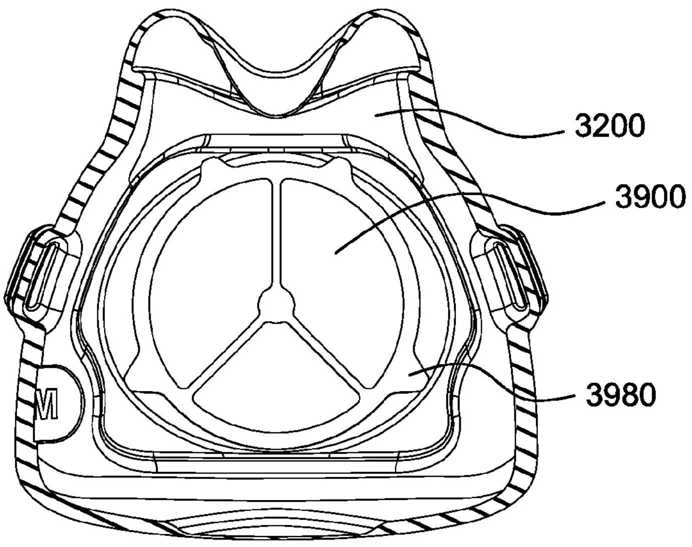

FIG. 29I shows a cross-sectional view of an HMX and a patient interface according to an example of the present technology taken through line 29I-29I of FIG. 29C.

Figure 29J:
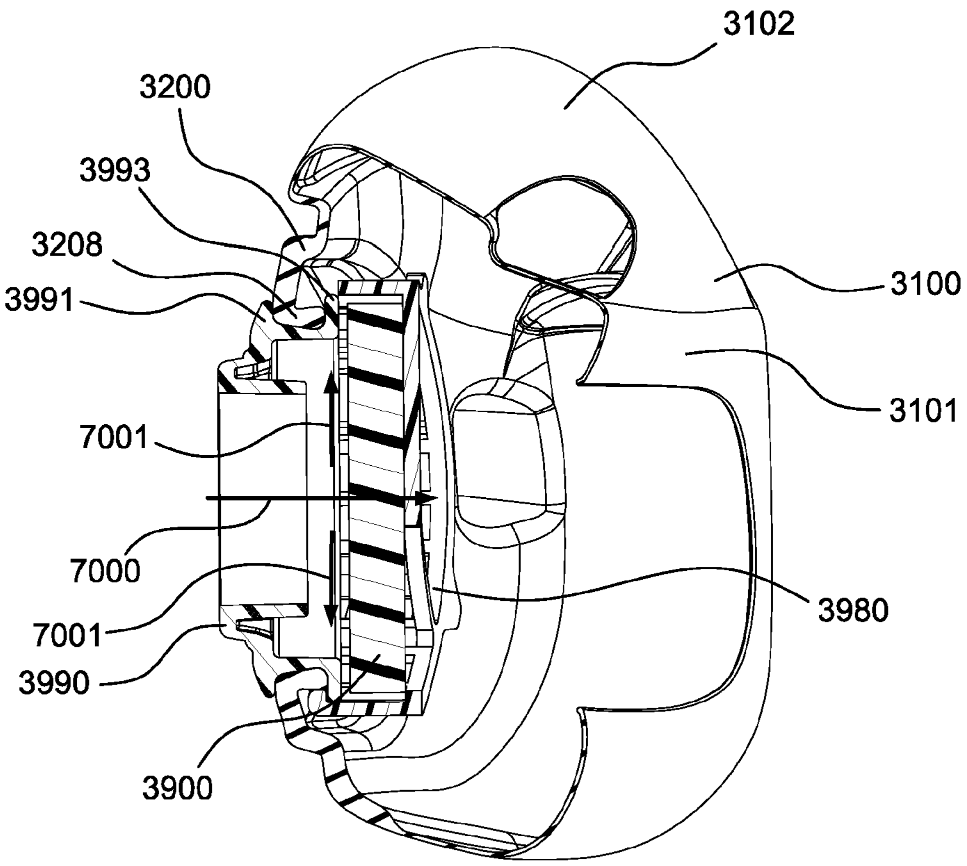

FIG. 29J shows a cross-sectional view of an HMX and a patient interface according to an example of the present technology taken through line 29H, J-29H, J of FIG. 29D.

Figure 30A:
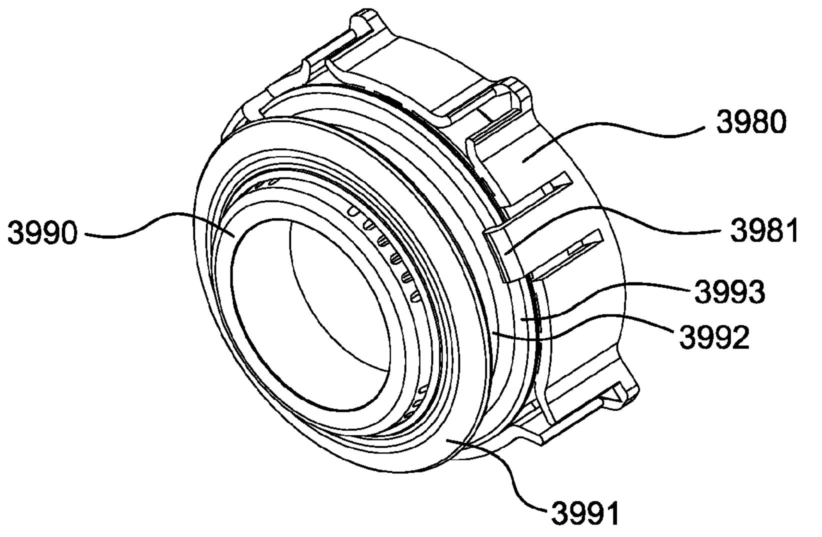

FIG. 30A shows a perspective view of a vent and frame assembly and an HMX material according to an example of the present technology.

Figure 30B:
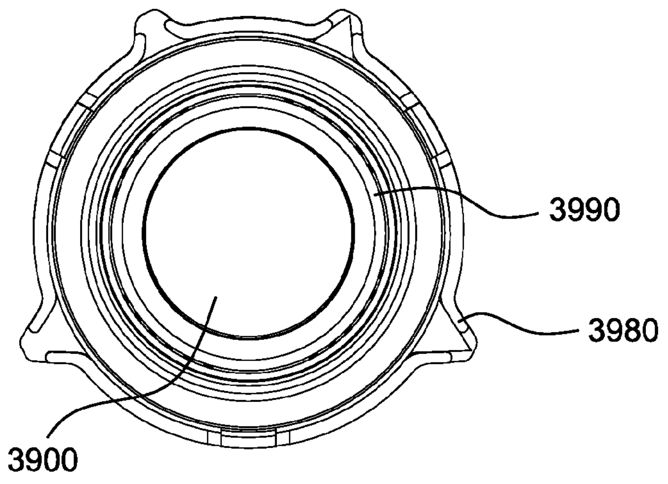

FIG. 30B shows an anterior view of a vent and frame assembly and an HMX material according to an example of the present technology.

Figure 30C:
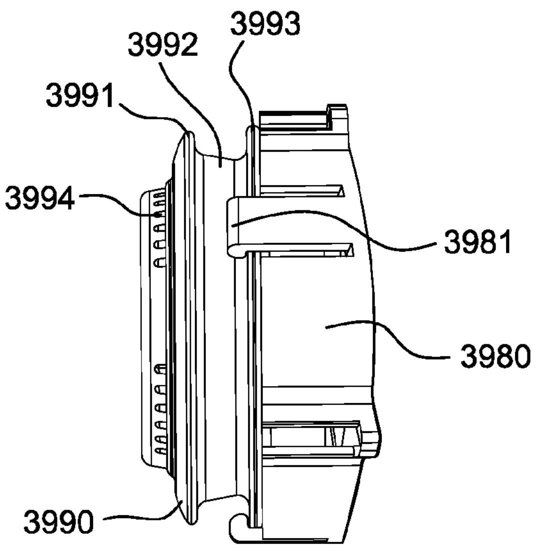

FIG. 30C shows a lateral view of a vent and frame assembly and an HMX material according to an example of the present technology.

Figure 30D:
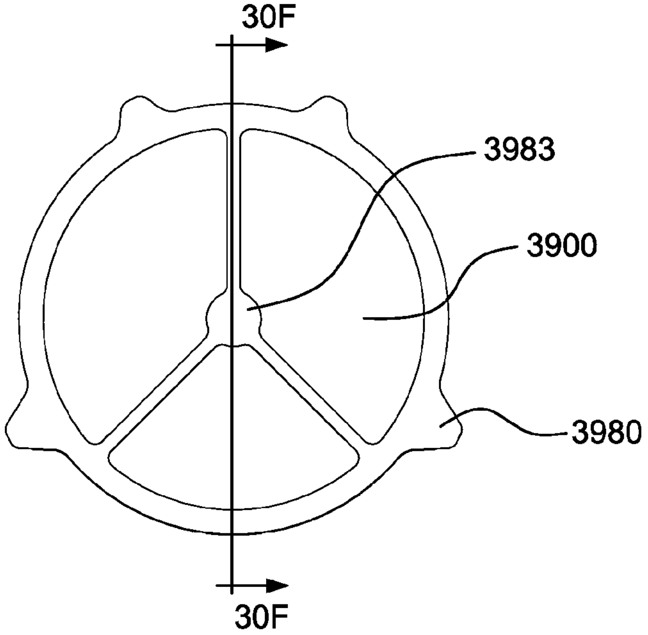

FIG. 30D shows a posterior view of a vent and frame assembly and an HMX material according to an example of the present technology.

Figure 30E:
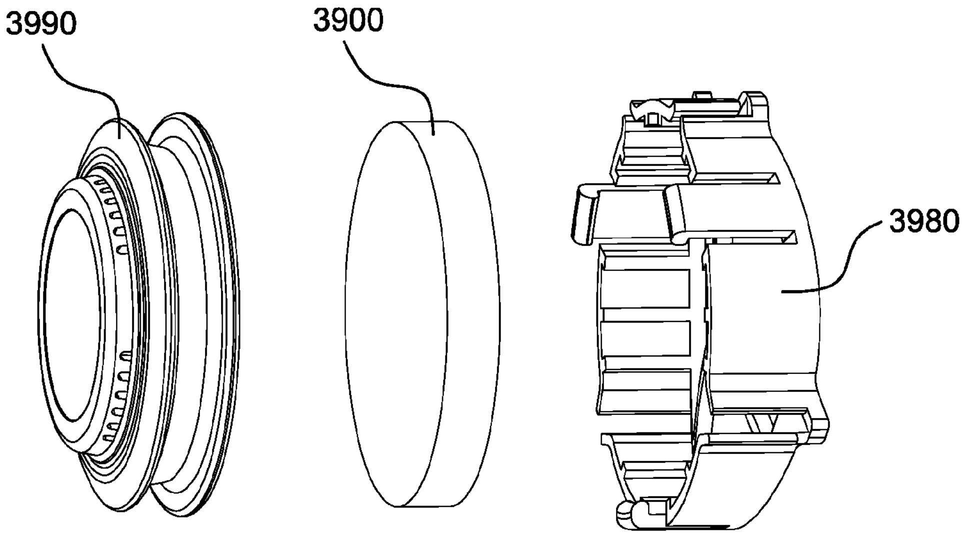

FIG. 30E shows an exploded view of a vent and frame assembly and an HMX material according to an example of the present technology.

Figure 30F:
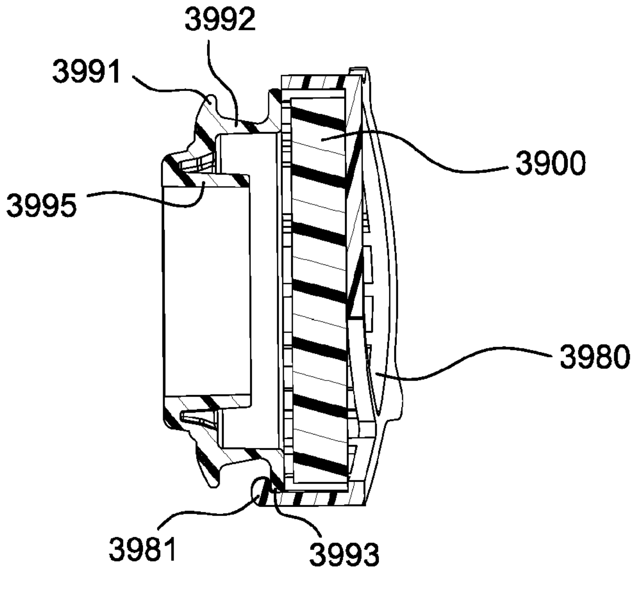

FIG. 30F shows a cross-sectional view of a vent and frame assembly and an HMX material according to an example of the present technology taken through line 30F-30F of FIG. 30D.

Figure 31A:
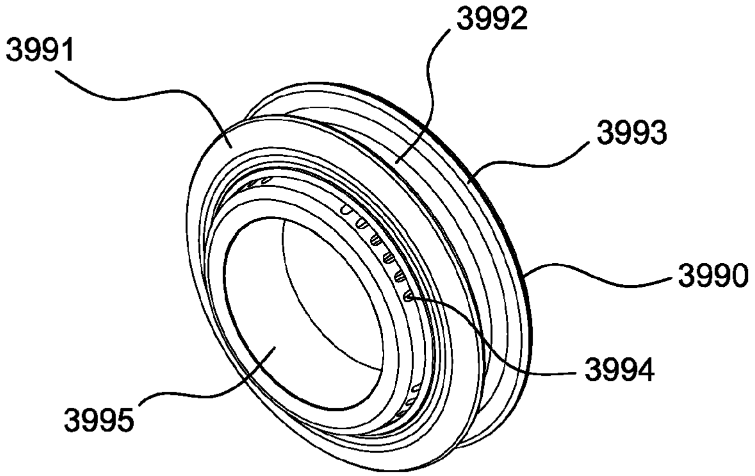

FIG. 31A shows a perspective view of an anterior HMX frame according to an example of the present technology.

Figure 31B:
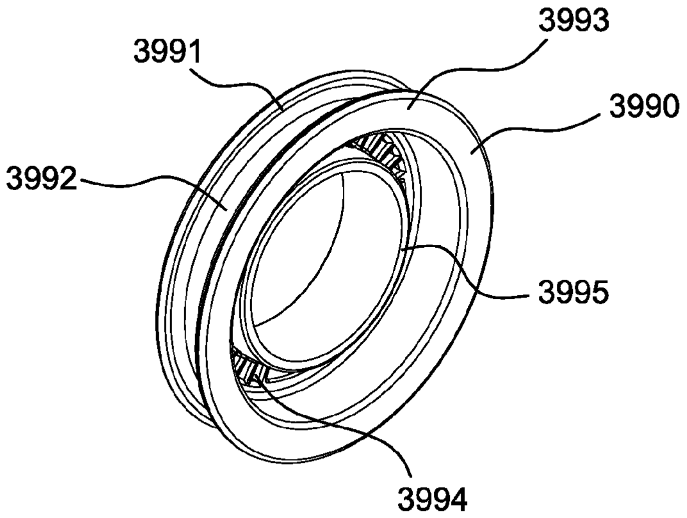

FIG. 31B shows another perspective view of an anterior HMX frame according to an example of the present technology.

Figure 31C:
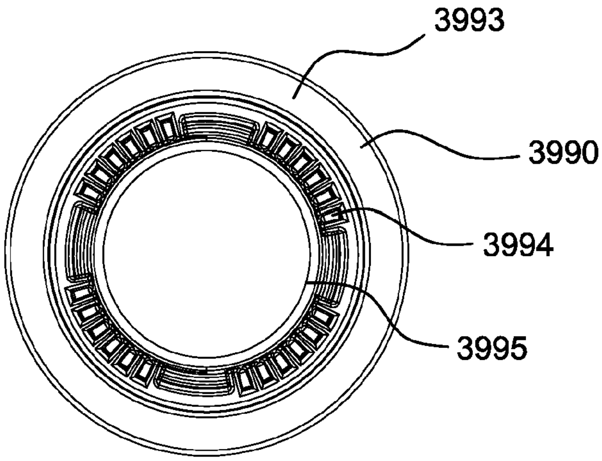

FIG. 31C shows a posterior view of an anterior HMX frame according to an example of the present technology.

Figure 32A:
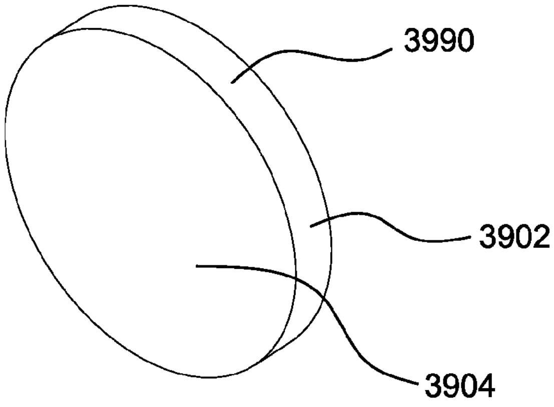

FIG. 32A shows a perspective view of an HMX material according to an example of the present technology.

Figure 32B:
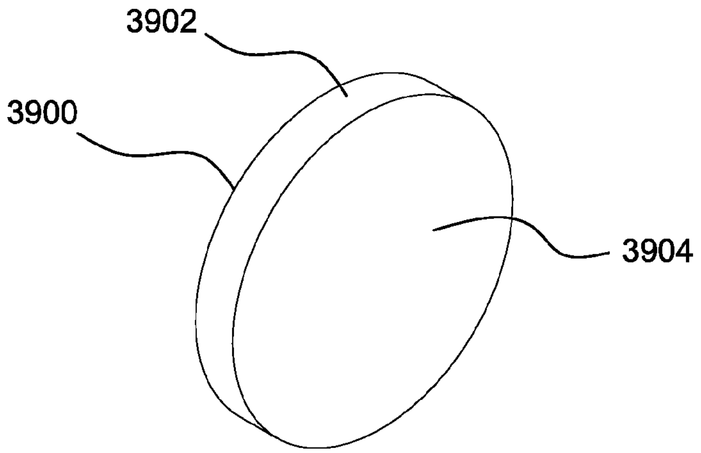

FIG. 32B shows another perspective view of an HMX material according to an example of the present technology.

Figure 33A:
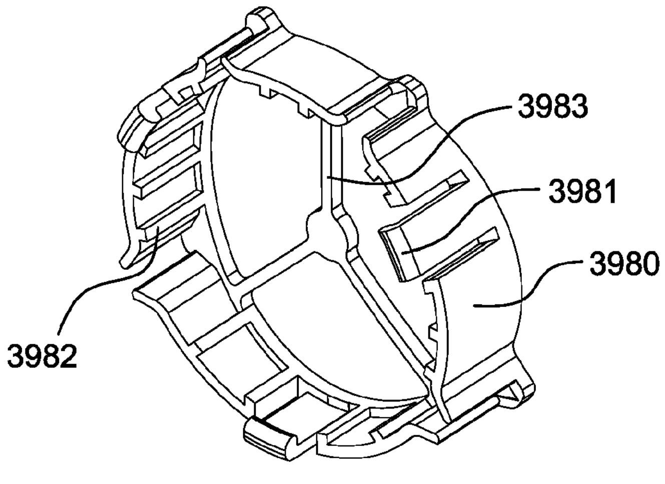

FIG. 33A shows a perspective view of a posterior HMX frame according to an example of the present technology.

Figure 33B:
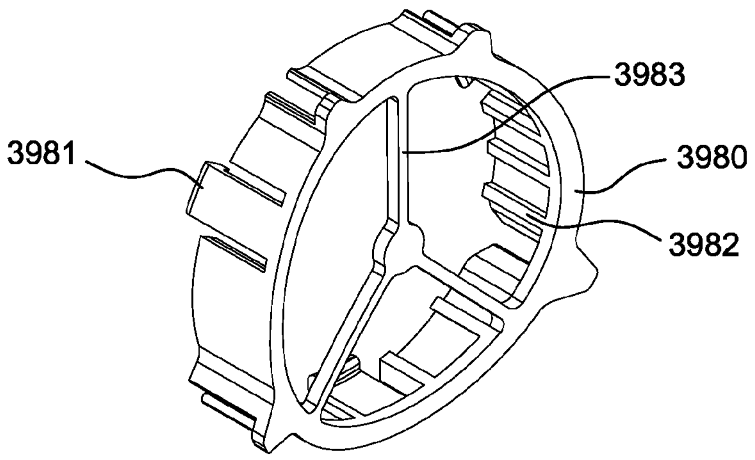

FIG. 33B shows another perspective view of a posterior HMX frame according to an example of the present technology.

Figure 34A:
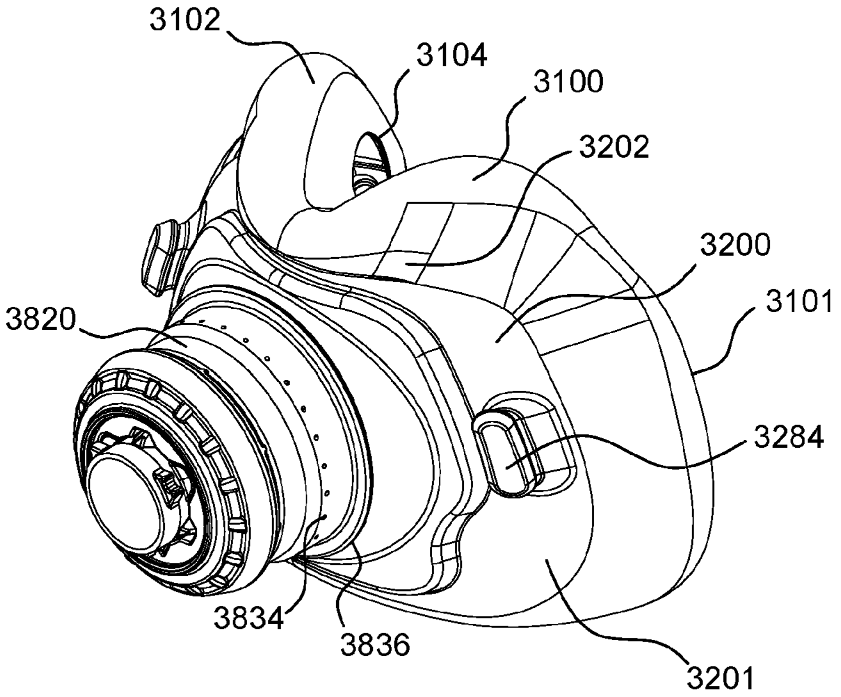

FIG. 34A shows a perspective view of an HMX and a patient interface according to an example of the present technology.

Figure 34B:
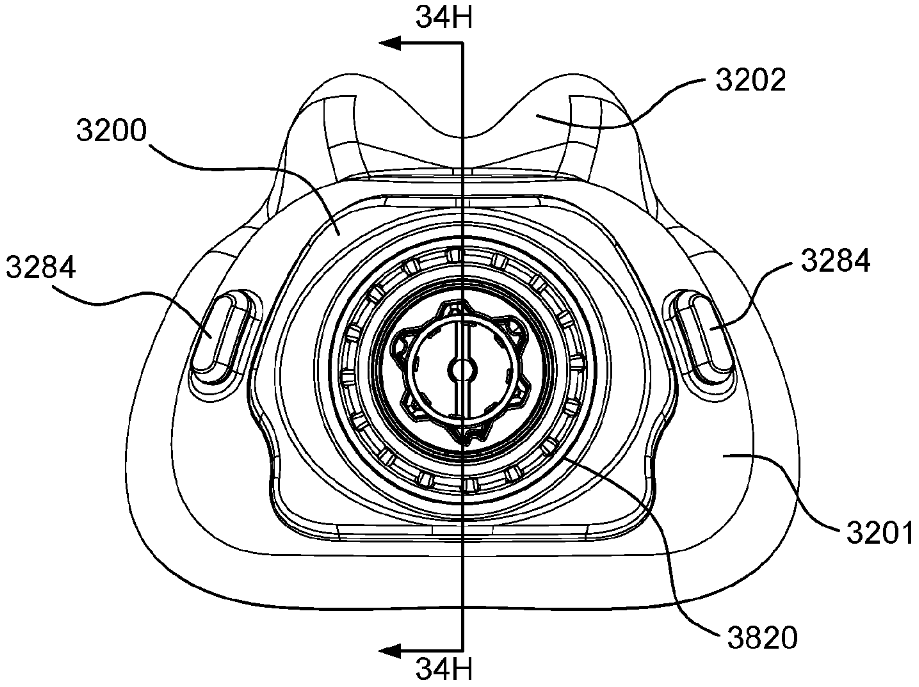

FIG. 34B shows an anterior view of an HMX and a patient interface according to an example of the present technology.

Figure 34C:
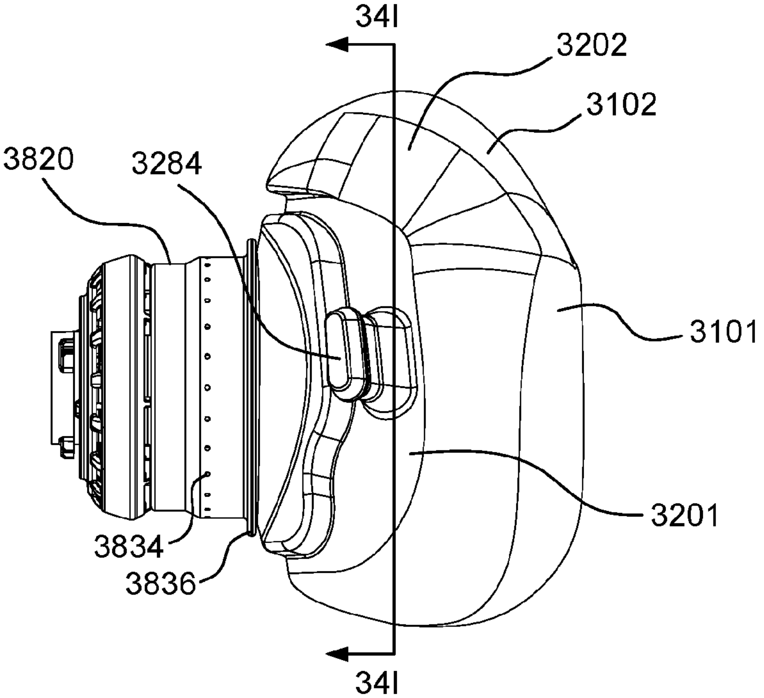

FIG. 34C shows a lateral view of an HMX and a patient interface according to an example of the present technology.

Figure 34D:
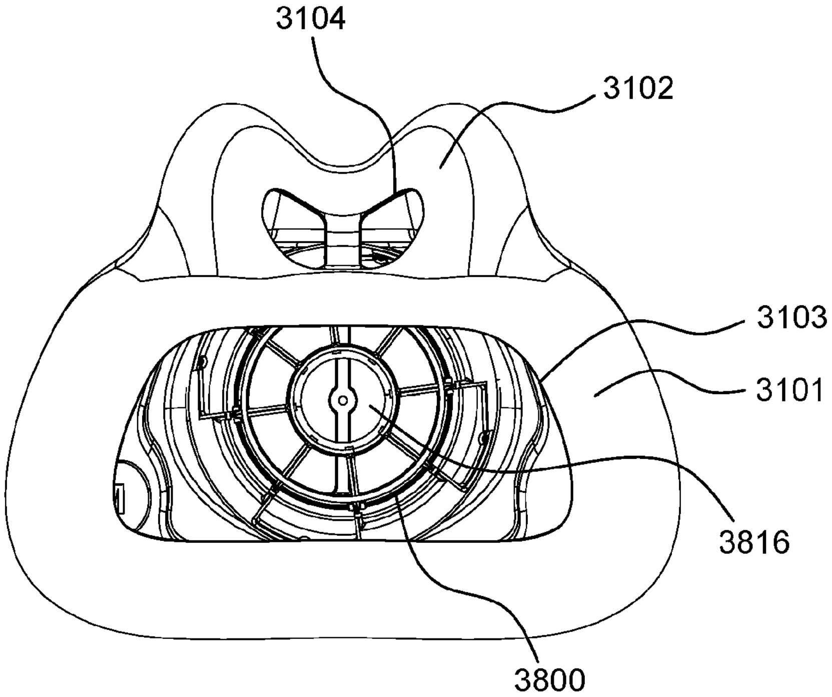

FIG. 34D shows a posterior view of an HMX and a patient interface according to an example of the present technology.

Figure 34E:
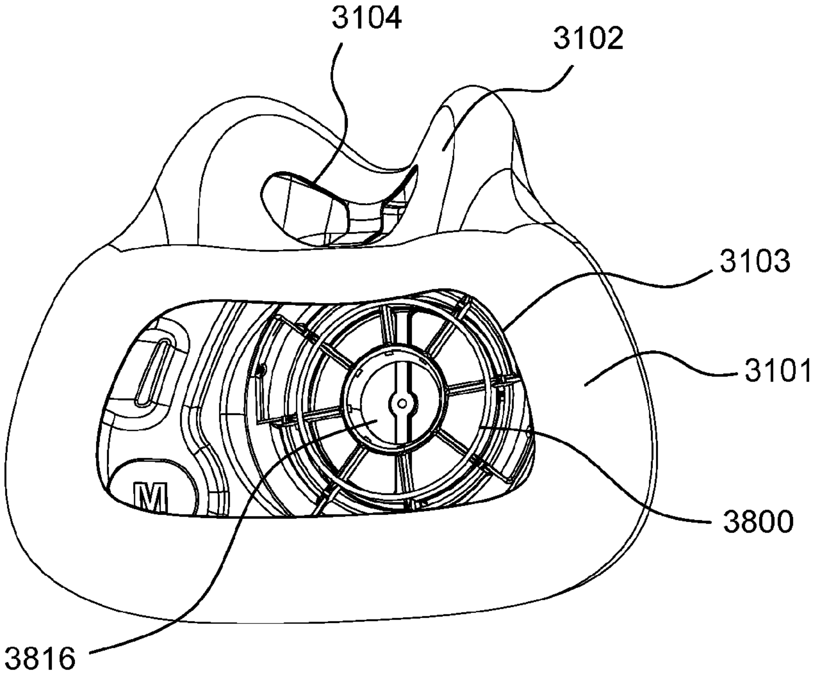

FIG. 34E shows another perspective view of an HMX and a patient interface according to an example of the present technology.

Figure 34F:
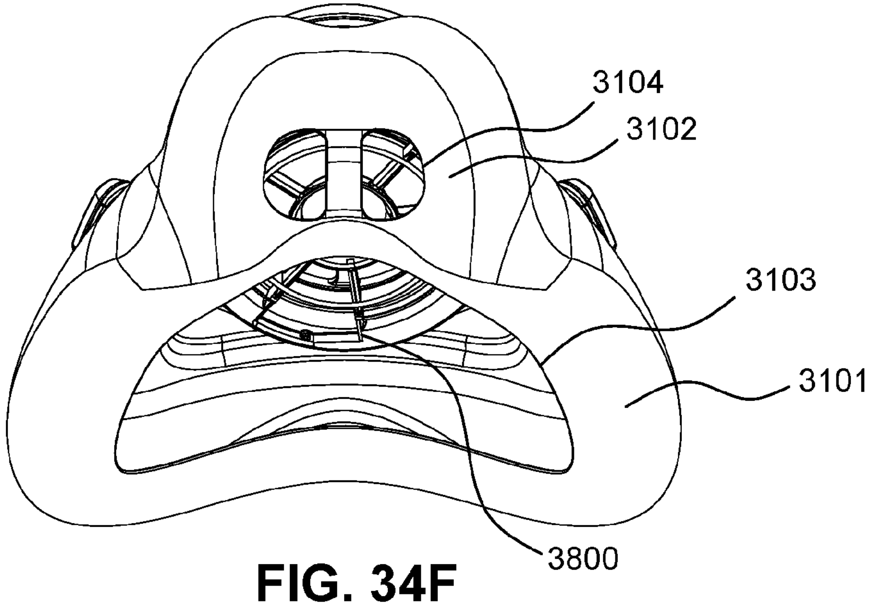

FIG. 34F shows a superior view of an HMX and a patient interface according to an example of the present technology.

Figure 34G:
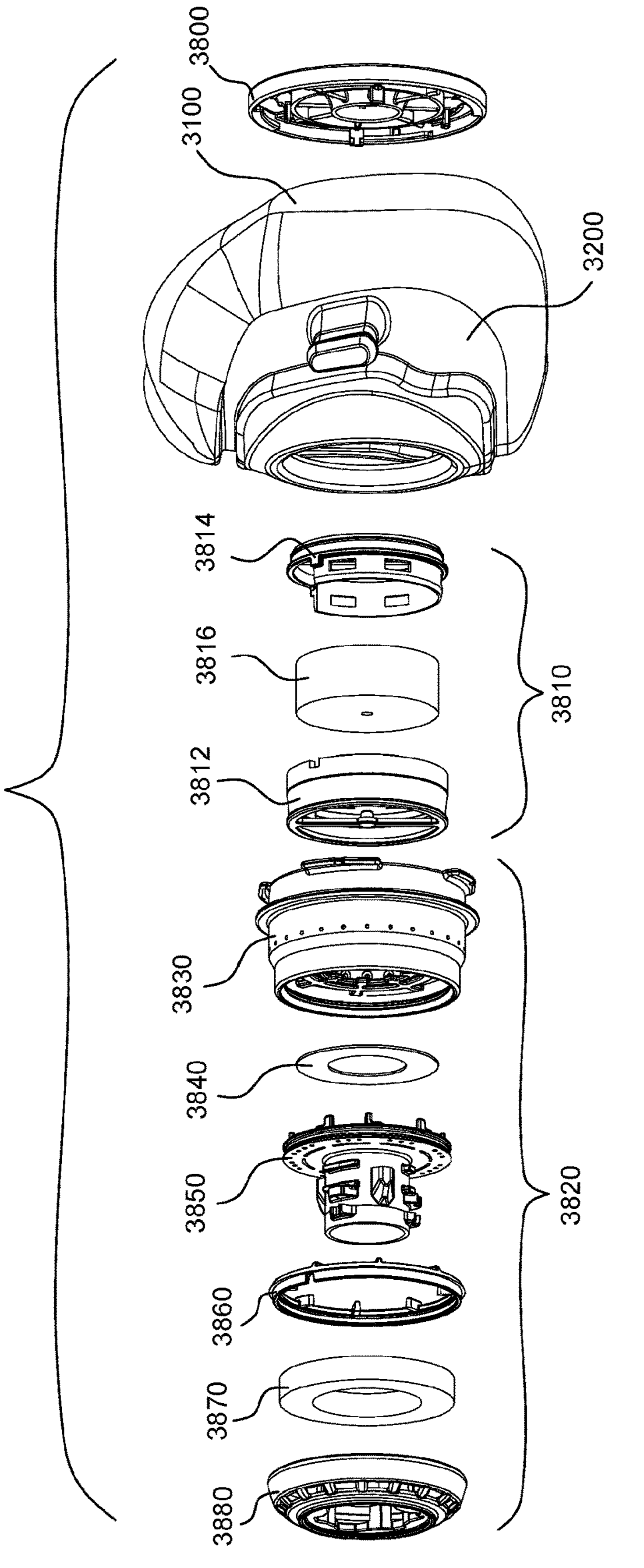

FIG. 34G shows an exploded view of an HMX and a patient interface according to an example of the present technology.

Figure 34H:
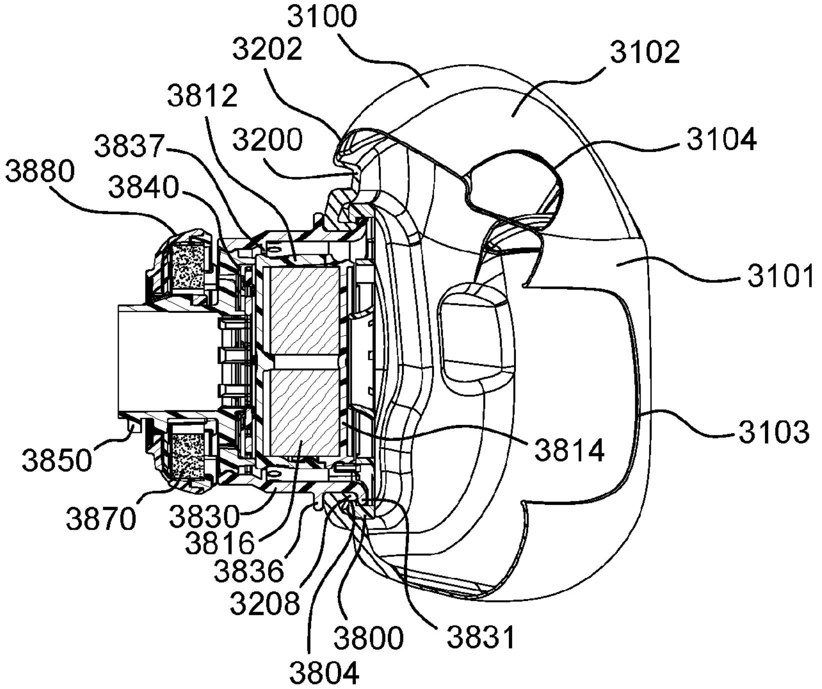

FIG. 34H shows a cross-sectional view of an HMX and a patient interface according to an example of the present technology taken through line 34H-34H of FIG. 34B.

Figure 34I:
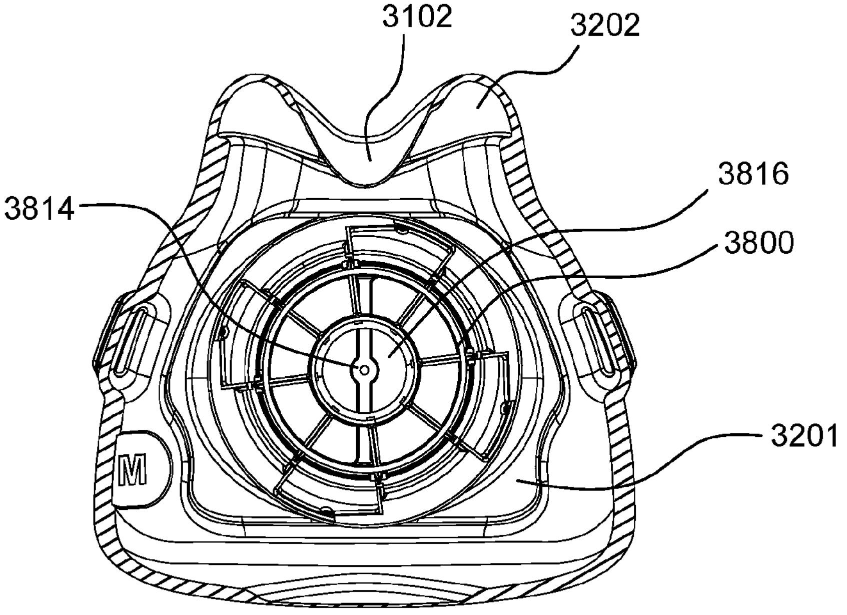

FIG. 34I shows a cross-sectional view of an HMX and a patient interface according to an example of the present technology taken through line 34I-34I of FIG. 34C.

Figure 34J:
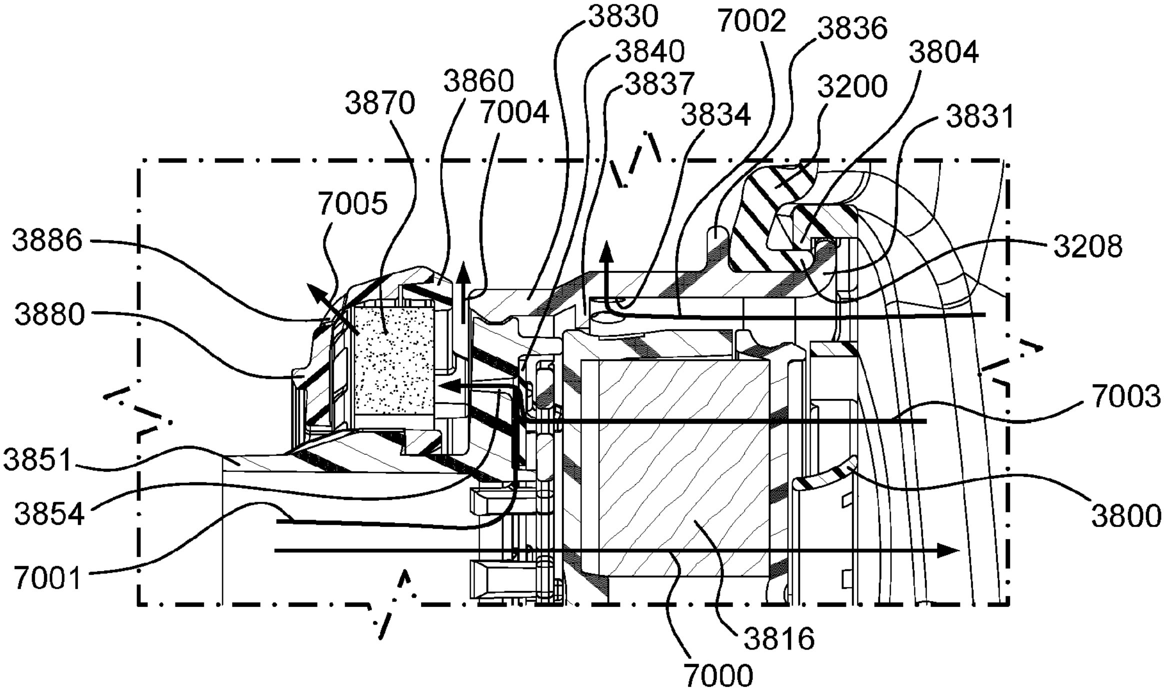

FIG. 34J shows a detailed view from FIG. 34H of an HMX and a patient interface according to an example of the present technology.

Figure 35A:
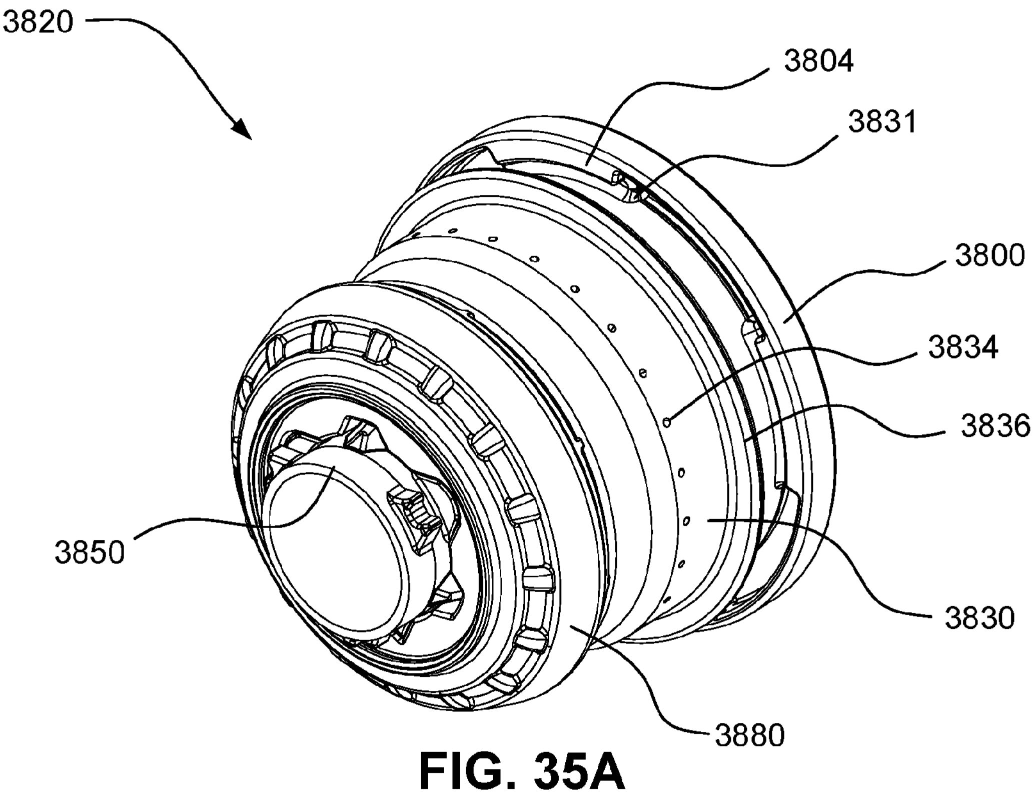

FIG. 35A shows a perspective view of a vent and conduit connector assembly and an HMX cartridge according to an example of the present technology.

Figure 35B:
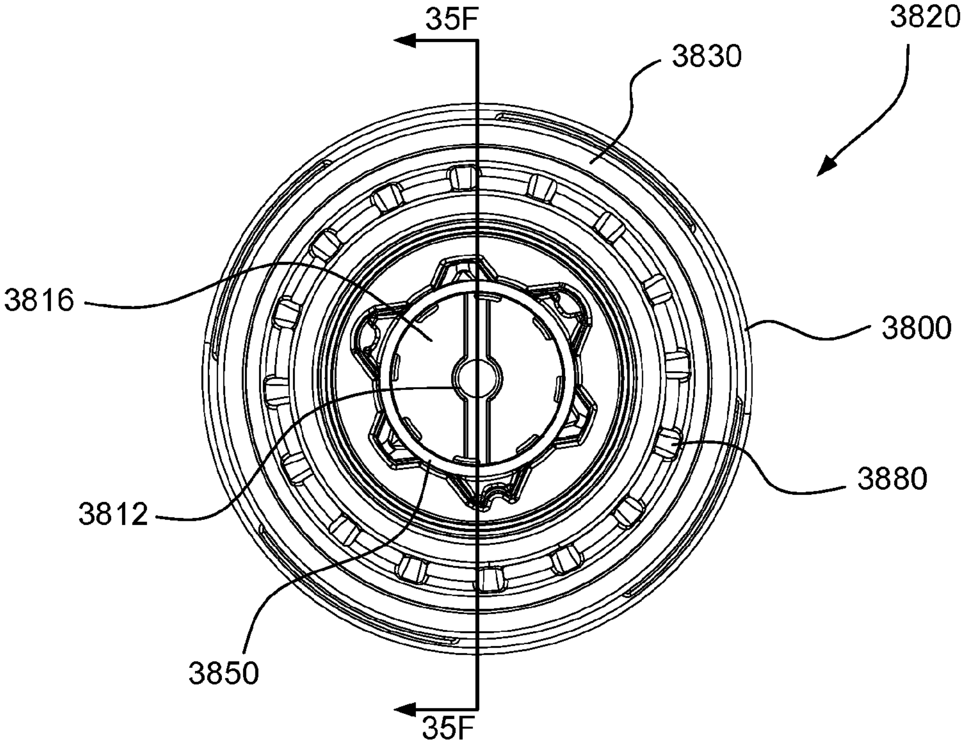

FIG. 35B shows an anterior view of a vent and conduit connector assembly and an HMX cartridge according to an example of the present technology.

Figure 35C:
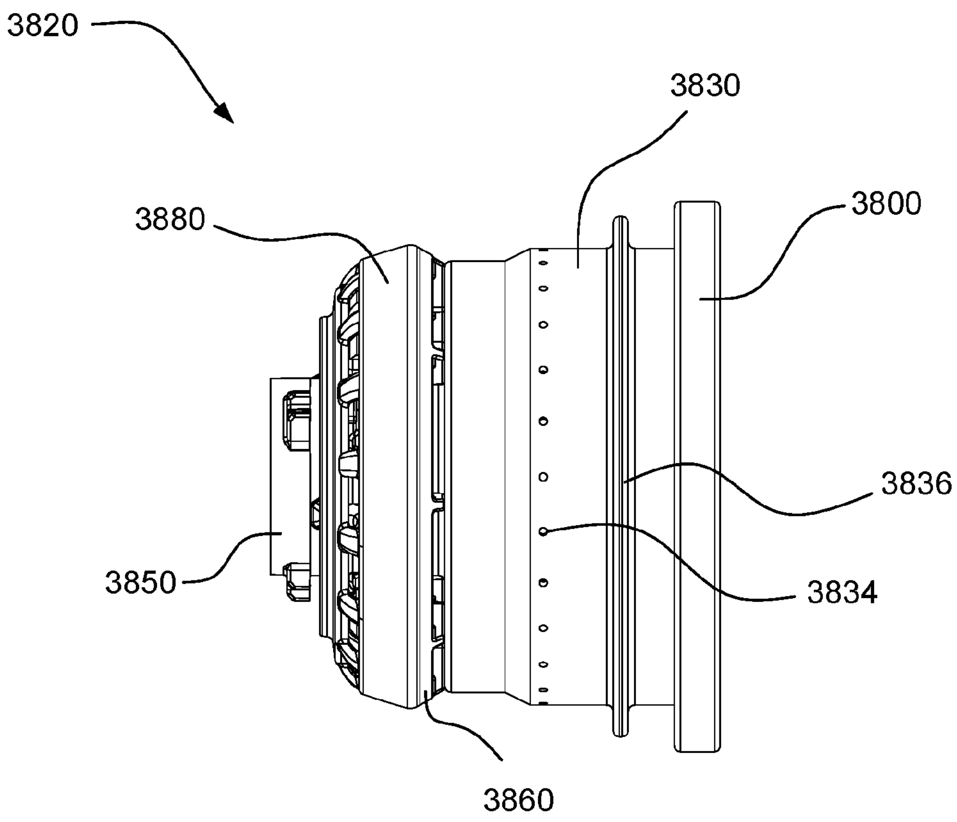

FIG. 35C shows a lateral view of a vent and conduit connector assembly and an HMX cartridge according to an example of the present technology.

Figure 35D:
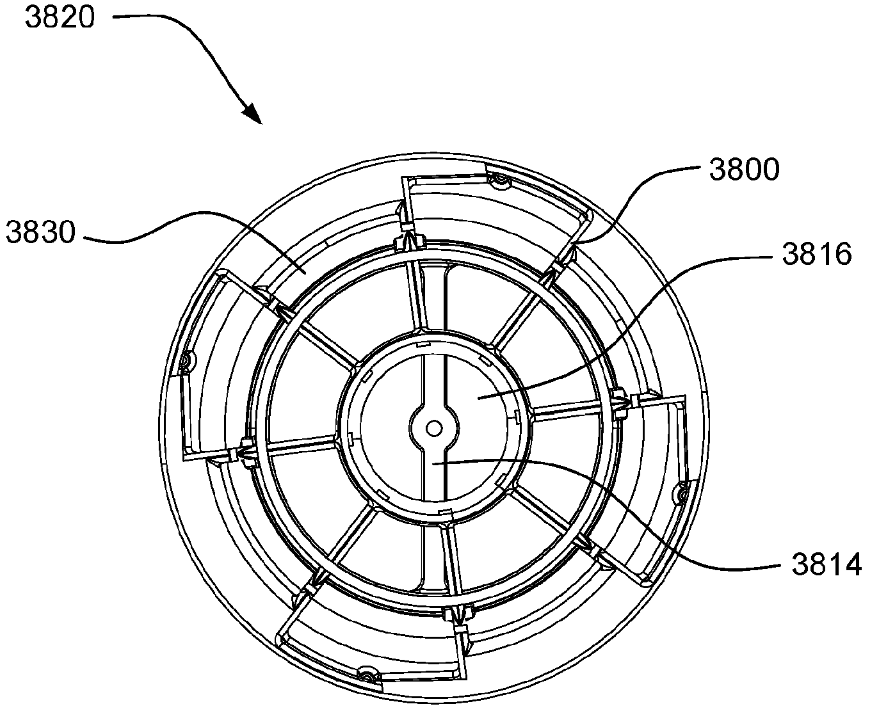

FIG. 35D shows a posterior view of a vent and conduit connector assembly and an HMX cartridge according to an example of the present technology.

Figure 35E:
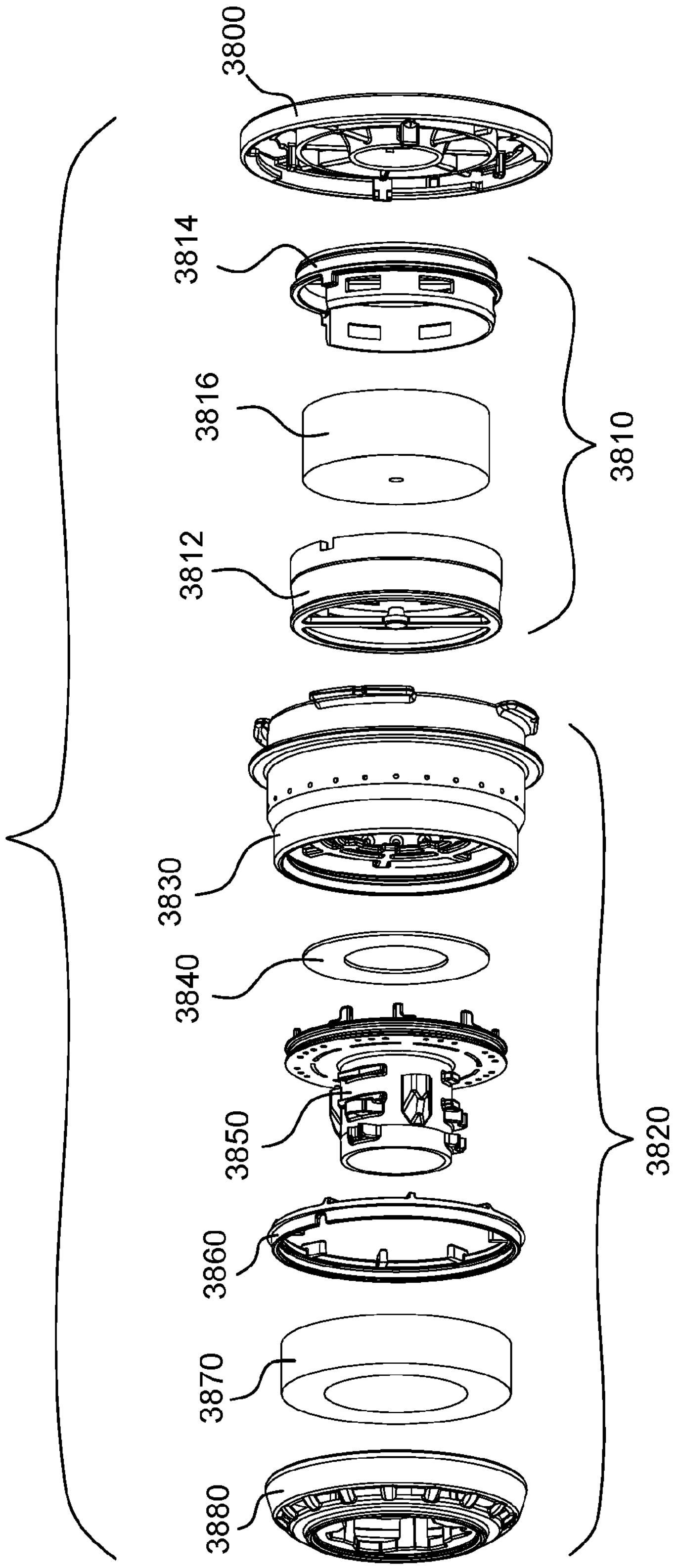

FIG. 35E shows an exploded view of a vent and conduit connector assembly and an HMX cartridge according to an example of the present technology.

Figure 35F:
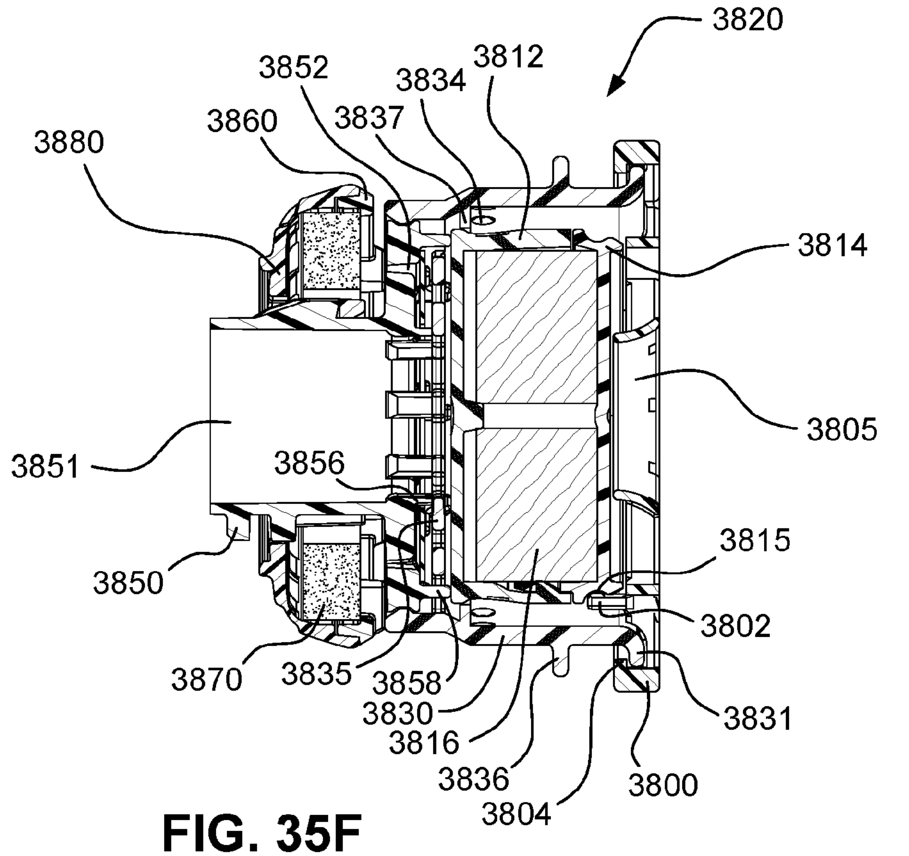

FIG. 35F shows a cross-sectional view of a vent and conduit connector assembly and an HMX cartridge according to an example of the present technology taken through line 35F-35F of FIG. 35B.

Figure 36A:
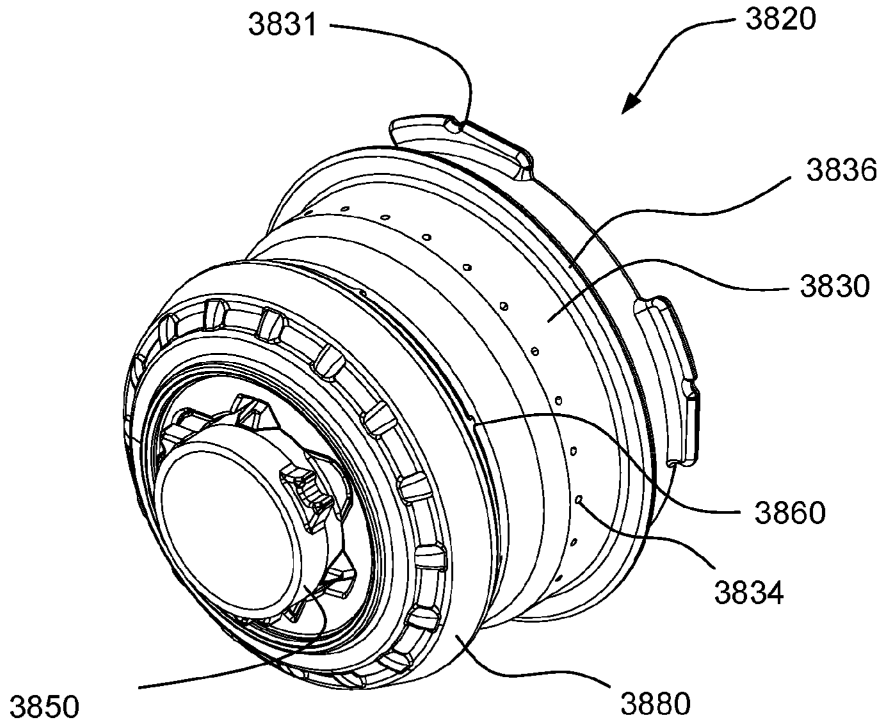

FIG. 36A shows a perspective view of a vent and conduit connector assembly according to an example of the present technology.

Figure 36B:
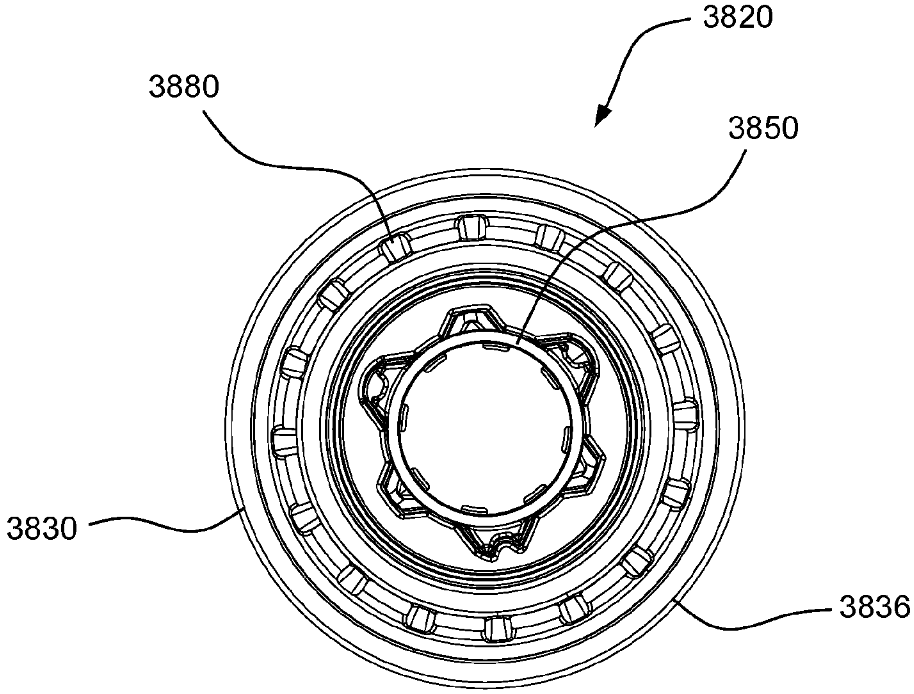

FIG. 36B shows an anterior view of a vent and conduit connector assembly according to an example of the present technology.

Figure 36C:
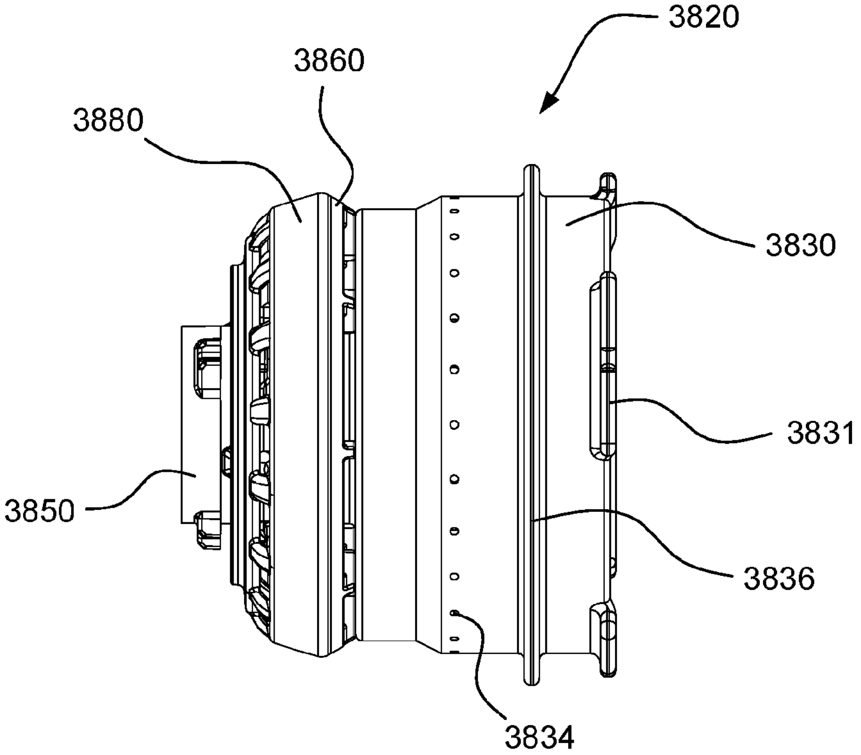

FIG. 36C shows a lateral view of a vent and conduit connector assembly according to an example of the present technology.

Figure 36D:
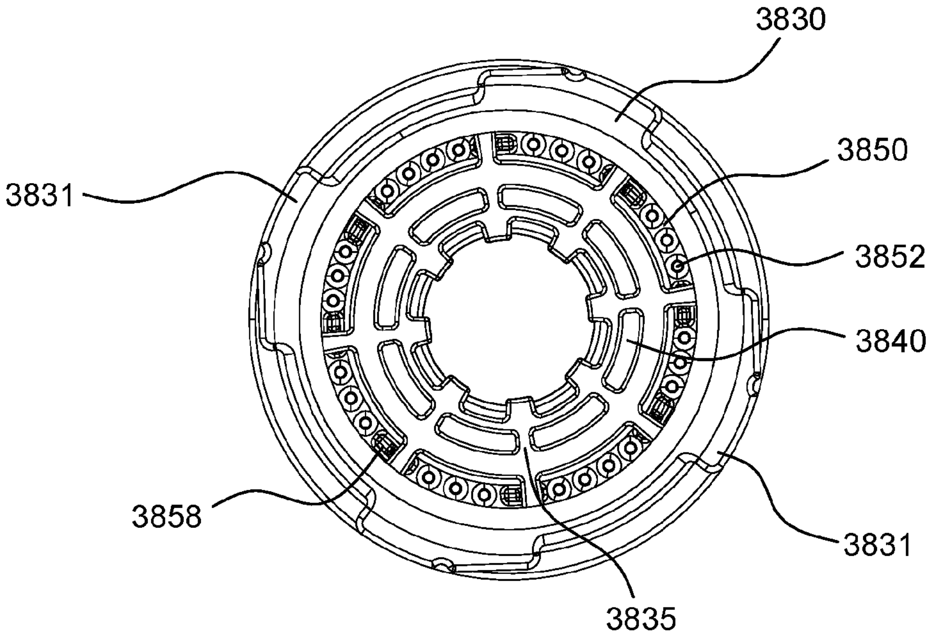

FIG. 36D shows a posterior view of a vent and conduit connector assembly according to an example of the present technology.

Figure 36E:
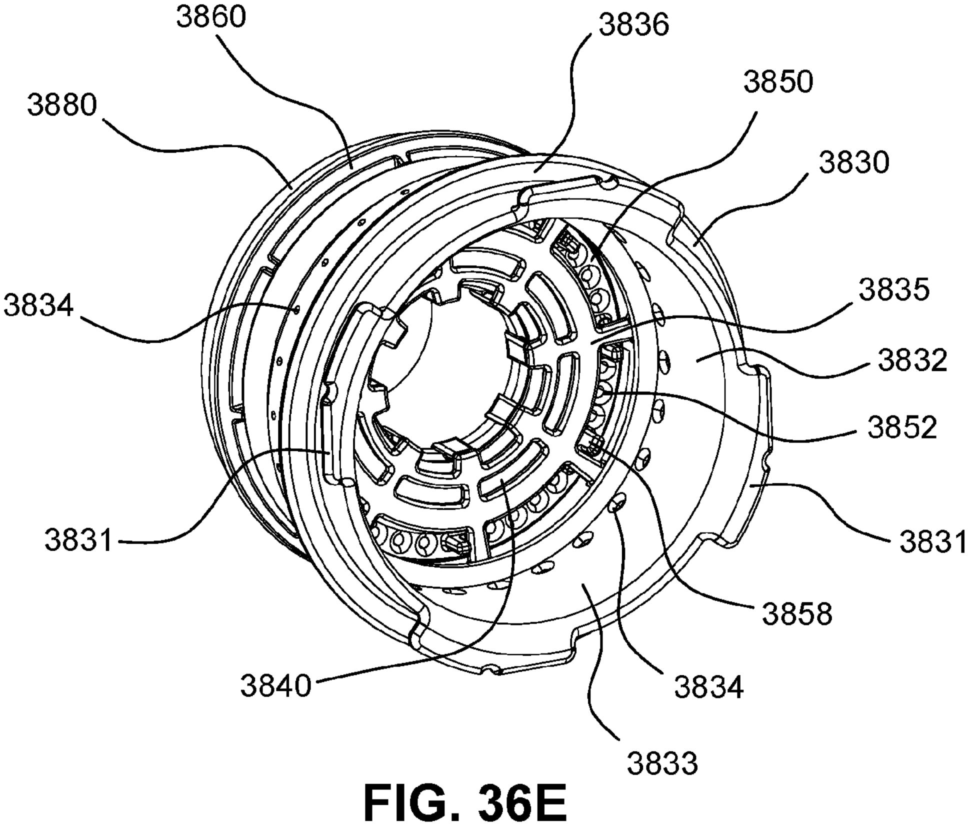

FIG. 36E shows another perspective view of a vent and conduit connector assembly according to an example of the present technology.

Figure 37A:
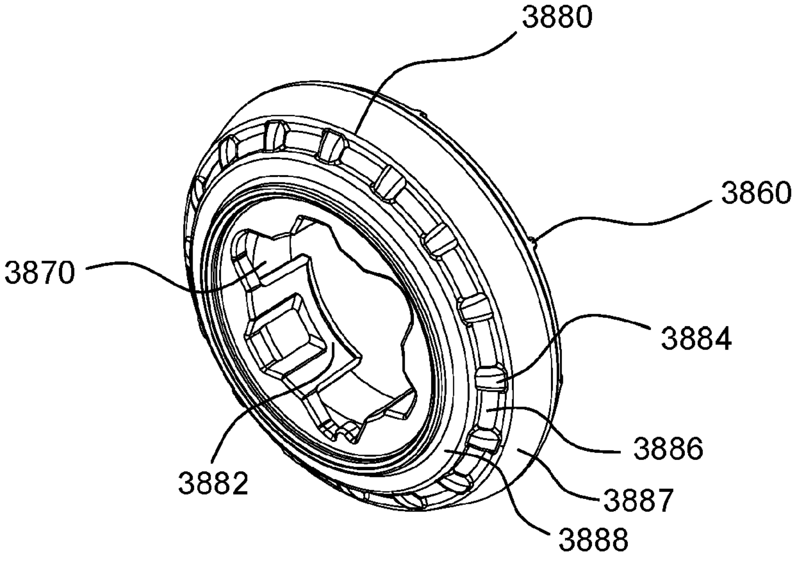

FIG. 37A shows a perspective view of an anterior diffuser retaining ring, a posterior diffuser retaining ring, and diffuser material according to an example of the present technology.

Figure 37B:
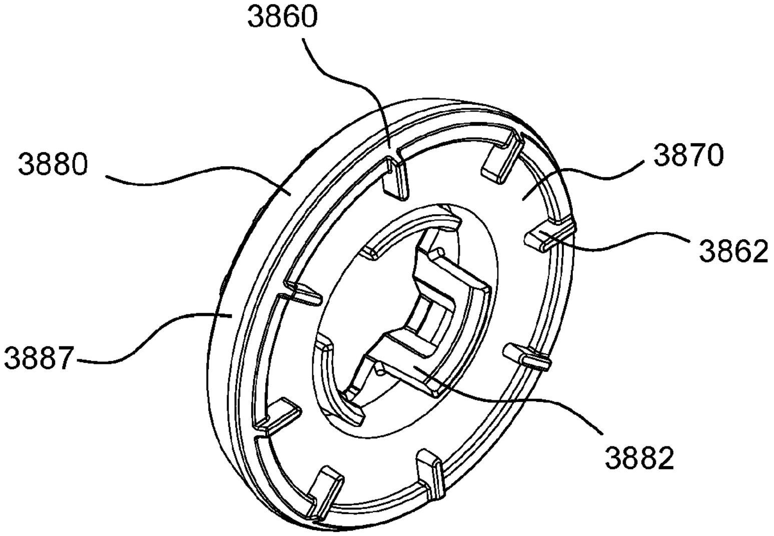

FIG. 37B shows another perspective view of an anterior diffuser retaining ring, a posterior diffuser retaining ring, and diffuser material according to an example of the present technology.

Figure 37C:
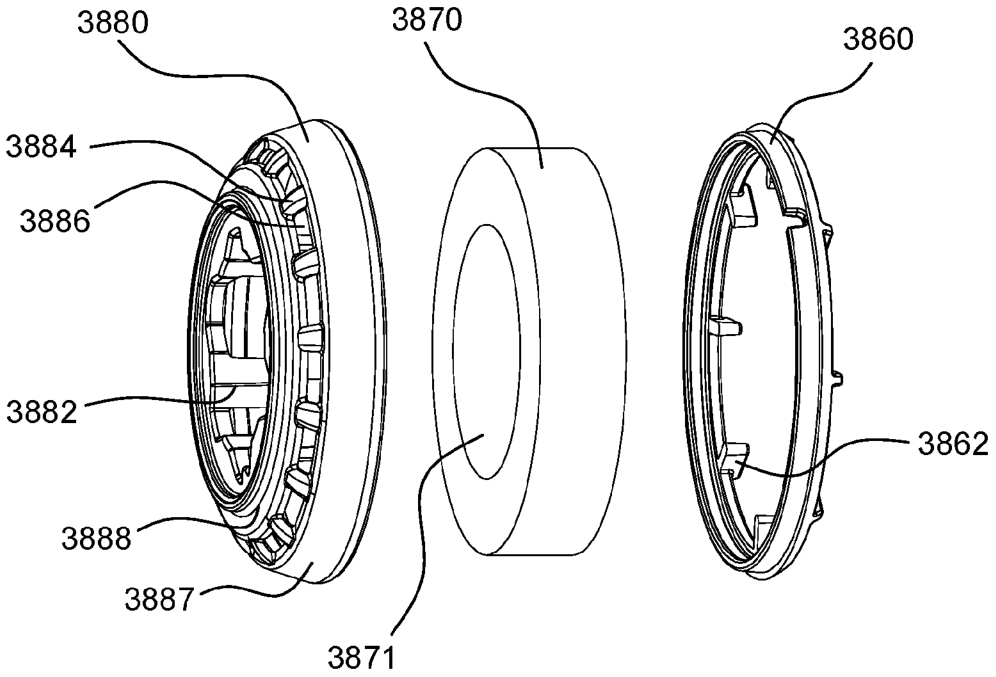

FIG. 37C shows an exploded view of an anterior diffuser retaining ring, a posterior diffuser retaining ring, and diffuser material according to an example of the present technology.

Figure 38A:
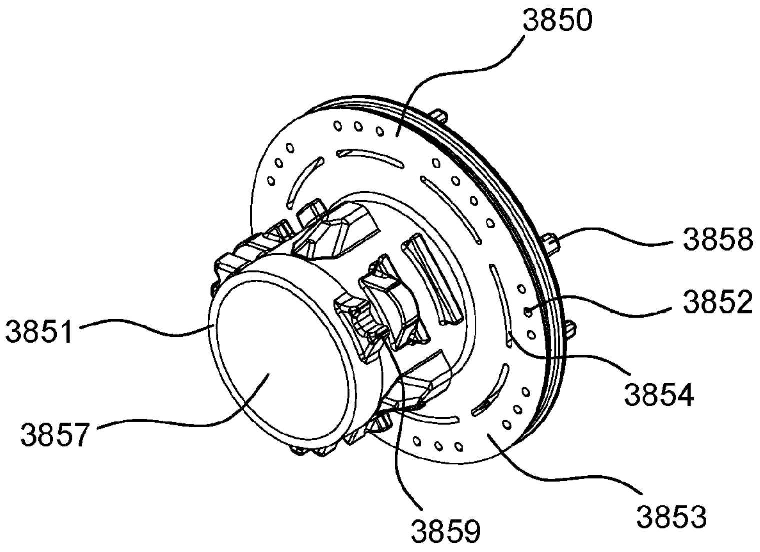

FIG. 38A shows a perspective view of a conduit connector and axial vent structure according to an example of the present technology.

Figure 38B:
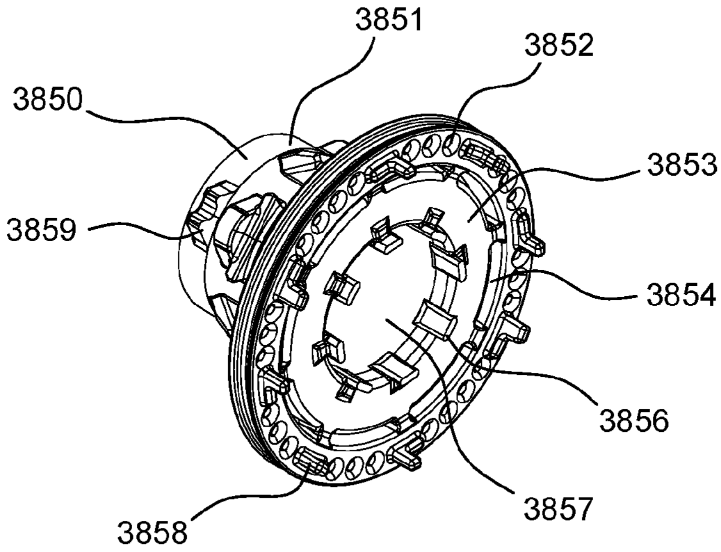

FIG. 38B shows another perspective view of a conduit connector and axial vent structure according to an example of the present technology.

Figure 39:
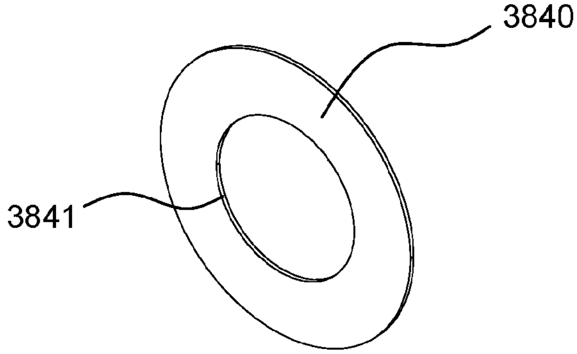

FIG. 39 shows a perspective view of a membrane according to an example of the present technology.

Figure 40A:
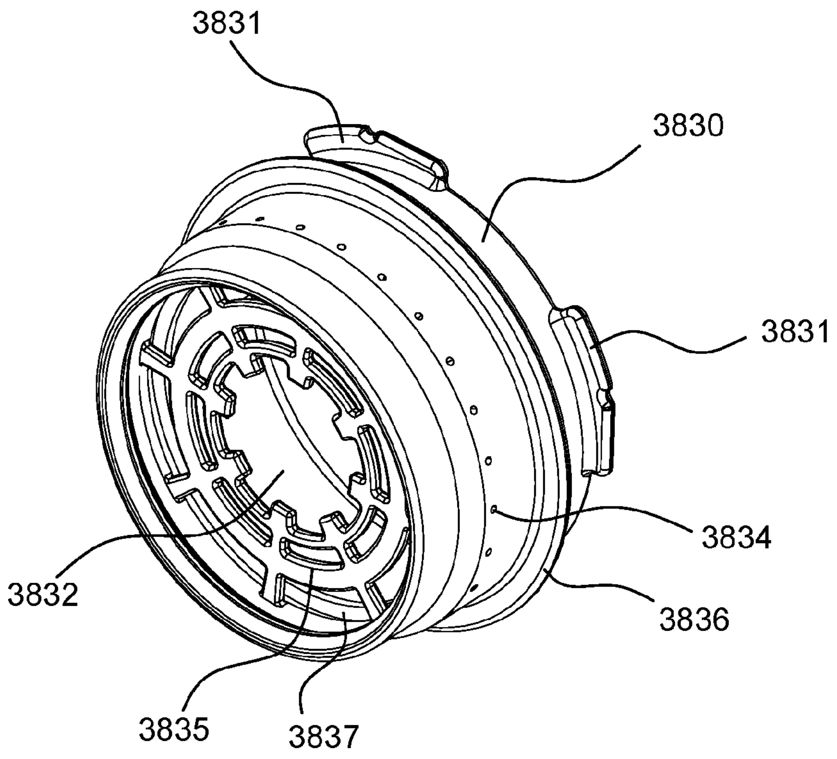

FIG. 40A shows a perspective view of an anterior frame according to an example of the present technology.

Figure 40B:
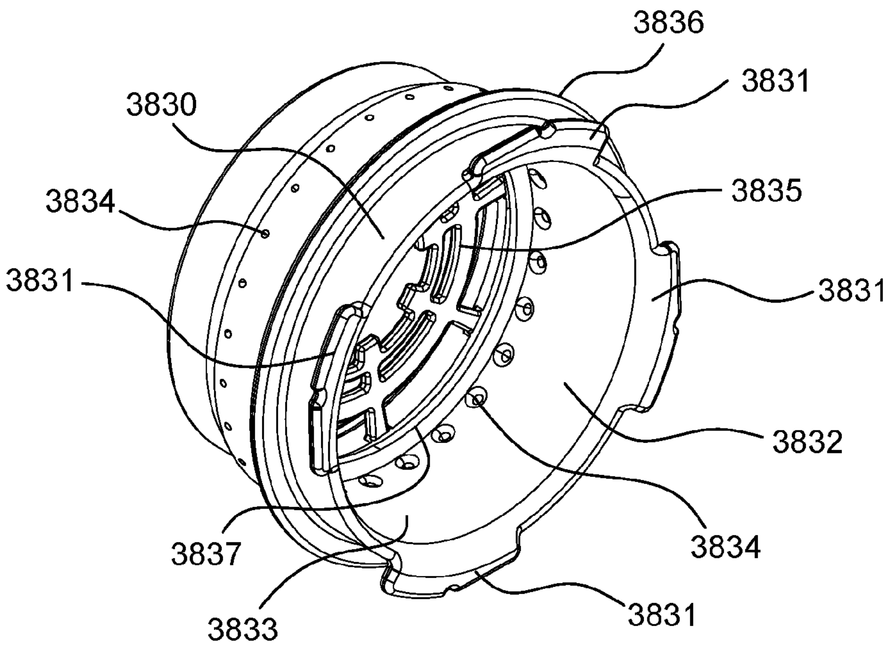

FIG. 40B shows another perspective view of an anterior frame according to an example of the present technology.

Figure 41A:
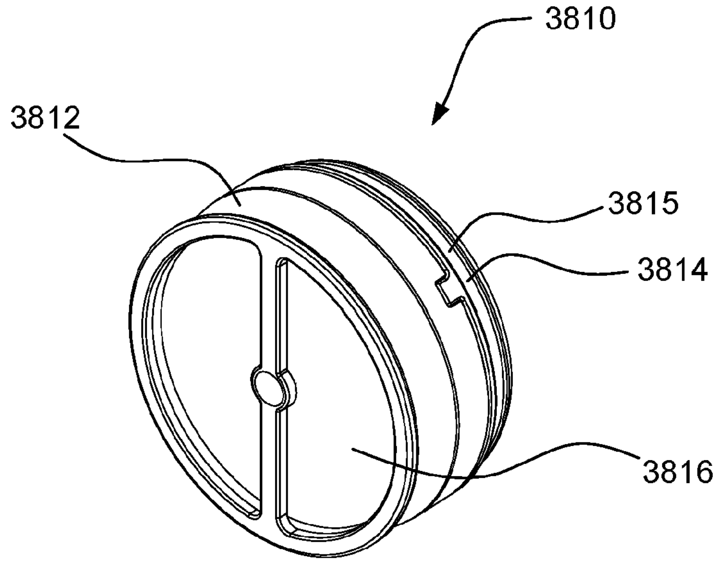

FIG. 41A shows a perspective view of an HMX cartridge according to an example of the present technology.

Figure 41B:
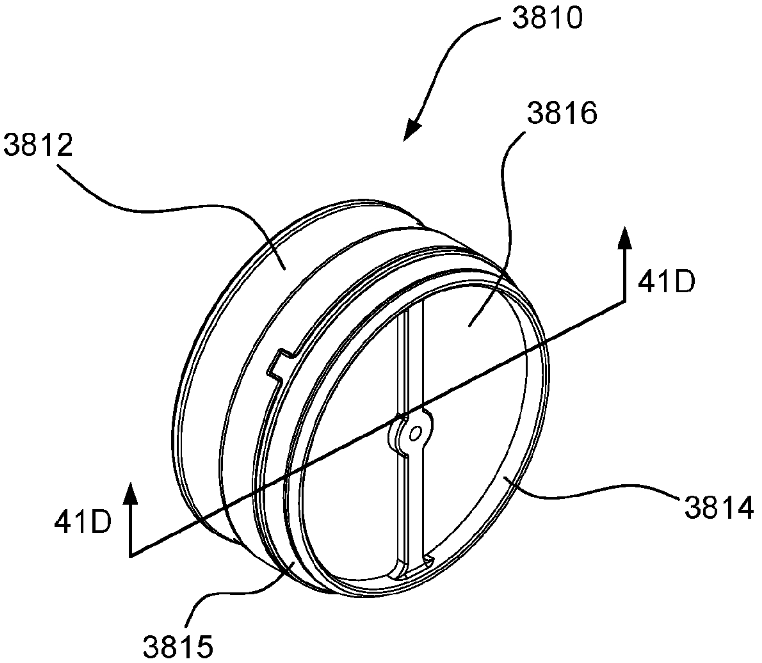

FIG. 41B shows another perspective view of an HMX cartridge according to an example of the present technology.

Figure 41C:
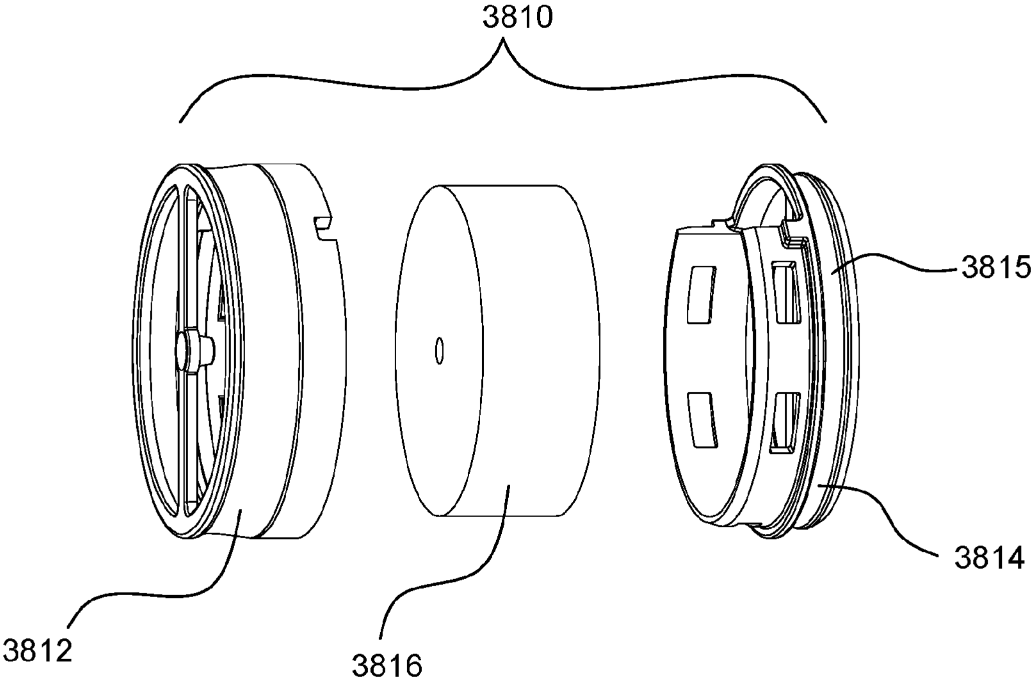

FIG. 41C shows an exploded view of an HMX cartridge according to an example of the present technology.

Figure 41D:
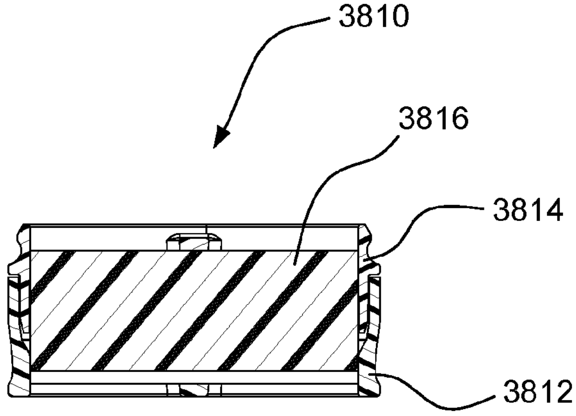

FIG. 41D shows a cross-sectional view of an HMX cartridge according to an example of the present technology taken through line 41D-41D of 41B.

Figure 42A:
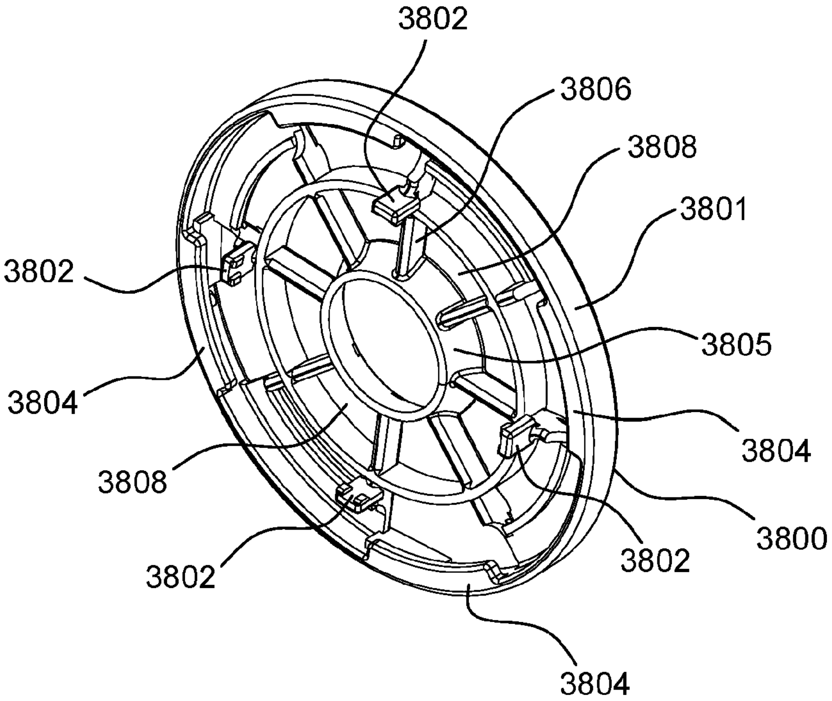

FIG. 42A shows a perspective view of a posterior frame according to an example of the present technology.

Figure 42B:
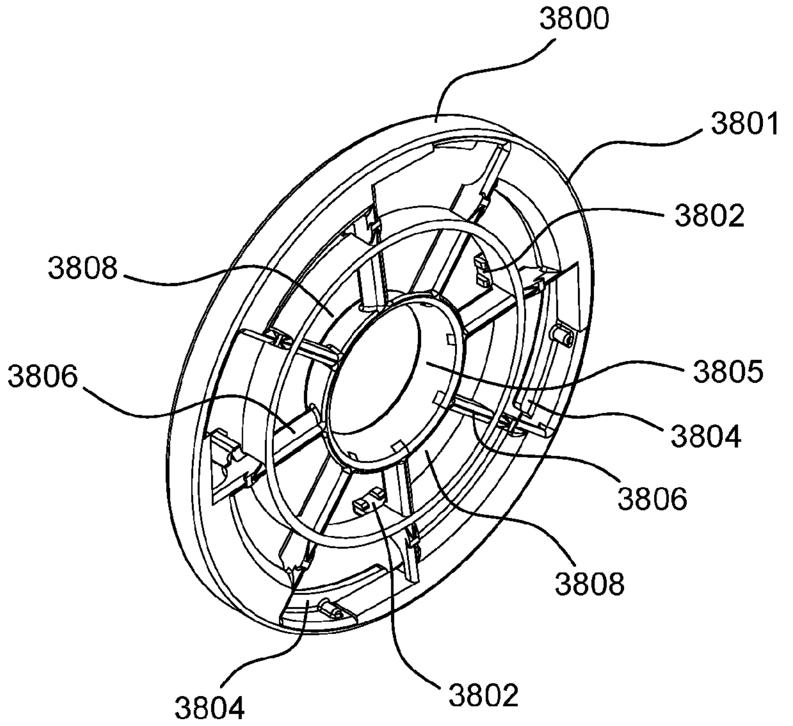

FIG. 42B shows another perspective view of a posterior frame according to an example of the present technology.

Figure 43A:
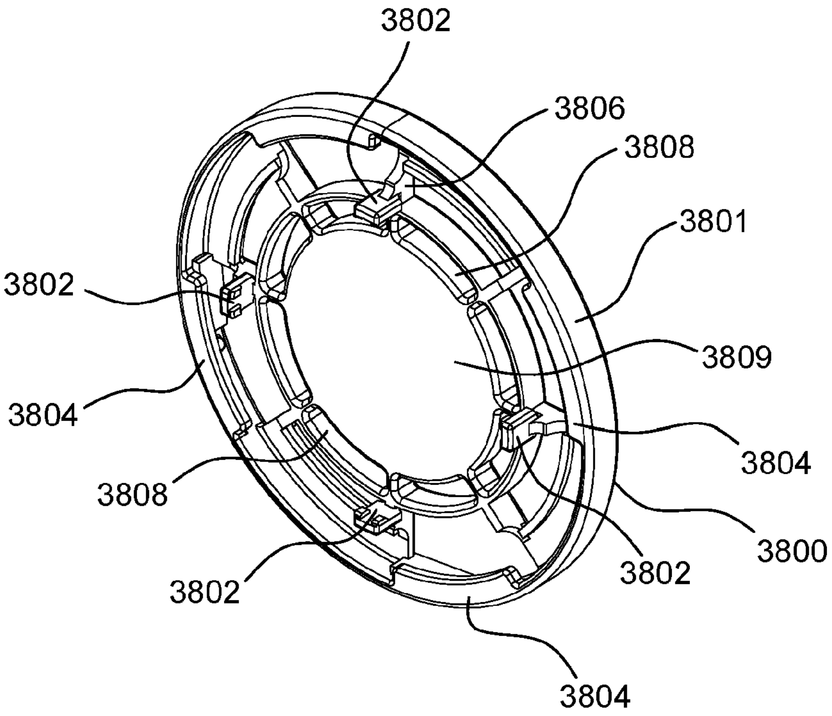

FIG. 43A shows a perspective view of a posterior frame according to an example of the present technology.

Figure 43B:
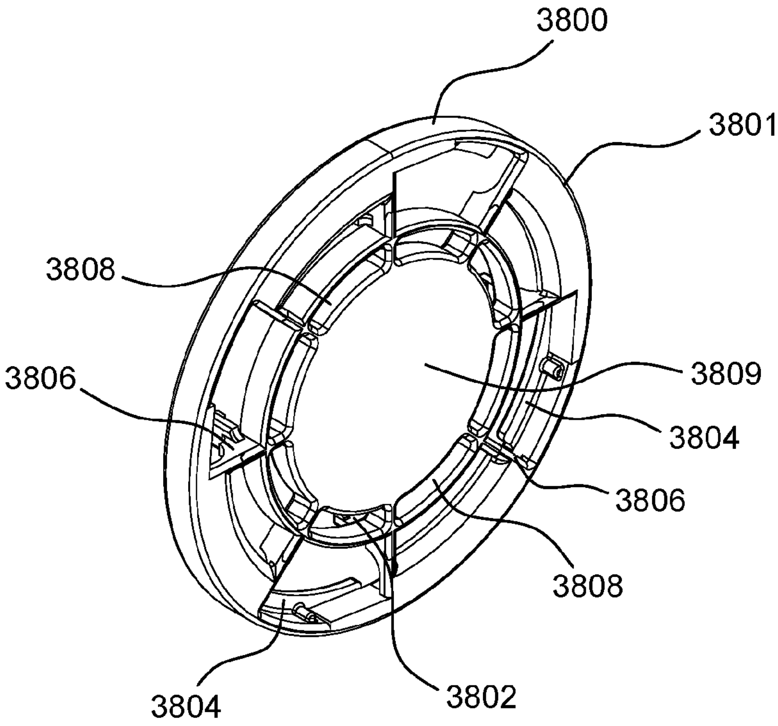

FIG. 43B shows another perspective view of a posterior frame according to an example of the present technology.

Figure 44A:
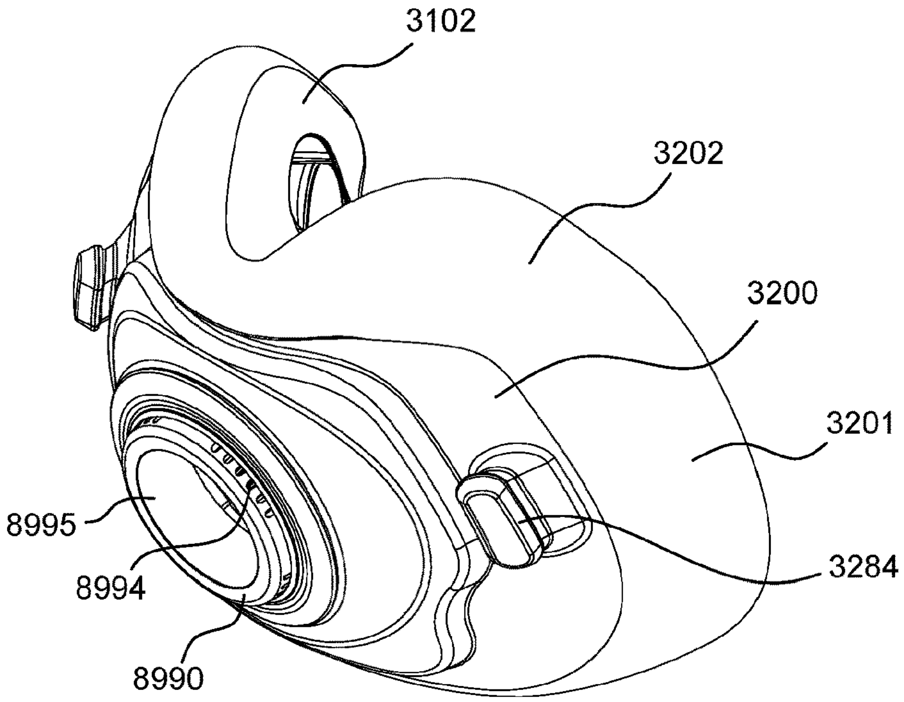

FIG. 44A shows a perspective view of a patient interface with an HMX and flow director assembly according to an example of the present technology.

Figure 44B:
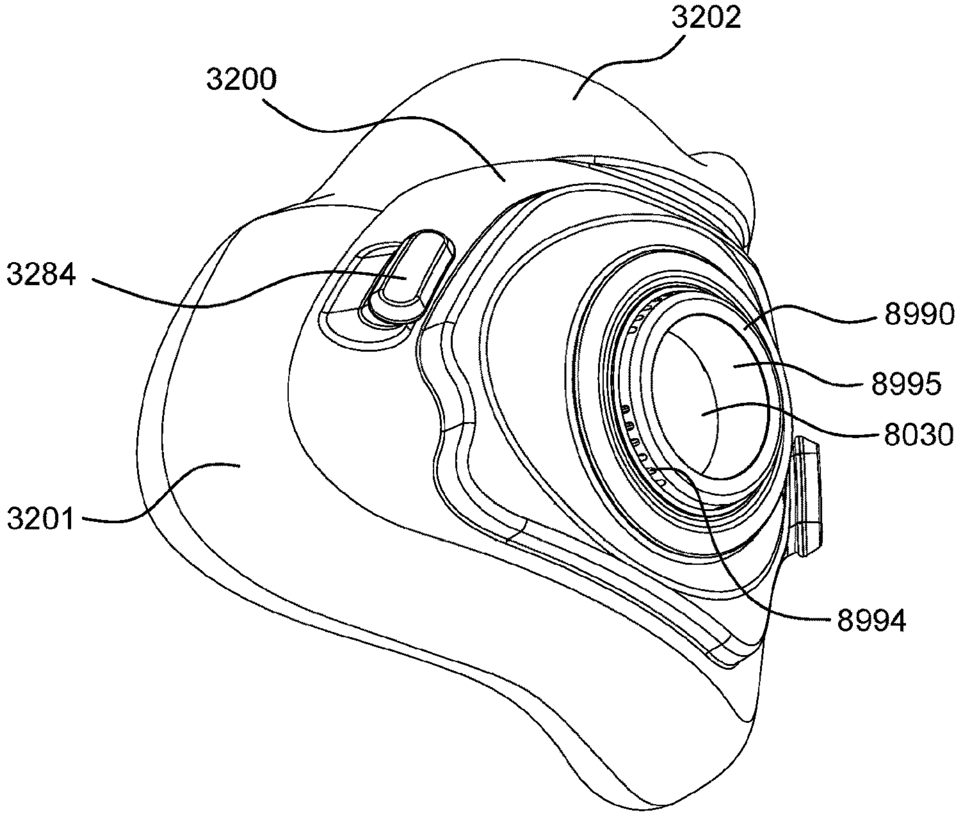

FIG. 44B shows another perspective view of a patient interface with an HMX and flow director assembly according to an example of the present technology.

Figure 44C:
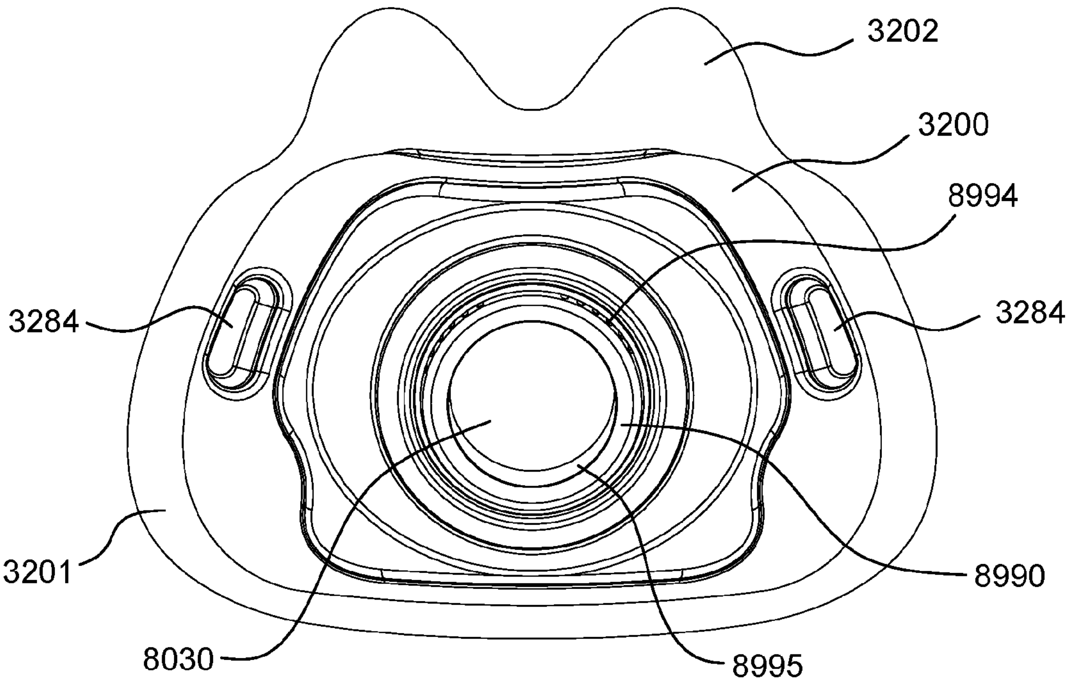

FIG. 44C shows an anterior view of a patient interface with an HMX and flow director assembly according to an example of the present technology.

Figure 44D:
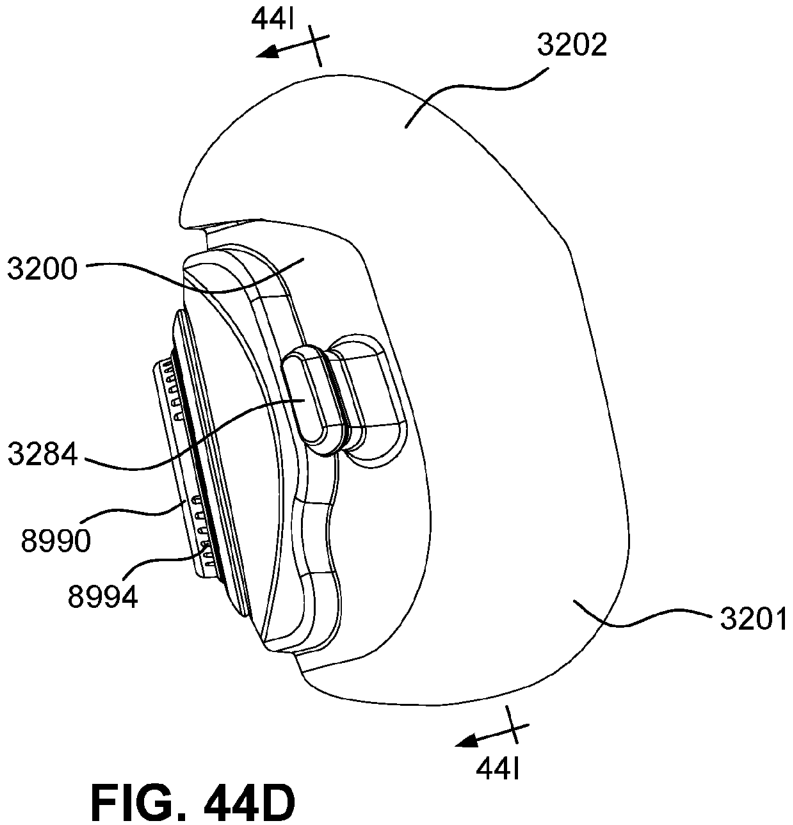

FIG. 44D shows a lateral view of a patient interface with an HMX and flow director assembly according to an example of the present technology.

Figure 44E:
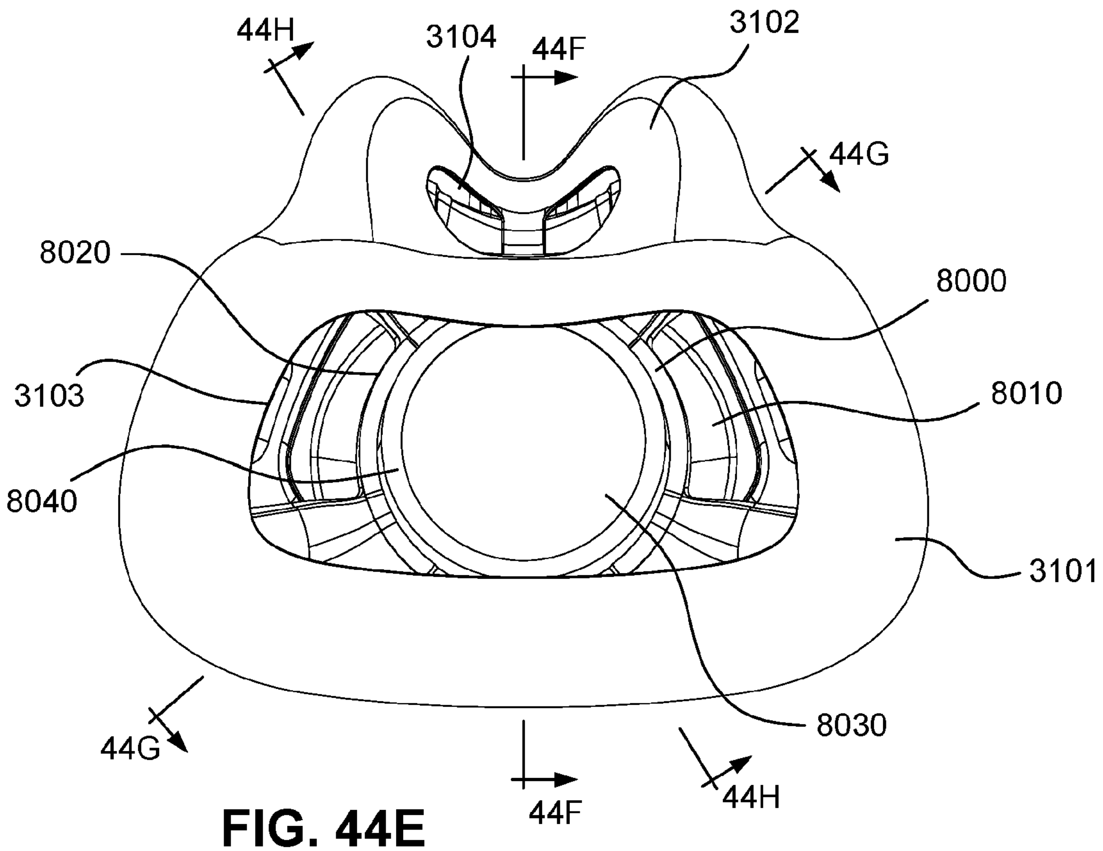

FIG. 44E shows a posterior view of a patient interface with an HMX and flow director assembly according to an example of the present technology.

Figure 44F:
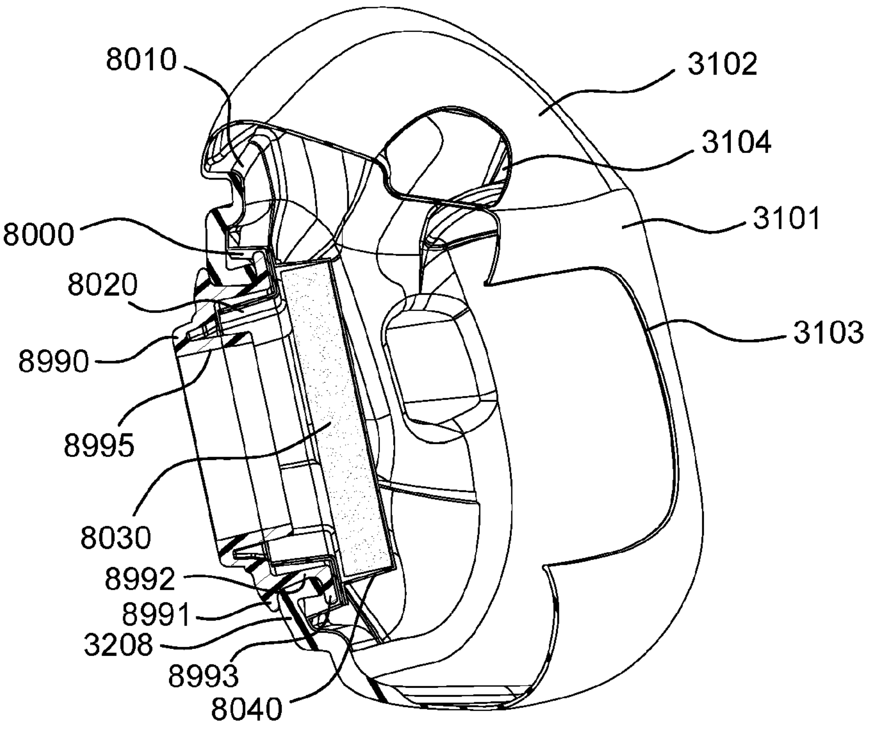

FIG. 44F shows a cross-sectional view of a patient interface with an HMX and flow director assembly taken through line 44F-44F of FIG. 44E according to an example of the present technology.

Figure 44G:
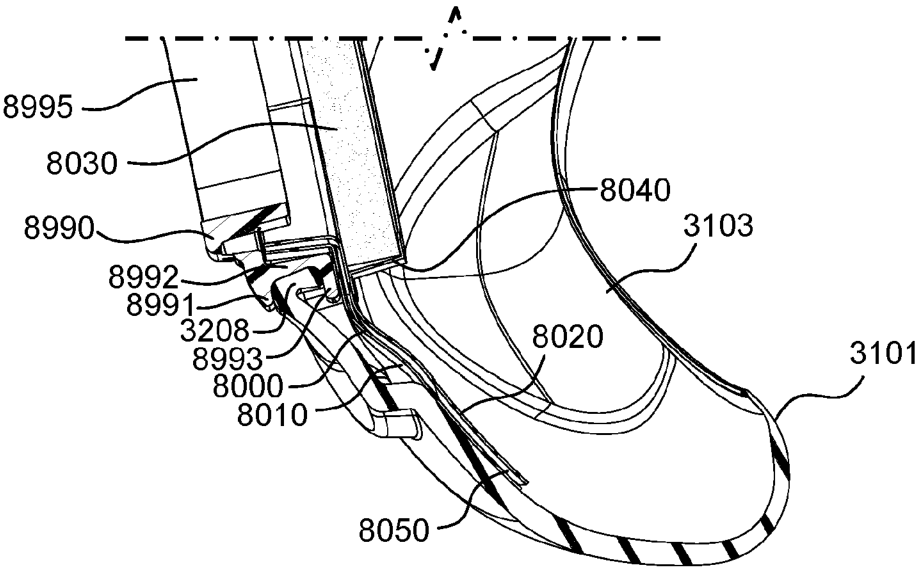

FIG. 44G shows a detailed cross-sectional view of a patient interface with an HMX and flow director assembly taken through line 44G-44G of FIG. 44E according to an example of the present technology.

Figure 44H:
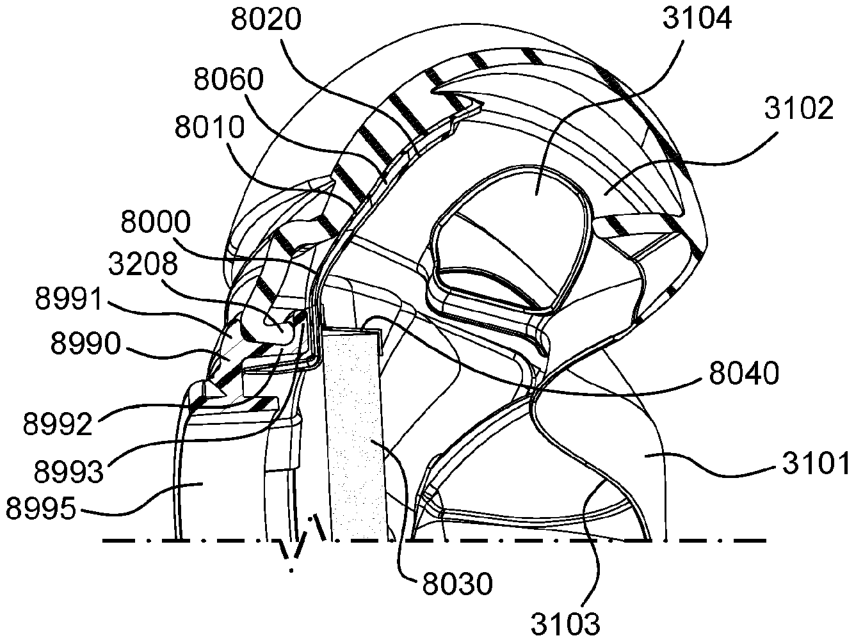

FIG. 44H shows a detailed cross-sectional view of a patient interface with an HMX and flow director assembly taken through line 44H-44H of FIG. 44E according to an example of the present technology.

Figure 44I:
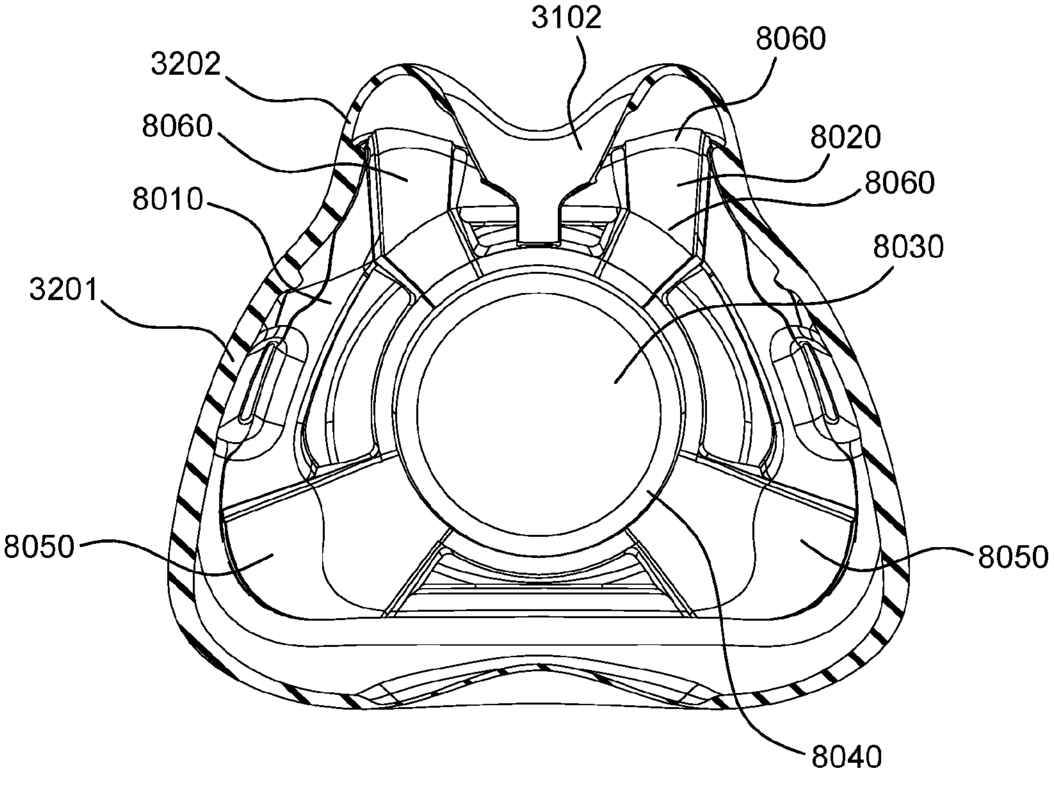

FIG. 44I shows a cross-sectional view of a patient interface with an HMX and flow director assembly taken through line 44I-44I of FIG. 44D according to an example of the present technology.

Figure 44J:
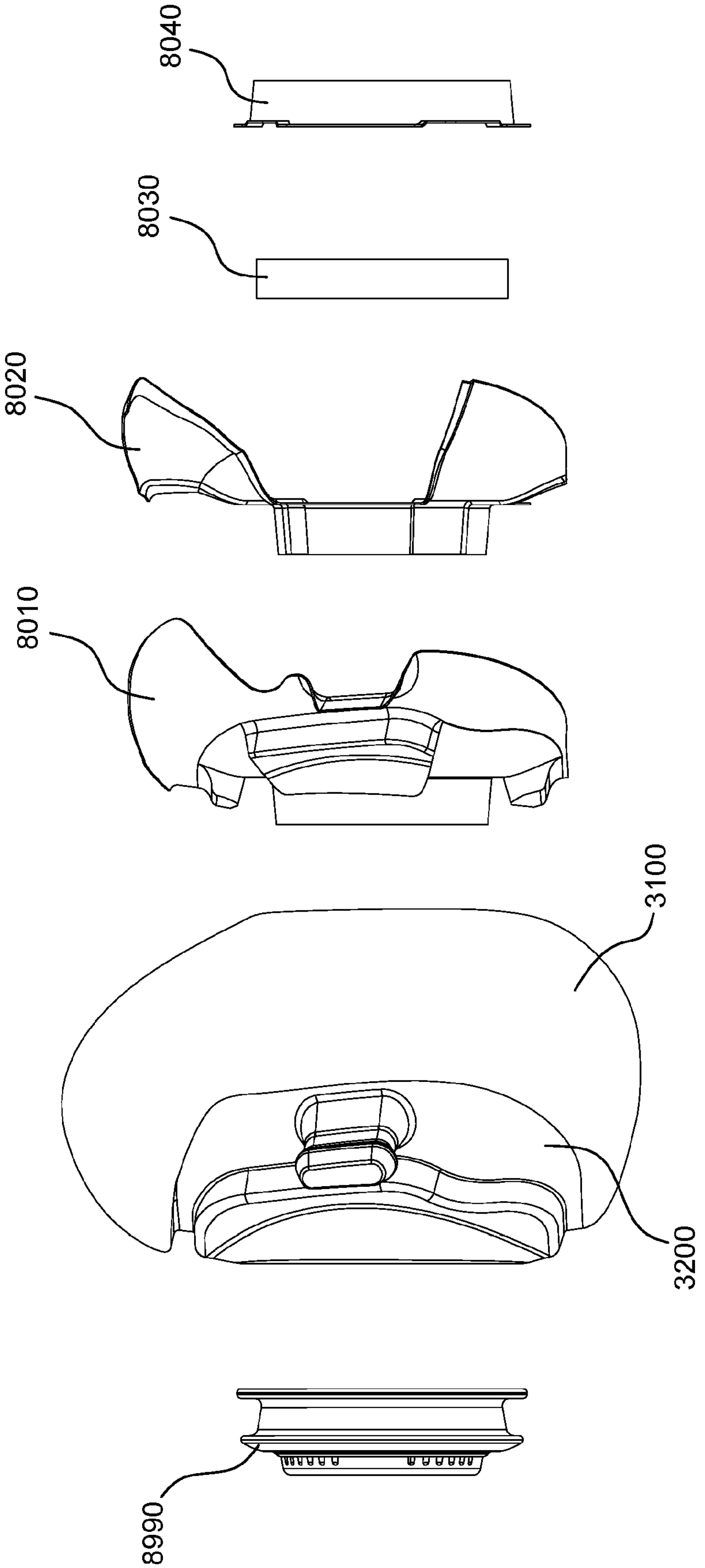

FIG. 44J shows an exploded view of a patient interface with an HMX and flow director assembly according to an example of the present technology.

Figure 45A:
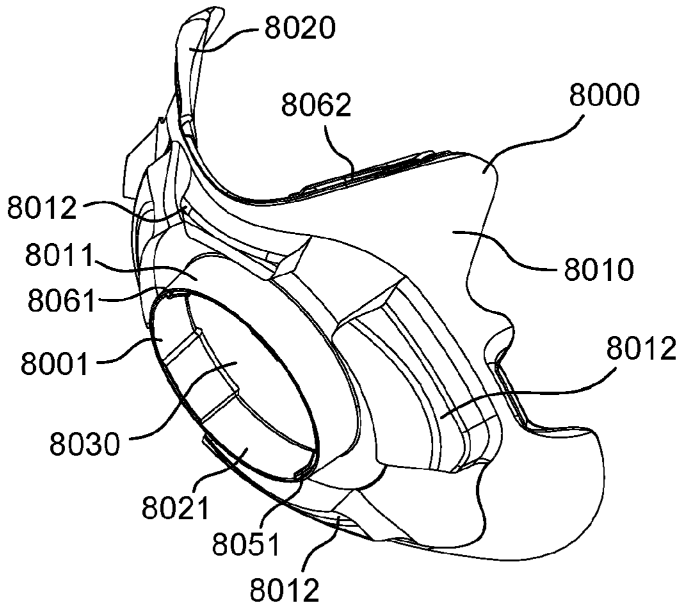

FIG. 45A shows a perspective view of an HMX and flow director assembly according to an example of the present technology.

Figure 45B:
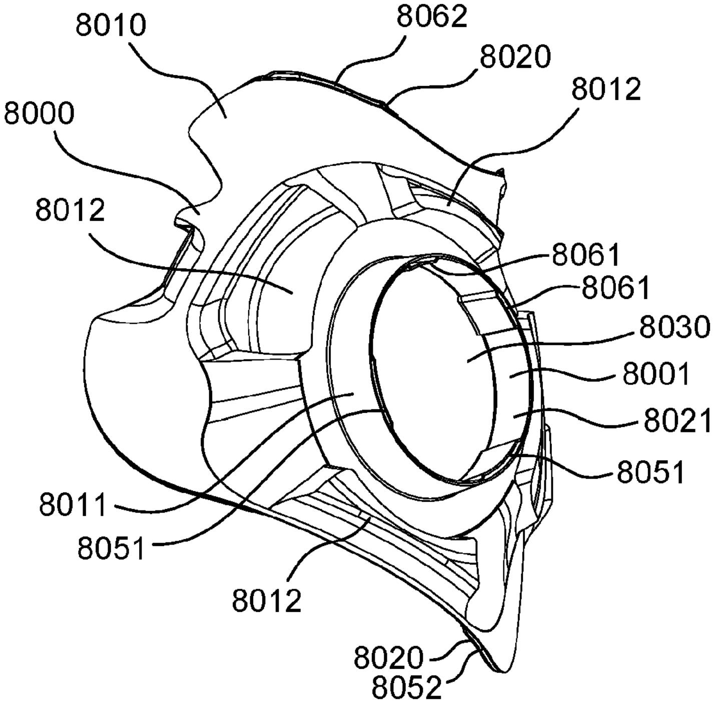

FIG. 45B shows another perspective view of an HMX and flow director assembly according to an example of the present technology.

Figure 45C:
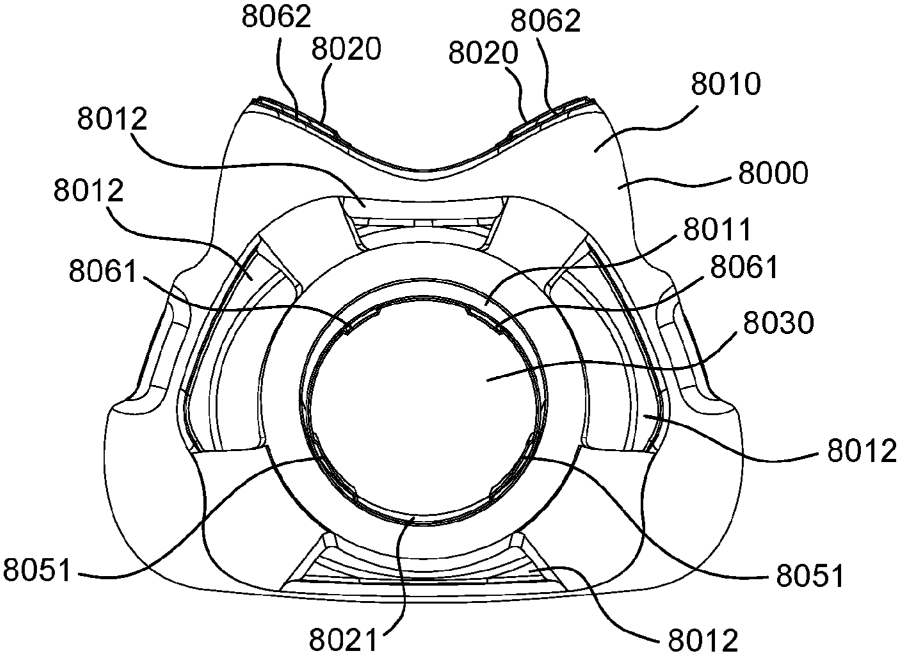

FIG. 45C shows an anterior view of an HMX and flow director assembly according to an example of the present technology.

Figure 45D:
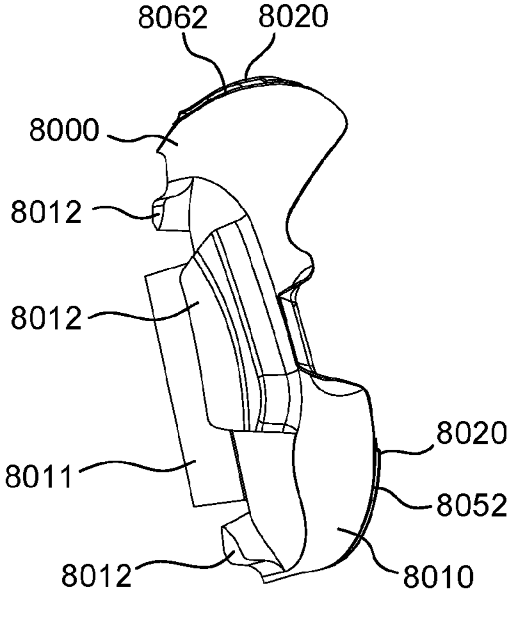

FIG. 45D shows a lateral view of an HMX and flow director assembly according to an example of the present technology.

Figure 45E:
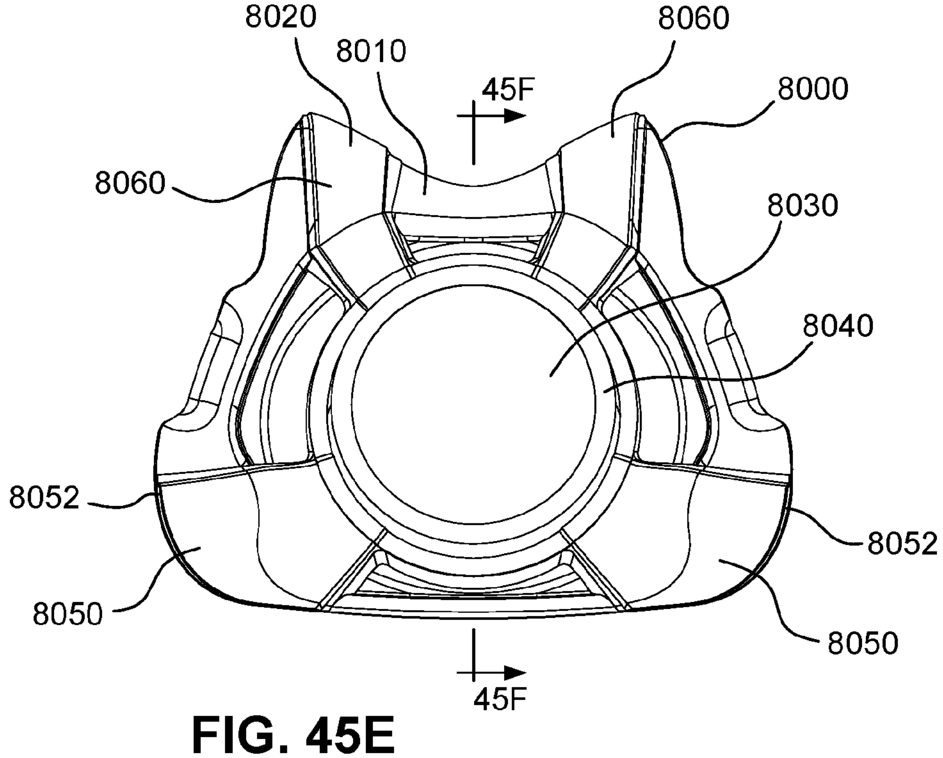

FIG. 45E shows a posterior view of an HMX and flow director assembly according to an example of the present technology.

Figure 45F:
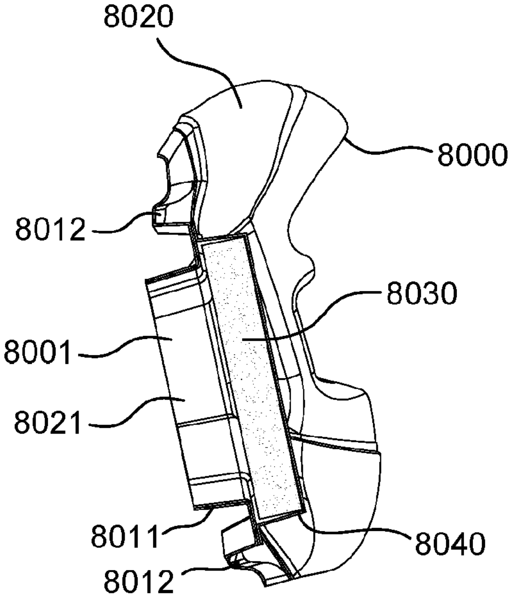

FIG. 45F shows a cross-sectional view of an HMX and flow director assembly taken through line 45F-45F of FIG. 45E according to an example of the present technology.

Figure 45G:
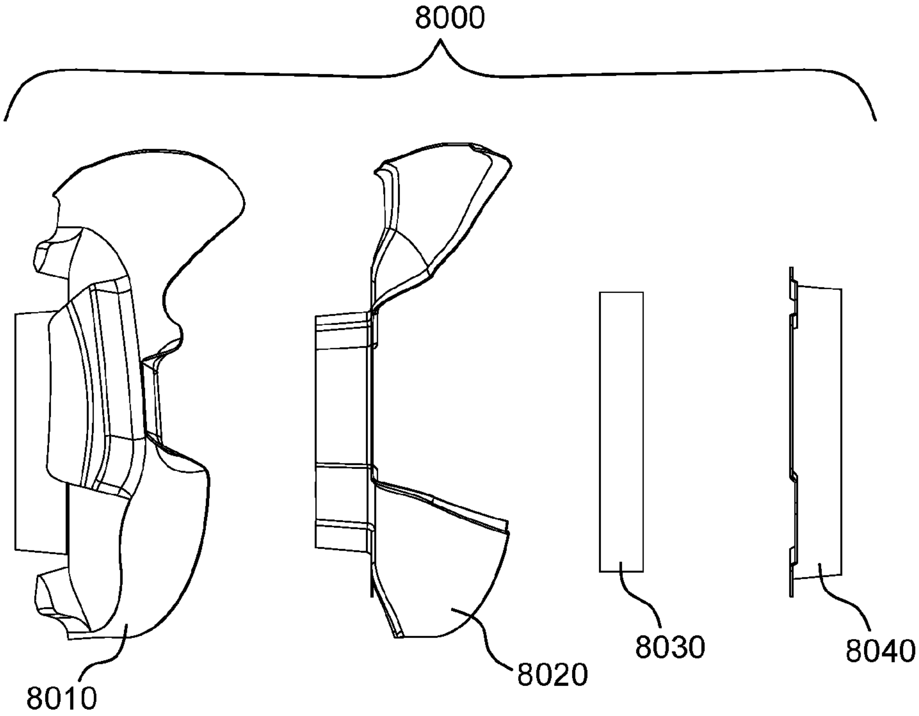

FIG. 45G shows an exploded view of an HMX and flow director assembly according to an example of the present technology.

Figure 46A:
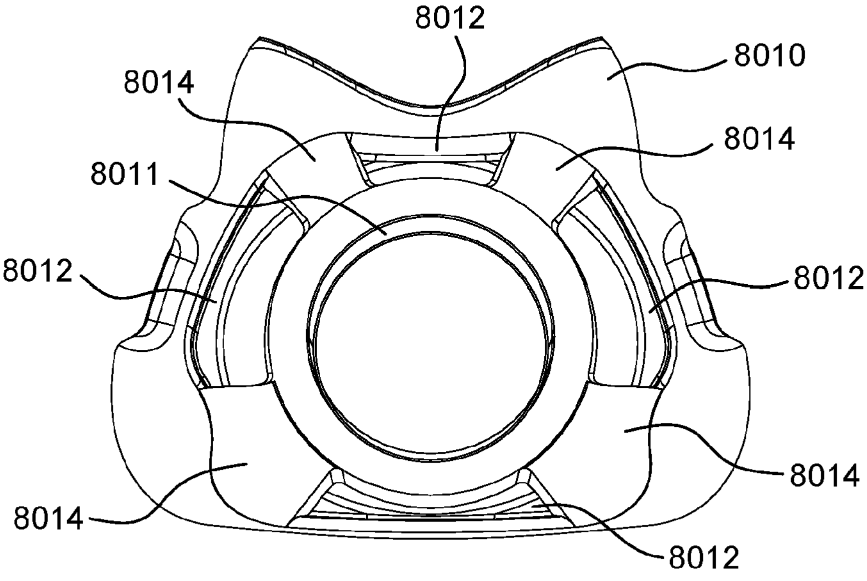

FIG. 46A shows an anterior view of an anterior shell of an HMX and flow director assembly according to an example of the present technology.

Figure 46B:
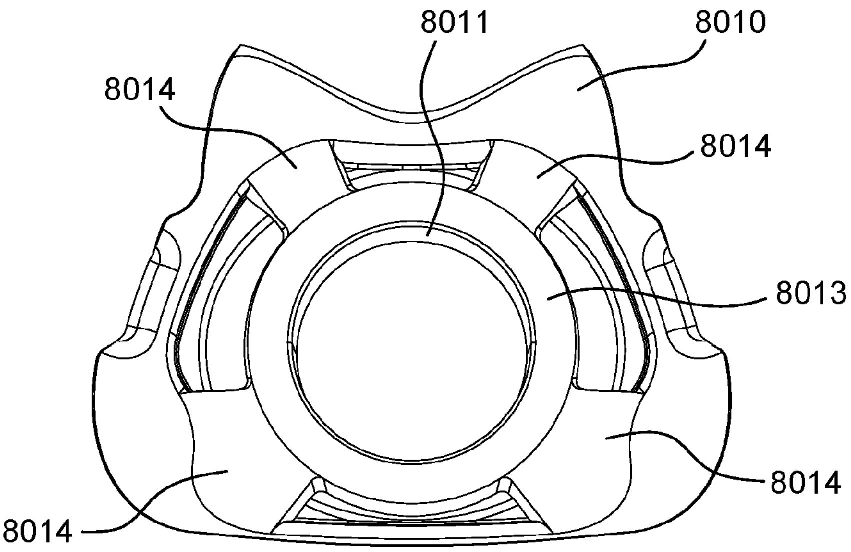

FIG. 46B shows a posterior view of an anterior shell of an HMX and flow director assembly according to an example of the present technology.

Figure 46C:
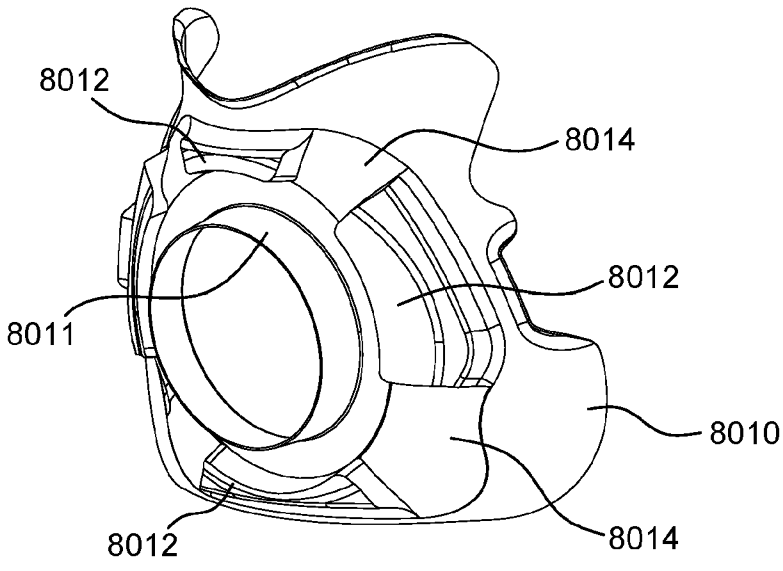

FIG. 46C shows a perspective view of an anterior shell of an HMX and flow director assembly according to an example of the present technology.

Figure 46D:
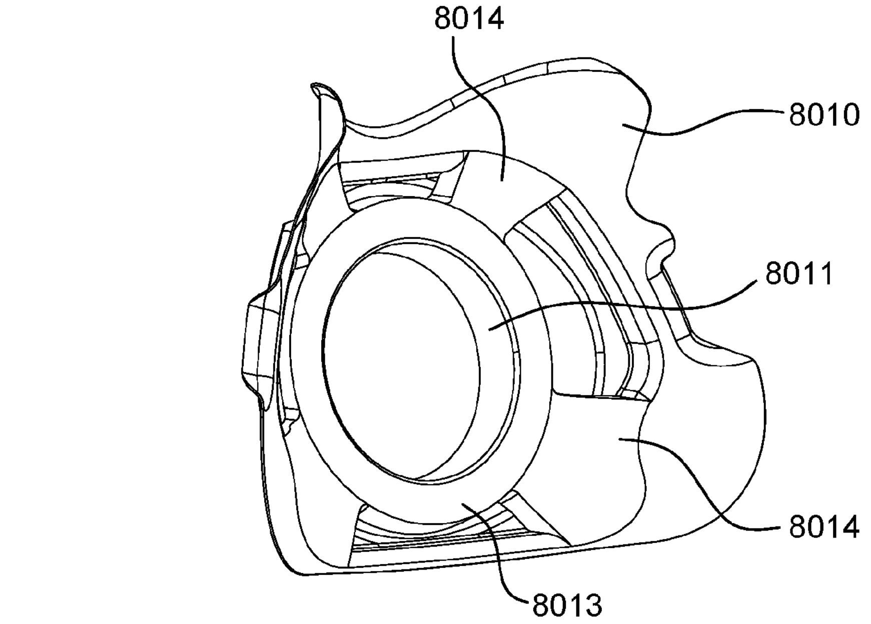

FIG. 46D shows another perspective view of an anterior shell of an HMX and flow director assembly according to an example of the present technology.

Figure 47A:
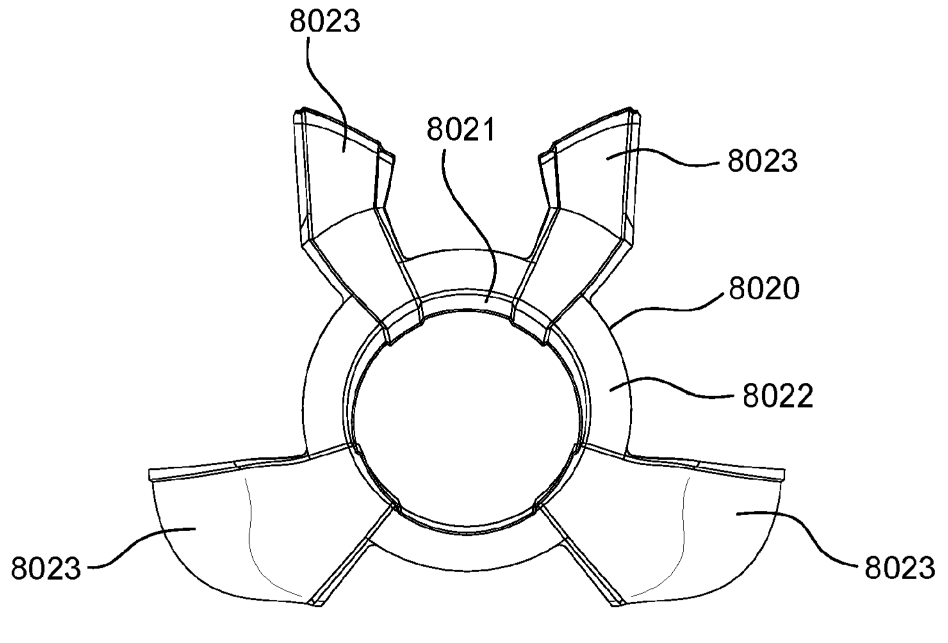

FIG. 47A shows an anterior view of a posterior shell of an HMX and flow director assembly according to an example of the present technology.

Figure 47B:
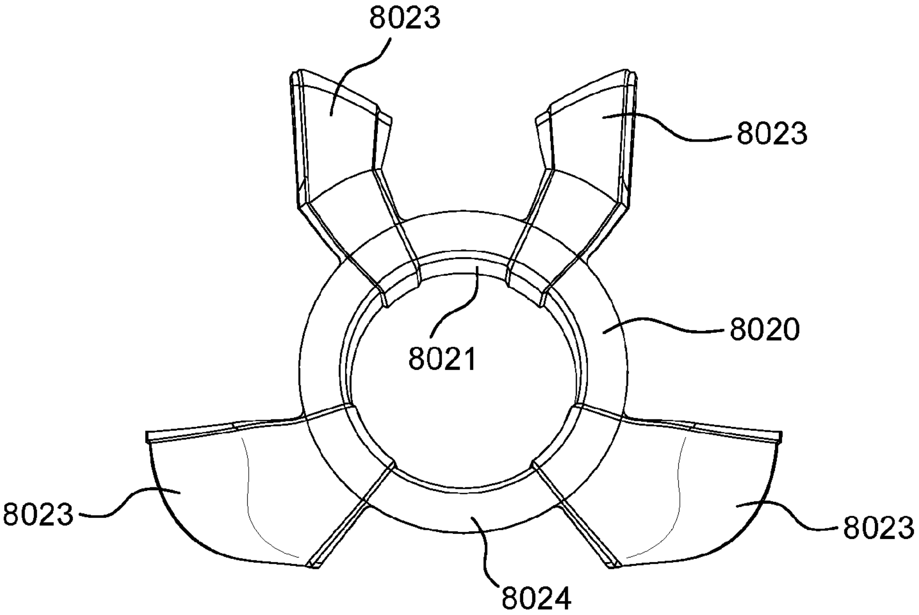

FIG. 47B shows a posterior view of a posterior shell of an HMX and flow director assembly according to an example of the present technology.

Figure 47C:
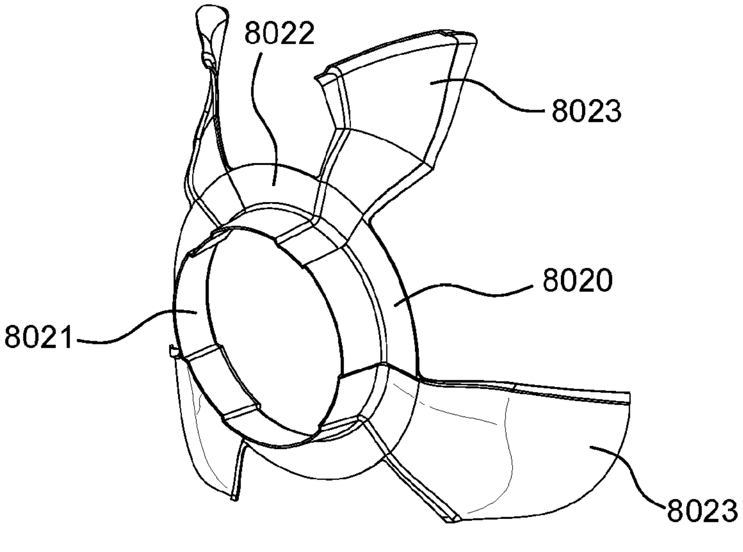

FIG. 47C shows a perspective view of a posterior shell of an HMX and flow director assembly according to an example of the present technology.

Figure 47D:
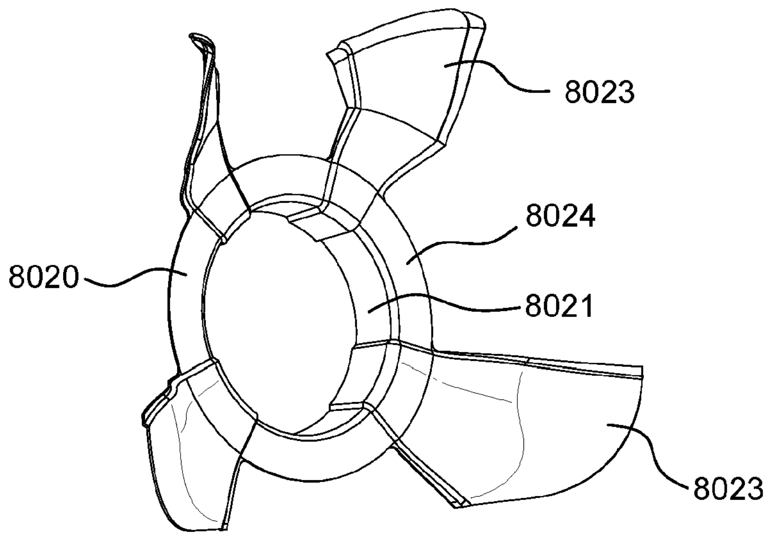

FIG. 47D shows another perspective view of a posterior shell of an HMX and flow director assembly according to an example of the present technology.

Figure 48A:
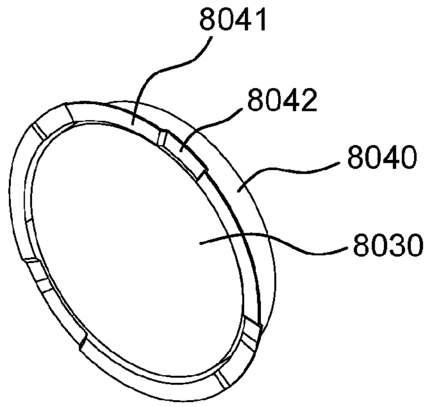

FIG. 48A shows a perspective view of a retainer and HMX material of an HMX and flow director assembly according to an example of the present technology.

Figure 48B:
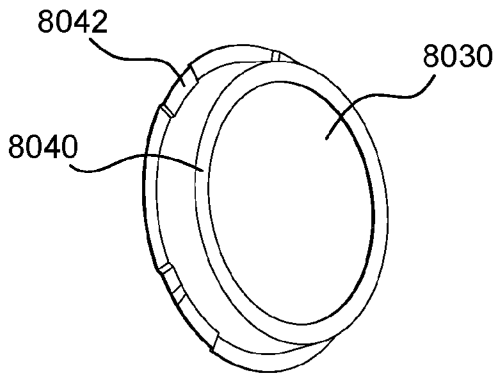

FIG. 48B shows a perspective view of a retainer and HMX material of an HMX and flow director assembly according to an example of the present technology.

5 DETAILED DESCRIPTION OF EXAMPLES OF THE TECHNOLOGY

Before the present technology is described in further detail, it is to be understood that the technology is not limited to the particular examples described herein, which may vary. It is also to be understood that the terminology used in this disclosure is for the purpose of describing only the particular examples discussed herein, and is not intended to be limiting.

The following description is provided in relation to various examples which may share one or more common characteristics and/or features. It is to be understood that one or more features of any one example may be combinable with one or more features of another example or other examples. In addition, any single feature or combination of features in any of the examples may constitute a further example.

5.1 Therapy

In one form, the present technology comprises a method for treating a respiratory disorder comprising applying positive pressure to the entrance of the airways of a patient 1000.

In certain examples of the present technology, a supply of air at positive pressure is provided to the nasal passages of the patient via one or both nares.

In certain examples of the present technology, mouth breathing is limited, restricted or prevented.

5.2 Respiratory Therapy Systems

In one form, the present technology comprises a respiratory therapy system for treating a respiratory disorder. The respiratory therapy system may comprise an RPT device 4000 for supplying a flow of air to the patient 1000 via an air circuit 4170 and a patient interface 3000.

5.3 Patient Interface

A non-invasive patient interface 3000 in accordance with one aspect of the present technology comprises the following functional aspects: a seal-forming structure 3100, a plenum chamber 3200, a positioning and stabilising structure 3300, a vent 3400, one form of connection port 3600 for connection to air circuit 4170, and a forehead support 3700. In some forms a functional aspect may be provided by one or more physical components. In some forms, one physical component may provide one or more functional aspects. In use the seal-forming structure 3100 is arranged to surround an entrance to the airways of the patient so as to maintain positive pressure at the entrance(s) to the airways of the patient 1000. The sealed patient interface 3000 is therefore suitable for delivery of positive pressure therapy.

If a patient interface is unable to comfortably deliver a minimum level of positive pressure to the airways, the patient interface may be unsuitable for respiratory pressure therapy.

The patient interface 3000 in accordance with one form of the present technology is constructed and arranged to be able to provide a supply of air at a positive pressure of at least 6 cmH2O with respect to ambient.

The patient interface 3000 in accordance with one form of the present technology is constructed and arranged to be able to provide a supply of air at a positive pressure of at least 10 cmH2O with respect to ambient.

The patient interface 3000 in accordance with one form of the present technology is constructed and arranged to be able to provide a supply of air at a positive pressure of at least 20 cmH2O with respect to ambient.

5.3.1 Seal-Forming Structure

In one form of the present technology, a seal-forming structure 3100 provides a target seal-forming region, and may additionally provide a cushioning function. The target seal-forming region is a region on the seal-forming structure 3100 where sealing may occur. The region where sealing actually occurs—the actual sealing surface—may change within a given treatment session, from day to day, and from patient to patient, depending on a range of factors including for example, where the patient interface was placed on the face, tension in the positioning and stabilising structure and the shape of a patient's face.

As is described in greater detail below, in certain forms of the invention the seal forming structure 3100 comprises a first seal forming structure 3101 connected to an oral portion 3201 of the plenum chamber and constructed and arranged to form seal with a region of the patient's face surrounding an entrance to the patient's mouth, and a second seal-forming structure 3102 connected to a nasal portion 3202 of the plenum chamber 3200 constructed and arranged to form a seal with a region of the patient's face surrounding an entrance to the patient's nose. The phrase "connected to" is used herein to refer to portions or components which are formed as a single piece as well as to portions or components which are formed separately and subsequently joined together. In some cases components may be connected by an intermediate component.

In certain forms, the first seal forming structure 3101 seals independently against the patient's face than the second seal forming structure 3102.

In certain forms, the first seal forming structure 3101 and the second seal forming structure 3102 cooperate to form a single common seal against the patient's face.

In one form the target seal-forming region is located on an outside surface of the seal-forming structure 3100.

In certain forms of the present technology, the seal-forming structure 3100 is constructed from a biocompatible material, e.g. silicone rubber.

A seal-forming structure 3100 in accordance with the present technology may be constructed from a soft, flexible, resilient material such as silicone.

In certain forms of the present technology, a system is provided comprising more than one a seal-forming structure 3100, each being configured to correspond to a different size and/or shape range. For example the system may comprise one form of a seal-forming structure 3100 suitable for a large sized head, but not a small sized head and another suitable for a small sized head, but not a large sized head.

5.3.1.1 Sealing Mechanisms

In one form, the seal-forming structure includes a sealing flange utilizing a pressure assisted sealing mechanism. In use, the sealing flange can readily respond to a system positive pressure in the interior of the plenum chamber 3200 acting on its underside to urge it into tight sealing engagement with the face. The pressure assisted mechanism may act in conjunction with elastic tension in the positioning and stabilising structure.

In one form, the seal-forming structure 3100 comprises a sealing flange and a support flange. The sealing flange comprises a relatively thin member with a thickness of less than about 1 mm, for example about 0.25 mm to about 0.45 mm, which extends around the perimeter of the plenum chamber 3200. Support flange may be relatively thicker than the sealing flange. The support flange is disposed between the sealing flange and the marginal edge of the plenum chamber 3200, and extends at least part of the way around the perimeter. The support flange is or includes a spring-like element and functions to support the sealing flange from buckling in use.

In one form, the seal-forming structure may comprise a compression sealing portion or a gasket sealing portion. In use the compression sealing portion, or the gasket sealing portion is constructed and arranged to be in compression, e.g. as a result of elastic tension in the positioning and stabilising structure.

In one form, the seal-forming structure comprises a tension portion. In use, the tension portion is held in tension, e.g. by adjacent regions of the sealing flange.

In one form, the seal-forming structure comprises a region having a tacky or adhesive surface.

In certain forms of the present technology, a seal-forming structure may comprise one or more of a pressure-assisted sealing flange, a compression sealing portion, a gasket sealing portion, a tension portion, and a portion having a tacky or adhesive surface.

5.3.1.2 Nose Bridge or Nose Ridge Region

In one form, the non-invasive patient interface 3000 comprises a seal-forming structure that forms a seal in use on a nose bridge region or on a nose-ridge region of the patient's face.

In one form, the seal-forming structure includes a saddle-shaped region constructed to form a seal in use on a nose bridge region or on a nose-ridge region of the patient's face.

5.3.1.3 Upper Lip Region

In one form, the non-invasive patient interface 3000 comprises a seal-forming structure that forms a seal in use on an upper lip region (that is, the lip superior) of the patient's face.

In one form, the seal-forming structure includes a saddle-shaped region constructed to form a seal in use on an upper lip region of the patient's face.

5.3.1.4 Chin-Region

In one form the non-invasive patient interface 3000 comprises a seal-forming structure that forms a seal in use on a chin-region of the patient's face.

In one form, the seal-forming structure includes a saddle-shaped region constructed to form a seal in use on a chin-region of the patient's face.

5.3.1.5 Forehead Region

In one form, the seal-forming structure that forms a seal in use on a forehead region of the patient's face. In such a form, the plenum chamber may cover the eyes in use.

5.3.1.6 Nasal Pillows

In one form the seal-forming structure of the non-invasive patient interface 3000 comprises a pair of nasal puffs, or nasal pillows, each nasal puff or nasal pillow being constructed and arranged to form a seal with a respective naris of the nose of a patient.

Nasal pillows in accordance with an aspect of the present technology include: a frusto-cone, at least a portion of which forms a seal on an underside of the patient's nose, a stalk, a flexible region on the underside of the frusto-cone and connecting the frusto-cone to the stalk. In addition, the structure to which the nasal pillow of the present technology is connected includes a flexible region adjacent the base of the stalk. The flexible regions can act in concert to facilitate a universal joint structure that is accommodating of relative movement both displacement and angular of the frusto-cone and the structure to which the nasal pillow is connected. For example, the frusto-cone may be axially displaced towards the structure to which the stalk is connected.

5.3.2 Plenum Chamber

The plenum chamber 3200 has a perimeter that is shaped to be complementary to the surface contour of the face of an average person in the region where a seal will form in use. In use, a marginal edge of the plenum chamber 3200 is positioned in close proximity to an adjacent surface of the face. Actual contact with the face is provided by the seal-forming structure 3100. The seal-forming structure 3100 may extend in use about the entire perimeter of the plenum chamber 3200. In some forms, the plenum chamber 3200 and the seal-forming structure 3100 are formed from a single homogeneous piece of material.

In certain forms of the present technology, the plenum chamber 3200 does not cover the eyes of the patient in use. In other words, the eyes are outside the pressurised volume defined by the plenum chamber. Such forms tend to be less obtrusive and/or more comfortable for the wearer, which can improve compliance with therapy.

In certain forms of the present technology, the plenum chamber 3200 is constructed from a transparent material, e.g. a transparent polycarbonate. The use of a transparent material can reduce the obtrusiveness of the patient interface, and help improve compliance with therapy. The use of a transparent material can aid a clinician to observe how the patient interface is located and functioning.

In certain forms of the present technology, the plenum chamber 3200 is constructed from a translucent material. The use of a translucent material can reduce the obtrusiveness of the patient interface, and help improve compliance with therapy.

5.3.3 Positioning and Stabilising Structure

The seal-forming structure 3100 of the patient interface 3000 of the present technology may be held in sealing position in use by the positioning and stabilising structure 3300.

In one form the positioning and stabilising structure 3300 provides a retention force at least sufficient to overcome the effect of the positive pressure in the plenum chamber 3200 to lift off the face.

In one form the positioning and stabilising structure 3300 provides a retention force to overcome the effect of the gravitational force on the patient interface 3000.

In one form the positioning and stabilising structure 3300 provides a retention force as a safety margin to overcome the potential effect of disrupting forces on the patient interface 3000, such as from tube drag, or accidental interference with the patient interface.

In one form of the present technology, a positioning and stabilising structure 3300 is provided that is configured in a manner consistent with being worn by a patient while sleeping. In one example the positioning and stabilising structure 3300 has a low profile, or cross-sectional thickness, to reduce the perceived or actual bulk of the apparatus. In one example, the positioning and stabilising structure 3300 comprises at least one strap having a rectangular cross-section. In one example the positioning and stabilising structure 3300 comprises at least one flat strap.

In one form of the present technology, a positioning and stabilising structure 3300 is provided that is configured so as not to be too large and bulky to prevent the patient from lying in a supine sleeping position with a back region of the patient's head on a pillow.

In one form of the present technology, a positioning and stabilising structure 3300 is provided that is configured so as not to be too large and bulky to prevent the patient from lying in a side sleeping position with a side region of the patient's head on a pillow.

In one form of the present technology, a positioning and stabilising structure 3300 is provided with a decoupling portion located between an anterior portion of the positioning and stabilising structure 3300, and a posterior portion of the positioning and stabilising structure 3300. The decoupling portion does not resist compression and may be, e.g. a flexible or floppy strap. The decoupling portion is constructed and arranged so that when the patient lies with their head on a pillow, the presence of the decoupling portion prevents a force on the posterior portion from being transmitted along the positioning and stabilising structure 3300 and disrupting the seal.

In one form of the present technology, a positioning and stabilising structure 3300 comprises a strap constructed from a laminate of a fabric patient-contacting layer, a foam inner layer and a fabric outer layer. In one form, the foam is porous to allow moisture, (e.g., sweat), to pass through the strap. In one form, the fabric outer layer comprises loop material to engage with a hook material portion.

In certain forms of the present technology, a positioning and stabilising structure 3300 comprises a strap that is extensible, e.g. resiliently extensible. For example the strap may be configured in use to be in tension, and to direct a force to draw a seal-forming structure into sealing contact with a portion of a patient's face. In an example the strap may be configured as a tie.

In one form of the present technology, the positioning and stabilising structure comprises a first tie, the first tie being constructed and arranged so that in use at least a portion of an inferior edge thereof passes superior to an otobasion superior of the patient's head and overlays a portion of a parietal bone without overlaying the occipital bone.

In one form of the present technology suitable for a nasal-only mask or for a full-face mask, the positioning and stabilising structure includes a second tie, the second tie being constructed and arranged so that in use at least a portion of a superior edge thereof passes inferior to an otobasion inferior of the patient's head and overlays or lies inferior to the occipital bone of the patient's head.

In one form of the present technology suitable for a nasal-only mask or for a full-face mask, the positioning and stabilising structure includes a third tie that is constructed and arranged to interconnect the first tie and the second tie to reduce a tendency of the first tie and the second tie to move apart from one another.

In certain forms of the present technology, a positioning and stabilising structure 3300 comprises a strap that is bendable and e.g. non-rigid. An advantage of this aspect is that the strap is more comfortable for a patient to lie upon while the patient is sleeping.

In certain forms of the present technology, a positioning and stabilising structure 3300 comprises a strap constructed to be breathable to allow moisture vapour to be transmitted through the strap, In certain forms of the present technology, a system is provided comprising more than one positioning and stabilizing structure 3300, each being configured to provide a retaining force to correspond to a different size and/or shape range. For example the system may comprise one form of positioning and stabilizing structure 3300 suitable for a large sized head, but not a small sized head, and another. suitable for a small sized head, but not a large sized head.

FIGS. 21 and 22 show embodiments which are provided with connectors 3310, e.g. magnetic connectors, for connection to a positioning and stabilising structure.

In certain forms, the frame 3350 includes two secondary connection points 3364. The secondary connection points 3364 may be inferior to the loops 3352 while the patient interface 3000 is worn by the patient. The headgear straps 3354 may further include a left inferior headgear straps 3366 and a right inferior headgear strap 3368, each configured to couple to the respective secondary connection points 3364. The headgear straps 3354 as a whole may then be able to provide a force to the superior and inferior regions of the seal-forming structure 3100 and/or the plenum chamber 3200.

In certain forms, the secondary connection points 3364 are formed directly on the central portion 3360. The secondary connection points 3364 may be more anterior than the loops 3352 while the patient interface 3000 is worn by the patient.

In certain forms, the secondary connection points 3364 may be constructed from a single component, which may assist in reducing tooling and/or manufacturing costs.

In certain forms, the left and/or right inferior headgear straps 3366, 3368 are removably coupled to the respective secondary connection points 3364. The secondary connection points 3364 may be magnetic, and a left and/or right inferior headgear straps 3366, 3368 may be threaded through a clip 3370 with an opposite polarity as the secondary connection points 3364. The length of the left and/or right inferior headgear straps 3366, 3368 may be adjusted by folding the respective strap 3366, 3368 on itself (e.g., as done with the left and/or right superior headgear straps 3356, 3358). Each clip 3370 may be removed from the respective secondary connection point 3364, without changing the length adjustment of the left and/or right inferior headgear straps 3366, 3368. A patient may be able to don and/or doff the patient interface 3000 while only removing the clip 3370 from the respective secondary connection points 3364 (e.g., without having to remove the left and/or right superior headgear straps 3356, 3358 from the respective loops 3352).

5.3.3.1 Frame

As shown in FIGS. 23 to 28-2, a frame 3350 is coupled to the plenum chamber 3200 and assists in maintaining the therapeutically effective position of the seal-forming structure 3100. The plenum chambers 3200 illustrated in FIGS. 23 to 28-2 specifically illustrate an elbow 3500 connected in front of the patient's face, although the frame may be used with other styles of plenum chambers 3200 (e.g., plenum chambers 3200 of FIGS. 21-22 used with conduit headgear).

In some forms, the frame 3350 is constructed from a rigid or semi-rigid material, and provides support to the seal-forming structure 3100 and/or the plenum chamber 3200. For example, the frame 3350 may assist in maintaining the shape of the seal-forming structure 3100 and/or the plenum chamber 3200 in order to reduce leaks of pressurized air as a result of folding and/or creasing as the seal-forming structure 3100 engages the patient's face.

In some forms, the frame 3350 provides at least one loop 3352, which may assist in indirectly connecting the headgear straps 3354 to the plenum chamber 3200 and/or seal-forming structure 3100. The loop 3352 (e.g., with a fully formed perimeter) may receive a portion of the headgear straps 3354. For example, a length of a left superior headgear strap 3356 may be threaded through one of the loops 3352, and pulled away from the plenum chamber 3200 in order to apply tension through the left superior headgear strap 3356. The left superior headgear strap 3356 may be folded against itself and retained in the selected length (e.g., using Velcro, magnets, adhesives, etc.) in order to maintain the applied tension. Similar steps may be performed regarding adjusting the tension in the right superior headgear strap 3358 in a corresponding loop 3352.

In some forms, each loop 3352 may be oriented so that a force vector applied by the respective superior headgear strap 3356, 3358 is substantially perpendicular to a loop inner surface, against which the superior headgear straps 3356, 3358 contact. As shown in FIG. 23, the right superior headgear strap 3358 engages the corresponding loop 3352 in substantially the center of the loop inner surface. When the right superior headgear strap 3358 is tightened, the force vector is applied in a substantially straight direction, and not oblique relative to the loop inner surface. This may improve the sealing of the seal-forming structure 3100, as the forces are directed along the arms 3362, and not oblique relative to the arms 3362, which may require the superior headgear straps 3356, 3358 to be further tightened to receive the same sealing effects (e.g., at the detriment to patient comfort), and/or may prevent the seal-forming structure 3100 from properly engaging the patient's face (e.g., leading to leaks).

Returning to FIGS. 26 to 26-2, the plenum chamber 3200 may include projections 3284 on the oral portion 3201. The projections may be elongated, and may have a similar shape to the slots 3372 (e.g., tapered). The projections 3284 may be disposed within the groove 3280 so that they cooperate with the frame 3350 during assembly.

5.3.4 Vent

In one form, the patient interface 3000 includes a vent 3400 constructed and arranged to allow for the washout of exhaled gases, e.g. carbon dioxide.

In certain forms the vent 3400 is configured to allow a continuous vent flow from an interior of the plenum chamber 3200 to ambient whilst the pressure within the plenum chamber is positive with respect to ambient. The vent 3400 is configured such that the vent flow rate has a magnitude sufficient to reduce rebreathing of exhaled CO2 by the patient while maintaining the therapeutic pressure in the plenum chamber in use.

One form of vent 3400 in accordance with the present technology comprises a plurality of holes, for example, about 20 to about 80 holes, or about 40 to about 60 holes, or about 45 to about 55 holes.

The vent 3400 may be located in the plenum chamber 3200. Alternatively, the vent 3400 is located in a decoupling structure, e.g., a swivel.

5.3.5 Decoupling Structure(s)

In one form the patient interface 3000 includes at least one decoupling structure, for example, a swivel or a ball and socket.

5.3.6 Connection Port

Connection port 3600 allows for connection to the air circuit 4170.

5.3.7 Forehead Support

In one form, the patient interface 3000 includes a forehead support 3700. Alternatively, the patient interface 3000 may not include a forehead support 3700.

5.3.8 Anti-Asphyxia Valve

In one form, the patient interface 3000 includes an anti-asphyxia valve.

5.3.9 Heat and Moisture Exchanger (HMX), Vent, and Conduit Connector

The present technology includes assemblies of a vent, a heat and moisture exchanger (HMX) material, a frame, and a conduit connector. FIGS. 8A-8C to show examples of a seal-forming structure 3100 and a plenum chamber 3200 to which the assemblies described below may be connected. Furthermore, the assemblies may be connected to the plenum chamber 3200 of a patient interface 3000 of FIGS. 7A-7C in place of the elbow 3500 or an elbow 3500 or a the cuff of an air circuit 4170 may be connected to one of the assemblies to connect the air circuit 4170 to the patient interface 3000. As will be explained below, a heat and moisture exchanger (HMX) material 3900 may be positioned inside of the assemblies to adsorb and desorb moisture in air traveling to and from the plenum chamber 3200. The HMX material 3900 may allow the patient interface 3000 to be used in a respiratory pressure therapy system with an RPT device 4000, as described below, but without a humidifier 5000. In these examples, a portion of the patient's exhaled gases may be diverted around the HMX material 3900 to atmosphere without passing through the HMX material 3900. That flow of exhaled gases bypassing the HMX material 3900 may pass through vent holes positioned radially around the assembly that holds the HMX material 3900. Such radial venting may diffuse the flow to reduce jetting, noise, and possible disruptions of the patient and any bed partner.

5.3.9.1 HMX Material Outside of Plenum Chamber

FIGS. 9A-16B and FIGS. 17A-21B show two examples of patient interfaces in which the heat and moisture exchanger material 3900 is positioned outside of the plenum chamber 3200 when the respective assemblies are connected to the plenum chamber 3200. The plenum chamber 3200 may include a lip 3208 that forms a plenum chamber hole 3206 on an anterior side of the plenum chamber 3200.

In the example of FIGS. 9A-16B, a frame assembly 3910 includes a heat and moisture exchanger (HMX) frame 3930 that includes an anterior HMX frame 3931 and a posterior HMX frame 3940 that may be releasably connected together. The posterior HMX frame 3940 may include one or more radial lip retainers 3941 that form a lip retaining channel 3942 to receive the lip 3208 to connect the frame assembly 3910 to the plenum chamber 3200. The radial lip retainers 3941 may extend radially from the posterior HMX frame 3940.

In the example of FIGS. 17A-21B, the frame assembly 3910 may include an anterior HMX frame 3970 and a posterior flow directing frame 3960 that may be releasably connected together. The anterior HMX frame 3970 may include an anterior annular rim 3971 and a posterior annular rim 3973 that form an annular channel 3972 to receive the lip 3208 to connect the frame assembly 3910 to the plenum chamber 3200. The posterior flow directing frame 3960 may also include one or more connection tabs 3963 to releasably connect the posterior flow directing frame 3960 to the anterior HMX frame 3970. Each of the connection tabs 3963 may extend in an axial direction to engage an interior surface of the anterior HMX frame 3970.

In both examples, the frame assembly 3910, including the posterior HMX frame 3940 and the anterior HMX frame 3970, may be formed from a relatively rigid material such as plastic, while at least the lip 3208 is formed from relatively flexible material such as silicone.

FIGS. 9H and 9J also show that when the posterior HMX frame 3940 is connected to the plenum chamber 3200, a portion of the posterior HMX frame 3940 may be positioned within the plenum chamber 3200. Also, the posterior flow directing structure 3920 may be positioned within the plenum chamber 3200.

FIGS. 17H and 17J also show that when the anterior HMX frame 3970 is connected to the plenum chamber 3200, a portion of the anterior HMX frame 3970 may be positioned within the plenum chamber 3200. Also, the posterior flow directing frame 3960 may be positioned within the plenum chamber 3200.

5.3.9.1.1 Bypass Flow Direction

In the example of FIGS. 9A-16B, the frame assembly 3910 may include a posterior flow directing structure 3920 having one or more flow directing tabs 3923 and one or more connection tabs 3921 to releasably connect the posterior flow directing structure 3920 to the posterior HMX frame 3940. Each of the connection tabs 3921 may include a notch 3922 to facilitate alignment of the connection tabs 3921 to the posterior HMX frame 3940. The posterior HMX frame 3940 may include one or more axial flow directing walls 3951 and two or more radial flow directing walls 3952. When the posterior flow directing structure 3920 is releasably connected to the posterior HMX frame 3940, The flow directing tabs 3923, the axial flow directing walls 3951, and the radial flow directing walls 3950 may form flow directing channels to direct gas into and out of the cavity of the plenum chamber 3200 without passing through the heat and moisture exchanger material 3900. In the cross-sectional views of FIGS. 9H and 9J, the HMX bypass vent flow path 7002 can be seen passing radially outward to atmosphere via the radial vent holes 3945 without passing through the HMX material 3900.

In the example of FIGS. 17A-21B, the posterior flow directing frame 3960 may include one or more flow directors 3961 extending radially therefrom. Each of the flow directors 3961 may form a flow directing hole 3962 to direct gas into and out of the cavity of the plenum chamber 3200 without passing through the heat and moisture exchanger material 3900. In the cross-sectional views of FIGS. 17H and 17J, the HMX bypass vent flow path 7002 can be seen passing radially outward to atmosphere via the vent holes 3975 without passing through the HMX material 3900.

Additionally, the cross-sectional views of FIGS. 9H and 9J and FIGS. 17H and 17J show that the HMX material 3900 may be spaced away from the conduit connector 3850 in an axial direction. That spacing may allow a portion of the incoming flow of pressurized air 7000 to travel directly to atmosphere via the outer axial vent holes 3852 and the inner axial vent holes 3854, which are described below, without passing through the HMX material 3900 and into the plenum chamber 3200.

Also, in the example of FIGS. 9A-16B, the posterior HMX frame 3940 may include one or more axial spacers 3947 extending axially to contact a posterior surface 3906 of the heat and moisture exchanger material 3900 and form gaps between the posterior HMX frame 3940 and the heat and moisture exchanger material 3900 to allow gases to flow around the heat and moisture exchanger material 3900. The posterior HMX frame 3940 may also include radial spacers 3946 extending radially inward to contact a circumferential surface 3902 of the heat and moisture exchanger material 3900 and form gaps between the posterior HMX frame 3940 and the heat and moisture exchanger material 3900 to allow gases to flow around the heat and moisture exchanger material 3900.

5.3.9.1.2 Conduit Connection and Constant Flow Vent (CFV)

A conduit connector 3850 may be connected to the anterior HMX frame 3931 or the anterior HMX frame 3970 to connect a conduit, such as the air circuit 4170 described elsewhere herein, to the patient interface 3000, as shown in the examples of FIGS. 9A-16B and FIGS. 17A-21B. Although the conduit connector 3850 and the membrane 3840, described below, are not shown in the example of FIGS. 17A-21B, it should be understood that those components may be included, attached, and operate similarly to the description below.

The conduit connector 3850 may include a conduit connection tube 3851 that forms a conduit connector hole. The conduit connector 3850 may be connected to the anterior HMX frame 3931 or the anterior HMX frame 3970 opposite the posterior HMX frame 3940 or the posterior flow directing structure 3920, respectively. The conduit connector 3850 may also include an anti-asphyxia valve, and in further examples the anti-asphyxia valve may be positioned on the conduit connection tube 3851. In further examples, an elbow may be connected to the conduit connection tube 3851, which may be connected to the air circuit 4170, and the elbow may include an anti-asphyxia valve.

As the therapeutic pressure increases within the frame assembly 3910 a membrane 3840 may be urged towards a vent base 3853 of the conduit connector 3850 to at least partially occlude the inner axial vent holes 3854. As the inner axial vent holes 3854 become occluded and flow therethrough reduced, outer axial vent holes 3852 remain completely open, as do the radial vent holes 3834. The progressive occlusion of the inner axial vent holes 3854 by the membrane 3840 may limit the increase of the combined vent flow to atmosphere through the outer axial vent holes 3852, the inner axial vent holes 3854, and the radial vent holes 3945 as the therapeutic pressure increases within the vent and conduit connector assembly 3820. Thus, by occluding the inner axial vent holes 3854, at least partially, as the therapeutic pressure increases, the combined vent flow throughout a range of therapeutic pressures (e.g., from as low as 4 $cmH_2O$ up to 20 $cmH_2O$ or 30 $cmH_2O$), may remain approximately constant.

In the depicted examples, the conduit connector 3850 includes outer axial vent holes 3852 and inner axial vent holes 3854 formed through a vent base 3853. The outer axial vent holes 3852 and the inner axial vent holes 3854 may be positioned radially around the conduit connection tube 3851, with the inner axial vent holes 3854 being radially inward of the outer axial vent holes 3852. The outer axial vent holes 3852 and the inner axial vent holes 3854 may be oriented on the conduit connector 3850 to direct the respective vent flows out of the vent and conduit connector assembly 3820 in an axial direction.

The membrane 3840 may be positioned between the conduit connector 3850 and a cage 3933 positioned within anterior frame 3830. The membrane 3840 may be free to move within the space between the conduit connector 3850 and the cage 3933. The membrane 3840 may be shaped and dimensioned to cover the inner axial vent holes 3854 while leaving the outer axial vent holes 3852 uncovered. The conduit connector 3850 may include one or more cage spacers 3856 and one or more HMX cartridge spacers 3858 that extend from the vent base 3853. The cage spacers 3856 may be positioned radially inward on the vent base 3853 and may pass through the membrane hole 3841 to contact the cage 3933 of the anterior frame 3830 to maintain adequate spacing between the vent base 3853 and the cage 3933 to allow the membrane 3840 to move freely therein. The HMX cartridge spacers 3858 may be positioned radially outward of the membrane 3840 and extend past it to contact the HMX cartridge 3810 and maintain its spacing from the cage 3933 within the anterior frame cavity 3832. The cage spacers 3856 and the HMX cartridge spacers 3858 may also be spaced apart radially such that the membrane 3840 fits between them radially, but with a minimal gap so as to allow the membrane 3840 to freely move but not become folded upon itself or displaced.

Below a predetermined threshold of therapeutic pressure, e.g., 4 $cmH_2O$, within the patient interface 3000 and the vent and conduit connector assembly 3820, the pressure may be low enough that the membrane 3840 is not forced against the conduit connector 3850 to occlude the inner axial vent holes 3854. As the therapeutic pressure increases, the membrane 3840 may be further urged against the conduit connector 3850, which increasingly occludes the inner axial vent holes 3854, although some amount of vent flow may be allow to escape to atmosphere therethrough. Once the therapeutic pressure increases further to exceed another predetermined threshold, the inner axial vent holes 3854 may be completely occluded by the membrane 3840 such that the only flow traveling to atmosphere through the conduit connector 3850 is via the outer axial vent holes 3852. Thus, depending on the therapeutic pressure within the vent and conduit connector assembly 3820, and therefore the position of the membrane 3840, the incoming pressurized bypass flow 7001 may travel to atmosphere through both the outer axial vent holes 3852 and inner axial vent holes 3854 or only the outer axial vent holes 3852, when the inner axial vent holes 3854 are occluded by the membrane 3840.

5.3.9.2 HMX Material Inside of Plenum Chamber

FIGS. 22A-28B and FIGS. 29A-33B show two examples of patient interfaces in which the heat and moisture exchanger material 3900 is positioned inside of the plenum chamber 3200 when the respective assemblies are connected to the plenum chamber 3200. In both of these examples, an anterior HMX frame 3990 and a posterior HMX frame 3980 may be releasably connected with the HMX material 3900 positioned therebetween.

The anterior HMX frame 3990 may include an anterior annular rim 3991 and a posterior annular rim 3993 that form an annular channel 3992 to receive the lip 3208 of the plenum chamber 3200. The anterior HMX frame 3990 also may include radial vent holes 3994 positioned radially to direct a vent flow of gas to atmosphere in a radial direction. As described above, such radial venting may reduce noise, jetting, and potential disruptions during sleep. The anterior HMX frame 3990 may include a central hole 3995 to which an elbow may be connected. The elbow may be rotatable. The elbow may be rotatable 360°. The anterior HMX frame 3990 comprises a central hole 3995 to receive the flow of air during therapy. The elbow may be connected at the central hole 3995.

The posterior HMX frame 3980 may include a plurality of radial spacers 3982 extending radially inward to contact a circumferential surface 3902 of the heat and moisture exchanger material 3900 and form gaps between the posterior HMX frame 3980 and the heat and moisture exchanger material 3900 to allow gases to flow around the heat and moisture exchanger material 3900.

The posterior HMX frame 3980 may include one or more posterior frame supports 3983 that form openings to allow gas to flow between the frame assembly and the plenum chamber 3200.

In the FIGS. 22A-28B example, when the frame assembly is assembled, the anterior HMX frame 3990 may contact the anterior surface 3904 and the posterior frame supports 3983 may contact the posterior surface 3906.

The posterior HMX frame 3980 may include one or more clips 3981 to releasably connect the posterior HMX frame 3980 to the anterior HMX frame 3990. The clips 3981 may releasably connect to the posterior annular rim 3993. The releasable connection may be snap fit.

In the FIGS. 29A-33B example, a bypass frame 3985 may be positioned between the anterior HMX frame 3990 and the heat and moisture exchanger material 3900. The bypass frame 3985 may include one or more bypass channels 3987 to direct gas into and out of the plenum chamber 3200 without passing through the heat and moisture exchanger material 3900. The bypass frame 3985 may include a tab 3988 to contact the anterior HMX frame 3990 and maintain spacing therefrom. The posterior HMX frame 3980 may include one or more alignment notches 3984 to receive a corresponding one of the bypass channels 3987 to align the bypass frame 3985 with the posterior HMX frame 3980. The bypass frame may include a central hole 3986 to allow the flow of air to pass through the bypass frame 3985 to reach the heat and moisture exchanger material 3900 and to allow exhaled gases to pass through the bypass frame 3985 after passing through the heat and moisture exchanger material 3900. The bypass frame 3985 may contact the anterior surface 3904 and the posterior frame supports 3983 may contact the posterior surface 3906 when the frame assembly is assembled.

5.3.9.3 Heat and Moisture Exchanger (HMX)

A heat and moisture exchanger (HMX) material 3900 may be positioned inside or outside of the plenum chamber 3200, but in either case along a flow path of pressurized air into the plenum chamber 3200 and exhaled gases out of the plenum chamber 3200, to adsorb and desorb moisture in air traveling to and from the plenum chamber 3200. In the depicted examples, the anterior frame 3830 may have an annular wall 3833 that forms an anterior frame cavity 3832, and the HMX cartridge 3810 may be positioned inside of the anterior frame cavity 3832. The HMX cartridge 3810 may be removable from the anterior frame 3830 when the vent and conduit connector assembly 3820 is disassembled so that it can be replaced periodically. The HMX cartridge 3810 may be approximately cylindrical in shape.

The HMX material 3900 may be foam or cellulose material or a combination of both. The foam may be an open cell foam. The cellulose material may be a corrugated structure. The cellulose material may be paper. The foam or cellulose material may be treated with a hygroscopic salt to enhance its ability to adsorb moisture.

Although the depicted examples show that the HMX material is positioned inside of the various assemblies during use, it should be understood that these assemblies may be designed to operate without the HMX material 3900 as well. For example, the vent flow and incoming flow to the patient via the plenum chamber 3200 may be sufficient for safe and effective therapy even in the absence of the HMX material.

The HMX material 3900 may have a circumferential or peripheral surface 3902, an anterior surface 3904, and a posterior surface 3906. In the examples of FIGS. 9A-16B and FIGS. 17A-21B the anterior surface 3904 is concave in shape and the posterior surface 3906 is convex in shape. In the example of FIGS. 22A-28B, the anterior surface 3904 is convex in shape and the posterior surface 3906 is concave in shape. By forming the anterior surface 3904 and the posterior surface 3906 with curvature, the surface area of each surface is increased which may enhance the ability of the HMX material 3900 to adsorb and desorb moisture. The examples of FIGS. 29A-33B shows the anterior surface 3904 and the posterior surface 3906 being flat.

5.3.9.4 Flow Paths

FIGS. 9J, 17J, 22J, and 29J depicts the various flow paths of air through the various assemblies during therapy. The flow of air at the therapeutic pressure directed into the various assemblies by the air circuit 4170 may follow two paths. The vent flow of air out of the various assemblies may also follow multiple different paths.

5.3.9.4.1 Incoming Pressurized Flows

A portion of the flow of air at the therapeutic pressure may pass through the frame assembly 3910, including the HMX material 3900, and this incoming pressurized flow 7000 may be warmed and humidified by the HMX material 3900 while passing therethrough before inhalation by the patient. Also, before reaching the HMX material 3900, the incoming pressurized flow 7000 may pass through a membrane hole 3841 in the membrane 3840.

Another portion of the flow of air at the therapeutic pressure may pass through the frame assembly 3910 while bypassing the HMX material 3900 before traveling to atmosphere, and this incoming pressurized bypass flow 7001 will not be warmed and humidified by the HMX material 3900 and will not be inhaled by the patient. The frame assembly 3910 may include vent holes through which the incoming pressurized bypass flow 7001 is directed to atmosphere. The conduit connector 3850 may include the vent holes. Also, before exiting to atmosphere through the conduit connector 3850, the incoming pressurized bypass flow 7001 may pass through the membrane hole 3841 in the membrane 3840, the operation of which will be described below, or the incoming pressurized bypass flow 7001 may bypass the membrane 3840 and travel to atmosphere without passing through the membrane hole 3841.

5.3.9.4.2 Vent Flows

Air exhaled with carbon dioxide from the patient may be vented to atmosphere through multiple different paths.

A portion of the air exhaled by the patient may be vented to atmosphere through vent holes in the anterior frames 3830. In the depicted examples, the vent holes are radial vent holes 3945 positioned radially around the anterior frame 3830. In an alternative example, the vent holes may be oriented axially. This HMX bypass vent flow 7002 passes directly to atmosphere without traveling through the HMX material 3900. The HMX material 3900 may have a smaller outer diameter than the inner diameter of the anterior frame, depending on the example, such that a gap is formed therebetween to allow the HMX bypass vent flow 7002 to travel from the patient's airways to the radial vent holes 3945, 3975, 3994 and then to atmosphere.

Another portion of the air exhaled by the patient may be vented to atmosphere through the conduit connector 3850 via both the outer axial vent holes 3852 and the inner axial vent holes 3854 or only the outer axial vent holes 3852, when the inner axial vent holes 3854 are occluded by the membrane 3840. This HMX vent flow 7003 may heat and moisten the HMX material 3900 as it passes therethrough. That heat and moisture may be released into the incoming pressurized flow 7000 before reaching the patient.

5.3.10 Heat and Moisture Exchanger (HMX), Vent, and Conduit Connector with a Flow-Controlled Vent Further examples of the present technology include a vent and conduit connector assembly 3820 that may be connected to the plenum chamber 3200, as shown in FIGS. 34A-34J. The vent and conduit connector assembly 3820 may be connected to the plenum chamber 3200 of a patient interface 3000 of FIGS. 7A-7C in place of the elbow 3500. FIGS. 35A-43B show examples of sub-assemblies and individual components of the vent and conduit connector assembly 3820. FIGS. 8A-8C to show examples of a seal-forming structure 3100 and a plenum chamber 3200 to which the vent and conduit connector assembly 3820 may be connected. As will be explained below, a heat and moisture exchanger (HMX) cartridge 3810 may be positioned inside of the vent and conduit connector assembly 3820 to adsorb and desorb moisture in air traveling to and from the plenum chamber 3200. The HMX cartridge 3810 may allow the patient interface 3000 to be used in a respiratory pressure therapy system with an RPT device 4000, as described below, but without a humidifier 5000.

5.3.10.1 Connection to Plenum Chamber

The vent and conduit connector assembly 3820 may include an anterior frame 3830 and a posterior frame 3800 that may be connected together to join the vent and conduit connector assembly 3820 to the plenum chamber 3200. FIGS. 8A-8C show a plenum chamber 3200 with a lip 3208 that forms a plenum chamber hole 3206 on an anterior side of the plenum chamber 3200. The anterior frame 3830 and the posterior frame 3800 may include an anterior connector 3831 and a posterior connector 3804, respectively, that may be connected to connect the anterior frame 3830 and the posterior frame 3800 together. When the anterior connector 3831 and the posterior connector 3804 are connected, the lip 3208 may be positioned between the anterior frame 3830 and the posterior frame 3800. When the lip 3208 is positioned between the anterior frame 3830 and the posterior frame 3800, the vent and conduit connector assembly 3820 may be secured to the plenum chamber 3200, e.g., by compressing the lip 3208 between the anterior frame 3830 and the posterior frame 3800. This arrangement can be seen in FIGS. 34H and 34J.

The lip 3208 may be constructed from a deformable and resilient material, such as silicone, that would be compressible between the anterior frame 3830 and the posterior frame 3800. A more rigid material, such as polyurethane or polycarbonate, may instead be used for the lip 3208, but a more rigid material that is less able to be compressed may require more precise manufacturing tolerances of the lip 3208, the anterior frame 3830, and the posterior frame 3800 to ensure that these components can be assembled and secured together. The anterior frame 3830 and the posterior frame 3800 may each be constructed from a plastic material.

FIGS. 34H and 34J also show that when the vent and conduit connector assembly 3820 is connected to the plenum chamber 3200, the posterior frame 3800 may be positioned within the plenum chamber 3200. Also, a portion of the anterior frame 3830 may extend through the plenum chamber hole 3206 and that portion may be positioned within the plenum chamber 3200 as well. Thus, the connection between the anterior frame 3830 and the posterior frame 3800 may be located inside of the plenum chamber 3200.

FIGS. 34H and 34J also show that the lip 3208 may be secured radially between the anterior frame 3830 and the posterior frame 3800. Additionally, a portion of the anterior frame 3830 may be positioned radially inward of the lip 3208 and a portion of the posterior frame 3800 may be positioned radially outward of the lip 3208.

FIGS. 34H and 34J also show that an outer annular rim 3836 extends from the exterior periphery of the anterior frame 3830, and the lip 3208 may be secured in an axial direction between the outer annular rim 3836 and the anterior connector 3831.

In the depicted examples, the anterior connector 3831 and the posterior connector 3804 form a bayonet connection. One of the anterior connector 3831 and the posterior connector 3804 is a male bayonet connector and the other is a female bayonet connector. The bayonet connection may be releasable to allow disassembly of the vent and conduit connector assembly 3820 and for the vent and conduit connector assembly 3820 to be removed from the plenum chamber 3200. Alternatively, the connection between the anterior frame 3830 and the posterior frame 3800 may be permanent such that the anterior frame 3830 and the posterior frame 3800 cannot be separated once assembled to the plenum chamber 3200.

The depicted examples also show that there may be a plurality of anterior connectors 3831 and a corresponding plurality of posterior connectors 3804 that connect to each other. Alternatively, there may be just one of each.

A conduit connector 3850 may be connected to the anterior frame 3830 to connect a conduit, such as the air circuit 4170 described elsewhere herein, to the patient interface 3000. The conduit connector 3850 may include a conduit connection tube 3851 that forms a conduit connector hole 3857. The conduit connector 3850 may be connected to the anterior frame 3830 opposite the posterior frame 3800. The conduit connector 3850 may also include an anti-asphyxia valve, and in further examples the anti-asphyxia valve may be positioned on the conduit connection tube 3851. In further examples, an elbow may be connected to the conduit connection tube 3851, which may be connected to the air circuit 4170, and the elbow may include an anti-asphyxia valve.

FIGS. 42A and 42B show a first example of the posterior frame 3800, and FIGS. 43A and 43B show a second example of the posterior frame 3800. In the first example, an inner annulus 3805 is joined to posterior frame supports 3806, which form posterior frame holes 3808 through air flows. In the second example, the posterior frame supports 3806 are joined to a plate 3809 that blocks a portion of the flow passing through the posterior frame 3800, while allowing flow to through posterior frame holes 3808 radially outward of the plate 3809. The inner annulus 3805 and the plate 3809 may be positioned centrally on the posterior frame 3800 in the respective examples.

5.3.10.2 Heat and Moisture Exchanger (HMX)

A heat and moisture exchanger (HMX) cartridge 3810 may be positioned inside of the vent and conduit connector assembly 3820 to adsorb and desorb moisture in air traveling to and from the plenum chamber 3200. In the depicted examples, the anterior frame 3830 may have an annular wall 3833 that forms an anterior frame cavity 3832, and the HMX cartridge 3810 may be positioned inside of the anterior frame cavity 3832. The HMX cartridge 3810 may be removable from the anterior frame 3830 when the vent and conduit connector assembly 3820 is disassembled so that it can be replaced periodically. The HMX cartridge 3810 may be approximately cylindrical in shape.

The HMX cartridge 3810 may include an anterior HMX cartridge frame 3812 and a posterior HMX cartridge frame 3814 that may be releasably or permanently connected. An HMX material 3816 may be positioned inside of the anterior HMX cartridge frame 3812 and the posterior HMX cartridge frame 3814, which may provide structural support for the HMX material 3816. The anterior HMX cartridge frame 3812 and the posterior HMX cartridge frame 3814 may each be constructed from a plastic material.

The HMX material 3816 may be foam. The foam may be an open cell foam. The HMX material 3816 may, alternatively, be a corrugated structure of cellulose material, such as paper. The foam or cellulose material may be treated with a hygroscopic salt to enhance its ability to adsorb moisture.

The HMX cartridge 3810 may also include an annular notch 3815 around the periphery of the anterior HMX cartridge frame 3812 or the posterior HMX cartridge frame 3814. To connect the HMX cartridge 3810 to the vent and conduit connector assembly 3820. In the depicted examples, the posterior HMX cartridge frame 3814 includes the annular notch 3815, and the annular notch 3815 connects the HMX cartridge 3810 to the posterior frame 3800 at one or more HMX cartridge connectors 3802. When the HMX cartridge 3810 is connected to the posterior frame 3800 and the posterior frame 3800 is connected to the anterior frame 3830, the HMX cartridge will be positioned inside of the anterior frame cavity 3832. Additionally, it can be seen in the depicted examples that because the anterior frame 3830 is positioned predominantly outside of the plenum chamber 3200, the HMX cartridge 3810 will be positioned externally of the plenum chamber 3200.

Although the depicted examples show that the HMX cartridge 3810 is positioned inside of the anterior frame 3830 during use, it should be understood that the vent and conduit connector assembly 3820 may be designed to operate without the HMX cartridge 3810. For example, the vent flow and incoming flow to the patient via the plenum chamber 3200 may be sufficient for safe and effective therapy even in the absence of the HMX cartridge 3810.

5.3.10.3 Flow Paths

FIG. 34J depicts the various flow paths of air through the vent and conduit connector assembly 3820 during therapy. The flow of air at the therapeutic pressure directed into the vent and conduit connector assembly 3820 by the air circuit 4170 may follow two paths. The vent flow of air out of the vent and conduit connector assembly 3820 may also follow multiple different paths.

5.3.10.3.1 Incoming Pressurized Flows

A portion of the flow of air at the therapeutic pressure may pass through the vent and conduit connector assembly 3820, including the HMX cartridge 3810, and this incoming pressurized flow 7000 may be warmed and humidified by the HMX cartridge 3810 while passing therethrough before inhalation by the patient. The anterior HMX cartridge frame 3812 and the posterior HMX cartridge frame 3814 may each be substantially open in the axial direction of the HMX cartridge 3810 to allow the incoming pressurized flow 7000 to pass through those components and the HMX material 3816. Also, before reaching the HMX cartridge 3810, the incoming pressurized flow 7000 may pass through a membrane hole 3841 in a membrane 3840, the operation of which will be described below.

Another portion of the flow of air at the therapeutic pressure may pass through the vent and conduit connector assembly 3820 while bypassing the HMX cartridge 3810 before traveling to atmosphere, and this incoming pressurized bypass flow 7001 will not be warmed and humidified by the HMX cartridge 3810 and will not be inhaled by the patient. The vent and conduit connector assembly 3820 may include vent holes through which the incoming pressurized bypass flow 7001 is directed to atmosphere. The conduit connector 3850 may include the vent holes. Also, before exiting to atmosphere through the conduit connector 3850, the incoming pressurized bypass flow 7001 may pass through the membrane hole 3841 in the membrane 3840, the operation of which will be described below, or the incoming pressurized bypass flow 7001 may bypass the membrane 3840 and travel to atmosphere without passing through the membrane hole 3841.

In the depicted examples, the conduit connector 3850 includes outer axial vent holes 3852 and inner axial vent holes 3854 formed through a vent base 3853. The outer axial vent holes 3852 and the inner axial vent holes 3854 may be positioned radially around the conduit connection tube 3851, with the inner axial vent holes 3854 being radially inward of the outer axial vent holes 3852. The outer axial vent holes 3852 and the inner axial vent holes 3854 may be oriented on the conduit connector 3850 to direct the respective vent flows out of the vent and conduit connector assembly 3820 in an axial direction.

The membrane 3840 may be positioned between the conduit connector 3850 and a cage 3835 positioned within anterior frame 3830. The membrane 3840 may be free to move within the space between the conduit connector 3850 and the cage 3835. The membrane 3840 may be shaped and dimensioned to cover the inner axial vent holes 3854 while leaving the outer axial vent holes 3852 uncovered. The conduit connector 3850 may include one or more cage spacers 3856 and one or more HMX cartridge spacers 3858 that extend from the vent base 3853. The cage spacers 3856 may be positioned radially inward on the vent base 3853 and may pass through the membrane hole 3841 to contact the cage 3835 of the anterior frame 3830 to maintain adequate spacing between the vent base 3853 and the cage 3835 to allow the membrane 3840 to move freely therein. The HMX cartridge spacers 3858 may be positioned radially outward of the membrane 3840 and extend past it to contact the HMX cartridge 3810 and maintain its spacing from the cage 3835 within the anterior frame cavity 3832. The cage spacers 3856 and the HMX cartridge spacers 3858 may also be spaced apart radially such that the membrane 3840 fits between them radially, but with a minimal gap so as to allow the membrane 3840 to freely move but not become folded upon itself or displaced.

Below a predetermined threshold of therapeutic pressure, e.g., 4 $cmH_2O$, within the patient interface 3000 and the vent and conduit connector assembly 3820, the pressure may be low enough that the membrane 3840 is not forced against the conduit connector 3850 to occlude the inner axial vent holes 3854. As the therapeutic pressure increases, the membrane 3840 may be further urged against the conduit connector 3850, which increasingly occludes the inner axial vent holes 3854, although some amount of vent flow may be allow to escape to atmosphere therethrough. Once the therapeutic pressure increases further to exceed another predetermined threshold, the inner axial vent holes 3854 may be completely occluded by the membrane 3840 such that the only flow traveling to atmosphere through the conduit connector 3850 is via the outer axial vent holes 3852. Thus, depending on the therapeutic pressure within the vent and conduit connector assembly 3820, and therefore the position of the membrane 3840, the incoming pressurized bypass flow 7001 may travel to atmosphere through both the outer axial vent holes 3852 and inner axial vent holes 3854 or only the outer axial vent holes 3852, when the inner axial vent holes 3854 are occluded by the membrane 3840.

5.3.10.3.2 Vent Flows

Air exhaled with carbon dioxide from the patient may be vented to atmosphere through multiple different paths.

A portion of the air exhaled by the patient may be vented to atmosphere through vent holes in the anterior frame 3830. In the depicted examples, the vent holes are radial vent holes 3834 positioned radially around the anterior frame 3830. In an alternative example, the vent holes may be oriented axially. This HMX bypass vent flow 7002 passes directly to atmosphere without traveling through the HMX cartridge 3810. The HMX cartridge 3810 may have a smaller outer diameter than the inner diameter of the annular wall 3833 such that a gap is formed therebetween to allow the HMX bypass vent flow 7002 to travel from the patient's airways to the radial vent holes 3834 and then to atmosphere. The anterior frame 3830 may include an inner annular rim 3837 that extends radially inward from the annular wall 3833. The inner annular rim 3837 may be adjacent to the HMX cartridge 3810 to block the HMX bypass vent flow 7002 and direct it to atmosphere via the radial vent holes 3834. In some examples, the inner annular rim 3837 may contact the anterior HMX cartridge frame 3812.

Another portion of the air exhaled by the patient may be vented to atmosphere through the conduit connector 3850 via both the outer axial vent holes 3852 and the inner axial vent holes 3854 or only the outer axial vent holes 3852, when the inner axial vent holes 3854 are occluded by the membrane 3840. This HMX vent flow 7003 may heat and moisten the HMX material 3816 as it passes through the HMX cartridge 3810. That heat and moisture may be released into the incoming pressurized flow 7000 before reaching the patient.

5.3.10.3.3 Constant-Flow Vent

As described above, as the therapeutic pressure increases within the vent and conduit connector assembly 3820 the membrane 3840 may be urged towards the vent base 3853 to at least partially occlude the inner axial vent holes 3854. As the inner axial vent holes 3854 become occluded and flow therethrough reduced, the outer axial vent holes 3852 remain completely open, as do the radial vent holes 3834. The progressive occlusion of the inner axial vent holes 3854 by the membrane 3840 may limit the increase of the combined vent flow to atmosphere through the outer axial vent holes 3852, the inner axial vent holes 3854, and the radial vent holes 3834 as the therapeutic pressure increases within the vent and conduit connector assembly 3820. Thus, by occluding the inner axial vent holes 3854, at least partially, as the therapeutic pressure increases, the combined vent flow throughout a range of therapeutic pressures (e.g., from as low as 4 $cmH_2O$ up to 20 $cmH_2O$ or 30 $cmH_2O$), may remain approximately constant.

5.3.10.3.4 Diffuser and Diffuser Bypass

Once the vent flows pass through the conduit connector 3850, e.g., the incoming pressurized bypass flow 7001 and the HMX vent flow 7003, a portion of those flows may travel directly to atmosphere in the form of a diffuser bypass vent flow 7004. Another portion of those flows may be directed to atmosphere after passing through a diffuser material 3870 in the form of a diffuser vent flow 7005.

An anterior diffuser retaining ring 3880 and a posterior diffuser retaining ring 3860 may be connected with the diffuser material 3870 therebetween. The diffuser material 3870 may be a porous material such as foam, and when the vent flows reach the diffuser material 3870, the velocity of the diffuser vent flow 7005 is reduced and the diffuser vent flow 7005 is diffused to reduce noise and jetting. The posterior diffuser retaining ring 3860 may have an open construction to allow the vent flows to pass into the diffuser material 3870, and the posterior diffuser retaining ring 3860 may have diffuser retainers 3862 to hold the diffuser material 3870 in position. The anterior diffuser retaining ring 3880 may have an attachment portion 3882 to attach the anterior diffuser retaining ring 3880 to the conduit connector 3850, e.g., around the conduit connection tube 3851. The anterior diffuser retaining ring 3880 may also have diffused vent holes 3886 formed by an outer portion 3887, an inner portion 3888, and a plurality of anterior retaining ring supports 3884 that join the outer portion 3887 and the inner portion 3888. The diffuser vent flow 7005 may pass to atmosphere through the diffused vent holes 3886.

5.3.11 Heat and Moisture Exchanger (HMX), Vent, and Bypass Channel(s)

FIGS. 44A-48B show examples of a patient interface 3000 and a HMX and flow director assembly 8000. FIGS. 44A-44J show the HMX and flow director assembly 8000 assembled to the patient interface 3000. FIGS. 45A-45G show the HMX and flow director assembly 8000 alone. FIGS. 46A-46D show an anterior shell 8010 of the HMX and flow director assembly 8000. FIGS. 47A-47D show a posterior shell 8020 of the HMX and flow director assembly 8000. FIGS. 48A and 48B show a retainer 8040 and HMX material of the HMX and flow director assembly 8000.

In these examples, the HMX and flow director assembly 8000 may be positioned inside of the plenum chamber 3200 to direct air from within the plenum chamber 3200 to atmosphere without passing through HMX material 8030 in the HMX and flow director assembly 8000. Because the HMX material 8030 adsorbs moisture from exhaled gases from the patient, directing the exhaled gases through the HMX material 8030 before passing to atmosphere may cause a loss of moisture to atmosphere in the vented, exhaled gas, in which case it cannot desorb into the incoming flow of air for breathing by the patient. By bypassing the HMX material 8030 through channels in the HMX and flow director assembly 8000, the vented, exhaled gases can pass to atmosphere while minimizing drying of the HMX material 8030.

The HMX and flow director assembly 8000 may include one or more channels to direct the vent to atmosphere. In the depicted examples, the HMX and flow director assembly 8000 includes four channels, but in other examples the HMX and flow director assembly 8000 may have 1, 2, or 3 channels depending on the shape of the patient interface. The patient interface 3000 in the depicted examples is an ultra-compact full-face or oro-nasal patient interface 3000 in that it is shaped and dimensioned to cover and provide the flow of air to the patient's nose and mouth and it has separate holes for the nose (nasal hole(s) 3104) and the mouth (oral hole 313). The ultra-compact full-face or oro-nasal patient interface 3000 may have four corners or regions of more complex geometry, and each channel corresponds to one such corner to provide a pathway for exhaled gases that may accumulate, e.g., due to stagnated flow, in those areas to exit to atmosphere.

A full-face patient interface 3000 (i.e., one hole for nose and mouth) could also include the HMX and flow director assembly 8000, but it may have three channels. A full-face patient interface 3000 may be approximately triangular in shape such that each of the three channels corresponds to one of the corners. The principle of operation is similar to the ultra-compact full-face or oro-nasal patient interface 3000 in that each channel may provide a pathway for exhaled gases that may accumulate, e.g., due to stagnated flow, in those areas to exit to atmosphere.

A nasal, nasal cradle, or nasal pillows patient interface 3000, which leave the patient's mouth uncovered, may also include the HMX and flow director assembly 8000, except that only two channels may be provided, each corresponding to a lateral side of the patient interface 3000 where the geometry is complex. Again, the principle of operation is similar to the ultra-compact full-face or oro-nasal patient interface 3000 in that each channel may provide a pathway for exhaled gases that may accumulate, e.g., due to stagnated flow, in those areas to exit to atmosphere.

In the depicted examples, the HMX and flow director assembly 8000 may have an anterior shell 8010 and a posterior shell 8020. The anterior shell 8010 and the posterior shell 8020 may be joined together. The anterior shell 8010 and the posterior shell 8020 may be joined together permanently, e.g., by heat staking, at adjacent surfaces. The HMX and flow director assembly 8000 may include a retainer 8040 joined to the anterior shell 8010 and/or the posterior shell 8020 to hold the HMX material 8030 in place. The retainer 8040 may also be joined, e.g., permanently via heat staking, to the anterior shell 8010 and/or the posterior shell 8020 to hold the HMX material 8030 in place.

The HMX material 8030 may be held over a port 8001 formed in the anterior shell 8010 and the posterior shell 8020. The incoming flow of air may pass through the port 8001 before passing through the HMX material 8030 for humidification prior to reaching the patient's airways. The HMX material 8030 may be shaped and dimensioned to completely cover the port 8001 so that all of the incoming flow of air must pass through the HMX material 8030 for humidification before reaching the patient's airways. In an alternative example, there may be one or more gaps around the HMX material 8030 so that some portion of the incoming flow of air can bypass the HMX material 8030 before reaching the patient's airways.

In another example, there may be no HMX material 8030 in the flow director assembly 8000 such that it is just a flow director that allows exhaled gases to be directed to vent holes along a path separate from the incoming flow of air. Thus, the incoming flow of air may be directed primarily towards the entrance to the patient's airways without a substantial portion being directed out to atmosphere via vents before reaching the patient. The retainer 8040 would also be unnecessary in this arrangement. This arrangement may still provide enhanced extraction of carbon dioxide from within the plenum chamber 3200 for a patient interface 3000 that does not use HMX material 8030 for humidification. This may be advantageous where the patient interface 3000 is used with an RPT device 4000 that includes a humidifier 5000, as contrasted with the examples that include the HMX material 8030 and may be used with an RPT device 4000 that does not include a humidifier 5000.

When the anterior shell 8010 and the posterior shell 8020 of the HMX and flow director assembly 8000 are joined together, they may form one or more inferior channels 8050 and one or more superior channels 8060. Each of the inferior channels 8050 and each of the superior channels 8060 may be formed between an anterior channel wall 8014 of the anterior shell 8010 and a posterior channel wall 8023 of the posterior shell 8020. The joining of the anterior shell 8010 and the posterior shell 8020 described above, e.g., via heat staking, may bond the anterior shell 8010 and the posterior shell 8020 together on opposing sides of each inferior channel 8050 and each superior channel 8060 such that respective anterior channel walls 8014 and posterior channel walls 8023 are spaced apart to form the inferior channels 8050 and the superior channels 8060 therebetween. The inferior channel(s) 8050 and the superior channel(s) 8060 may extend radially outward from the port 8001.

Additionally, the anterior shell 8010 may have a posterior mating surface 8013 that is positioned adjacent to and joined to an anterior mating surface 8022 of the posterior shell 8020, and the posterior shell 8020 may have a posterior mating surface 8024 that is positioned adjacent to and joined to an anterior mating surface 8041 of the retainer 8040. The joint between the posterior mating surface 8024 of the posterior shell 8020 and the anterior mating surface 8041 of the retainer 8040 may be sealed 360° so that all of the flow of air is directed through the HMX material 8030. Also, bumps 8042 may be formed on the anterior mating surface 8041 of the retainer 8040 to allow space for the inferior channels 8050 and the superior channels 8060. Between the posterior mating surface 8013 of the anterior shell 8010 and the anterior mating surface 8022 of the posterior shell 8020 there may be gaps, i.e., these surfaces are not sealed together 360°, so that the inferior channels 8050 and the superior channels 8060 can pass between the surfaces.

The inferior channels 8050 and the superior channels 8060 each include a proximal opening 8052, 8062, respectively, that is inside of the plenum chamber 3200 when the HMX and flow director assembly 8000 is assembled to the patient interface 3000 and that is proximal to the patient when the patient interface 3000 is worn by the patient. The proximal openings 8052, 8062 are the entrances to the respective inferior channels 8050 and superior channels 8060 for the extraction of exhaled gases from within the plenum chamber 3200. The inferior channels 8050 and the superior channels 8060 each include a distal opening 8051, 8061, respectively, that is outside of the plenum chamber 3200 when the HMX and flow director assembly 8000 is assembled to the patient interface 3000 and that is distal to the patient when the patient interface 3000 is worn by the patient. The distal openings 8051, 8061 are the outlets for the respective inferior channels 8050 and superior channels 8060 for discharge of exhaled gases to a vent.

The HMX and flow director assembly 8000 may be removably connected to the patient interface 3000, e.g., to a vent ring 8990 or to an interior surface of the plenum chamber 3200. The anterior shell 8010 may include one or more protrusions 8012 shaped and dimensioned to fit into corresponding portions of the plenum chamber 3200 to provide stability between the plenum chamber 3200 and the HMX and flow director assembly 8000. In some examples, the protrusion(s) 8012 may removably connect the HMX and flow director assembly 8000 to the plenum chamber 3200 with a friction fit.

The HMX and flow director assembly 8000 may, in some examples, removably connect to the vent ring 8990 such that the plenum chamber 3200 is sandwiched between the vent ring 8990 and the HMX and flow director assembly 8000. The vent ring 8990 may include an anterior annular rim 8991 and a posterior annular rim 8993 that form an annular channel 8992 to receive the lip 3208 of the plenum chamber 3200. The vent ring 8990 also may include radial vent holes 8994 positioned radially to direct a vent flow of gas to atmosphere in a radial direction. The inferior channels 8050 and the superior channels 8060 may direct the flow of exhaled gases to the radial vent holes 8994 before discharge to atmosphere. The inferior channels 8050 and the superior channels 8060 may direct the flow of exhaled gases directly to the radial vent holes 8994 without passing through the HMX material 8030 before discharge to atmosphere. The distal openings 8051, 8061 may be proximal to the radial vent holes 8994 when the HMX and flow director assembly 8000 is connected to the vent ring 8990. As described above, such radial venting may reduce noise, jetting, and potential disruptions during sleep. The vent ring 8990 may include a central hole 8995 to which an elbow or an air delivery conduit may be connected. The elbow or the air delivery conduit may be removably and/or rotatably connected to the vent ring 8990. The elbow or the air delivery conduit may be rotatable 360° about the vent ring 8990. The central hole 3995 may receive the flow of air during therapy.

The anterior shell 8010 may have an outer rim 8011 and the posterior shell 8020 may have an inner rim 8021, and the distal openings 8051, 8061 may be formed between the outer rim 8011 and the inner rim 8021. The port 8001 may be formed through the inner rim 8021. The outer rim 8011 may be removably connected to the vent ring 8990. The outer rim 8011 and the inner rim 8021 may partially extend into the vent ring 8990 so that the distal openings 8051, 8061 are as close as possible to the radial vent holes 8994 for direct discharge of exhaled gases from the inferior channels 8050 and the superior channels 8060.

One or more of the anterior shell 8010, the posterior shell 8020, and the retainer 8040 may be constructed from a polymer. The polymer may be one of: Polycarbonate (PC), Polypropylene (PP), Acrylic (PMMA), Acrylonitrile butadiene styrene (ABS), Polyethylene (PE), Polyethylene terephthalate glycol (PETG), and Polystyrene (PS). One or more of the anterior shell 8010, the posterior shell 8020, and the retainer 8040 may be constructed from the same polymer or the polymer of one or more of the anterior shell 8010, the posterior shell 8020, and the retainer 8040 may different in at least one aspect, property, or composition. One or more of the anterior shell 8010, the posterior shell 8020, and the retainer 8040 may be formed by vacuum forming, thermoforming, or pressure forming. These processes allow the components to be with considerably thinner walls than if made by injection molding, e.g., 0.25 mm for vacuum forming, thermoforming, or pressure forming vs. 1.00 mm to 1.25 mm for injection molding, which also allows for a more compact assembly to fit inside of the plenum chamber 3200. Additionally, these processes allow greater control of the wall thicknesses of the components. For example, one or more of the anterior shell 8010, the posterior shell 8020, and the retainer 8040 may have a uniform wall thickness throughout or the wall thickness may be variable. In a further example, one or more of the anterior shell 8010, the posterior shell 8020, and the retainer 8040 may have a wall thickness of approximately 0.25 mm that is constant throughout. In a still further example, one or more of the anterior shell 8010, the posterior shell 8020, and the retainer 8040 may have a wall thickness that is less than approximately 1.00 mm to approximately 1.25 mm and that is uniform throughout.

The HMX material 8030 may be foam, paper, or a combination of foam and paper. The HMX material 8030 may include a salt applied thereto. The HMX material 8030 may be disc-shaped.

The HMX and flow director assembly 8000 may have a concave shape on its posterior or patient-facing side to avoid contact with the patient's face during use. The HMX and flow director assembly 8000 may have a convex shape on its anterior side or the side proximal to the plenum chamber 3200 to conform as closely as possible with the interior surface of the plenum chamber 3200 and maintain a low profile.

5.4 RPT Device

An RPT device 4000 in accordance with one aspect of the present technology comprises mechanical, pneumatic, and/or electrical components and is configured to execute one or more algorithms, such as any of the methods, in whole or in part, described herein. The RPT device 4000 may be configured to generate a flow of air for delivery to a patient's airways, such as to treat one or more of the respiratory conditions described elsewhere in the present document.

In one form, the RPT device 4000 is constructed and arranged to be capable of delivering a flow of air in a range of −20 L/min to +150 L/min while maintaining a positive pressure of at least 6 cmH2O, or at least 10 cmH2O, or at least 20 cmH2O.

The RPT device may have an external housing 4010, formed in two parts, an upper portion 4012 and a lower portion 4014. Furthermore, the external housing 4010 may include one or more panel(s) 4015. The RPT device 4000 comprises a chassis 4016 that supports one or more internal components of the RPT device 4000. The RPT device 4000 may include a handle 4018.

The pneumatic path of the RPT device 4000 may comprise one or more air path items, e.g., an inlet air filter 4112, an inlet muffler 4122, a pressure generator 4140 capable of supplying air at positive pressure (e.g., a blower 4142), an outlet muffler 4124 and one or more transducers 4270, such as pressure sensors 4272 and flow rate sensors 4274.

One or more of the air path items may be located within a removable unitary structure which will be referred to as a pneumatic block 4020. The pneumatic block 4020 may be located within the external housing 4010. In one form a pneumatic block 4020 is supported by, or formed as part of the chassis 4016.

The RPT device 4000 may have an electrical power supply 4210, one or more input devices 4220, a central controller 4230, a therapy device controller 4240, a pressure generator 4140, one or more protection circuits 4250, memory 4260, transducers 4270, data communication interface 4280 and one or more output devices 4290. Electrical components 4200 may be mounted on a single Printed Circuit Board Assembly (PCBA) 4202. In an alternative form, the RPT device 4000 may include more than one PCBA 4202.

5.4.1 RPT Device Mechanical & Pneumatic Components

An RPT device may comprise one or more of the following components in an integral unit. In an alternative form, one or more of the following components may be located as respective separate units.

5.4.1.1 Air Filter(s)

An RPT device in accordance with one form of the present technology may include an air filter 4110, or a plurality of air filters 4110.

In one form, an inlet air filter 4112 is located at the beginning of the pneumatic path upstream of a pressure generator 4140.

In one form, an outlet air filter 4114, for example an antibacterial filter, is located between an outlet of the pneumatic block 4020 and a patient interface 3000.

5.4.1.2 Muffler(s)

An RPT device in accordance with one form of the present technology may include a muffler 4120, or a plurality of mufflers 4120.

In one form of the present technology, an inlet muffler 4122 is located in the pneumatic path upstream of a pressure generator 4140.

In one form of the present technology, an outlet muffler 4124 is located in the pneumatic path between the pressure generator 4140 and a patient interface 3000.

5.4.1.3 Pressure Generator

In one form of the present technology, a pressure generator 4140 for producing a flow, or a supply, of air at positive pressure is a controllable blower 4142. For example, the blower 4142 may include a brushless DC motor 4144 with one or more impellers. The impellers may be located in a volute. The blower may be capable of delivering a supply of air, for example at a rate of up to about 120 litres/minute, at a positive pressure in a range from about 4 cmH2O to about 20 cmH2O, or in other forms up to about 30 cmH2O when delivering respiratory pressure therapy. The blower may be as described in any one of the following patents or patent applications the contents of which are incorporated herein by reference in their entirety: U.S. Pat. Nos. 7,866,944; 8,638,014; 8,636,479; and PCT Patent Application Publication No. WO 2013/020167.

5.4.1.4 Transducer(s)

Transducers may be internal of the RPT device, or external of the RPT device. External transducers may be located for example on or form part of the air circuit, e.g., the patient interface. External transducers may be in the form of non-contact sensors such as a Doppler radar movement sensor that transmit or transfer data to the RPT device.

In one form of the present technology, one or more transducers 4270 are located upstream and/or downstream of the pressure generator 4140. The one or more transducers 4270 may be constructed and arranged to generate signals representing properties of the flow of air such as a flow rate, a pressure or a temperature at that point in the pneumatic path.

In one form of the present technology, one or more transducers 4270 may be located proximate to the patient interface 3000=.

In one form, a signal from a transducer 4270 may be filtered, such as by low-pass, high-pass or band-pass filtering.

5.4.1.4.1 Flow Rate Sensor

A flow rate sensor 4274 in accordance with the present technology may be based on a differential pressure transducer, for example, an SDP600 Series differential pressure transducer from SENSIRION.

In one form, a signal generated by the flow rate sensor 4274 and representing a flow rate is received by the central controller 4230.

5.4.1.4.2 Pressure Sensor

A pressure sensor 4272 in accordance with the present technology is located in fluid communication with the pneumatic path. An example of a suitable pressure sensor is a transducer from the HONEYWELL ASDX series. An alternative suitable pressure sensor is a transducer from the NPA Series from GENERAL ELECTRIC.

In one form, a signal generated by the pressure sensor 4272 and representing a pressure is received by the central controller 4230.

5.4.1.4.3 Motor Speed Transducer

In one form of the present technology a motor speed transducer 4276 is used to determine a rotational velocity of the motor 4144 and/or the blower 4142. A motor speed signal from the motor speed transducer 4276 may be provided to the therapy device controller 4240. The motor speed transducer 4276 may, for example, be a speed sensor, such as a Hall effect sensor.

5.4.1.5 Anti-Spill Back Valve

In one form of the present technology, an anti-spill back valve 4160 is located between the humidifier 5000 and the pneumatic block 4020. The anti-spill back valve is constructed and arranged to reduce the risk that water will flow upstream from the humidifier 5000, for example to the motor 4144.

5.4.2 RPT Device Electrical Components 5.4.2.1 Power Supply

A power supply 4210 may be located internal or external of the external housing 4010 of the RPT device 4000.

In one form of the present technology, power supply 4210 provides electrical power to the RPT device 4000 only. In another form of the present technology, power supply 4210 provides electrical power to both RPT device 4000 and humidifier 5000.

5.4.2.2 Input Devices

In one form of the present technology, an RPT device 4000 includes one or more input devices 4220 in the form of buttons, switches or dials to allow a person to interact with the device. The buttons, switches or dials may be physical devices, or software devices accessible via a touch screen. The buttons, switches or dials may, in one form, be physically connected to the external housing 4010, or may, in another form, be in wireless communication with a receiver that is in electrical connection to the central controller 4230.

In one form, the input device 4220 may be constructed and arranged to allow a person to select a value and/or a menu option.

5.4.2.3 Central Controller

In one form of the present technology, the central controller 4230 is one or a plurality of processors suitable to control an RPT device 4000.

Suitable processors may include an x86 INTEL processor, a processor based on ARM® Cortex®-M processor from ARM Holdings such as an STM32 series microcontroller from ST MICROELECTRONIC. In certain alternative forms of the present technology, a 32-bit RISC CPU, such as an STR9 series microcontroller from ST MICROELECTRONICS or a 16-bit RISC CPU such as a processor from the MSP430 family of microcontrollers, manufactured by TEXAS INSTRUMENTS may also be suitable.

In one form of the present technology, the central controller 4230 is a dedicated electronic circuit.

In one form, the central controller 4230 is an application-specific integrated circuit. In another form, the central controller 4230 comprises discrete electronic components.

The central controller 4230 may be configured to receive input signal(s) from one or more transducers 4270, one or more input devices 4220, and the humidifier 5000.

The central controller 4230 may be configured to provide output signal(s) to one or more of an output device 4290, a therapy device controller 4240, a data communication interface 4280, and the humidifier 5000.

5.4.2.4 Clock

The RPT device 4000 may include a clock 4232 that is connected to the central controller 4230.

5.4.2.5 Protection Circuits

The one or more protection circuits 4250 in accordance with the present technology may comprise an electrical protection circuit, a temperature and/or pressure safety circuit.

5.4.2.6 Memory

In accordance with one form of the present technology the RPT device 4000 includes memory 4260, e.g., non-volatile memory. In some forms, memory 4260 may include battery powered static RAM. In some forms, memory 4260 may include volatile RAM.

Memory 4260 may be located on the PCBA 4202. Memory 4260 may be in the form of EEPROM, or NAND flash.

Additionally, or alternatively, RPT device 4000 includes a removable form of memory 4260, for example a memory card made in accordance with the Secure Digital (SD) standard.

5.4.2.7 Data Communication Systems

In one form of the present technology, a data communication interface 4280 is provided, and is connected to the central controller 4230. Data communication interface 4280 may be connectable to a remote external communication network 4282 and/or a local external communication network 4284. The remote external communication network 4282 may be connectable to a remote external device 4286. The local external communication network 4284 may be connectable to a local external device 4288.

In one form, data communication interface 4280 is part of the central controller 4230. In another form, data communication interface 4280 is separate from the central controller 4230, and may comprise an integrated circuit or a processor.

In one form, remote external communication network 4282 is the Internet. The data communication interface 4280 may use wired communication (e.g. via Ethernet, or optical fibre) or a wireless protocol (e.g. CDMA, GSM, LTE) to connect to the Internet.

In one form, local external communication network 4284 utilises one or more communication standards, such as Bluetooth, or a consumer infrared protocol.

In one form, remote external device 4286 is one or more computers, for example a cluster of networked computers. In one form, remote external device 4286 may be virtual computers, rather than physical computers. In either case, such a remote external device 4286 may be accessible to an appropriately authorised person such as a clinician.

The local external device 4288 may be a personal computer, mobile phone, tablet or remote control.

5.4.2.8 Output Devices Including Optional Display, Alarms

An output device 4290 in accordance with the present technology may take the form of one or more of a visual, audio and haptic unit. A visual display may be a Liquid Crystal Display (LCD) or Light Emitting Diode (LED) display.

5.4.2.8.1 Display Driver

A display driver 4292 receives as an input the characters, symbols, or images intended for display on the display 4294, and converts them to commands that cause the display 4294 to display those characters, symbols, or images.

5.4.2.8.2 Display

A display 4294 is configured to visually display characters, symbols, or images in response to commands received from the display driver 4292. For example, the display 4294 may be an eight-segment display, in which case the display driver 4292 converts each character or symbol, such as the figure "0", to eight logical signals indicating whether the eight respective segments are to be activated to display a particular character or symbol.

5.5 Air Circuit

An air circuit 4170 in accordance with an aspect of the present technology is a conduit or a tube constructed and arranged to allow, in use, a flow of air to travel between two components such as RPT device 4000 and the patient interface 3000.

In particular, the air circuit 4170 may be in fluid connection with the outlet of the pneumatic block 4020 and the patient interface. The air circuit may be referred to as an air delivery tube. In some cases there may be separate limbs of the circuit for inhalation and exhalation. In other cases a single limb is used.

In some forms, the air circuit 4170 may comprise one or more heating elements configured to heat air in the air circuit, for example to maintain or raise the temperature of the air. The heating element may be in a form of a heated wire circuit, and may comprise one or more transducers, such as temperature sensors. In one form, the heated wire circuit may be helically wound around the axis of the air circuit 4170. The heating element may be in communication with a controller such as a central controller 4230. One example of an air circuit 4170 comprising a heated wire circuit is described in U.S. Pat. No. 8,733,349, which is incorporated herewithin in its entirety by reference.

5.6 Humidifier 5.6.1 Humidifier Overview

In one form of the present technology there is provided a humidifier 5000 (e.g. as shown in FIG. 5A) to change the absolute humidity of air or gas for delivery to a patient relative to ambient air. Typically, the humidifier 5000 is used to increase the absolute humidity and increase the temperature of the flow of air (relative to ambient air) before delivery to the patient's airways.

The humidifier 5000 may comprise a humidifier reservoir 5110, a humidifier inlet 5002 to receive a flow of air, and a humidifier outlet 5004 to deliver a humidified flow of air. In some forms, as shown in FIG. 5A and FIG. 5B, an inlet and an outlet of the humidifier reservoir 5110 may be the humidifier inlet 5002 and the humidifier outlet 5004 respectively. The humidifier 5000 may further comprise a humidifier base 5006, which may be adapted to receive the humidifier reservoir 5110 and comprise a heating element 5240.

5.7 Breathing Waveforms

FIG. 6 shows a model typical breath waveform of a person while sleeping. The horizontal axis is time, and the vertical axis is respiratory flow rate. While the parameter values may vary, a typical breath may have the following approximate values: tidal volume Vt 0.5 L, inhalation time Ti 1.6 s, peak inspiratory flow rate Qpeak 0.4 L/s, exhalation time Te 2.4 s, peak expiratory flow rate Qpeak−0.5 L/s. The total duration of the breath, Ttot, is about 4 s. The person typically breathes at a rate of about 15 breaths per minute (BPM), with Ventilation Vent about 7.5 L/min. A typical duty cycle, the ratio of Ti to Ttot, is about 40%.

5.8 Glossary

For the purposes of the present technology disclosure, in certain forms of the present technology, one or more of the following definitions may apply. In other forms of the present technology, alternative definitions may apply.

5.8.1 General

Air: In certain forms of the present technology, air may be taken to mean atmospheric air, and in other forms of the present technology air may be taken to mean some other combination of breathable gases, e.g. oxygen enriched air.

Ambient: In certain forms of the present technology, the term ambient will be taken to mean (i) external of the treatment system or patient, and (ii) immediately surrounding the treatment system or patient.

For example, ambient humidity with respect to a humidifier may be the humidity of air immediately surrounding the humidifier, e.g. the humidity in the room where a patient is sleeping. Such ambient humidity may be different to the humidity outside the room where a patient is sleeping.

In another example, ambient pressure may be the pressure immediately surrounding or external to the body.

In certain forms, ambient (e.g., acoustic) noise may be considered to be the background noise level in the room where a patient is located, other than for example, noise generated by an RPT device or emanating from a mask or patient interface. Ambient noise may be generated by sources outside the room.

Automatic Positive Airway Pressure (APAP) therapy: CPAP therapy in which the treatment pressure is automatically adjustable, e.g. from breath to breath, between minimum and maximum limits, depending on the presence or absence of indications of SDB events.

Continuous Positive Airway Pressure (CPAP) therapy: Respiratory pressure therapy in which the treatment pressure is approximately constant through a respiratory cycle of a patient. In some forms, the pressure at the entrance to the airways will be slightly higher during exhalation, and slightly lower during inhalation. In some forms, the pressure will vary between different respiratory cycles of the patient, for example, being increased in response to detection of indications of partial upper airway obstruction, and decreased in the absence of indications of partial upper airway obstruction.

Flow rate: The volume (or mass) of air delivered per unit time. Flow rate may refer to an instantaneous quantity. In some cases, a reference to flow rate will be a reference to a scalar quantity, namely a quantity having magnitude only. In other cases, a reference to flow rate will be a reference to a vector quantity, namely a quantity having both magnitude and direction. Flow rate may be given the symbol Q. 'Flow rate' is sometimes shortened to simply 'flow' or 'airflow'.

In the example of patient respiration, a flow rate may be nominally positive for the inspiratory portion of a breathing cycle of a patient, and hence negative for the expiratory portion of the breathing cycle of a patient. Device flow rate, Qd, is the flow rate of air leaving the RPT device. Total flow rate, Qt, is the flow rate of air and any supplementary gas reaching the patient interface via the air circuit. Vent flow rate, Qv, is the flow rate of air leaving a vent to allow washout of exhaled gases. Leak flow rate, Ql, is the flow rate of leak from a patient interface system or elsewhere. Respiratory flow rate, Or, is the flow rate of air that is received into the patient's respiratory system.

Flow therapy: Respiratory therapy comprising the delivery of a flow of air to an entrance to the airways at a controlled flow rate referred to as the treatment flow rate that is typically positive throughout the patient's breathing cycle.

Humidifier: The word humidifier will be taken to mean a humidifying apparatus constructed and arranged, or configured with a physical structure to be capable of providing a therapeutically beneficial amount of water ($H_2O$) vapour to a flow of air to ameliorate a medical respiratory condition of a patient.

Leak: The word leak will be taken to be an unintended flow of air. In one example, leak may occur as the result of an incomplete seal between a mask and a patient's face. In another example leak may occur in a swivel elbow to the ambient.

Noise, conducted (acoustic): Conducted noise in the present document refers to noise which is carried to the patient by the pneumatic path, such as the air circuit and the patient interface as well as the air therein. In one form, conducted noise may be quantified by measuring sound pressure levels at the end of an air circuit.

Noise, radiated (acoustic): Radiated noise in the present document refers to noise which is carried to the patient by the ambient air. In one form, radiated noise may be quantified by measuring sound power/pressure levels of the object in question according to ISO 3744.

Noise, vent (acoustic): Vent noise in the present document refers to noise which is generated by the flow of air through any vents such as vent holes of the patient interface.

Oxygen enriched air: Air with a concentration of oxygen greater than that of atmospheric air (21%), for example at least about 50% oxygen, at least about 60% oxygen, at least about 70% oxygen, at least about 80% oxygen, at least about 90% oxygen, at least about 95% oxygen, at least about 98% oxygen, or at least about 99% oxygen. "Oxygen enriched air" is sometimes shortened to "oxygen".

Medical Oxygen: Medical oxygen is defined as oxygen enriched air with an oxygen concentration of 80% or greater.

Patient: A person, whether or not they are suffering from a respiratory condition.

Pressure: Force per unit area. Pressure may be expressed in a range of units, including $cmH_2O$, g-f/$cm^2$ and hectopascal. 1 $cmH_2O$ is equal to 1 g-f/$cm^2$ and is approximately 0.98 hectopascal (1 hectopascal=100 Pa=100 N/$m^2$=1 millibar~0.001 atm). In this specification, unless otherwise stated, pressure is given in units of $cmH_2O$.

The pressure in the patient interface is given the symbol Pm, while the treatment pressure, which represents a target value to be achieved by the interface pressure Pm at the current instant of time, is given the symbol Pt.

Respiratory Pressure Therapy: The application of a supply of air to an entrance to the airways at a treatment pressure that is typically positive with respect to atmosphere.

Ventilator: A mechanical device that provides pressure support to a patient to perform some or all of the work of breathing.

5.8.1.1 Materials

Silicone or Silicone Elastomer: A synthetic rubber. In this specification, a reference to silicone is a reference to liquid silicone rubber (LSR) or a compression moulded silicone rubber (CMSR). One form of commercially available LSR is SILASTIC (included in the range of products sold under this trademark), manufactured by Dow Corning. Another manufacturer of LSR is Wacker. Unless otherwise specified to the contrary, an exemplary form of LSR has a Shore A (or Type A) indentation hardness in the range of about 35 to about 45 as measured using ASTM D2240.

Polycarbonate: a thermoplastic polymer of Bisphenol-A Carbonate.

5.8.1.2 Mechanical Properties

Resilience: Ability of a material to absorb energy when deformed elastically and to release the energy upon unloading.

Resilient: Will release substantially all of the energy when unloaded. Includes e.g. certain silicones, and thermoplastic elastomers.

Hardness: The ability of a material per se to resist deformation (e.g. described by a Young's Modulus, or an indentation hardness scale measured on a standardised sample size).

- 'Soft' materials may include silicone or thermo-plastic elastomer (TPE), and may, e.g. readily deform under finger pressure.
- 'Hard' materials may include polycarbonate, polypropylene, steel or aluminium, and may not e.g. readily deform under finger pressure.

Stiffness (or rigidity) of a structure or component: The ability of the structure or component to resist deformation in response to an applied load. The load may be a force or a moment, e.g. compression, tension, bending or torsion. The structure or component may offer different resistances in different directions. The inverse of stiffness is flexibility.

Floppy structure or component: A structure or component that will change shape, e.g. bend, when caused to support its own weight, within a relatively short period of time such as 1 second.

Rigid structure or component: A structure or component that will not substantially change shape when subject to the loads typically encountered in use. An example of such a use may be setting up and maintaining a patient interface in sealing relationship with an entrance to a patient's airways, e.g. at a load of approximately 20 to 30 $cmH_2O$ pressure.

As an example, an I-beam may comprise a different bending stiffness (resistance to a bending load) in a first direction in comparison to a second, orthogonal direction. In another example, a structure or component may be floppy in a first direction and rigid in a second direction.

5.8.2 Respiratory Cycle

Apnea: According to some definitions, an apnea is said to have occurred when flow falls below a predetermined threshold for a duration, e.g. 10 seconds. An obstructive apnea will be said to have occurred when, despite patient effort, some obstruction of the airway does not allow air to flow. A central apnea will be said to have occurred when an apnea is detected that is due to a reduction in breathing effort, or the absence of breathing effort, despite the airway being patent. A mixed apnea occurs when a reduction or absence of breathing effort coincides with an obstructed airway.

Breathing rate: The rate of spontaneous respiration of a patient, usually measured in breaths per minute.

Duty cycle: The ratio of inhalation time, Ti to total breath time, Ttot.

Effort (breathing): The work done by a spontaneously breathing person attempting to breathe.

Expiratory portion of a breathing cycle: The period from the start of expiratory flow to the start of inspiratory flow.

Inspiratory portion of a breathing cycle: The period from the start of inspiratory flow to the start of expiratory flow will be taken to be the inspiratory portion of a breathing cycle.

Patency (airway): The degree of the airway being open, or the extent to which the airway is open. A patent airway is open. Airway patency may be quantified, for example with a value of one (1) being patent, and a value of zero (0), being closed (obstructed).

Peak flow rate (Qpeak): The maximum value of flow rate during the inspiratory portion of the respiratory flow waveform.

Respiratory flow rate, patient airflow rate, respiratory airflow rate (Or): These terms may be understood to refer to the RPT device's estimate of respiratory flow rate, as opposed to "true respiratory flow rate" or "true respiratory flow rate", which is the actual respiratory flow rate experienced by the patient, usually expressed in litres per minute.

Tidal volume (Vt): The volume of air inhaled or exhaled during normal breathing, when extra effort is not applied. In principle the inspiratory volume Vi (the volume of air inhaled) is equal to the expiratory volume Ve (the volume of air exhaled), and therefore a single tidal volume It may be defined as equal to either quantity. In practice the tidal volume Vt is estimated as some combination, e.g. the mean, of the inspiratory volume Vi and the expiratory volume Ve.

Inhalation Time (Ti): The duration of the inspiratory portion of the respiratory flow rate waveform.

Exhalation Time (Te): The duration of the expiratory portion of the respiratory flow rate waveform.

Total Time (Ttot): The total duration between the start of one inspiratory portion of a respiratory flow rate waveform and the start of the following inspiratory portion of the respiratory flow rate waveform.

Typical recent ventilation: The value of ventilation around which recent values of ventilation Vent over some predetermined timescale tend to cluster, that is, a measure of the central tendency of the recent values of ventilation.

Upper airway obstruction (UAO): includes both partial and total upper airway obstruction. This may be associated with a state of flow limitation, in which the flow rate increases only slightly or may even decrease as the pressure difference across the upper airway increases (Starling resistor behaviour).

Ventilation (Vent): A measure of a rate of gas being exchanged by the patient's respiratory system. Measures of ventilation may include one or both of inspiratory and expiratory flow, per unit time. When expressed as a volume per minute, this quantity is often referred to as "minute ventilation". Minute ventilation is sometimes given simply as a volume, understood to be the volume per minute.

5.8.3 Anatomy 5.8.3.1 Anatomy of the Face

Ala: the external outer wall or "wing" of each nostril (plural: alar)

Alar angle:

Alare: The most lateral point on the nasal ala.

Alar curvature (or alar crest) point: The most posterior point in the curved base line of each ala, found in the crease formed by the union of the ala with the cheek.

Auricle: The whole external visible part of the ear.

(nose) Bony framework: The bony framework of the nose comprises the nasal bones, the frontal process of the maxillae and the nasal part of the frontal bone.

(nose) Cartilaginous framework: The cartilaginous framework of the nose comprises the septal, lateral, major and minor cartilages.

Columella: the strip of skin that separates the nares and which runs from the pronasale to the upper lip.

Columella angle: The angle between the line drawn through the midpoint of the nostril aperture and a line drawn perpendicular to the Frankfort horizontal while intersecting subnasale.

Frankfort horizontal plane: A line extending from the most inferior point of the orbital margin to the left tragion. The tragion is the deepest point in the notch superior to the tragus of the auricle.

Glabella: Located on the soft tissue, the most prominent point in the midsagittal plane of the forehead.

Lateral nasal cartilage: A generally triangular plate of cartilage. Its superior margin is attached to the nasal bone and frontal process of the maxilla, and its inferior margin is connected to the greater alar cartilage.

Lip, lower (labrale inferius):

Lip, upper (labrale superius):

Greater alar cartilage: A plate of cartilage lying below the lateral nasal cartilage. It is curved around the anterior part of the naris. Its posterior end is connected to the frontal process of the maxilla by a tough fibrous membrane containing three or four minor cartilages of the ala.

Nares (Nostrils): Approximately ellipsoidal apertures forming the entrance to the nasal cavity. The singular form of nares is naris (nostril). The nares are separated by the nasal septum.

Naso-labial sulcus or Naso-labial fold: The skin fold or groove that runs from each side of the nose to the corners of the mouth, separating the cheeks from the upper lip.

Naso-labial angle: The angle between the columella and the upper lip, while intersecting subnasale.

Otobasion inferior: The lowest point of attachment of the auricle to the skin of the face.

Otobasion superior: The highest point of attachment of the auricle to the skin of the face.

Pronasale: the most protruded point or tip of the nose, which can be identified in lateral view of the rest of the portion of the head.

Philtrum: the midline groove that runs from lower border of the nasal septum to the top of the lip in the upper lip region.

Pogonion: Located on the soft tissue, the most anterior midpoint of the chin.

Ridge (nasal): The nasal ridge is the midline prominence of the nose, extending from the Sellion to the Pronasale.

Sagittal plane: A vertical plane that passes from anterior (front) to posterior (rear). The midsagittal plane is a sagittal plane that divides the body into right and left halves.

Sellion: Located on the soft tissue, the most concave point overlying the area of the frontonasal suture.

Septal cartilage (nasal): The nasal septal cartilage forms part of the septum and divides the front part of the nasal cavity.

Subalare: The point at the lower margin of the alar base, where the alar base joins with the skin of the superior (upper) lip.

Subnasal point: Located on the soft tissue, the point at which the columella merges with the upper lip in the midsagittal plane.

Supramenton: The point of greatest concavity in the midline of the lower lip between labrale inferius and soft tissue pogonion Anatomy of the Skull Frontal bone: The frontal bone includes a large vertical portion, the squama frontalis, corresponding to the region known as the forehead.

Mandible: The mandible forms the lower jaw. The mental protuberance is the bony protuberance of the jaw that forms the chin.

Maxilla: The maxilla forms the upper jaw and is located above the mandible and below the orbits. The frontal process of the maxilla projects upwards by the side of the nose, and forms part of its lateral boundary.

Nasal bones: The nasal bones are two small oblong bones, varying in size and form in different individuals; they are placed side by side at the middle and upper part of the face, and form, by their junction, the "bridge" of the nose.

Nasion: The intersection of the frontal bone and the two nasal bones, a depressed area directly between the eyes and superior to the bridge of the nose.

Occipital bone: The occipital bone is situated at the back and lower part of the cranium. It includes an oval aperture, the foramen magnum, through which the cranial cavity communicates with the vertebral canal. The curved plate behind the foramen magnum is the squama occipitalis.

Orbit: The bony cavity in the skull to contain the eyeball.

Parietal bones: The parietal bones are the bones that, when joined together, form the roof and sides of the cranium.

Temporal bones: The temporal bones are situated on the bases and sides of the skull, and support that part of the face known as the temple.

Zygomatic bones: The face includes two zygomatic bones, located in the upper and lateral parts of the face and forming the prominence of the cheek.

5.8.3.2 Anatomy of the Respiratory System

Diaphragm: A sheet of muscle that extends across the bottom of the rib cage. The diaphragm separates the thoracic cavity, containing the heart, lungs and ribs, from the abdominal cavity. As the diaphragm contracts the volume of the thoracic cavity increases and air is drawn into the lungs.

Larynx: The larynx, or voice box houses the vocal folds and connects the inferior part of the pharynx (hypopharynx) with the trachea.

Lungs: The organs of respiration in humans. The conducting zone of the lungs contains the trachea, the bronchi, the bronchioles, and the terminal bronchioles. The respiratory zone contains the respiratory bronchioles, the alveolar ducts, and the alveoli.

Nasal cavity: The nasal cavity (or nasal fossa) is a large air filled space above and behind the nose in the middle of the face. The nasal cavity is divided in two by a vertical fin called the nasal septum. On the sides of the nasal cavity are three horizontal outgrowths called nasal conchae (singular "concha") or turbinates. To the front of the nasal cavity is the nose, while the back blends, via the choanae, into the nasopharynx.

Pharynx: The part of the throat situated immediately inferior to (below) the nasal cavity, and superior to the oesophagus and larynx. The pharynx is conventionally divided into three sections: the nasopharynx (epipharynx) (the nasal part of the pharynx), the oropharynx (mesopharynx) (the oral part of the pharynx), and the laryngopharynx (hypopharynx).

5.8.4 Patient Interface

Anti-asphyxia valve (AAV): The component or sub-assembly of a mask system that, by opening to atmosphere in a failsafe manner, reduces the risk of excessive $CO_2$ rebreathing by a patient.

Elbow: An elbow is an example of a structure that directs an axis of flow of air travelling therethrough to change direction through an angle. In one form, the angle may be approximately 90 degrees. In another form, the angle may be more, or less than 90 degrees. The elbow may have an approximately circular cross-section. In another form the elbow may have an oval or a rectangular cross-section. In certain forms an elbow may be rotatable with respect to a mating component, e.g. about 360 degrees. In certain forms an elbow may be removable from a mating component, e.g. via a snap connection. In certain forms, an elbow may be assembled to a mating component via a one-time snap during manufacture, but not removable by a patient.

Frame: Frame will be taken to mean a mask structure that bears the load of tension between two or more points of connection with a headgear. A mask frame may be a non-airtight load bearing structure in the mask. However, some forms of mask frame may also be air-tight.

Functional dead space: (description to be inserted here)

Headgear: Headgear will be taken to mean a form of positioning and stabilizing structure designed for use on a head. For example the headgear may comprise a collection of one or more struts, ties and stiffeners configured to locate and retain a patient interface in position on a patient's face for delivery of respiratory therapy. Some ties are formed of a soft, flexible, elastic material such as a laminated composite of foam and fabric.

Membrane: Membrane will be taken to mean a typically thin element that has, preferably, substantially no resistance to bending, but has resistance to being stretched.

Plenum chamber: a mask plenum chamber will be taken to mean a portion of a patient interface having walls at least partially enclosing a volume of space, the volume having air therein pressurised above atmospheric pressure in use. A shell may form part of the walls of a mask plenum chamber.

Seal: May be a noun form ("a seal") which refers to a structure, or a verb form ("to seal") which refers to the effect. Two elements may be constructed and/or arranged to 'seal' or to effect 'sealing' therebetween without requiring a separate 'seal' element per se.

Shell: A shell will be taken to mean a curved, relatively thin structure having bending, tensile and compressive stiffness. For example, a curved structural wall of a mask may be a shell. In some forms, a shell may be faceted. In some forms a shell may be airtight. In some forms a shell may not be airtight.

Stiffener: A stiffener will be taken to mean a structural component designed to increase the bending resistance of another component in at least one direction.

Strut: A strut will be taken to be a structural component designed to increase the compression resistance of another component in at least one direction.

Swivel (noun): A subassembly of components configured to rotate about a common axis, preferably independently, preferably under low torque. In one form, the swivel may be constructed to rotate through an angle of at least 360 degrees. In another form, the swivel may be constructed to rotate through an angle less than 360 degrees. When used in the context of an air delivery conduit, the sub-assembly of components preferably comprises a matched pair of cylindrical conduits. There may be little or no leak flow of air from the swivel in use.

Tie (noun): A structure designed to resist tension.

Vent: (noun): A structure that allows a flow of air from an interior of the mask, or conduit, to ambient air for clinically effective washout of exhaled gases. For example, a clinically effective washout may involve a flow rate of about 10 litres per minute to about 100 litres per minute, depending on the mask design and treatment pressure.

5.8.5 Shape of Structures

Products in accordance with the present technology may comprise one or more three-dimensional mechanical structures, for example a mask cushion or an impeller. The three-dimensional structures may be bounded by two-dimensional surfaces. These surfaces may be distinguished using a label to describe an associated surface orientation, location, function, or some other characteristic. For example a structure may comprise one or more of an anterior surface, a posterior surface, an interior surface and an exterior surface. In another example, a seal-forming structure may comprise a face-contacting (e.g. outer) surface, and a separate non-face-contacting (e.g. underside or inner) surface. In another example, a structure may comprise a first surface and a second surface.

To facilitate describing the shape of the three-dimensional structures and the surfaces, we first consider a cross-section through a surface of the structure at a point, p. See FIG. 3B to FIG. 3F, which illustrate examples of cross-sections at point p on a surface, and the resulting plane curves. FIGS. 3B to 3F also illustrate an outward normal vector at p. The outward normal vector at p points away from the surface. In some examples we describe the surface from the point of view of an imaginary small person standing upright on the surface.

5.8.5.1 Curvature in One Dimension

The curvature of a plane curve at p may be described as having a sign (e.g. positive, negative) and a magnitude (e.g. 1/radius of a circle that just touches the curve at p).

Positive curvature: If the curve at p turns towards the outward normal, the curvature at that point will be taken to be positive (if the imaginary small person leaves the point p they must walk uphill). See FIG. 3B (relatively large positive curvature compared to FIG. 3C) and FIG. 3C (relatively small positive curvature compared to FIG. 3B). Such curves are often referred to as concave.

Zero curvature: If the curve at p is a straight line, the curvature will be taken to be zero (if the imaginary small person leaves the point p, they can walk on a level, neither up nor down). See FIG. 3D.

Negative curvature: If the curve at p turns away from the outward normal, the curvature in that direction at that point will be taken to be negative (if the imaginary small person leaves the point p they must walk downhill). See FIG. 3E (relatively small negative curvature compared to FIG. 3F) and FIG. 3F (relatively large negative curvature compared to FIG. 3E). Such curves are often referred to as convex.

5.8.5.2 Curvature of Two Dimensional Surfaces

A description of the shape at a given point on a two-dimensional surface in accordance with the present technology may include multiple normal cross-sections. The multiple cross-sections may cut the surface in a plane that includes the outward normal (a "normal plane"), and each cross-section may be taken in a different direction. Each cross-section results in a plane curve with a corresponding curvature. The different curvatures at that point may have the same sign, or a different sign. Each of the curvatures at that point has a magnitude, e.g. relatively small. The plane curves in FIGS. 3B to 3F could be examples of such multiple cross-sections at a particular point.

Principal curvatures and directions: The directions of the normal planes where the curvature of the curve takes its maximum and minimum values are called the principal directions. In the examples of FIG. 3B to FIG. 3F, the maximum curvature occurs in FIG. 3B, and the minimum occurs in FIG. 3F, hence FIG. 3B and FIG. 3F are cross sections in the principal directions. The principal curvatures at p are the curvatures in the principal directions.

Region of a surface: A connected set of points on a surface. The set of points in a region may have similar characteristics, e.g. curvatures or signs.

Saddle region: A region where at each point, the principal curvatures have opposite signs, that is, one is positive, and the other is negative (depending on the direction to which the imaginary person turns, they may walk uphill or downhill).

Dome region: A region where at each point the principal curvatures have the same sign, e.g. both positive (a "concave dome") or both negative (a "convex dome").

Cylindrical region: A region where one principal curvature is zero (or, for example, zero within manufacturing tolerances) and the other principal curvature is non-zero.

Planar region: A region of a surface where both of the principal curvatures are zero (or, for example, zero within manufacturing tolerances).

Edge of a surface: A boundary or limit of a surface or region.

Path: In certain forms of the present technology, 'path' will be taken to mean a path in the mathematical-topological sense, e.g. a continuous space curve from f(0) to f(1) on a surface. In certain forms of the present technology, a 'path' may be described as a route or course, including e.g. a set of points on a surface. (The path for the imaginary person is where they walk on the surface, and is analogous to a garden path).

Path length: In certain forms of the present technology, 'path length' will be taken to mean the distance along the surface from f(0) to f(1), that is, the distance along the path on the surface. There may be more than one path between two points on a surface and such paths may have different path lengths. (The path length for the imaginary person would be the distance they have to walk on the surface along the path).

Straight-line distance: The straight-line distance is the distance between two points on a surface, but without regard to the surface. On planar regions, there would be a path on the surface having the same path length as the straight-line distance between two points on the surface. On non-planar surfaces, there may be no paths having the same path length as the straight-line distance between two points. (For the imaginary person, the straight-line distance would correspond to the distance 'as the crow flies'.)

5.8.5.3 Space Curves

Space curves: Unlike a plane curve, a space curve does not necessarily lie in any particular plane. A space curve may be closed, that is, having no endpoints. A space curve may be considered to be a one-dimensional piece of three-dimensional space. An imaginary person walking on a strand of the DNA helix walks along a space curve. A typical human left ear comprises a helix, which is a left-hand helix, see FIG. 3Q. A typical human right ear comprises a helix, which is a right-hand helix, see FIG. 3R. FIG. 3S shows a right-hand helix. The edge of a structure, e.g. the edge of a membrane or impeller, may follow a space curve. In general, a space curve may be described by a curvature and a torsion at each point on the space curve. Torsion is a measure of how the curve turns out of a plane. Torsion has a sign and a magnitude. The torsion at a point on a space curve may be characterised with reference to the tangent, normal and binormal vectors at that point.

Tangent unit vector (or unit tangent vector): For each point on a curve, a vector at the point specifies a direction from that point, as well as a magnitude. A tangent unit vector is a unit vector pointing in the same direction as the curve at that point. If an imaginary person were flying along the curve and fell off her vehicle at a particular point, the direction of the tangent vector is the direction she would be travelling.

Unit normal vector: As the imaginary person moves along the curve, this tangent vector itself changes. The unit vector pointing in the same direction that the tangent vector is changing is called the unit principal normal vector. It is perpendicular to the tangent vector.

Binormal unit vector: The binormal unit vector is perpendicular to both the tangent vector and the principal normal vector. Its direction may be determined by a right-hand rule (see e.g. FIG. 3P), or alternatively by a left-hand rule (FIG. 3O).

Osculating plane: The plane containing the unit tangent vector and the unit principal normal vector. See FIGS. 3O and 3P.

Torsion of a space curve: The torsion at a point of a space curve is the magnitude of the rate of change of the binormal unit vector at that point. It measures how much the curve deviates from the osculating plane. A space curve which lies in a plane has zero torsion. A space curve which deviates a relatively small amount from the osculating plane will have a relatively small magnitude of torsion (e.g. a gently sloping helical path). A space curve which deviates a relatively large amount from the osculating plane will have a relatively large magnitude of torsion (e.g. a steeply sloping helical path). With reference to FIG. 3S, since T2>T1, the magnitude of the torsion near the top coils of the helix of FIG. 3S is greater than the magnitude of the torsion of the bottom coils of the helix of FIG. 3S With reference to the right-hand rule of FIG. 3P, a space curve turning towards the direction of the right-hand binormal may be considered as having a right-hand positive torsion (e.g. a right-hand helix as shown in FIG. 3S). A space curve turning away from the direction of the right-hand binormal may be considered as having a right-hand negative torsion (e.g. a left-hand helix).

Equivalently, and with reference to a left-hand rule (see FIG. 3O), a space curve turning towards the direction of the left-hand binormal may be considered as having a left-hand positive torsion (e.g. a left-hand helix). Hence left-hand positive is equivalent to right-hand negative. See FIG. 3T.

5.8.5.4 Holes

A surface may have a one-dimensional hole, e.g. a hole bounded by a plane curve or by a space curve. Thin structures (e.g. a membrane) with a hole, may be described as having a one-dimensional hole. See for example the one dimensional hole in the surface of structure shown in FIG. 3I, bounded by a plane curve.

A structure may have a two-dimensional hole, e.g. a hole bounded by a surface. For example, an inflatable tyre has a two dimensional hole bounded by the interior surface of the tyre. In another example, a bladder with a cavity for air or gel could have a two-dimensional hole. See for example the cushion of FIG. 3L and the example cross-sections therethrough in FIG. 3M and FIG. 3N, with the interior surface bounding a two dimensional hole indicated. In a yet another example, a conduit may comprise a one-dimension hole (e.g. at its entrance or at its exit), and a two-dimension hole bounded by the inside surface of the conduit. See also the two dimensional hole through the structure shown in FIG. 3K, bounded by a surface as shown.

5.9 Other Remarks

Unless the context clearly dictates otherwise and where a range of values is provided, it is understood that each intervening value, to the tenth of the unit of the lower limit, between the upper and lower limit of that range, and any other stated or intervening value in that stated range is encompassed within the technology. The upper and lower limits of these intervening ranges, which may be independently included in the intervening ranges, are also encompassed within the technology, subject to any specifically excluded limit in the stated range. Where the stated range includes one or both of the limits, ranges excluding either or both of those included limits are also included in the technology.

Furthermore, where a value or values are stated herein as being implemented as part of the technology, it is understood that such values may be approximated, unless otherwise stated, and such values may be utilized to any suitable significant digit to the extent that a practical technical implementation may permit or require it.

Unless defined otherwise, all technical and scientific terms used herein have the same meaning as commonly understood by one of ordinary skill in the art to which this technology belongs. Although any methods and materials similar or equivalent to those described herein can also be used in the practice or testing of the present technology, a limited number of the exemplary methods and materials are described herein.

When a particular material is identified as being used to construct a component, obvious alternative materials with similar properties may be used as a substitute. Furthermore, unless specified to the contrary, any and all components herein described are understood to be capable of being manufactured and, as such, may be manufactured together or separately.

It must be noted that as used herein and in the appended claims, the singular forms "a", "an", and "the" include their plural equivalents, unless the context clearly dictates otherwise.

All publications mentioned herein are incorporated herein by reference in their entirety to disclose and describe the methods and/or materials which are the subject of those publications. The publications discussed herein are provided solely for their disclosure prior to the filing date of the present application. Nothing herein is to be construed as an admission that the present technology is not entitled to antedate such publication by virtue of prior invention. Further, the dates of publication provided may be different from the actual publication dates, which may need to be independently confirmed.

The terms "comprises" and "comprising" should be interpreted as referring to elements, components, or steps in a non-exclusive manner, indicating that the referenced elements, components, or steps may be present, or utilized, or combined with other elements, components, or steps that are not expressly referenced.

The subject headings used in the detailed description are included only for the ease of reference of the reader and should not be used to limit the subject matter found throughout the disclosure or the claims. The subject headings should not be used in construing the scope of the claims or the claim limitations.

Although the technology herein has been described with reference to particular examples, it is to be understood that these examples are merely illustrative of the principles and applications of the technology. In some instances, the terminology and symbols may imply specific details that are not required to practice the technology. For example, although the terms "first" and "second" may be used, unless otherwise specified, they are not intended to indicate any order but may be utilised to distinguish between distinct elements. Furthermore, although process steps in the methodologies may be described or illustrated in an order, such an ordering is not required. Those skilled in the art will recognize that such ordering may be modified and/or aspects thereof may be conducted concurrently or even synchronously.

It is therefore to be understood that numerous modifications may be made to the illustrative examples and that other arrangements may be devised without departing from the spirit and scope of the technology.

5.10 REFERENCE SIGNS LIST

| | |
|---|---|
| patient | 1000 |
| bed partner | 1100 |
| patient interface | 3000 |
| seal - forming structure | 3100 |
| first seal forming structure | 3101 |
| second seal - forming structure | 3102 |
| oral hole | 3103 |
| nasal hole | 3104 |
| plenum chamber | 3200 |
| oral portion | 3201 |
| nasal portion | 3202 |
| plenum chamber hole | 3206 |
| lip | 3208 |
| groove | 3280 |
| projection | 3284 |
| positioning and stabilising structure | 3300 |
| connector | 3310 |
| frame | 3350 |
| connection point | 3352 |
| headgear straps | 3354 |
| right superior headgear strap | 3356 |
| left superior headgear strap | 3358 |
| central portion | 3360 |
| arm | 3362 |
| secondary connection points | 3364 |
| right inferior headgear strap | 3366 |
| left inferior headgear strap | 3368 |
| clip | 3370 |
| slots | 3372 |
| vent | 3400 |
| elbow | 3500 |
| connection port | 3600 |
| forehead support | 3700 |
| posterior frame | 3800 |
| outer annulus | 3801 |
| HMX cartridge connector | 3802 |
| posterior connector | 3804 |
| inner annulus | 3805 |
| posterior frame support | 3806 |
| posterior frame hole | 3808 |
| plate | 3809 |
| heat and moisture exchanger (HMX) cartridge | 3810 |
| anterior HMX cartridge frame | 3812 |
| posterior HMX cartridge frame | 3814 |
| annular notch | 3815 |
| HMX material | 3816 |
| vent and conduit connector assembly | 3820 |
| anterior frame | 3830 |
| anterior connector | 3831 |
| anterior frame cavity | 3832 |
| annular wall | 3833 |
| radial vent hole | 3834 |
| cage | 3835 |
| outer annular rim | 3836 |
| inner annular rim | 3837 |
| membrane | 3840 |
| membrane hole | 3841 |
| conduit connector | 3850 |
| conduit connection tube | 3851 |
| outer axial vent hole | 3852 |
| vent base | 3853 |
| inner axial vent hole | 3854 |
| cage spacer | 3856 |

-continued

| 5.10 REFERENCE SIGNS LIST | |
|---|---|
| conduit connector hole | 3857 |
| HMX cartridge spacer | 3858 |
| posterior diffuser retaining ring | 3860 |
| diffuser retainer | 3862 |
| diffuser material | 3870 |
| anterior diffuser retaining ring | 3880 |
| attachment portion | 3882 |
| anterior retaining ring support | 3884 |
| diffused vent hole | 3886 |
| outer portion | 3887 |
| inner portion | 3888 |
| heat and moisture exchanger (HMX) material | 3900 |
| circumferential surface | 3902 |
| anterior surface | 3904 |
| posterior surface | 3906 |
| frame assembly | 3910 |
| posterior flow directing structure | 3920 |
| connection tab | 3921 |
| notch | 3922 |
| flow directing tab | 3923 |
| locating protrusion | 3924 |
| central hole | 3925 |
| heat and moisture exchanger (HMX) frame | 3930 |
| anterior HMX frame | 3931 |
| annular lip | 3932 |
| HMX frame cage | 3933 |
| peripheral hole | 3934 |
| central hole | 3935 |
| posterior HMX frame | 3940 |
| radial lip retainer | 3941 |
| lip retaining channel | 3942 |
| locating recess | 3943 |
| peripheral wall | 3944 |
| peripheral vent hole | 3945 |
| radial HMX spacer | 3946 |
| axial HMX spacer | 3947 |
| HMX support | 3948 |
| posterior HMX frame hole | 3949 |
| radial flow directing wall | 3950 |
| axial flow directing wall | 3951 |
| posterior flow directing frame | 3960 |
| flow director | 3961 |
| flow directing hole | 3962 |
| connection tab | 3963 |
| HMX support | 3964 |
| flow directing posterior frame hole | 3965 |
| alignment indicator | 3966 |
| anterior HMX frame | 3970 |
| anterior annular rim | 3971 |
| annular channel | 3972 |
| posterior annular rim | 3973 |
| annular wall | 3974 |
| radial vent hole | 3975 |
| anterior frame and connector cage | 3976 |
| anterior HMX support | 3977 |
| peripheral hole | 3978 |
| central hole | 3979 |
| posterior HMX frame | 3980 |
| clip | 3981 |
| radial spacer | 3982 |
| posterior frame support | 3983 |
| alignment notch | 3984 |
| bypass frame | 3985 |
| central hole | 3986 |
| bypass channel | 3987 |
| tab | 3988 |
| anterior HMX frame | 3990 |
| anterior annular rim | 3991 |
| annular channel | 3992 |
| posterior annular rim | 3993 |
| vent hole | 3994 |
| central hole | 3995 |
| RPT device | 4000 |
| external housing | 4010 |
| upper portion | 4012 |

-continued

| 5.10 REFERENCE SIGNS LIST | |
|---|---|
| lower portion | 4014 |
| panel | 4015 |
| chassis | 4016 |
| handle | 4018 |
| pneumatic block | 4020 |
| air filter | 4110 |
| inlet air filter | 4112 |
| outlet air filter | 4114 |
| muffler | 4120 |
| inlet muffler | 4122 |
| outlet muffler | 4124 |
| pressure generator | 4140 |
| blower | 4142 |
| controllable blower | 4142 |
| motor | 4144 |
| anti - spill back valve | 4160 |
| air circuit | 4170 |
| electrical components | 4200 |
| PCBA | 4202 |
| power supply | 4210 |
| input device | 4220 |
| central controller | 4230 |
| clock | 4232 |
| therapy device controller | 4240 |
| protection circuits | 4250 |
| memory | 4260 |
| transducer | 4270 |
| pressure sensor | 4272 |
| flow rate sensor | 4274 |
| motor speed transducer | 4276 |
| data communication interface | 4280 |
| remote external communication network | 4282 |
| local external communication network | 4284 |
| remote external device | 4286 |
| local external device | 4288 |
| output device | 4290 |
| display driver | 4292 |
| display | 4294 |
| humidifier | 5000 |
| humidifier inlet | 5002 |
| humidifier outlet | 5004 |
| humidifier base | 5006 |
| humidifier reservoir | 5110 |
| humidifier reservoir dock | 5130 |
| heating element | 5240 |
| incoming pressurized flow | 7000 |
| incoming pressurized vent flow | 7001 |
| HMX bypass vent flow | 7002 |
| HMX vent flow | 7003 |
| HMX and flow director assembly | 8000 |
| port | 8001 |
| anterior shell | 8010 |
| outer rim | 8011 |
| protrusion | 8012 |
| posterior mating surface | 8013 |
| anterior channel wall | 8014 |
| posterior shell | 8020 |
| inner rim | 8021 |
| anterior mating surface | 8022 |
| posterior channel wall | 8023 |
| posterior mating surface | 8024 |
| HMX material | 8030 |
| retainer | 8040 |
| anterior mating surface | 8041 |
| bump | 8042 |
| inferior channel | 8050 |
| distal opening | 8051 |
| proximal opening | 8052 |
| superior channel | 8060 |
| distal opening | 8061 |
| proximal opening | 8062 |
| vent ring | 8990 |
| anterior annular rim | 8991 |
| annular channel | 8992 |
| posterior annular rim | 8993 |

-continued

| 5.10 REFERENCE SIGNS LIST | |
|---|---|
| vent hole | 8994 |
| central hole | 8995 |

The invention claimed is:

1. A patient interface comprising:

a plenum chamber pressurisable to a therapeutic pressure of at least 4 cmH2O above ambient air pressure by a flow of air at the therapeutic pressure for breathing by a patient;

a seal-forming structure connected to the plenum chamber, the seal-forming structure being constructed and arranged to seal with a region of the patient's face that at least partly surrounds an entrance to the patient's airways, the seal-forming structure having a nasal hole therein to deliver the flow of air at the therapeutic pressure to at least the patient's nares during use, the seal-forming structure being constructed and arranged to maintain the therapeutic pressure within the plenum chamber throughout the patient's respiratory cycle in use;

a positioning and stabilising structure comprising at least one tie configured to hold the seal-forming structure in a therapeutically effective position on the patient's head;

a heat and moisture exchanger cartridge including a heat and moisture exchanger material positioned within a heat and moisture exchanger cartridge frame; and a vent and conduit connector assembly connected to the plenum chamber and comprising:

an anterior frame that forms a cavity configured to receive the heat and moisture exchanger cartridge;

a conduit connector configured to be connected to a conduit to receive the flow of air at the therapeutic pressure;

a first plurality of vent holes configured to direct a first portion of gas exhaled by the patient from the plenum chamber to atmosphere after passing through the heat and moisture exchanger cartridge; and a second plurality of vent holes configured to direct a second portion of gas exhaled by the patient from the plenum chamber to atmosphere without passing through the heat and moisture exchanger cartridge, wherein the patient interface is configured to leave the patient's mouth uncovered, or the seal-forming structure is configured to seal around the patient's mouth and the patient interface is configured to allow the patient to breath from ambient in the absence of the flow of air at the therapeutic pressure.

2. The patient interface of claim 1, wherein the plenum chamber further comprises a plenum chamber hole, and wherein the vent and conduit connector assembly further comprises a posterior frame configured to be releasably connected to the anterior frame to join the vent and conduit connector assembly to the plenum chamber at the plenum chamber hole.

3. The patient interface of claim 2, wherein the heat and moisture exchanger cartridge is configured to be releasably connected to the posterior frame.

4. The patient interface of claim 2, wherein the posterior frame is configured to retain the heat and moisture exchanger cartridge within the cavity of the anterior frame.

5. The patient interface of claim 2, wherein the posterior frame includes a plate positioned centrally thereon to block a portion of the flow of air at the therapeutic pressure passing from the heat and moisture exchanger cartridge into the plenum chamber.

6. The patient interface of claim 1, wherein the vent and conduit connector assembly is configured such that the heat and moisture exchanger cartridge is positioned externally of the plenum chamber when received in the cavity of the anterior frame.

7. The patient interface of claim 1, wherein the anterior frame comprises an annular wall around the cavity.

8. The patient interface of claim 7, wherein the second plurality of vent holes are positioned on the annular wall.

9. The patient interface of claim 7, wherein the annular wall and the heat and moisture exchanger cartridge form a path, when the heat and moisture exchanger cartridge is positioned within the cavity, to allow the second portion of gas exhaled by the patient to travel from the plenum chamber to atmosphere without passing through the heat and moisture exchanger cartridge.

10. The patient interface of claim 7, wherein the second plurality of vent holes are positioned radially around the annular wall.

11. The patient interface of claim 1, wherein the conduit connector is positioned on the anterior frame.

12. The patient interface of claim 1, wherein the first plurality of vent holes are positioned on the conduit connector.

13. The patient interface of claim 1, wherein the first plurality of vent holes are oriented on the conduit connector axially relative to the flow of air therethrough.

14. The patient interface of claim 1, wherein the conduit connector comprises a conduit connection tube configured to be connected to a conduit to receive the flow of air at the therapeutic pressure, and wherein the first plurality of vent holes are positioned radially outward of the conduit connection tube on the conduit connector.

15. The patient interface of claim 1, wherein the first plurality of vent holes comprise inner axial vent holes and outer axial vent holes that are positioned radially outward of the inner axial vent holes.

16. The patient interface of claim 15, wherein the anterior frame includes a cage, wherein a membrane is positioned between the cage and the conduit connector and is freely movable between the cage and the conduit connector, and wherein the membrane is configured to be urged against the conduit connector in response to an increase in pressure within the patient interface to at least partially occlude a portion of the first plurality of vent holes while leaving another portion of the first plurality of vent holes unoccluded.

17. The patient interface of claim 16, wherein the membrane is shaped and dimensioned to at least partially cover the inner axial vent holes while leaving the outer axial vent holes uncovered.

18. The patient interface of claim 16, wherein the membrane includes a membrane hole configured to allow the flow of air at the therapeutic pressure to travel from the conduit connector, through the anterior frame, and into the plenum chamber.

19. The patient interface of claim 1, wherein the heat and moisture exchanger cartridge, when positioned within the cavity of the anterior frame, is spaced from the conduit connector such that a portion of the incoming flow of air at the therapeutic pressure travels through the first plurality of vent holes to atmosphere without passing through the heat and moisture exchanger cartridge.

20. The patient interface of claim 1, wherein a diffuser material is positioned opposite the anterior frame relative to the conduit connector such that a first portion of a vent flow passing through the first plurality of vent holes is directed into the diffuser material.

21. The patient interface of claim 20, wherein the diffuser material is spaced from the conduit connector such that a second portion of the vent flow passing through the second plurality of vent holes travels to atmosphere without being directed into the diffuser material.

22. The patient interface of claim 1, further comprising an anti-asphyxia valve.

23. The patient interface of claim 22, wherein the anti-asphyxia valve is positioned on the conduit connector.

* * * * *